(12) United States Patent
Myaji et al.

(10) Patent No.: US 8,134,013 B2
(45) Date of Patent: Mar. 13, 2012

(54) AMIDE COMPOUND AND THROMBOPOIETIN RECEPTOR ACTIVATOR

(75) Inventors: Katsuaki Myaji, Funabashi (JP); Shunsuke Iwamoto, Funabashi (JP); Satoshi Nakano, Funabashi (JP); Hirofumi Ota, Funabashi (JP); Yukihiro Shigeta, Funabashi (JP); Yutaka Hirokawa, Funabashi (JP); Kazufumi Yanagihara, Funabashi (JP); Koji Toyama, Funabashi (JP); Shingo Owada, Funabashi (JP); Masato Horikawa, Minamisaitama-gun (JP); Norihisa Ishiwata, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 705 days.

(21) Appl. No.: 11/721,786

(22) PCT Filed: Dec. 14, 2005

(86) PCT No.: PCT/JP2005/023425
§ 371 (c)(1), (2), (4) Date: Jun. 14, 2007

(87) PCT Pub. No.: WO2006/064957
PCT Pub. Date: Jun. 22, 2006

(65) Prior Publication Data
US 2009/0131659 A1 May 21, 2009

(30) Foreign Application Priority Data

Dec. 14, 2004 (JP) ................. 2004-361750
May 2, 2005 (JP) ................. 2005-134643

(51) Int. Cl.
*C07D 409/02* (2006.01)
*A61K 31/40* (2006.01)

(52) U.S. Cl. ........................ 548/527; 514/422
(58) Field of Classification Search .......... 548/527; 514/422
See application file for complete search history.

(56) References Cited

U.S. PATENT DOCUMENTS

| | | |
|---|---|---|
| 2003/0195231 A1 | 10/2003 | Takemoto et al. |
| 2004/0063764 A1 | 4/2004 | Takemoto et al. |
| 2004/0077697 A1 | 4/2004 | Koshio et al. |
| 2004/0082626 A1 | 4/2004 | Takemoto et al. |
| 2005/0153977 A1 | 7/2005 | Sugasawa et al. |
| 2005/0282730 A1 | 12/2005 | Miyaji et al. |
| 2006/0069140 A1 | 3/2006 | Miyaji et al. |
| 2006/0094694 A1 | 5/2006 | Owada et al. |

FOREIGN PATENT DOCUMENTS

| | | |
|---|---|---|
| EP | 1 207 155 A1 | 5/2002 |
| JP | 10-72492 | 3/1998 |
| JP | 11-1477 | 1/1999 |
| JP | 11-152276 | 6/1999 |
| JP | 2001-097948 | 4/2001 |
| JP | 2003 513965 | 4/2003 |
| JP | 2003-238565 | 8/2003 |
| JP | 2004 520302 | 7/2004 |
| WO | WO 96/40189 | 12/1996 |
| WO | WO 96/40750 | 12/1996 |
| WO | WO 98/25965 | 6/1998 |
| WO | WO 99/11262 | 3/1999 |
| WO | WO 00/35446 | 6/2000 |
| WO | WO 00/66112 | 11/2000 |
| WO | WO 01/07423 A1 | 2/2001 |
| WO | WO 01/17349 A1 | 3/2001 |
| WO | WO 01/21180 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |
| WO | WO 02/49413 A2 | 6/2002 |
| WO | WO 02/059099 A1 | 8/2002 |
| WO | WO 02/059100 A1 | 8/2002 |
| WO | WO 02/062775 A1 | 8/2002 |
| WO | WO 02/085343 | 10/2002 |
| WO | WO 03/062233 A1 | 7/2003 |
| WO | 2004 033433 | 4/2004 |
| WO | 2004 108683 | 12/2004 |
| WO | WO 2006/062240 A1 | 6/2006 |

OTHER PUBLICATIONS

Owada et al. (CAPLUS Abstract of WO 2004108683, published Dec. 16, 2004).*
Kimura et al. (FEBS Lett., 428, 250-54 (1998)).*
Kubinyi (3D QSAR in Drug Design: Ligand-Protein Interactions and Molecular Similarity, vol. 2-3, Springer, 1998, 800 pages), TOC and pp. 243-244 provided.*
Bundgaard (Design and application of prodrugs, In a Textbook of Drug Design and Development, (1991), p. 113-191).*
Byrn et al., Pharm. Res., v. 12, n. 7, p945-54, 1995.*

(Continued)

*Primary Examiner* — Robert Havlin
(74) *Attorney, Agent, or Firm* — Oblon, Spivak, McClelland, Maier & Neustadt, L.L.P.

(57) ABSTRACT

The present invention provides compounds useful for prevention, treatment or alleviation of diseases against which activation of the thrombopoietin receptor is effective.

A compound represented by the formula (1):

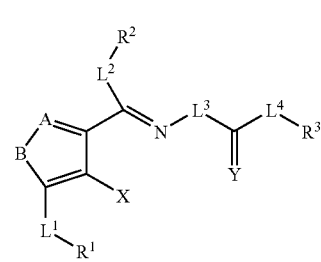

(1)

wherein A, B, $R^1$, $L^1$, $R^2$, $L^2$, $L^3$, Y, $L^4$, $R^3$ and X are the same as defined in the description, a tautomer, prodrug or pharmaceutically acceptable salt of the compound or a solvate thereof.

9 Claims, 1 Drawing Sheet

OTHER PUBLICATIONS

Wermuth, The Practice of Medicinal Chemsitry, 2d ed. (2003). Chs. 9-10 provided.*
Park et al. (Toxicology Lett., 120 (2001), 281-91).*
Park et al., Toxicology Lett., 120 (2001), 281-91.*
U.S. Appl. No. 12/303,436, filed Dec. 4, 2008, Miyaji, et al.
U.S. Appl. No. 11/721,252, filed Jun. 8, 2007, Miyaji, et al.
U.S. Appl. No. 11/837,659, filed Aug. 13, 2007, Owada, et al.
U.S. Appl. No. 12/492,435, filed Jun. 26, 2009, Owada, et al.
J. E. Cardier, "Effects of Megakaryocyte Growth and Development Factor (Thrombopoietin) on Liver Endothelial Cells in Vitro", Microvascular Reasearch, vol. 58, 1999, pp. 108-113.
M. F. Brizzi, et al., "Thrombopoietin Stimulates Endothelial Cell Motility and Neoangiogenesis by a Platelet-Activating Factor-Dependent Mechanism", Circulation Research, vol. 84, 1999, pp. 785-796.
"Blood", Journal of the American Society of Hematology vol. 98, No. 11, Nov. 16, 2001, pp. 71-72.

* cited by examiner

AMIDE COMPOUND AND THROMBOPOIETIN RECEPTOR ACTIVATOR

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation or vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3.

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 25).

1) Applications filed by Hokuriku Seiyaku Co., Ltd. relating to 1,4-benzodiazepine derivatives (patent documents 5 and 6)
2) International Laid-open Patent Applications filed by Shionogi a Co., Ltd (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application filed by Roche Diagnostics GMBH (patent document 21)
6) International Laid-open Patent Applications filed by Yamanouchi Pharmaceutical Co., Ltd. (patent documents 22 and 23)
7) Japanese Laid-open Patent Application filed by Japan Tabacco Inc. (patent document 24)
8) Japanese Laid-open Patent Applications filed by Nissan Chemical Industries, Ltd. (patent documents 25 and 26)

Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO01/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Patent document 25 WO04/033433
Patent document 26 WO04/108683
Non-patent document 1 Microvasc. Res., 1999: 58, p. 108-113
Non-patent document 2 Circ. Res., 1999: 84, p. 785-796
Non-patent document 3 Blood 2001:98, p. 71a-72a

DISCLOSURE OF THE INVENTION

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely the present invention relates to:
1. A compound represented by the formula (1):

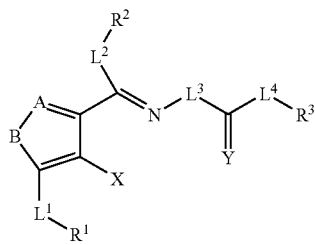

(1)

wherein A is a nitrogen atom or $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{4-14}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms, $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), B is an oxygen atom, a sulfur atom or $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) (provided that when A is a nitrogen atom, B is not NH), $R^1$ is a $C_{2-14}$ aryl group (the $C_{2-14}$ aryl group may be substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkylcarbonyloxy groups and the $C_{1-10}$ alkoxycarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups (the $C_{2-14}$ aryl groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), thiol groups and amino groups (the thiol groups and the amino groups may be optionally substituted with one or two substituents selected from the group consisting of: formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), $L^1$ is a bond, $CR^{10}R^{11}$ (wherein each of $R^{10}$ and $R^{11}$ is independently a hydrogen atom or a $C_{1-6}$ alkyl group (the $C_{1-6}$ alkyl group may be substituted with one or more halogen atoms)), an oxygen atom, a sulfur atom or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), X is $OR^{13}$, $SR^{13}$ or $NR^{14}R^{15}$ (wherein $R^{13}$ is a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), and each of $R^{14}$ and $R^{15}$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $R^2$ is a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $L^2$ is a bond, $CR^{34}R^{35}$ (wherein each of $R^{34}$ and $R^{35}$ is independently a hydrogen atom or a $C_{1-6}$ alkyl group (the $C_{1-6}$ alkyl group may be substituted with one or more halogen atoms)), an oxygen atom, a sulfur atom or $NR^{16}$ (wherein $R^{16}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $L^3$ is a bond, $CR^{17}R^{18}$ (wherein each of $R^{17}$ and $R^{18}$ is independently a hydrogen atom, a $C_{1-10}$ alkyl group, a $C_{2-6}$ alkenyl group; a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), an oxygen atom, a sulfur atom or $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), L is a bond, $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-10}$ alkyl groups (the $C_{1-10}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), an oxygen atom, a sulfur atom or $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), Y is an oxygen atom, a sulfur atom or $NR^{23}$ (wherein $R^{23}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is a $C_{2-14}$ aryl group (the $C_{2-14}$ aryl group is optionally substituted with one or more substituents independently represented by —$V^1$ (wherein $V^1$ is a hydrogen atom, a hydroxyl group, a protected hydroxyl group, an amino group, a thiol group, a nitro group, a cyano group, a halogen atom, a carboxyl group, a carbamoyl group, a sulfamoyl group, a sulfo group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a C alkylcarbonyl group, a $C_{1-10}$ alkylcarbonylamino group, a mono- or di-$C_{1-10}$ alkylamino group, a $C_{1-10}$ alkylaminosulfonyl group, a $C_{1-10}$ alkylaminocarbonyl group, a $C_{1-10}$ alkylsulfonylamino group, a $C_{1-10}$ thioalkyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group, the $C_{1-10}$ alkylcarbonyl group, the $C_{1-10}$ alkylcarbonylamino group, the mono- or di-$C_{1-10}$ alkylamino group, the $C_{1-10}$ alkylaminosulfonyl group, the $C_{1-10}$ alkylaminocarbonyl group, the $C_{1-10}$ alkylsulfonylamino group and the $C_{1-10}$ thioalkyl group may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{2-14}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^3$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $CR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{2-14}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the amino group, the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups $C_{1-10}$ alkylcarbonyloxy groups, $C_{1-10}$ alkoxycarbonyl groups, alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5), or $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms, $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or a substituted $C_{2-9}$ heterocyclyl group (the substituted $C_{2-9}$ heterocyclyl group may be optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))), a $C_{2-14}$ aryl group (the $C_{2-14}$ aryl group is optionally substituted with one or more substituents independently represented by —$V^1$ (wherein $V^1$ is the same as defined above) and with one or more substituents selected from the group consisting of: $C_{1-6}$ alkyl groups, $C_{2-6}$ alkenyl groups and $C_{2-16}$ alkynyl groups (the $C_{1-6}$ alkyl groups, the $C_{2-6}$ alkenyl groups and the $C_{2-6}$ alkynyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents independently represented by —$V^2$ (wherein $V^2$ is the same as $V^1$, and $V^1$ is the same as defined above) and with —$W^5$ (wherein $W^5$ is $SO_2R^{42}$, $SOR^{42}$, $COR^{42}$ (wherein $R^{42}$ is a hydrogen atom, a hydroxyl group or $NR^{43}R^{44}$, $R^{43}$ is the same as $R^6$, $R^{44}$ is the same as $R^7$ and $R^6$ and $R^7$ are the same as defined above) or $W^4$, and $W^4$ is the same as defined above))), a $C_{2-14}$ aryl group (the $C_{2-14}$ aryl group is optionally substituted with one or more substituents independently represented by —$V^1$ (wherein $V^1$ is the same as defined above) and with one or more substituents selected from the group consisting of: $C_{1-6}$ alkyl groups, $C_{2-6}$ alkenyl groups, $C_{2-6}$ alkynyl groups $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents independently represented by $-V^2$ (wherein $V^2$ is the same as $V^1$ and $V^1$ is the same as defined above) and with one or more substituents selected from $C_{2-9}$ heterocyclyl groups (the $C_{2-9}$ heterocyclyl groups are optionally substituted with one or more substituents independently represented by $-V^3$ (wherein $V^3$ is the same as $V^1$, and $V^1$ is the same as defined above)))), a $C_{2-14}$ aryl group (the $C_{2-14}$ aryl group is optionally substituted with one or more substituents independently represented by $-V^1$ (wherein $V^1$ is the same as defined above) and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the C alkylcarbonyl groups, the $C_{1-10}$ alkylthiocarbonyl groups and the $C_{1-10}$ alkylsulfonyl groups are optionally substituted with one or more substituents independently represented by $-V^2$ (wherein $V^2$ is the same as $V^1$, and $V^1$ is the same as defined above) and with one or more substituents selected from the group consisting of: amino groups (the amino groups are substituted with a $C_{1-10}$ alkyl group (the $C_{1-10}$ alkyl group is optionally substituted with one or more substituents independently represented by $-V^3$ (wherein $V^3$ is the same as $V^1$, and $V^1$ is the same as defined above)) and with a $C_{2-9}$ heterocyclyl group or a $C_{2-14}$ aryl group (the $C_{2-9}$ heterocyclyl group and the $C_{2-14}$ aryl group are optionally substituted with one or more substituents independently represented by $-V^4$ (wherein $V^4$ is the same as $V^1$, and $V^1$ is the same as defined above))), amino groups, mono- or di-$C_{1-10}$ alkylamino groups, $C_{1-10}$ alkoxy groups, $C_{1-10}$ thioalkyl groups, $C_{1-10}$ alkylsulfonyl groups, sulfonyl groups, sulfinyl groups and thiol groups (the amino groups, the mono- or di-$C_{1-10}$ alkylamino groups, the $C_{1-10}$ alkoxy groups, the $C_{1-10}$ thioalkyl groups, the $C_{1-10}$ alkylsulfonyl groups, the sulfonyl groups, the sulfinyl groups and the thiol groups are optionally substituted with one or more $C_{2-9}$ heterocyclyl groups or one or more $C_{2-14}$ aryl groups (the $C_{2-9}$ heterocyclyl groups and the $C_{2-14}$ aryl groups are optionally substituted with one or more substituents independently represented by $-V^5$ (wherein $V^5$ is the same as $V^1$, and $V^1$ is the same as defined above)))) or a $C_{2-14}$ substituted aryl group (the $C_{2-14}$ substituted aryl group may be optionally substituted with one or more substituents independently represented by $-V^1$ wherein $V^1$ is the same as defined above)), a tautomer, prodrug or pharmaceutically acceptable salt of the compound or a solvate thereof.

2. The compound according to 1, wherein A is a nitrogen atom, and B is a sulfur atom, a tautomer, prodrug or pharmaceutically acceptable salt of the compound or a solvate thereof.

3. The compound according to 1, wherein A is a nitrogen atom, and B is an oxygen atom, a tautomer, prodrug or pharmaceutically acceptable salt of the compound or a solvate thereof.

4. The compound according to 1, wherein A is a nitrogen atom, and B is $NR^9$ other than NH (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

5. The compound according to 1 wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) $SO_2R^5$, $SOR^5$ or $COR^5$ (wherein 5 is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, n nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, $C_{2-6}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is an oxygen atom, a tautomer, prodrug or pharmaceutically acceptable salt of the compound or a solvate thereof.

6. The compound according to 1, wherein A is the same as defined in 5, and B is a sulfur atom, a tautomer, prodrug or pharmaceutically acceptable salt of the compound or a solvate thereof.

7. The compound according to 1, wherein A is the same as defined in 5, and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

8. The compound according to any one of 1 to 7, wherein $L^1$ is a bond, a tautomer, prodrug or pharmaceutically acceptable salt of the compound or a solvate thereof.

9. The compound according to any one of 1 to 8, wherein $L^2$ is a bond a tautomer, prodrug or pharmaceutically acceptable salt of the compound or a solvate thereof.

10. The compound according to any one of 1 to 9, wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

11. The compound according to any one of 1 to 10, wherein $L^3$ is NH, a tautomer, prodrug or pharmaceutically acceptable salt of the compound or a solvate thereof.

12. The compound according to 10, wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

13. The compound according to 11, wherein $L^4$ is the same as defined in 12, a tautomer, prodrug or pharmaceutically acceptable salt of the compound or a solvate thereof.

14. The compound according to 10 or 11, wherein $L^4$ is NH, a tautomer, prodrug or pharmaceutically acceptable salt of the compound or a solvate thereof.

15. The compound according to 10 or 11, wherein $L^4$ is a bond, a tautomer, prodrug or pharmaceutically acceptable salt of the compound or a solvate thereof.

16. The compound according to any one of 12 to 15, wherein Y is an oxygen atom, a tautomer, prodrug or pharmaceutically acceptable salt of the compound or a solvate thereof.

17. The compound according to any one of 12 to 15, wherein Y is a sulfur atom, a tautomer, prodrug or pharmaceutically acceptable salt of the compound or a solvate thereof.

18. The compound according to 16, wherein X is a hydroxyl group, a tautomer, prodrug or pharmaceutically acceptable salt of the compound or a solvate thereof.

19. The compound according to 17, wherein X is a hydroxyl group, a tautomer, prodrug or pharmaceutically acceptable salt of the compound or a solvate thereof.

20. The compound according to 16 or 18, wherein $R^3$ is a $C_{2-14}$ aryl group (the $C_{2-14}$ aryl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{26}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the amino group, the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))))), a tautomer, prodrug or pharmaceutically acceptable salt of the compound or a solvate thereof.

21. The compound according to 17 or 19, wherein $R^3$ is the same as defined in 20, a tautomer, prodrug or pharmaceutically acceptable salt of the compound or a solvate thereof.

22. The compound according to 16 or 18, wherein $R^3$ is a $C_{2-14}$ aryl group (wherein the $C_{2-14}$ aryl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^6$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms; $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups; $C_{2-6}$ alkynyl groups, $C_{1-10}$ alkylcarbonyloxy groups, $C_{1-10}$ alkoxycarbonyl groups, $C_{1-10}$ alkoxycarbonyl groups; $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), a tautomer, prodrug or pharmaceutically acceptable salt of the compound or a solvate thereof.

23. The compound according to 17 or 19, wherein $R^3$ is the same as defined in 22, a tautomer, prodrug or pharmaceutically acceptable salt of the compound or a solvate thereof.

24. The compound according to 16 or 18, wherein $R^3$ is a $C_{2-14}$ aryl group (the $C_{2-14}$ aryl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups $C_{1-10}$ fluoroalkyl groups, sulfamoyl groups, carbamoyl groups and $C_{1-10}$ alkylcarbonylamino groups and with one or more substituents independently represented by $-W^1(CW^2W^3)_m W^4$ (wherein $W^1$ is $(CR^{24}R^{25})_n$ (wherein each of $R^{24}$ and $R^{25}$ is independently a hydrogen atom, a hydroxyl group an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))), a tautomer, prodrug or pharmaceutically acceptable salt of the compound or a solvate thereof.

25. The compound according to 17 or 19, wherein $R^3$ is the same as defined in 24, a tautomer, prodrug or pharmaceutically acceptable salt of the compound or a solvate thereof.

26. The compound according to 16 or 18, wherein $R^3$ is a $C_{2-14}$ aryl group (the $C_{2-14}$ aryl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups $C_{1-10}$ fluoroalkyl groups, sulfamoyl groups, carbamoyl groups and $C_{1-10}$ alkylcarbonylamino groups and with one or more substituents independently represented by $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents independently represented by —$V^1$ (wherein $V^1$ is the same as defined in 1) and with —$W^5$ (wherein We is $SO_2R^{42}$, $SOR^{42}$, $COR^{42}$ (wherein $R^{42}$ is a hydroxyl group or $NR^{43}R^{44}$ and $R^{43}$ and $R^{44}$ are the same as defined in 1) or $W^4$ wherein $W^4$ is the same as defined in 1))), a tautomer, prodrug or pharmaceutically acceptable salt of the compound or a solvate thereof.

27. The compound according to 17 or 19 wherein $R^3$ is the same as defined in 26, a tautomer, prodrug or pharmaceutically acceptable salt of the compound or a solvate thereof.

28. The compound according to 16 or 18, wherein $R^3$ is a $C_{2-14}$ substituted aryl group (the $C_{2-14}$ substituted aryl group may be optionally substituted with one or more substituents independently represented by —$V^1$ (wherein $V^1$ is the same as defined in 1)), a tautomer, prodrug or pharmaceutically acceptable salt of the compound or a solvate thereof.

29. The compound according to 17 or 19, wherein $R^3$ is the same as defined in 28, a tautomer, prodrug or pharmaceutically acceptable salt of the compound or a solvate thereof.

30. The compound according to 16 or 18, wherein $R^3$ is a $C_{2-14}$ aryl group (the $C_{2-14}$ aryl group is optionally substituted with one or more substituents selected from the group consisting of: hydrogen atoms, nitro groups, cyano groups, halogen atoms, amino groups, hydroxy groups $C_{1-10}$ alkylaminocarbonyl groups, $C_{1-10}$ alkylaminosulfonyl groups, $C_{1-10}$ fluoroalkyl groups, $C_{1-10}$ alkoxy groups, sulfamoyl groups, carbamoyl groups and $C_{1-10}$ alkylcarbonylamino groups and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents selected from the group consisting of: hydrogen atoms, $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups and with one or more substituents selected from $C_{2-9}$ heterocyclyl groups (the $C_{2-9}$ heterocyclyl groups may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), a tautomer, prodrug or pharmaceutically acceptable salt of the compound or a solvate thereof.

31. The compound according to 17 or 19, wherein $R^3$ is the same as defined in 30, a tautomer, prodrug or pharmaceutically acceptable salt of the compound or a solvate thereof.

32. The compound according to 16 or 18, wherein $R^3$ is a $C_{2-14}$ aryl group (the $C_{2-14}$ aryl group is optionally substituted with one or more substituents selected from the group consisting of: hydrogen atoms, nitro groups, cyano groups, halogen atoms, amino groups, hydroxyl groups, $C_{1-10}$ alkylaminocarbonyl groups, $C_{1-10}$ alkylaminosulfonyl groups, $C_{1-10}$ fluoroalkyl groups, $C_{1-10}$ fluoroalkoxy groups, sulfamoyl groups, carbamoyl groups and $C_{1-10}$ alkylcarbonylamino groups and with one or more groups selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents selected from the group consisting of: amino groups (the amino groups are substituted with a $C_{1-10}$ alkyl group and with a $C_{2-6}$ heterocyclyl group or a $C_{2-14}$ aryl group (the $C_{2-9}$ heterocyclyl group and the $C_{2-14}$ aryl group may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), amino groups, mono- or di-$C_{1-10}$ alkylamino groups, $C_{1-10}$ alkoxy groups, $C_{1-10}$ thioalkyl groups, $C_{1-10}$ alkylsulfonyl groups, sulfonyl groups, sulfinyl groups and thiol groups (the amino groups, the mono- or di-$C_{1-10}$ alkylamino groups, the $C_{1-10}$ alkoxy groups, the $C_{1-10}$ thioalkyl groups, the $C_{1-10}$ alkylsulfonyl groups, the sulfonyl groups, the sulfinyl groups and the thiol groups are optionally substituted one or more $C_{2-9}$ heterocyclyl groups or one or more $C_{2-14}$ aryl groups (the $C_{2-9}$ heterocyclyl groups and the $C_{2-14}$ aryl groups may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))), a tautomer, prodrug or pharmaceutically acceptable salt of the compound or a solvate thereof.

33. The compound according to 17 or 19, wherein $R^3$ is the same as defined in 32, a tautomer prodrug or pharmaceutically acceptable salt of the compound or a solvate thereof.

34. Medicament containing the compound according to any one of 1 to 33, a tautomer, prodrug or pharmaceutically acceptable salt of the compound or a solvate thereof, as an active ingredient.

35. A thrombopoietin receptor activator containing the compound according to any one of 1 to 33, a tautomer, prodrug or pharmaceutically acceptable salt of the compound or a solvate thereof, as an active ingredient.

36. A preventive, therapeutic or improving agent for diseases against which activation of the thrombopoietin receptor is effective, which contains the compound according to any one of 1 to 33, a tautomer, prodrug or pharmaceutically acceptable salt of the activator or a solvate thereof, as an active ingredient.

37. A platelet increasing agent containing the compound according to any one of 1 to 33, a tautomer, prodrug or pharmaceutically acceptable salt of the activator or a solvate thereof, as an active ingredient.

BEST MODE FOR CARRYING OUT THE INVENTION

Figure 1:
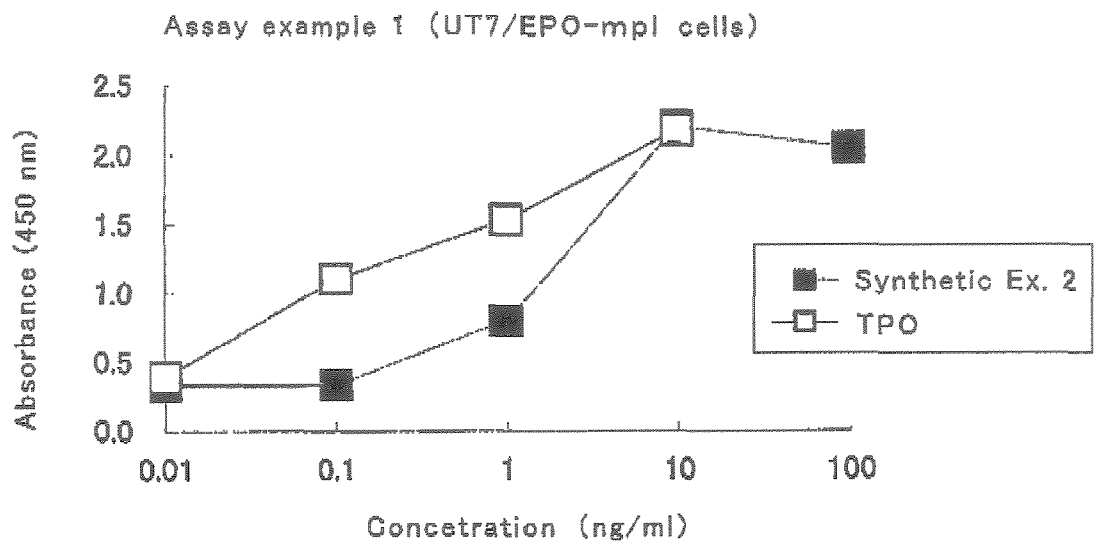
FIG. 1 shows the proliferation of UT7/EPO-mpl cells when stimulated by the compound of the present invention (Synthetic Example 2).

In the present invention, "n" denotes normal, "i" denotes iso, "s" denotes secondary, "t" denotes tertiary "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, "Bu" denotes butyl and "Ac" denotes acetyl.

First the terms in the respective substituents $R^1$ to $R^{44}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl-1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 2-methyl-1-c-pentenyl, 2-methyl-3-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-9}$ heterocyclyl group may be a heteromonocyclic or fused heterobicyclic group consisting of at least one atom optionally selected from nitrogen atoms, oxygen atoms and sulfur atoms and from 2 to 9 carbon atoms, and specifically mentioned are:

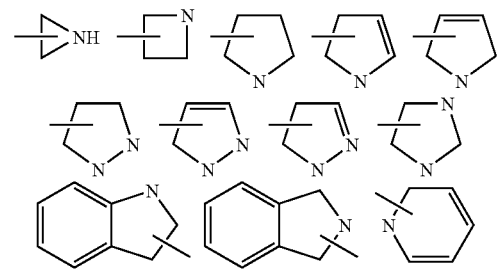

-continued
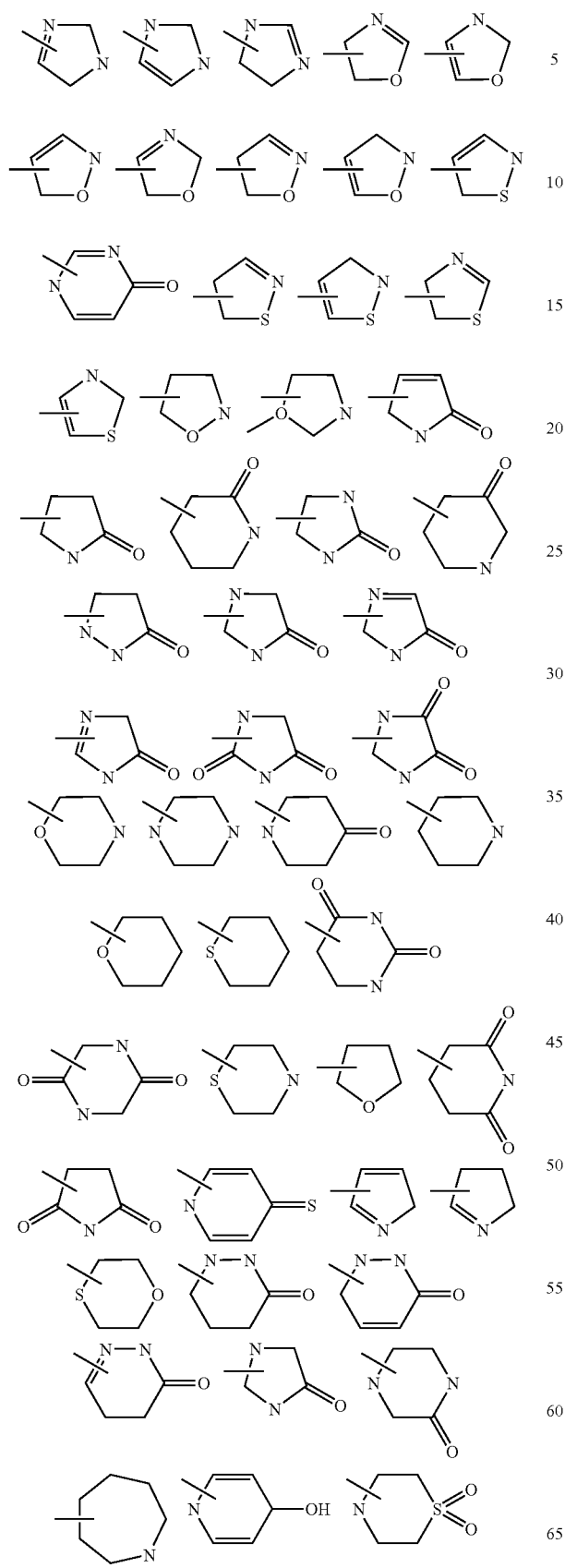
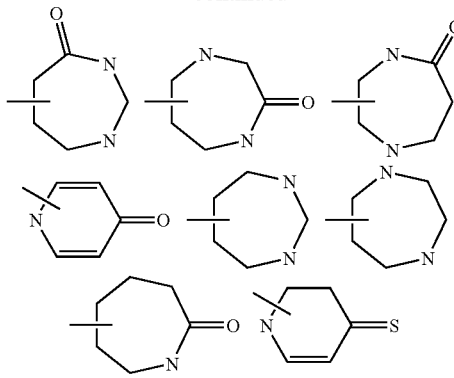
A nitrogen-containing $C_{2-9}$ heterocyclyl group may be, among those give above, a heteromonocyclic or fused heterobicyclic group which contains least one nitrogen atom, may contain at least one atom optionally selected from oxygen atoms and sulfur atoms and contains from 2 to 9 carbon atoms, and specifically mentioned are:
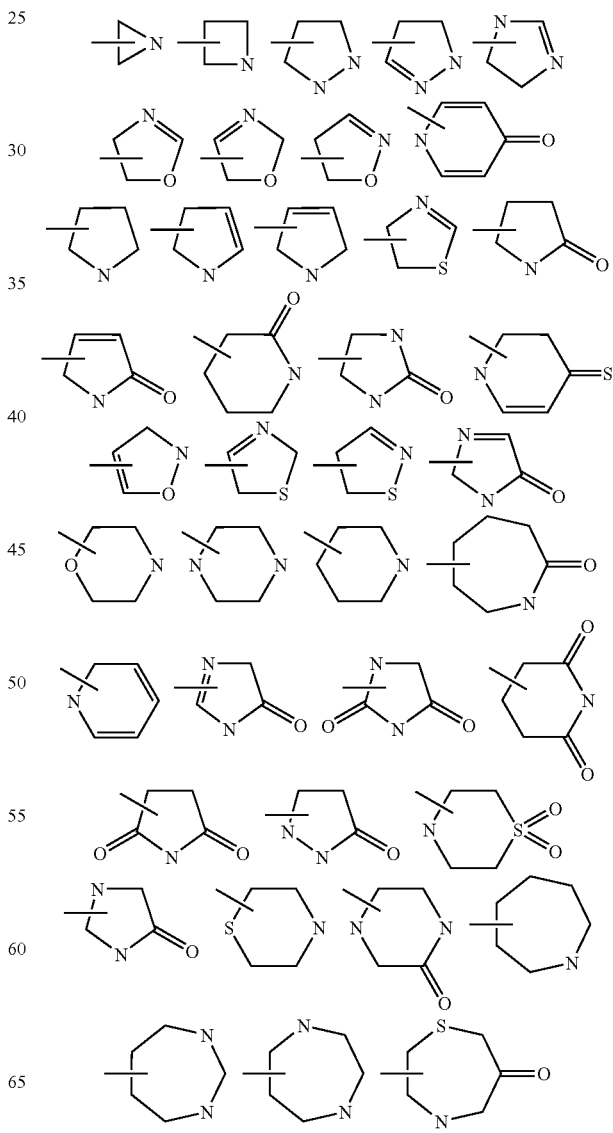

-continued

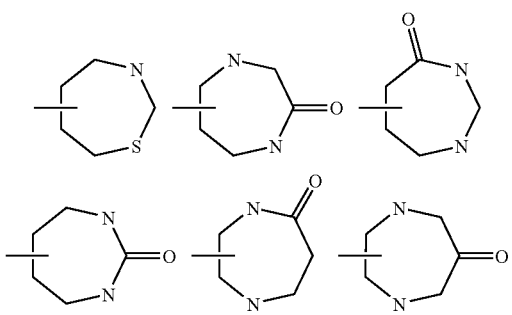

A substituted $C_{2-9}$ heterocyclyl group may be, among the $C_{2-9}$ heterocyclyl groups and the nitrogen-containing $C_{2-9}$ heterocyclyl groups, a heteromonocyclic or fused heterobicyclic group which has no nitrogen atoms and one or three carbonyl groups or thiocarbonyl groups as ring constituting carbon atoms, and specifically mentioned are:

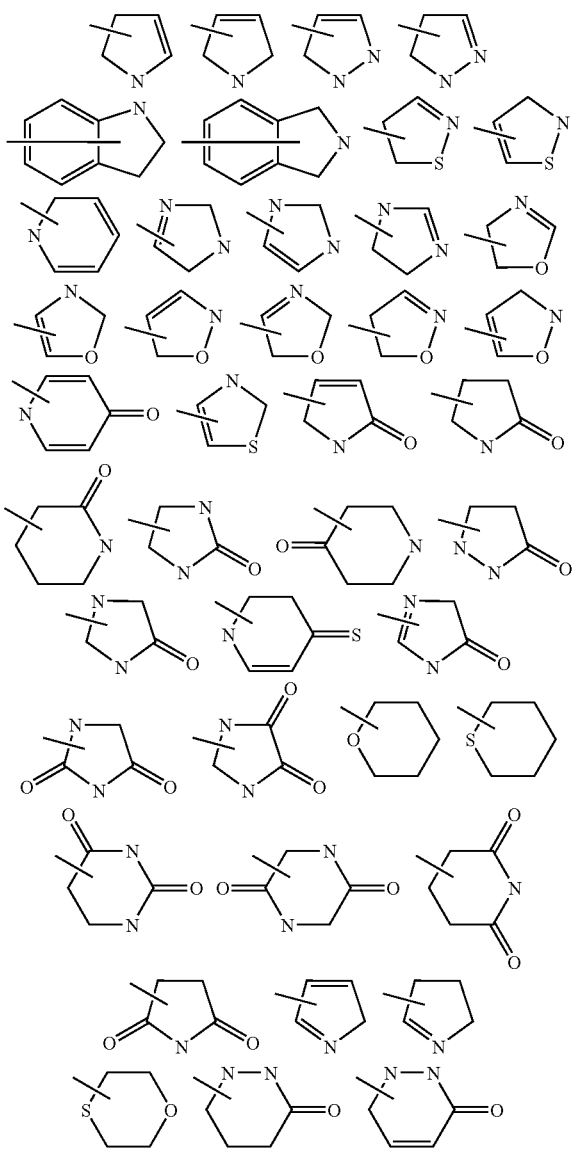

-continued

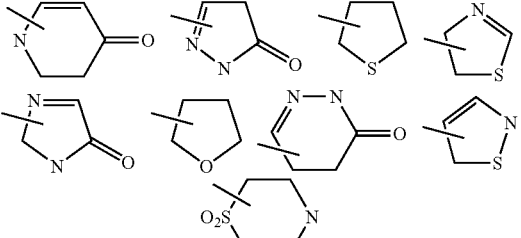

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered $C_{5-9}$ fused heterocyclic group may be a 2-benzofuranyl group, a 3-benzofuranyl group, a 4-benzofuranyl group, a 5-benzofuranyl group, a 6-benzofuranyl group, a 7-benzofuranyl group, a 1-Isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like.

A $C_{2-14}$ substituted aryl group may be a fused bicyclic or tricyclic group resulting from fusion of the above-mentioned $C_{2-14}$ aryl group with a $C_{2-9}$ heterocyclyl group, a nitrogen-containing $C_{2-9}$ heterocyclyl group or a substituted $C_{2-9}$ heterocyclyl group, and specifically mentioned are:

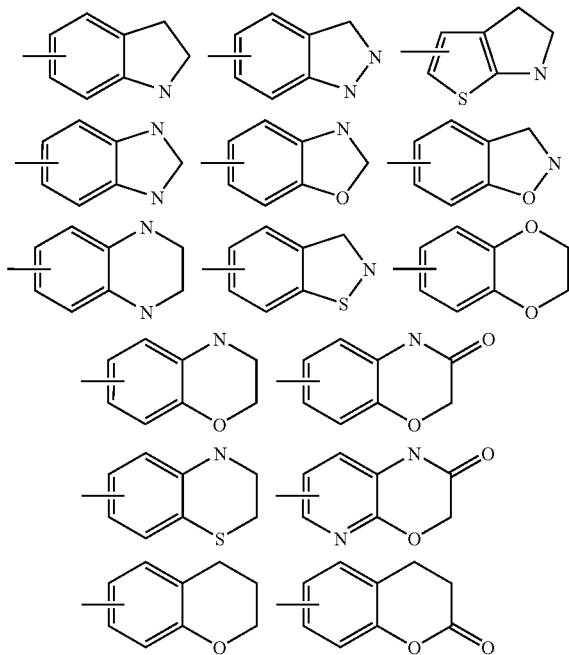

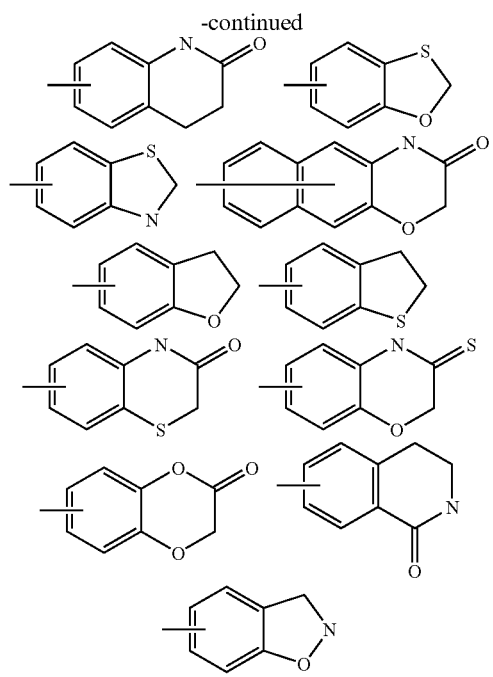

A $C_{2-14}$ aryloxy group may be a $C_{6-14}$ aryloxy group containing no hetero atoms as ring constituting atoms or a $C_{2-9}$ aromatic heterocyclyloxy group, and a $C_{2-9}$ aromatic heterocyclyloxy group may be a 5 to 7-membered $C_{2-6}$ monocyclic heterocyclyloxy group or 8 to 10-membered $C_{5-9}$ fused bicyclic heterocyclyloxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ monocyclic heterocyclyloxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazol-yloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused bicyclic heterocyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group a 8-1,6-naphthyridinyloxy group, a 2-1,5-naphthyridinyloxy group, a 3-1,5-naphthyridinyloxy group, a 4-1, 5-naphthyridinyloxy group, a 6-1,5-naphthyridinyloxy group, a 7-1,5-naphthyridinyloxy group a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pterdinyloxy group, a 4-pterdinyloxy group, a 6-pterdinyloxy group, a 7-pterdinyloxy group or the like.

A $C_{1-6}$ alkylcarbonyl group may linear, branched or a $C_{3-6}$ cycloalkylcarbonyl group, and be methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butyl-carbonyl, 2,3-dimethyl-c-butylcarbonyl, 2,4-dimethyl-c-butylcarbonyl, 3,3-dimethyl-c-butyl carbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl may be linear, branched or a $C_{3-10}$ cycloalkylcarbonyl group and in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-10}$ alkyl group may linear, branched or a $C_{3-10}$ cyclothioalkyl group, and be methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 23-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-6}$ alkylsulfonylamino group may be linear, branched or a $C_{3-6}$ cycloalkylsulfonylamino group, and methylsulfonylamino, ethylsulfonylamino, n-propylsulfonylamino, i-propylsulfonylamino, c-propylsulfonylamino, n-butylsulfonylamino, i-butylsulfonylamino, s-butylsulfonylamino, t-butylsulfonylamino, c-butylsulfonylamino, 1-methyl-c-propylsulfonylamino, 2-methyl-c-propylsulfonylamino, n-pentylsulfonylamino, 1-methyl-n-butylsulfonylamino, 2-methyl-n-butylsulfonylamino, 3-methyl-n-butylsulfonylamino, 1,1-dimethyl-n-propylsulfonylamino, 1,2-dimethyl-n-propylsulfonylamino, 2,2-dimethyl-n-propylsulfonylamino, 1-ethyl-n-propylsulfonylamino, c-pentylsulfonylamino, 1-methyl-c-butylsulfonylamino, 2-methyl-c-butylsulfonylamino, 3-methyl-c-butylsulfonylamino, 1,2-dimethyl-c-propylsulfonylamino, 2,3-dimethyl-c-propylsulfonylamino, 1-ethyl-c-propylsulfonylamino, 2-ethyl-c-propylsulfonylamino, n-hexylsulfonylamino, 1-methyl-n-pentylsulfonylamino, 2-methyl-n-pentylsulfonylamino, 3-methyl-n-pentylsulfonylamino, 4-methyl-n-pentylsulfonylamino, 1,1-dimethyl-n-butylsulfonylamino, 1,2-dimethyl-n-butylsulfonylamino, 1,3-dimethyl-n-butylsulfonylamino, 2,2-dimethyl-n-butylsulfonylamino, 2,3-dimethyl-n-butylsulfonylamino, 3,3-dimethyl-n-butylsulfonylamino, 1-ethyl-n-butylsulfonylamino, 2-ethyl-n-butylsulfonylamino, 1,1,2-trimethyl-n-propylsulfonylamino, 1,2,2-trimethyl-n-propylsulfonylamino, 1-ethyl-1-methyl-n-propylsulfonylamino, 1-ethyl-2-methyl-n-propylsulfonylamino, c-hexylsulfonylamino, 1-methyl-c-pentylsulfonylamino, 2-methyl-c-pentylsulfonylamino, 3-methyl-c-pentylsulfonylamino, 1-ethyl-c-butylsulfonylamino, 2-ethyl-c-butylsulfonylamino, 3-ethyl-c-butylsulfonylamino, 1,2-dimethyl-c-butylsulfonylamino, 1,3-dimethyl-c-butylsulfonylamino, 2,2-dimethyl-c-butylsulfonylamino, 2,3-dimethyl-c-butylsulfonylamino, 2,4-dimethyl-c-butylsulfonylamino, 3,3-dimethyl-c-butylsulfonylamino, 1-n-propyl-c-propylsulfonylamino, 2-n-propyl-c-propylsulfonylamino, 1-i-propyl-c-propylsulfonylamino, 2-i-propyl-c-propylsulfonylamino, 1,2,2-trimethyl-c-propylsulfonylamino, 1,2,3-trimethyl-c-propylsulfonylamino, 2,2,3-trimethyl-c-propylsulfonylamino, 1-ethyl-2-methyl-c-propylsulfonylamino, 2-ethyl-1-methyl-c-propylsulfonylamino, 2-ethyl-2-methyl-c-propylsulfonylamino, 2-ethyl-3-methyl-c-propylsulfonylamino or the like may be mentioned.

A $C_{1-10}$ alkylsulfonylamino group may be linear, branched or a $C_{3-10}$ cycloalkylsulfonylamino group, and in addition to those mentioned above, 1-methyl-1-ethyl-n-pentylsulfonylamino, 1-heptylsulfonylamino, 2-heptylsulfonylamino, 1-ethyl-1,2-dimethyl-n-propylsulfonylamino, 1-ethyl-2,2-dimethyl-n-propylsulfonylamino, 1-octylsulfonylamino, 3-octylsulfonylamino, 4-methyl-3-n-heptylsulfonylamino, 6-methyl-2-n-heptylsulfonylamino, 2-propyl-1-n-n-heptylsulfonylamino, 2,4,4-trimethyl-1-n-pentylsulfonylamino, 1-nonylsulfonylamino, 2-nonylsulfonylamino, 2,6-dimethyl-4-n-heptylsulfonylamino, 3-ethyl-2,2-dimethyl-3-n-pentylsulfonylamino, 3,5,5-trimethyl-1-n-hexylsulfonylamino, 1-decylsulfonylamino, 2-decylsulfonylamino, 4-decylsulfonylamino, 3,7-dimethyl-1-n-octylsulfonylamino, 3,7-dimethyl-3-n-octylsulfonylamino, c-heptylsulfonylamino, c-octylsulfonylamino, 1-methyl-c-hexylsulfonylamino, 2-methyl-c-hexylsulfonylamino, 3-methyl-c-hexylsulfonylamino, 1,2-dimethyl-c-hexylsulfonylamino, 1-ethyl-c-hexylsulfonylamino, 1-methyl-c-pentylsulfonylamino, 2-methyl-c-pentylsulfonylamino, 3-methyl-c-pentylsulfonylamino or the like may be mentioned.

A $C_{1-6}$ alkoxy group may be linear, branched or a $C_{3-10}$ cycloalkoxy group, and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-1-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-10}$ alkoxy group may be linear, branched or a $C_{3-10}$ cycloalkoxy group, and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-1-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, 1-methyl-1-ethyl-n-pentyloxy, 1-heptyloxy, 2-heptyloxy, 1-ethyl-1,2-dimethyl-n-propyloxy, 1-ethyl-2,2- dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1 decyloxy, 2-decyloxy, 4-decyloxy, 3,7-dimethyl-1-n-octyloxy, 3,7-dimethyl-3-n-octyloxy or the like may be mentioned.

A $C_{1-6}$ alkylthiocarbonyl group is a $C_{1-6}$ alkylcarbonyl group having a sulfur atom instead of an oxygen atom and may be linear, branched or a $C_{3-6}$ cycloalkylthiocarbonyl group Methyl(thiocarbonyl)ethyl(thiocarbonyl), n-propyl(thiocarbonyl), i-propyl(thiocarbonyl), c-propyl (thiocarbonyl), n-butyl(thiocarbonyl), i-butyl(thiocarbonyl), s-butyl(thiocarbonyl), t-butyl(thiocarbonyl), c-butyl(thiocarbonyl), 1-methyl-c-propyl(thiocarbonyl), 2-methyl-c-propyl(thiocarbonyl), n-pentyl(thiocarbonyl), 1-methyl-n-butyl(thiocarbonyl), 2-methyl-n-butyl(thiocarbonyl), 3-methyl-n-butyl(thiocarbonyl), 1,1-dimethyl-n-propyl(thiocarbonyl), 1,2-dimethyl-n-propyl(thiocarbonyl), 2,2-dimethyl-n-propyl(thiocarbonyl), 1-ethyl-n-propyl(thiocarbonyl), c-pentyl(thiocarbonyl), 1-methyl-c-butyl(thiocarbonyl), 2-methyl-c-butyl(thiocarbonyl), 3-methyl-c-butyl(thiocarbonyl), 1,2-dimethyl-c-propyl(thiocarbonyl), 2,3-dimethyl-c-propyl(thiocarbonyl), 1-ethyl-c-propyl(thiocarbonyl), 2-ethyl-c-propyl(thiocarbonyl), n-hexyl(thiocarbonyl), 1-methyl-n-pentyl(thiocarbonyl), 2-methyl-n-pentyl(thiocarbonyl), 3-methyl-n-pentyl(thiocarbonyl), 4-methyl-n-pentyl(thiocarbonyl), 1,1-dimethyl-n-butyl(thiocarbonyl), 1,2-dimethyl-n-butyl(thiocarbonyl), 1,3-dimethyl-n-butyl(thiocarbonyl), 2,2-dimethyl-n-butyl(thiocarbonyl), 2,3-dimethyl-n-butyl(thiocarbonyl), 3,3-dimethyl-n-butyl(thiocarbonyl), 1-ethyl-n-butyl(thiocarbonyl), 2-ethyl-n-butyl(thiocarbonyl) 1,1,2-trimethyl-n-propyl(thiocarbonyl), 1,2,2-trimethyl-n-propyl(thiocarbonyl), 1-ethyl-1-methyl-n-propyl(thiocarbonyl), 1-ethyl-2-methyl-n-propyl(thiocarbonyl), c-hexyl(thiocarbonyl), 1-methyl-c-pentyl(thiocarbonyl), 2-methyl-c-pentyl(thiocarbonyl), 3-methyl-c-pentyl(thiocarbonyl), 1-ethyl-c-butyl(thiocarbonyl), 2-ethyl-c-butyl(thiocarbonyl), 3-ethyl-c-butyl(thiocarbonyl), 1,2-dimethyl-c-butyl(thiocarbonyl), 1,3-dimethyl-c-butyl(thiocarbonyl), 2,2-dimethyl-c-butyl(thiocarbonyl), 2,3-dimethyl-c-butyl(thiocarbonyl), 2,4-dimethyl-c-butyl(thiocarbonyl), 3,3-dimethyl-c-butyl(thiocarbonyl), 1-n-propyl-c-propyl(thiocarbonyl), 2-n-propyl-c-propyl(thiocarbonyl), 1-i-propyl-c-propyl(thiocarbonyl), 2-i-propyl-c-propyl(thiocarbonyl), 1,2,2-trimethyl-c-propyl(thiocarbonyl), 1,2,3-trimethyl-c-propyl(thiocarbonyl), 2,2,3-trimethyl-c-propyl(thiocarbonyl), 1-ethyl-2-methyl-c-propyl(thiocarbonyl), 2-ethyl-1-methyl-c-propyl(thiocarbonyl), 2-ethyl-2-methyl-c-propyl(thiocarbonyl), 2-ethyl-3-methyl-c-propyl(thiocarbonyl) and the like may be mentioned.

A $C_{1-10}$ alkylthiocarbonyl group may be linear, branched or a $C_{3-10}$ cycloalkylthiocarbonyl group, and in addition to those mentioned above, 1-methyl-1-ethyl-n-pen-yl(thiocarbonyl), 1-heptyl(thiocarbonyl), 2-heptyl(thiocarbonyl), 1-ethyl-1,2-dimethyl-n-propyl(thiocarbonyl), 1-ethyl-2,2-dimethyl-n-propyl(thiocarbonyl), 1-octyl(thiocarbonyl), 3-octyl(thiocarbonyl), 4-methyl-3-n-heptyl(thiocarbonyl), 6-methyl-2-n-heptyl(thiocarbonyl), 2-propyl-1-n-heptyl(thiocarbonyl), 2,4,4-trimethyl-1-n-pentyl(thiocarbonyl), 1-nonyl(thiocarbonyl), 2-nonyl(thiocarbonyl), 2,6-dimethyl-4-n-heptyl(thiocarbonyl), 3-ethyl-2,2-dimethyl-3-n-pentyl (thiocarbonyl), 3,5,5-trimethyl-1-n-hexyl(thiocarbonyl), 1-decyl(thiocarbonyl), 2-decyl(thiocarbonyl), 4-decyl(thiocarbonyl), 3,7-dimethyl-1-n-octyl(thiocarbonyl), 3,7-dimethyl-3-n-octyl(thiocarbonyl) or the like may be mentioned.

A $C_{1-6}$ alkylsulfonyl group may be linear, branched or a $C_{3-6}$ cycloalkylsulfonyl group, and methylsulfonyl, ethylsulfonyl, n-propylsulfonyl, 4-propylsulfonyl, c-propylsulfonyl, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl or the like may be mentioned.

A $C_{1-10}$ alkylsulfonyl group may be linear, branched or a $C_{3-10}$ cycloalkylsulfonyl group, and in addition to those mentioned above, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2, 2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl, c-heptylsulfonyl, c-octylsulfonyl, 1-methyl-c-hexylsulfonyl, 2-methyl-c-hexylsulfonyl, 3-methyl-c-hexylsulfonyl, 1,2-dimethyl-c-hexylsulfonyl, 1-ethyl-c-hexylsulfonyl, 1-methyl-c-pentylsulfonyl, 2-methyl-c-pentylsulfonyl, 3-methyl-c-pentylsulfonyl or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propoxylcarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyln-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl-2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-tri-methyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino 2-n-propyl-c-propylcarbonylamino, 1-i-propyl-c-propylcarbonylamino, 2-i-propyl-c-propylcarbonylamino, 1,2,2-trimethyl-c-propyl-carbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c- propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2 ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(3,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group and (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (C-propyl, n-butyl)amino, (c-propyl, i-butyl)amino, (c-propyl, s-butyl)amino, (C-propyl, t-butyl)amino, (c-propyl, n-pentyl)amino, (c-propyl, c-pentyl)amino, (c-propyl, n-hexyl)amino, (C-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)

amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonyl)amino, (methyl, n-decyl)amino, (methyl, n-heptyl)amino, (ethyl, n-octyl)amino, (ethyl, n-nonyl)amino, (ethyl, n-decyl)amino or the like may be mentioned.

A $C_{1-10}$ alkylaminocarbonyl group may be linear, branched or a $C_{3-10}$ alkylaminocarbonyl group, and methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7-dimethyl-1-n-octylaminocarbonyl, 3,7-dimethyl-3-n-octylaminocarbonyl or the like may be mentioned.

A $C_{1-10}$ dialkylaminocarbonyl group may be symmetric or asymmetric. A symmetric $C_{1-10}$ dialkylaminocarbonyl group may be linear, branched or a $C_{3-10}$ cycloalkylaminocarbonyl group, and dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-(1-methyl-c-propylaminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propylaminocarbonyl, di-(1,2-dimethyl-n-propyl)aminocarbonyl, di-(2,2-dimethyl-n-propyl)aminocarbonyl, di-(1-ethyl-n-propyl)aminocarbonyl di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propyl)aminocarbonyl, di-(2-ethyl-c-propyl)aminocarbonyl, di-n-hexylaminocarbonyl, di-(1-methyl-n-pentyl)aminocarbonyl, di-4-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonylaminocarbonyl, di-(2,6-dimethyl-4-n-heptyl)aminocarbonyl, di-(3-ethyl-2,2-dimethyl-3-n-pentyl)aminocarbonyl, di-(3,55-trimethyl-1-n-hexyl)

aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

An asymmetric $C_{1-10}$ dialkylaminocarbonyl group may be linear, branched or a $C_{3-10}$ cycloalkylaminocarbonyl group, and (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonyl)aminocarbonyl, (methyl, n-decyl)aminocarbonyl, (methyl, n-heptyl)aminocarbonyl, (ethyl, n-octyl)aminocarbonyl, (ethyl, n-nonyl)aminocarbonyl, (ethyl, n-decyl)aminocarbonyl or the like may be mentioned.

A $C_{1-6}$ alkylaminosulfonyl group may be linear, branched or a $C_{3-6}$ cycloalkylaminosulfonyl group, and methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyln-propylaminosulfonyl, 2,2-dimethyln-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosulfonyl, 1,1-dimethyl-n-butylaminosulfonyl, 1,2-dimethyl-n-butylaminosulfonyl, 1,3-dimethyl-n-butylaminosulfonyl, 2,2-dimethyl-n-butylaminosulfonyl, 2,3-dimethyl-n-butylaminosulfonyl, 3,3-dimethyl-n-butylaminosulfonyl, 1 ethyl-n-butylaminosulfonyl, 2-ethyl-n-butylaminosulfonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 2-ethyl-3-methyl-c-propylaminosulfonyl or the like may be mentioned.

A $C_{1-10}$ alkylaminosulfonyl group may be linear, branched or a $C_{3-10}$ cycloalkylsulfonylamino group, and in addition to those mentioned above, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimethyl-1-n-octylaminosulfonyl, 3,7-dimethyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

The protecting group in a protected hydroxyl group may be a $C_{1-4}$ alkoxymethyl group (such as MOM: methoxymethyl, MEM: 2-methoxyethoxymethyl ethoxymethyl, n-propoxymethyl, i-propoxymethyl, n-butoxymethyl, iBM: isobutyloxymethyl, BUM: t-butoxymethyl, POM: pivaloyloxytethyl, SEM: trimethylsilylethoxymethyl and the like, preferably a $C_{1-2}$ alkoxymethyl or the like), an aryloxymethyl (such as BOM: benzyloxymethyl, PMBM: P-methoxybenzyloxymethyl, p-AOM: p-anisyloxymethyl and the like, preferably benzyloxymethyl), a $C_{1-4}$ alkylaminomethyl group (such as dimethylaminomethyl), a substituted acetamidomethyl group (such as Acm: acetamidomethyl Tacm: trimethylacetamidomethyl and the like) a substituted thiomethyl group (such as MTM: methylthiomethyl PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl dichloroacetyl, trichloroacetyl, propionyl, Pv: pivaloyl, tigloyl and the like), an arylcarbonyl group (such as benzoyl, p-bromobenzoyl, 2,3-dinitrobenzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, 1-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TEDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TEMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MS: p-methoxybenzenesulfonyl, m-nitrobenzenesulfonyl, o-nitrobenzenesulfonyl, p-nitrobenzenesulfonyl, 2,4-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

In addition, a 1-methyl-1-methoxyethyl group, a 1-ethoxyethylgroup, a 2,22-trichloroethyl group, a 2-trimethylsilylethoxy group, a t-butyl group, an allyl group, a benzyl group, a p-methoxybenzyl group, a 2,4-dinitrophenyl group, a p-chlorophenyl group, a p-methoxyphenyl group, a tetrahydropyranyl group and a tetrahydrofuranyl group may be mentioned.

Specific preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group), and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents a $C_{1-10}$ alkyl group, a halogen atom, a $C_{1-10}$ alkyl group substituted with one or more halogen atoms, a nitro group, an amino group, an amino group substituted with one or two $C_{1-10}$ alkyl groups, an amino group substituted with a $C_{1-10}$ alkylcarbonyl group, a thiol group substituted with a $C_{1-10}$ alkyl group, a thiol group substituted with a $C_{1-10}$ alkylcarbonyl group, a hydroxyl group, a $C_{1-6}$ alkoxy group, a $C_{1-10}$ alkylcarbonyloxy group, a $C_{1-10}$ alkoxycarbonyl group and a $C_{1-10}$ alkylcarbonyl group.

Particularly preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a methyl group, a t-butyl group, a trifluoromethyl group, a chlorine atom, a fluorine atom, a bromine atom, a trifluoromethoxy group, a methoxy group, a methylamino group, a dimethylamino group, a t-butyloxy group and a t-butylamino group.

Still further preferred specific examples of the substituent are a 3-methyl-phenyl group, a 4-methyl-phenyl group, a 3,4-dimethyl-phenyl group, a 4-bromo-phenyl group, a 4-trifluoromethoxy-phenyl group, a 3-t-butyl-phenyl group, a 4-t-butyl-phenyl group, a 3-trifluoromethyl-phenyl group, a 4-trifluoromethyl-phenyl group, a 4-trifluoromethoxy-phenyl group, a 3,4-ditrifluoromethyl-phenyl group, a 3-chlorophenyl group, a 4-chloro-phenyl group, a 3-fluoro-phenyl group, a 4-fluoro-phenyl group, a 3,4-dichloro-phenyl group, a 4-methoxy-phenyl group, a 4-methylamino-phenyl group, a 3-methyl-thienyl group, a 4-methyl-thienyl group, a 3,4-dimethyl-thienyl group, a 3-t-butyl-thienyl group, a 4-t-butyl-thienyl group, a 3-trifluoromethyl-thienyl group, a 4-trifluoromethyl-thienyl group, a 3,4-ditrifluoromethyl-thienyl group, a 3-chloro-thienyl group, a 4-chloro-thienyl group, a 3-fluoro-thienyl group, a 4-fluoro-thienyl group, a 3,4-dichloro-thienyl group, a 4-methoxy-thienyl group, a 4-methylamino-thienyl group, a 3-methyl-furyl group, a 4-methyl-furyl group, a 3,4-dimethyl-furyl group, a 3-t-butyl-furyl group, a 4-t-butyl-furyl group, a 3-trifluoromethyl-furyl group, a 4-trifluoromethyl-furyl group, a 3,4-ditrifluoromethyl-furyl group, a 3-chloro-furyl group, a 4-chloro-furyl group, a 3-fluoro-furyl group, a 4-fluoro-furyl group, a 3,4-dichloro-furyl group, a 4-methoxy-furyl group, a 4-methylamino-furyl group, a 5-chloro-pyridazinyl group, a 5-methyl-pyridazinyl group, a 5-methoxy-pyridazinyl group, a 4-chloro-pyridazinyl group, a 4-methylpyridazinyl group, a 4-methoxy-pyridazinyl group, a 4-t-butoxy-pyridazinyl group and the like.

Specific preferable examples of $L^1$ are a bond, $CH_2$, an oxygen atom, a sulfur atom, NH, N-Me, N—CHO, CHMe, $CMe_2$, N—$CH_2Ph$ and the like, and particularly preferable examples are a bond, $CH_2$, an oxygen atom, a sulfur atom, NH, NMe and the like.

Specific preferable examples of the substituent $R^2$ are hydrogen, a methyl group, an ethyl group, a n-propyl group, an i-propyl group, a t-butyl group and a phenyl group (the methyl group, the ethyl group, the n-propyl group, the i-propyl group, the t-butyl group and the phenyl group may be optionally substituted with an amino group, a monomethylamino group, a dimethylamino group, a monoethylamino group, a diethylamino group, a methoxy group, an ethoxy group, a methoxycarbonyl group, an ethoxycarbonyl group, a methylcarbonyloxy group, an ethylcarbonyloxy group, a methylcarbonylamino group or an ethylcarbonylamino group), and particularly preferable examples are hydrogen, a methyl group, an ethyl group, a n-propyl group, an i-propyl group, a t-butyl group, a phenyl group and the like.

Specific preferable examples of $L^2$ are a bond, $CH_2$, an oxygen atom, a sulfur atom, NH, N-Me, N—CHO, CHMe, $CMe_2$, N—$CH_2$Ph and the like, and particularly preferable examples are a bond, $CH_2$, an oxygen atom, a sulfur atom, NH, NMe and the like.

Specific preferable examples of $L^3$ are a bond, $CH_2$, an oxygen atom, a sulfur atom, NH, NH—OH, N-Me, N—CHO, CHMe, $CMe_2$, N—$CH_2$PH and the like, and particularly preferred examples are a bond, $CH_2$, an oxygen atom, a sulfur atom, NH, NMe and the like.

Specific preferable examples of the substituent $R^3$ are a $C_{2-14}$ aryl group which is optionally substituted with one or more substituents selected from the following substituent set A and may be optionally substituted with one or more substituents independently selected from the following substituent set B and a $C_{2-14}$ substituted aryl group which may be optionally substituted with one or more substituents selected from the following substituent set B.

Substituent Set A:

—$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3) an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^3$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the amino group, the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-4}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group, a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5), or $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or a substituted $C_{2-9}$ heterocyclyl group (the substituted $C_{2-9}$ heterocyclyl group may be optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halo-en atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))), and $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfo groups, $C_{1-10}$ alkylaminocarbonyl groups $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino groups, the $C_{1-10}$ alkylaminosulfo groups, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with —$W^5$ (wherein $W^5$ is $SO_2R^{42}$, $SOR^{42}$, $COR^{42}$ (wherein $R^{42}$ is a hydrogen atom, a hydroxyl group or $NR^{43}R^{44}$, and each of $R^{43}$ and $R^{44}$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^{43}$ and $R^{44}$ mean, together with each other, —$(CH_2)_{m1}$-E-$(CH_2)_{m2}$— (wherein E is an oxygen atom, a sulfur atom, $CR^{26}R^{27}$ (wherein each of $R^{20}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alk-ylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)) or $W^4$, and $W^4$ is the same as defined above)) may be mentioned.

Substituent Set B

Hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino groups, the $C_{1-10}$ alkylaminosulfonyl groups, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) may be mentioned.

Specific particularly preferable examples of the substituent $R^3$ are $C_{2-14}$ aryl groups which are optionally substituted with one or more substituents selected from the following substituent set A and may be optionally substituted with one or more substituents independently selected from the following substituent set B.

Substituent Set A:

$C_{1-6}$ alkyl groups, $C_{2-6}$ alkenyl groups and $C_{2-6}$ alkynyl groups (the $C_{1-6}$ alkyl groups, the $C_{2-6}$ alkenyl groups and the $C_{2-6}$ alkynyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents independently represented by —$V^2$ (wherein $V^2$ is the same as $V^1$, and $V^1$ is the same as defined above) and with —$W^5$ (wherein $W^5$ is $SO_2R^{42}$, $SOR^{42}$, $COR^{42}$ (wherein $R^{42}$ is a hydrogen atom, a hydroxyl group or $NR^{43}R^{44}$, $R^{43}$ is the same as $R^6$, $R^{44}$ is the same as $R^7$, and $R^6$ and $R^7$ are the same as defined above) or $W^4$, and $W^4$ is the same as defined above)), $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents independently represented by —$V^2$ (Wherein $V^2$ is the same as $V^1$, and $V^1$ is the same as defined above) and with one or more substituents selected from $C_{2-9}$ heterocyclyl groups (the $C_{2-9}$ heterocyclyl groups are optionally substituted with one or more substituents independently represented by —$V^3$ (wherein $V^3$ is the same as $V^1$, and $V^1$ is the same as defined above))), $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents independently represented by —$V^2$ (wherein $V^2$ is the same as $V^1$ and $V^1$ is the same as defined above) and with one or more substituents selected from the group consisting of: amino groups (the amino groups are substituted with a $C_{1-10}$ alkyl group (the $C_{1-10}$ alkyl group is optionally substituted with one or more substituents independently represented by —$V^3$ (wherein $V^3$ is the same as $V^1$ and $V^1$ is the same as defined above)) and with a $C_{2-9}$ heterocyclyl group or a $C_{2-14}$ aryl group (the $C_{2-9}$ heterocyclyl group and the $C_{2-14}$ aryl group are optionally substituted with one or more substituents independently represented by —$V^4$ (wherein $V^4$ is the same as $V^1$, and $V^1$ is the same as defined above))), amino groups, mono- or di-$C_{1-10}$ alkylamino groups, $C_{1-10}$ alkoxy groups, $C_{1-10}$ thioalkyl groups, $C_{1-10}$ alkylsulfonyl groups, sulfonyl groups, sulfinyl groups and thiol groups (the amino groups, the mono- or di-$C_{1-10}$ alkylamino groups, the $C_{1-10}$ alkoxy groups, the $C_{1-10}$ thioalkyl groups, the $C_{1-10}$ alkylsulfonyl groups, the sulfonyl groups, the sulfinyl groups and the thiol groups are optionally substituted with one or more $C_{2-9}$ heterocyclyl groups or one or more $C_{2-14}$ aryl groups (the $C_{2-9}$ heterocyclyl groups and the $C_{2-14}$ aryl groups are optionally substituted with one or more substituents independently represented by —$V^5$ (wherein $V^5$ is the same as $V^1$, and $V^1$ is the same as defined above)))) may be mentioned.

Substituent Set B:

Hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono or di-$C_{1-10}$ alkylamino groups, the $C_{1-10}$ alkylaminosulfonyl groups, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups, may be mentioned.

Still further specific preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) which are substituted with one or more substituents selected from the following substituent set A and may be optionally substituted with one or more substituents independently selected from the following substituent set B and the following structures which may be optionally substituted with one or more substituents selected from the following substituent set B.

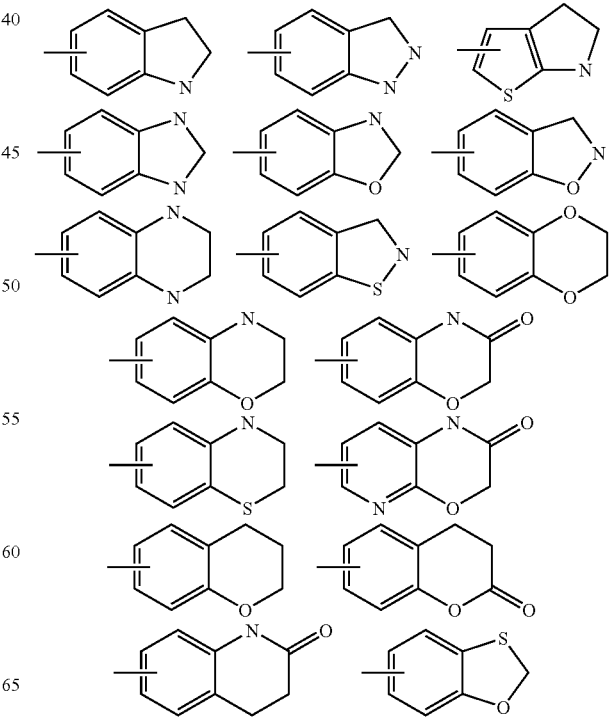

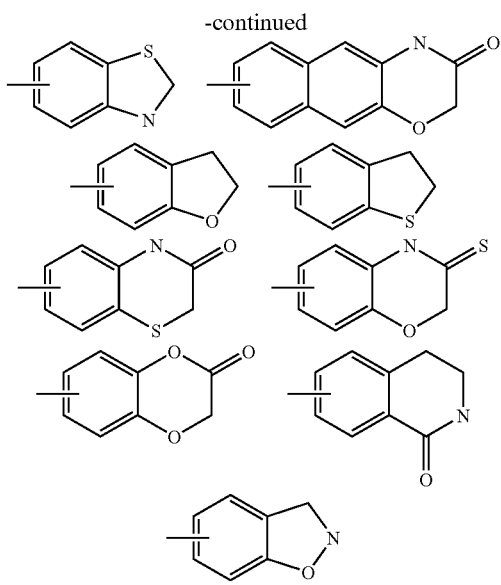

Substituent Set A:

$SO_2R^{28}$, $SOR^{28}$ or $COR^{28}$ (wherein $R^{21}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the amino group, the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-9}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $R^{29}$ and $R^{30}$ mean together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group, a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl so group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m3 and m4 is independently an integer of from 0 to 5, provided that m3+m4 is 3, 4 or 5), or $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ alkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or a substituted $C_{2-9}$ heterocyclyl group (the substituted $C_{2-9}$ heterocyclyl group may be optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino groups, the $C_{1-10}$ alkylaminosulfonyl groups, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with —$W^5$ (wherein $W^5$ is $SO_2R^{42}$, $SOR^{42}$, $COR^{42}$ (wherein $R^{42}$ is a hydrogen atom, a hydroxyl group or $NR^{43}R^{44}$, and each of $R^{43}$ and $R^{44}$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^{43}$ and $R^{44}$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)), $SO_2R^{28}$, $SOR^{28}$ or $COR^{28}$ (wherein $R^{28}$ is the same as defined above))) may be mentioned.

Substituent Set B:

Hydrogen atoms, hydroxyl groups, amino groups, thiol groups, nitro groups, cyano groups, halogen atoms, carboxyl groups, carbamoyl groups, sulfamoyl groups, sulfo groups, formyl groups, Clay alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino groups, the $C_{1-10}$ alkylaminosulfonyl groups, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) may be mentioned.

Specific preferable examples of $L^4$ are a bond, $CH_2$, an oxygen atom, a sulfur atom, NH, N-Me, N—CHO, CHMe, $CMe_2$, N—$CH_2Ph$ and the like, and particularly preferred examples are a bond, $CH_2$, an oxygen atom, a sulfur atom, NH, NMe and the like.

Specific preferable examples of X are OH, SH, $NH_2$, OMe, SMe, NHMe, NHEt, NH—CHO, NH—$CH_2Ph$, $OCH_2Ph$, $SCH_2Ph$, OC(=O)$CH_3$, SC(=O)$CH_3$, NHC(=O)$CH_3$ and the like, and particularly preferable examples are OH, SH, $NH_2$ and the like.

Specific preferable examples of Y are an oxygen atom, a sulfur atom, NH, N—OH, N—CHO, N-Me, N—$CH_2Ph$, N—OMe, N—$OCH_2Ph$ an the like, and particularly preferred examples are an oxygen atom, a sulfur atom, NH, N—OH and the like.

Favorable compounds as the thrombopoietin receptor activator, the preventive, therapeutic or improving agent for diseases against which activation of the thrombopoietin receptor is effective and the platelet increasing agent of the present invention are as follows.

1) Compounds represented by the formula II) wherein A is a nitrogen atom, and B is a sulfur atom, tautomers, prodrugs or pharmaceutically acceptable salts of the compounds or solvates thereof.

2) Compounds represented by the formula (1) wherein A is a nitrogen atom, and B is an oxygen atom, tautomers, prodrugs or pharmaceutically acceptable salts of the compounds or solvates thereof.

3) Compounds represented by the formula (1) wherein A is a nitrogen atom, and B is $NR^9$ other than NH (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of; carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

4) Compounds represented by the formula (1) wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $R^6$ and $R^7$ mean, together with each other, —$(CH_2)_{m1}$-E-$(CH_2)_{m2}$— wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein 8 is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is an oxygen atom, tautomers, prodrugs or pharmaceutically acceptable salts of the compounds or solvates thereof.

5) Compounds represented by the formula (1) wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, clay alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$ $SOR^5$ or $COR^5$ (wherein R is a hydroxyl group, a $C_{1-10}$ alkyl group, a $C_{2-5}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 3 to 5 provided that m1+m2 is 3, 4 or 5)))), and B is a sulfur atom, tautomers, prodrugs or pharmaceutically acceptable salts of the compounds or solvates thereof.

6) Compounds represented by the formula (1) wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

7) The compounds represented by the formula (1) according to 4), 5) or 6), wherein A is $CR^{37}$ (wherein $R^{37}$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group) an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonylamino group and the mono- or di-$C_{1-10}$ alkylamino group may be substituted with one or more substituents selected from the group consisting of: halogen atoms, carboxyl groups, nitro groups and cyano groups), $SO_2R^{38}$, $SOR^{38}$ or $COR^{38}$ (wherein $R^{38}$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be substituted with one or more substituents selected from the group consisting of: halogen atoms, carboxyl groups, nitro groups and cyano groups), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl groups may be substituted with one or more halogen atoms) or one or more halogen atoms))), tautomers, prodrugs or pharmaceutically acceptable salts of the compounds or solvates thereof. The terms in the respective substituents $R^{37}$ and $R^{38}$ are the same as those in the respective substituents $R^1$ to $R^{36}$.

8) The compounds represented by the formula (1) according to 3) or 6), wherein B is $NR^{39}$ (wherein $R^{39}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be substituted with one or more substituents selected from the group consisting of: carboxyl groups, halogen atoms, nitro groups and cyano groups), a $C_{2-14}$ aryl group or a $C_{2-14}$ aryloxy group (the $C_{2-14}$ aryl group and the $C_{2-14}$ aryloxy group may be substituted with one or more substituents selected from the group consisting of: $C_{1-6}$ alkyl groups (the $C_{1-6}$ alkyl groups may be substituted with one or more halogen atoms), $C_{2-6}$ alkenyl groups, $C_{2-6}$ alkynyl groups, carboxyl groups, nitro groups, cyano groups and halogen atoms)), tautomers prodrugs or pharmaceutically acceptable salts of the compounds or solvates thereof. The terms in the substituent $R^{39}$ are the same as those in the respective substituents $R^1$ to $R^{36}$.

9) The compounds represented by the formula (1) according to 1), 2), 3), 4), 5), 6), 7) or 8), wherein $L^1$ is a bond, tautomers prodrugs or pharmaceutically acceptable salts of the compounds or solvates thereof.

10) The compounds represented by the formula (1) according to 1), 2), 3), 4), 5), 6), 7), 8) or 9), wherein $L^2$ is a bond, tautomers, prodrugs or pharmaceutically acceptable salts of the compounds or solvates thereof.

11) The compounds represented by the formula (1) according to 1), 2), 3), 4), 5), 6) 7), 8), 9) or 10), wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

12) The compounds according to 1), 2), 3), 4), 5), 6), 7), 8), 9) or 10), wherein $L^3$ is NH, tautomers, prodrugs or pharmaceutically acceptable salts of the compounds or solvates thereof.

13) The compounds according to 1), 2), 3), 4), 5), 6) 7) 8), 9) or 10), wherein $L^3$ is $CH_2$, tautomers, prodrugs or pharmaceutically acceptable salts of the compounds or solvates thereof.

14) The compounds according to 11), 12) or 13), wherein $L^4$ is a bond, tautomers prodrugs or pharmaceutically acceptable salts of the compounds or solvates thereof.

15) The compounds according to 11), 12, or 13), wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

16) The compounds according to 11), 12) or 13), wherein $L^4$ is NH, tautomers prodrugs or pharmaceutically acceptable salts of the compounds or solvates thereof.

17) The compounds according to 11), 12) or 13), wherein $L^4$ is $CH_2$, tautomers, prodrugs or pharmaceutically acceptable salts of the compounds or solvates thereof.

18) The compounds according to 14), 15), 16) or 17), wherein $R^2$ is a hydrogen atom, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl groups may be substituted with one or more halogen atoms) or one or more halogen atoms), tautomers, prodrugs or pharmaceutically acceptable salts of the compounds or solvates thereof.

19) The compounds according to 14), 15), 16) or 17), wherein $R^2$ is a hydrogen atom, a $C_{1-10}$ alkyl group, a $C_{2-6}$ alkenyl group, a $C_{2-6}$ alkynyl group, a $C_{1-3}$ alkoxy group (the $C_{1-10}$ alkyl group, the $C_{2-6}$ alkenyl group, the $C_{2-6}$ alkynyl group and the $C_{1-3}$ alkoxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, phenyl groups and phenyloxyl groups (the phenyl groups and the phenyloxyl groups may be substituted with one or more $C_{1-6}$ alkyl groups (the $C_{1-6}$ alkyl groups may be substituted with one or more halogen atoms) or one or more halogen atoms), a phenyl group or a phenyloxy group (the phenyl group and the phenyloxy group may be substituted with one or more $C_{1-6}$ alkyl groups (the $C_{1-6}$ alkyl groups may be substituted with one or more halogen atoms) or one or more halogen atoms), tautomers, prodrugs or pharmaceutically acceptable salts of the compounds or solvates thereof.

20) The compounds according to 14), 15), 16) or 17), wherein $R^2$ is a hydrogen atom, a $C_{1-10}$ alkyl group, a $C_{2-6}$ alkenyl group or a $C_{2-6}$ alkynyl group (the $C_{1-10}$ alkyl group, the $C_{2-6}$ alkenyl group and the $C_{2-6}$ alkynyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers prodrugs or pharmaceutically acceptable salts of the compounds or solvates thereof.

21) The compounds according to 14), 15) 16) or 17), wherein $R^2$ is a hydrogen atom or a $C_{1-6}$ alkyl group (the $C_{1-6}$ alkyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers prodrugs or pharmaceutically acceptable salts of the compounds or solvates thereof.

22) The compounds according to 14), 15), 16) or 17), wherein $R^2$ is a hydrogen atom or a $C_{1-3}$ alkyl group (the $C_{1-3}$ alkyl group may be optionally substituted with one or more substituents selected from the group consisting of halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers, prodrugs or pharmaceutically acceptable salts of the compounds or solvates thereof.

23) The compounds according to 18), 19), 20) 21) or 22), wherein $R^1$ is a $C_{2-14}$ aryl group (the $C_{2-14}$ aryl group may be optionally substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), tautomers, prodrugs or pharmaceutically acceptable salts of the compounds or solvates thereof.

24) The compounds according to 18), 19), 20) 21) or 22), wherein $R^1$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkylcarbonyloxy groups and the $C_{1-10}$ alkoxycarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), thiol groups and amino groups (the thiol groups and the amino groups may be optionally substituted with one or more substituents selected from the group consisting of: formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), tautomers, prodrugs or pharmaceutically acceptable salts of the compounds or solvates thereof.

25) The compounds according to 18), 19), 20) 21) or 22), wherein $R^1$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkoxycarbonyl groups and the $C_{1-10}$ alkylcarbonyloxy groups may be optionally substituted with one or more substituents selected from the group consisting of: halogen atoms, carboxyl groups, nitro groups and cyano groups), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of: formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: halogen atoms, carboxyl groups, nitro groups, cyano groups, hydroxyl groups and protected hydroxyl groups))), tautomers, prodrugs or pharmaceutically acceptable salts of the compounds or solvates thereof.

26) The compounds according to 18), 19), 20) 21) or 22), wherein $R^1$ is a phenyl group (the phenyl group may be optionally substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkoxycarbonyl groups and the $C_{1-10}$ alkylcarbonyloxy groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), thiol groups and amino groups (the thiol groups and the amino groups may be optionally substituted with one or more substituents selected from the group consisting of: formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: carboxyl group-s nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), tautomers, prodrugs or pharmaceutically acceptable salts of the compounds or solvates thereof.

27) The compounds according to 18), 19), 20) 21) or 22), wherein $R^1$ is a phenyl group (the phenyl group may be optionally substituted with one or more substituents selected from the group consisting of: halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkoxycarbonyl groups and the $C_{1-10}$ alkylcarbonyloxy groups may be optionally substituted with one or more substituents selected from the group consisting of: halogen atoms, carboxyl groups, nitro groups and cyano groups), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of: formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of: halogen atoms, carboxyl groups, nitro groups, cyano groups, hydroxyl groups and protected hydroxyl groups))), tautomers, prodrugs or pharmaceutically acceptable salts of the compounds or solvates thereof.

28) The compounds according to 23), 24), 25), 26) or 27), wherein Y is an oxygen atom, tautomers, prodrugs or pharmaceutically acceptable salts of the compounds or solvates thereof.

29) The compounds according to 23), 24), 25), 26) or 27), wherein Y is a sulfur atom, tautomers, prodrugs or pharmaceutically acceptable salts of the compounds or solvates thereof.

30) The compounds according to 28) or 29), wherein X is a hydroxyl group, tautomers, prodrugs or pharmaceutically acceptable salts of the compounds or solvates thereof.

31) The compounds according to 28) 29) or 30), wherein $R^3$ is a $C_{2-14}$ aryl group (the $C_{2-14}$ aryl group is optionally substituted with one or more substituents independently represented by —$V^1$ (wherein $V^1$ is a hydrogen atom, a hydroxyl group, a protected hydroxyl group, an amino group, a thiol group, a nitro group, a cyano group, a halogen atom, a carboxyl group, a carbamoyl group, a sulfamoyl group, a sulfo group a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylaminosulfonyl group, a $C_{1-10}$ alkylaminocarbonyl group, a $C_{1-10}$ alkylsulfonylamino group, a $C_{1-10}$ thioalkyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group, the $C_{1-10}$ alkylcarbonyl group, the $C_{1-10}$ alkylcarbonylamino group, the mono- or di-$C_{1-10}$ alkylamino group, the $C_{1-10}$ alkylaminosulfonyl group, the $C_{1-10}$ alkylaminocarbonyl group, the $C_{1-10}$ alkylsulfonylamino group and the $C_{1-10}$ thioalkyl group may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) and with one or more substituents independently represented by —$W^1(CW^2W^3)_mW^4$ (wherein $W^1$ is (—$R^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{26}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the amino group, the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms, $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting off hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5), or $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $Cl_{11}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or a substituted $C_{2-9}$ heterocyclyl group (the substituted $C_{2-9}$ heterocyclyl group may be optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))), a $C_{2-14}$ aryl group (the $C_{2-14}$ aryl group is optionally substituted with one or more substituents independently represented by —$V^1$ (wherein $V^1$ is the same as defined above) and with one or more substituents selected from the group consisting of: $C_{1-6}$ alkyl groups, $C_{2-6}$ alkenyl groups and $C_{2-6}$ alkynyl groups (the $C_{1-6}$ alkyl groups, the $C_{2-6}$ alkenyl groups and the $C_{2-6}$ alkynyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more substituents independently represented by —$V^2$ (wherein $V^2$ is the same as $V^1$, and $V^1$ is the same as defined above) and with —$W^5$ (wherein $W^5$ is $SO_2R^{42}$, $SOR^{42}$, $COR^{42}$ wherein $R^2$ is a hydrogen atom, a hydroxyl group or $NR^{43}R^{44}$, $R^{41}$ is the same as $R^6$, $R^{44}$ is the same as $R^7$, and $R^6$ and $R^7$ are the same as defined above) or $W^4$ and $W^4$ is the same as defined above))), a $C_{2-14}$ aryl group (the $C_{2-14}$ aryl group is optionally substituted with one or more substituents independently represented by —$V^1$ (wherein $V^1$ is the same as defined above) and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents independently represented by —$V^2$ (wherein $V^2$ is the same as $V^1$, and $V^1$ is the same as defined above) and with one or more substituents selected from $C_{2-9}$ heterocyclyl groups (the $C_{2-9}$ heterocyclyl groups are optionally substituted with one or more substituents independently represented by —$V^3$ (wherein $V^3$ is the same as $V^1$, and $V^1$ is the same as defined above)))), a $C_{2-14}$ aryl group (the $C_{2-14}$ aryl group is optionally substituted with one or more substituents independently represented by —$V^1$ (wherein $V^1$ is the same as defined above) and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents independently represented by —$V^2$ (wherein $V^2$ is the same as $V^1$, and $V^1$ is the same as defined above) and with one or more substituents selected from the group consisting of: amino groups (the amino groups are substituted with a $C_{1-10}$ alkyl group (the $C_{1-10}$ alkyl group is optionally substituted with one or more substituents independently represented by —$V^3$ (wherein $V^3$ is the same as $V^1$, and $V^1$ is the same as defined above)) and with a $C_{2-9}$ heterocyclyl group or a $C_{2-14}$ aryl group (the $C_{2-9}$ heterocyclyl group and the $C_{2-14}$ aryl group are optionally substituted with one or more substituents independently represented by —$V^4$ (wherein $V^4$ is the same as $V^1$, and $V^1$ is the same as defined above))), amino groups, mono- or di-$C_{1-10}$ alkylamino groups, $C_{1-10}$ alkoxy groups, $C_{1-10}$ thioalkyl groups, $C_{1-10}$ alkylsulfonyl groups, sulfonyl groups, sulfinyl groups and thiol groups (the amino groups, the mono- or di-$C_{1-10}$ alkylamino groups, the $C_{1-10}$ alkoxy groups, the $C_{1-10}$ thioalkyl groups, the $C_{1-10}$ alkylsulfonyl groups, the sulfonyl groups, the sulfinyl groups and the thiol groups are optionally substituted with one or more $C_{2-9}$ heterocyclyl groups or one or more $C_{2-14}$ aryl groups (the $C_{2-9}$ heterocyclyl groups and the $C_{2-14}$ aryl groups are optionally substituted with one or more substituents independently represented by —$V^5$ (wherein $V^5$ is the same as $V^1$, and $V^1$ is the same as defined above))))) or a $C_{2-14}$ substituted aryl group (the $C_{2-14}$ substituted aryl group may be optionally substituted with one or more substituents independently represented by —$V^1$ (wherein $V^1$ is the same as defined above)), tautomers, prodrugs or pharmaceutically acceptable salts of the compounds or solvates thereof.

32) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^3$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{21}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))))), tautomers, prodrugs or pharmaceutically acceptable salts of the compounds or solvates thereof.

33) The compounds according to 28) 29) or 30), wherein $R^3$ is a phenyl group (the phenyl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms. $C_{1-10}$ alkoxy groups, $C_{1-10}$ alkylcarbonyl groups, $C_{1-10}$ alkylcarbonyloxy groups $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-10}$ alkyl groups (the $C_{2-14}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))))), tautomers, prodrugs or pharmaceutically acceptable salts of the compounds or solvates thereof.

34) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups; nitro groups; cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from Q to 5, provided that m3+m4 is 3, 4 or 5))))), tautomers, prodrugs or pharmaceutically acceptable salts of the compounds or solvates thereof.

35) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents independently represented by —$V^1$ (wherein $V^1$ is the same as defined in Claim 1) and with —$W^5$ (wherein $W^5$ is $SO_2R^{42}$, $SOR^{42}$, $COR^{42}$ (wherein $R^{42}$ is a hydroxyl group or $NR^{43}R^{44}$, and $R^{43}$ and $R^{44}$ are the same as defined in Claim 1) or $W^4$ (wherein $W^4$ is the same as defined in Claim 1))), tautomers, prodrugs or pharmaceutically acceptable salts of the compounds or solvates thereof.

36) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group/the pyridyl group, the quinolyl group and the Isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, $C_{1-10}$ fluoroalkoxy groups, sulfamoyl groups, carbamoyl groups and $C_{1-10}$ alkylcarbonylamino groups and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents selected from the group consisting of: amino groups (the amino groups are substituted with a $C_{1-10}$ alkyl group and with a $C_{2-9}$ heterocyclyl group or a $C_{2-14}$ aryl group (the $C_{2-9}$ heterocyclyl group and the $C_{2-14}$ aryl group may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), amino groups, mono- or di-$C_{1-10}$ alkylamino groups, $C_{1-10}$ alkoxy groups, $C_{1-10}$ thioalkyl groups, $C_{1-10}$ alkylsulfonyl groups, sulfonyl groups, sulfinyl groups and thiol groups (the amino groups, the mono- or di-$C_{1-10}$ alkylamino groups, the $C_{1-10}$ alkoxy groups, the $C_{1-10}$ thioalkyl groups, the $C_{1-10}$ alkylsulfonyl groups, the sulfonyl groups, the sulfinyl groups and the thiol groups are optionally substituted one or more $C_{2-9}$ heterocyclyl groups or one or more $C_{2-14}$ aryl groups (the $C_{2-9}$ heterocyclyl groups and the $C_{2-14}$ aryl groups may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))), tautomers, prodrugs or pharmaceutically acceptable salts of the compounds or solvates thereof.

37) The compounds according to 28) 29) or 30), wherein $R^3$ is a phenyl group (the phenyl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom, a hydroxyl group an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group) each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{32}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers prodrugs or pharmaceutically acceptable salts of the compounds or solvates thereof.

38) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by $—W^1(CW^2W^3)_mW^4$ (wherein $W^1$ is $(CR^{24}R^{25})_n$ (wherein each of $R^{24}$ and $R^{25}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n is 0, 1, 2 or 3), an oxygen atom, a sulfur atom or $NR^{36}$ (wherein 36 is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $NR^{23}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

39) The compounds according to 28) 29) or 30), wherein $R^3$ is a phenyl group (the phenyl group is optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, sulfamoyl groups, carbamoyl groups and $C_{1-10}$ alkylcarbonylamino groups and with one or more substituents independently represented by $—W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{38}$ or $COR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

40) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{2-6}$ alkylcarbonyl group are substituted with one or more $C_{2-9}$ heterocyclyl groups (the $C_{2-9}$ heterocyclyl groups may be substituted with one or more substituents selected from the group consisting of: hydroxyl groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))))), tautomers, prodrugs or pharmaceutically acceptable salts of the compounds or solvates thereof.

41) The compounds according to 28) 29) or 30), wherein $R^3$ is a phenyl group (the phenyl group is optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_m W^4$ (wherein $W^1$ is $CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group) each of $W^2$ and $W^3$ is independently a hydrogen atom or a $C_{1-3}$ alkyl group (the $C_{1-3}$ alkyl group may be substituted with one or more halogen atoms) m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are substituted with one or more $C_{2-9}$ heterocyclyl groups (the $C_{2-9}$ heterocyclyl groups may be substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

42) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups; the $C_{2-6}$ alkenyl groups, the $C_{2-6}$ alkynyl groups; the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers, prodrugs or pharmaceutically acceptable salts of the compounds or solvates thereof.

43) The compounds according to 28) 29) or 30), wherein $R^3$ is a phenyl group (the phenyl group is optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halo-en atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers, prodrugs or pharmaceutically acceptable salts of the compounds or solvates thereof.

44) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-10}$ alkyl group may be substituted with one or more halogen atoms), m is 0, 1, 2 or 3, and $W^4$ is $SO_2R^{28}$, $SOR^{28}$ or $COR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers; prodrugs or pharmaceutically acceptable salts of the compounds or solvates thereof.

45) The compounds according to 28) 29) or 30), wherein $R^3$ is a phenyl group (the phenyl group is optionally substituted with one or more substituents selected from the group consisting of: nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3 and $W^4$ is $SO_2R^{28}$, $SOR^{28}$ or $CR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, $C_{1-10}$ amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

46) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or H) an oxygen atom, a sulfur atom or $NR^{36}$ (wherein $R^2$ is a hydrogen atom, a $C_{1-6}$ alkyl group, a formyl group or a $C_{1-10}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3 and $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are substituted with one or more $C_{2-9}$ heterocyclyl groups (the $C_{2-9}$ heterocyclyl groups may be substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

47) The compounds according to 28) 29) or 30), wherein $R^3$ is a phenyl group (the phenyl group is optionally substituted with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein 36 is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^{26}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups, and $R^{30}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are substituted with one or more $C_{2-9}$ heterocyclyl groups (the $C_{2-9}$ heterocyclyl groups may be substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))))), tautomers, prodrugs or pharmaceutically acceptable salts of the compounds or solvates thereof.

48) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms)), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3 and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers, prodrugs or pharmaceutically acceptable salts of the compounds or solvates thereof.

49) The compounds according to 28) 29) or 30), wherein $R^3$ is a phenyl group (the phenyl group is optionally substituted with one or more substituents independently represented by $W^1(CW^2W^3)_m W^4$ (wherein $W^1$ is $CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms) m is 0, 1, 2 or 3, and $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl (the mono- or di-$C_{1-10}$ alkylamino group, the $C_{1-10}$ alkylcarbonylamino group and the $C_{1-10}$ alkylaminocarbonyl group may be substituted with one or more substituents selected from the group consisting of: hydrogen atoms, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers, prodrugs or pharmaceutically acceptable salts of the compounds or solvates thereof.

50) The compounds according to 28) 29) or 30), wherein $R^3$ is a phenyl group, a thienyl group, a furyl group, a pyridazinyl group, a pyridyl group, a quinolyl group or an Isoquinolyl group (the phenyl group, the thienyl group, the furyl group, the pyridazinyl group, the pyridyl group, the quinolyl group and the isoquinolyl group are optionally substituted with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3/and $W^4$ is $SO_2R^{28}$, $SOR^{28}$ or $COR^{28}$ (wherein $R^{28}$ is $NR^{29}R^{30}$ (wherein $NR^{29}R^{30}$ as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))), tautomers, prodrugs or pharmaceutically acceptable salts of the compounds or solvates thereof.

51) The compounds according to 28) 29) or 30), wherein $R^3$ is a phenyl group (the phenyl group is optionally substituted with one or more substituents independently represented by $W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is $SO_2R^{28}$, $SOR^{28}$ or $COR^{28}$ (wherein $R^2$ is $NR^{29}R^{30}$ wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

52) The compounds according to 28) 29) or 30), wherein 3 is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with —$W^4$ (wherein $W^4$ is $SO_2R^{28}$, $SOR^{28}$ or $COR^{28}$ (wherein $R^{28}$ is $NR^{29}R^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))))), tautomers, prodrugs or pharmaceutically acceptable salts of the compounds or solvates thereof.

53) The compounds according to 28) 29) or 30), wherein $R^3$ is a phenyl group (the phenyl group is substituted with —$W^4$ (wherein $W^4$ is $SO_2R^{28}$, $SOR^{28}$ or $COR^{28}$ (wherein $R^{28}$ is $R^{29}NR^{30}$ (wherein $R^{29}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), and $R^{30}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may be optionally substituted with one or more substituents selected from the group consisting of: hydrogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may be optionally substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))))))), tautomers, prodrugs or pharmaceutically acceptable salts of the compounds or solvates thereof.

54) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with —$W^4$ (wherein $W^4$ is $SO_2R^{28}$, $SOR^{28}$ or $COR^{28}$ (wherein $R^{28}$ is $NR^{29}R^{30}$ (wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), a hydroxyl group or a protected hydroxyl group, and $R^{32}$ is an amino group, a mono- or di-$C_{1-10}$) alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5)))), tautomers, prodrugs or pharmaceutically acceptable salts of the compounds or solvates thereof.

55) The compounds according to 28) 29) or 30), wherein $R^3$ is a phenyl group (the phenyl group is optionally substituted with one or more substituents independently represented by —$W^4$— (wherein $W^4$ is $SO_2R^{28}$, $SOR^{28}$ or $COR^{28}$ (wherein $R^{28}$ is $NR^{29}R^{30}$ wherein $R^{29}$ and $R^{30}$ mean, together with each other, —$(CH_2)_{m3}$-G-$(CH_2)_{m4}$— (wherein G is $CR^{31}R^{32}$ (wherein $R^{31}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{32}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{33}$ (wherein $R^{33}$ is an amino group, a mono- or di-$C_{1-10}$ alkylamino group, a $C_{1-10}$ alkylcarbonylamino group, a $C_{2-9}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), tautomers, prodrugs or pharmaceutically acceptable salts of the compounds or solvates thereof.

56) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents independently represented by $W^4$ (wherein $W^4$ is $SO_2R^{28}$, $SOR^{28}$ or $COR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkyl carbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

57) The compounds according to 28) 29) or 30), wherein $R^3$ is a phenyl group (the phenyl group is optionally substituted with one or more substituents independently represented by —$W^4$ (wherein $W^4$ is $SO_2R^{28}$, $SOR^{28}$ or $COR^{28}$ (wherein $R^{28}$ is $NR^{29}R^{30}$ (wherein $NR^{29}R^{30}$, as a whole, means a nitrogen-containing $C_{2-9}$ cyclyl group (the nitrogen-containing $C_{2-9}$ cyclyl group may be optionally substituted with one or more hydrogen atoms and is substituted with two or three substituents independently selected from the group consisting of: hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may be optionally substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)))))), tautomers, prodrugs or pharmaceutically acceptable salts of the compounds or solvates thereof.

58) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents optionally selected from the group consisting of: hydrogen atoms, nitro groups, cyano groups, halogen atoms, $C_{1-10}$ fluoroalkyl groups, $C_{1-10}$ alkylaminosulfonyl groups, $C_{1-10}$ alkylaminocarbonyl groups and $C_{1-10}$ alkylcarbonylamino groups and with one or more $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms), with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino group, the $C_{1-10}$ alkylaminosulfonyl group, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkyl carbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) and with one or more substituents selected from the group consisting of: carboxyl groups, carbamoyl groups, sulfamoyl groups and sulfo groups)), tautomers, prodrugs or pharmaceutically acceptable salts of the compounds or solvates thereof.

59) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more $C_{1-6}$ alkyl groups (the $C_{1-6}$ alkyl groups are optionally substituted with one or more substituents selected from the group consisting of: hydroxyl groups, amino groups, mono- or di-$C_{1-10}$ alkylamino groups and $C_{1-6}$ alkoxy groups (the mono- or di-$C_{1-10}$ alkylamino groups and the $C_{1-6}$ alkoxy groups may be substituted with one or more halogen atoms) and with one or more substituents selected from the group consisting of: carboxyl groups, carbamoyl groups, sulfamoyl groups and sulfo groups)), tautomers, prodrugs or pharmaceutically acceptable salts of the compounds or solvates thereof.

60) The compounds according to 28) 29) or 30), wherein $R^3$ is a $C_{2-14}$ substituted aryl group (the $C_{2-14}$ substituted aryl group may be optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino group, the $C_{1-10}$ alkylaminosulfonyl group, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

61) The compounds according to 28) 29) or 30), wherein $R^3$ is any of the following structures (the following structures are optionally substituted with one or more substituents selected from the group consisting of: hydrogen atoms, hydroxyl groups, amino groups, thiol groups, nitro groups, cyano groups, halogen atoms, carboxyl groups, carbamoyl groups, sulfamoyl groups, sulfo groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkoxy groups, $C_{1-10}$ alkylcarbonyl groups, $C_{1-10}$ alkylcarbonylamino groups, mono- or di-$C_{1-10}$ alkylamino groups, $C_{1-10}$ alkylaminosulfonyl groups, $C_{1-10}$ alkylaminocarbonyl groups, $C_{1-10}$ alkylsulfonylamino groups, $C_{1-10}$ thioalkyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkoxy groups, the $C_{1-10}$ alkylcarbonyl groups, the $C_{1-10}$ alkylcarbonylamino groups, the mono- or di-$C_{1-10}$ alkylamino group, the $C_{1-10}$ alkylaminosulfonyl group, the $C_{1-10}$ alkylaminocarbonyl groups, the $C_{1-10}$ alkylsulfonylamino groups and the $C_{1-10}$ thioalkyl groups may be optionally substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

62) The compounds according to 28) 29) or 30), wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: hydrogen atoms, nitro groups, cyano groups, halogen atoms, amino groups, $C_{1-10}$ alkylaminocarbonyl groups, $C_{1-10}$ alkylaminosulfonyl groups, $C_{1-10}$ fluoroalkyl groups, $C_{1-10}$ fluoroalkoxy groups, sulfamoyl groups, carbamoyl groups and $C_{1-10}$ alkylcarbonylamino groups and with one or more substituents selected from the group consisting of: $C_{1-6}$ alkyl groups, $C_{2-6}$ alkenyl groups, $C_{2-6}$ alkynyl groups, $C_{1-10}$ alkylcarbonyl groups, $C_{1-10}$ alkylthiocarbonyl groups and $C_{1-10}$ alkylsulfonyl groups (the $C_{1-6}$ alkyl groups, the $C_{2-6}$ alkenyl groups, the $C_{2-6}$ alkynyl groups, the $C_{1-10}$ alkylcarbonyl groups, the $C_{1-10}$ alkylthiocarbonyl groups and the $C_{1-10}$ alkylsulfonyl groups are optionally substituted with one or more substituents selected from the group consisting of: hydrogen atoms, $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups and with one or more substituents selected from $C_{2-9}$ heterocyclyl groups (the $C_{2-9}$ heterocyclyl groups may be optionally substituted with one or more substituents selected from the group consisting of: $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups))), tautomers, prodrugs or pharmaceutically acceptable salts of the compounds or solvates thereof.

63) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof. The symbols in Table 1 denote the flowing substituents.

TABLE 1

| No | A | B | $R^1$ | $L^1$ | $R^2$ | $L^2$ | $L^3$ | Y | $L^4$ | $R^3$ | X |
|----|---|---|-------|-------|-------|-------|-------|---|-------|-------|---|
| 1 | N | NMe | Q1a | a bond | Me | a bond | NH | S | NH | T3a | OH |
| 2 | N | NMe | Q1a | a bond | Me | a bond | NH | S | NH | T3b | OH |
| 3 | N | NMe | Q1a | a bond | Me | a bond | NH | S | NH | T3c | OH |
| 4 | N | NMe | Q1a | a bond | Me | a bond | NH | S | NH | T3d | OH |
| 5 | N | NMe | Q1a | a bond | Me | a bond | NH | S | NH | T3e | OH |
| 6 | N | NMe | Q1a | a bond | Me | a bond | NH | S | NH | T3f | OH |
| 7 | N | NMe | Q1a | a bond | Me | a bond | NH | S | NH | T3g | OH |
| 8 | N | NMe | Q1a | a bond | Me | a bond | NH | S | NH | T3h | OH |
| 9 | N | NMe | Q1a | a bond | Me | a bond | NH | S | NH | T3i | OH |
| 10 | N | NMe | Q1a | a bond | Me | a bond | NH | S | NH | T3j | OH |
| 11 | N | NMe | Q1a | a bond | Me | a bond | NH | S | a bond | T3a | OH |
| 12 | N | NMe | Q1a | a bond | Me | a bond | NH | S | a bond | T3b | OH |
| 13 | N | NMe | Q1a | a bond | Me | a bond | NH | S | a bond | T3c | OH |
| 14 | N | NMe | Q1a | a bond | Me | a bond | NH | S | a bond | T3d | OH |
| 15 | N | NMe | Q1a | a bond | Me | a bond | NH | S | a bond | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 16 | N | NMe | Q1a | a bond | Me | a bond | NH | S | a bond | T3f | OH |
| 17 | N | NMe | Q1a | a bond | Me | a bond | NH | S | a bond | T3g | OH |
| 18 | N | NMe | Q1a | a bond | Me | a bond | NH | S | a bond | T3h | OH |
| 19 | N | NMe | Q1a | a bond | Me | a bond | NH | S | a bond | T3i | OH |
| 20 | N | NMe | Q1a | a bond | Me | a bond | NH | S | a bond | T3j | OH |
| 21 | N | NMe | Q1a | a bond | Me | a bond | NH | O | NH | T3a | OH |
| 22 | N | NMe | Q1a | a bond | Me | a bond | NH | O | NH | T3b | OH |
| 23 | N | NMe | Q1a | a bond | Me | a bond | NH | O | NH | T3c | OH |
| 24 | N | NMe | Q1a | a bond | Me | a bond | NH | O | NH | T3d | OH |
| 25 | N | NMe | Q1a | a bond | Me | a bond | NH | O | NH | T3e | OH |
| 26 | N | NMe | Q1a | a bond | Me | a bond | NH | O | NH | T3f | OH |
| 27 | N | NMe | Q1a | a bond | Me | a bond | NH | O | NH | T3g | OH |
| 28 | N | NMe | Q1a | a bond | Me | a bond | NH | O | NH | T3h | OH |
| 29 | N | NMe | Q1a | a bond | Me | a bond | NH | O | NH | T3i | OH |
| 30 | N | NMe | Q1a | a bond | Me | a bond | NH | O | NH | T3j | OH |
| 31 | N | NMe | Q1a | a bond | Me | a bond | NH | O | a bond | T3a | OH |
| 32 | N | NMe | Q1a | a bond | Me | a bond | NH | O | a bond | T3b | OH |
| 33 | N | NMe | Q1a | a bond | Me | a bond | NH | O | a bond | T3c | OH |
| 34 | N | NMe | Q1a | a bond | Me | a bond | NH | O | a bond | T3d | OH |
| 35 | N | NMe | Q1a | a bond | Me | a bond | NH | O | a bond | T3e | OH |
| 36 | N | NMe | Q1a | a bond | Me | a bond | NH | O | a bond | T3f | OH |
| 37 | N | NMe | Q1a | a bond | Me | a bond | NH | O | a bond | T3g | OH |
| 38 | N | NMe | Q1a | a bond | Me | a bond | NH | O | a bond | T3h | OH |
| 39 | N | NMe | Q1a | a bond | Me | a bond | NH | O | a bond | T3i | OH |
| 40 | N | NMe | Q1a | a bond | Me | a bond | NH | O | a bond | T3j | OH |
| 41 | N | NMe | Q1a | a bond | H | a bond | NH | S | NH | T3a | OH |
| 42 | N | NMe | Q1a | a bond | H | a bond | NH | S | NH | T3b | OH |
| 43 | N | NMe | Q1a | a bond | H | a bond | NH | S | NH | T3c | OH |
| 44 | N | NMe | Q1a | a bond | H | a bond | NH | S | NH | T3d | OH |
| 45 | N | NMe | Q1a | a bond | H | a bond | NH | 3 | NH | T3e | OH |
| 46 | N | NMe | Q1a | a bond | H | a bond | NH | S | NH | T3f | OH |
| 47 | N | NMe | Q1a | a bond | H | a bond | NH | S | NH | T3g | OH |
| 48 | N | NMe | Q1a | a bond | H | a bond | NH | S | NH | T3h | OH |
| 49 | N | NMe | Q1a | a bond | H | a bond | NH | S | NH | T3i | OH |
| 50 | N | NMe | Q1a | a bond | H | a bond | NH | S | NH | T3j | OH |
| 51 | N | NMe | Q1a | a bond | H | a bond | NH | S | a bond | T3a | OH |
| 52 | N | NMe | Q1a | a bond | H | a bond | NH | S | a bond | T3b | OH |
| 53 | N | NMe | Q1a | a bond | H | a bond | NH | S | a bond | T3c | OH |
| 54 | N | NMe | Q1a | a bond | H | a bond | NH | S | a bond | T3d | OH |
| 55 | N | NMe | Q1a | a bond | H | a bond | NH | S | a bond | T3e | OH |
| 56 | N | NMe | Q1a | a bond | H | a bond | NH | S | a bond | T3f | OH |
| 57 | N | NMe | Q1a | a bond | H | a bond | NH | S | a bond | T3g | OH |
| 58 | N | NMe | Q1a | a bond | H | a bond | NH | S | a bond | T3h | OH |
| 59 | N | NMe | Q1a | a bond | H | a bond | NH | S | a bond | T3i | OH |
| 60 | N | NMe | Q1a | a bond | H | a bond | NH | S | a bond | T3j | OH |
| 61 | N | NMe | Q1a | a bond | H | a bond | NH | O | NH | T3a | OH |
| 62 | N | NMe | Q1a | a bond | H | a bond | NH | O | NH | T3b | OH |
| 63 | N | NMe | Q1a | a bond | H | a bond | NH | O | NH | T3c | OH |
| 64 | N | NMe | Q1a | a bond | H | a bond | NH | O | NH | T3d | OH |
| 65 | N | NMe | Q1a | a bond | H | a bond | NH | O | NH | T3e | OH |
| 66 | N | NMe | Q1a | a bond | H | a bond | NH | O | NH | T3f | OH |
| 67 | N | NMe | Q1a | a bond | H | a bond | NH | O | NH | T3g | OH |
| 68 | N | NMe | Q1a | a bond | H | a bond | NH | O | NH | T3h | OH |
| 69 | N | NMe | Q1a | a bond | H | a bond | NH | O | NH | T3i | OH |
| 70 | N | NMe | Q1a | a bond | H | a bond | NH | O | NH | T3j | OH |
| 71 | N | NMe | Q1a | a bond | H | a bond | NH | O | a bond | T3a | OH |
| 72 | N | NMe | Q1a | a bond | H | a bond | NH | O | a bond | T3b | OH |
| 73 | N | NMe | Q1a | a bond | H | a bond | NH | O | a bond | T3c | OH |
| 74 | N | NMe | Q1a | a bond | H | a bond | NH | O | a bond | T3d | OH |
| 75 | N | NMe | Q1a | a bond | H | a bond | NH | O | a bond | T3e | OH |
| 76 | N | NMe | Q1a | a bond | H | a bond | NH | O | a bond | T3f | OH |
| 77 | N | NMe | Q1a | a bond | H | a bond | NH | O | a bond | T3g | OH |
| 78 | N | NMe | Q1a | a bond | H | a bond | NH | O | a bond | T3h | OH |
| 79 | N | NMe | Q1a | a bond | H | a bond | NH | O | a bond | T3i | OH |
| 80 | N | NMe | Q1a | a bond | H | a bond | NH | O | a bond | T3j | OH |
| 81 | N | NMe | Q1b | a bond | Me | a bond | NH | S | NH | T3a | OH |
| 82 | N | NMe | Q1b | a bond | Me | a bond | NH | S | NH | T3b | OH |
| 83 | N | NMe | Q1b | a bond | Me | a bond | NH | S | NH | T3c | OH |
| 84 | N | NMe | Q1b | a bond | Me | a bond | NH | S | NH | T3d | OH |
| 85 | N | NMe | Q1b | a bond | Me | a bond | NH | S | NH | T3e | OH |
| 86 | N | NMe | Q1b | a bond | Me | a bond | NH | S | NH | T3f | OH |
| 87 | N | NMe | Q1b | a bond | Me | a bond | NH | S | NH | T3g | OH |
| 88 | N | NMe | Q1b | a bond | Me | a bond | NH | S | NH | T3h | OH |
| 89 | N | NMe | Q1b | a bond | Me | a bond | NH | S | NH | T3i | OH |
| 90 | N | NMe | Q1b | a bond | Me | a bond | NH | S | NH | T3j | OH |
| 91 | N | NMe | Q1b | a bond | Me | a bond | NH | S | a bond | T3a | OH |
| 92 | N | NMe | Q1b | a bond | Me | a bond | NH | S | a bond | T3b | OH |
| 93 | N | NMe | Q1b | a bond | Me | a bond | NH | S | a bond | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 94 | N | NMe | Q1b | a bond | Me | a bond | NH | S | a bond | T3d | OH |
| 95 | N | NMe | Q1b | a bond | Me | a bond | NH | S | a bond | T3e | OH |
| 96 | N | NMe | Q1b | a bond | Me | a bond | NH | S | a bond | T3f | OH |
| 97 | N | NMe | Q1b | a bond | Me | a bond | NH | S | a bond | T3g | OH |
| 98 | N | NMe | Q1b | a bond | Me | a bond | NH | S | a bond | T3h | OH |
| 99 | N | NMe | Q1b | a bond | Me | a bond | NH | S | a bond | T3i | OH |
| 100 | N | NMe | Q1b | a bond | Me | a bond | NH | S | a bond | T3j | OH |
| 101 | N | NMe | Q1b | a bond | Me | a bond | NH | O | NH | T3a | OH |
| 102 | N | NMe | Q1b | a bond | Me | a bond | NH | O | NH | T3b | OH |
| 103 | N | NMe | Q1b | a bond | Me | a bond | NH | O | NH | T3c | OH |
| 104 | N | NMe | Q1b | a bond | Me | a bond | NH | O | NH | T3d | OH |
| 105 | N | NMe | Q1b | a bond | Me | a bond | NH | O | NH | T3e | OH |
| 106 | N | NMe | Q1b | a bond | Me | a bond | NH | O | NH | T3f | OH |
| 107 | N | NMe | Q1b | a bond | Me | a bond | NH | O | NH | T3g | OH |
| 108 | N | NMe | Q1b | a bond | Me | a bond | NH | O | NH | T3h | OH |
| 109 | N | NMe | Q1b | a bond | Me | a bond | NH | O | NH | T3i | OH |
| 110 | N | NMe | Q1b | a bond | Me | a bond | NH | O | NH | T3j | OH |
| 111 | N | NMe | Q1b | a bond | Me | a bond | NH | O | a bond | T3a | OH |
| 112 | N | NMe | Q1b | a bond | Me | a bond | NH | O | a bond | T3b | OH |
| 113 | N | NMe | Q1b | a bond | Me | a bond | NH | O | a bond | T3c | OH |
| 114 | N | NMe | Q1b | a bond | Me | a bond | NH | O | a bond | T3d | OH |
| 115 | N | NMe | Q1b | a bond | Me | a bond | NH | O | a bond | T3e | OH |
| 116 | N | NMe | Q1b | a bond | Me | a bond | NH | O | a bond | T3f | OH |
| 117 | N | NMe | Q1b | a bond | Me | a bond | NH | O | a bond | T3g | OH |
| 118 | N | NMe | Q1b | a bond | Me | a bond | NH | O | a bond | T3h | OH |
| 119 | N | NMe | Q1b | a bond | Me | a bond | NH | O | a bond | T3i | OH |
| 120 | N | NMe | Q1b | a bond | Me | a bond | NH | O | a bond | T3j | OH |
| 121 | N | NMe | Q1b | a bond | H | a bond | NH | S | NH | T3a | OH |
| 122 | N | NMe | Q1b | a bond | H | a bond | NH | S | NH | T3b | OH |
| 123 | N | NMe | Q1b | a bond | H | a bond | NH | S | NH | T3c | OH |
| 124 | N | NMe | Q1b | a bond | H | a bond | NH | S | NH | T3d | OH |
| 125 | N | NMe | Q1b | a bond | H | a bond | NH | S | NH | T3e | OH |
| 126 | N | NMe | Q1b | a bond | H | a bond | NH | S | NH | T3f | OH |
| 127 | N | NMe | Q1b | a bond | H | a bond | NH | S | NH | T3g | OH |
| 128 | N | NMe | Q1b | a bond | H | a bond | NH | S | NH | T3h | OH |
| 129 | N | NMe | Q1b | a bond | H | a bond | NH | S | NH | T3i | OH |
| 130 | N | NMe | Q1b | a bond | H | a bond | NH | S | NH | T3j | OH |
| 131 | N | NMe | Q1b | a bond | H | a bond | NH | S | a bond | T3a | OH |
| 132 | N | NMe | Q1b | a bond | H | a bond | NH | S | a bond | T3b | OH |
| 133 | N | NMe | Q1b | a bond | H | a bond | NH | S | a bond | T3c | OH |
| 134 | N | NMe | Q1b | a bond | H | a bond | NH | S | a bond | T3d | OH |
| 135 | N | NMe | Q1b | a bond | H | a bond | NH | S | a bond | T3e | OH |
| 136 | N | NMe | Q1b | a bond | H | a bond | NH | S | a bond | T3f | OH |
| 137 | N | NMe | Q1b | a bond | H | a bond | NH | S | a bond | T3g | OH |
| 138 | N | NMe | Q1b | a bond | H | a bond | NH | S | a bond | T3h | OH |
| 139 | N | NMe | Q1b | a bond | H | a bond | NH | S | a bond | T3i | OH |
| 140 | N | NMe | Q1b | a bond | H | a bond | NH | S | a bond | T3j | OH |
| 141 | N | NMe | Q1b | a bond | H | a bond | NH | O | NH | T3a | OH |
| 142 | N | NMe | Q1b | a bond | H | a bond | NH | O | NH | T3b | OH |
| 143 | N | NMe | Q1b | a bond | H | a bond | NH | O | NH | T3c | OH |
| 144 | N | NMe | Q1b | a bond | H | a bond | NH | O | NH | T3d | OH |
| 145 | N | NMe | Q1b | a bond | H | a bond | NH | O | NH | T3e | OH |
| 146 | N | NMe | Q1b | a bond | H | a bond | NH | O | NH | T3f | OH |
| 147 | N | NMe | Q1b | a bond | H | a bond | NH | O | NH | T3g | OH |
| 148 | N | NMe | Q1b | a bond | H | a bond | NH | O | NH | T3h | OH |
| 149 | N | NMe | Q1b | a bond | H | a bond | NH | O | NH | T3i | OH |
| 150 | N | NMe | Q1b | a bond | H | a bond | NH | O | NH | T3j | OH |
| 151 | N | NMe | Q1b | a bond | H | a bond | NH | O | a bond | T3a | OH |
| 152 | N | NMe | Q1b | a bond | H | a bond | NH | O | a bond | T3b | OH |
| 153 | N | NMe | Q1b | a bond | H | a bond | NH | O | a bond | T3c | OH |
| 154 | N | NMe | Q1b | a bond | H | a bond | NH | O | a bond | T3d | OH |
| 155 | N | NMe | Q1b | a bond | H | a bond | NH | O | a bond | T3e | OH |
| 156 | N | NMe | Q1b | a bond | H | a bond | NH | O | a bond | T3f | OH |
| 157 | N | NMe | Q1b | a bond | H | a bond | NH | O | a bond | T3g | OH |
| 158 | N | NMe | Q1b | a bond | H | a bond | NH | O | a bond | T3h | OH |
| 159 | N | NMe | Q1b | a bond | H | a bond | NH | O | a bond | T3i | OH |
| 160 | N | NMe | Q1b | a bond | H | a bond | NH | O | a bond | T3j | OH |
| 161 | N | NMe | Q1c | a bond | Me | a bond | NH | S | NH | T3a | OH |
| 162 | N | NMe | Q1c | a bond | Me | a bond | NH | S | NH | T3b | OH |
| 163 | N | NMe | Q1c | a bond | Me | a bond | NH | S | NH | T3c | OH |
| 164 | N | NMe | Q1c | a bond | Me | a bond | NH | S | NH | T3d | OH |
| 165 | N | NMe | Q1c | a bond | Me | a bond | NH | S | NH | T3e | OH |
| 166 | N | NMe | Q1c | a bond | Me | a bond | NH | S | NH | T3f | OH |
| 167 | N | NMe | Q1c | a bond | Me | a bond | NH | S | NH | T3g | OH |
| 168 | N | NMe | Q1c | a bond | Me | a bond | NH | S | NH | T3h | OH |
| 169 | N | NMe | Q1c | a bond | Me | a bond | NH | S | NH | T3i | OH |
| 170 | N | NMe | Q1c | a bond | Me | a bond | NH | S | NH | T3j | OH |
| 171 | N | NMe | Q1c | a bond | Me | a bond | NH | S | a bond | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 172 | N | NMe | Q1c | a bond | Me | a bond | NH | S | a bond | T3b | OH |
| 173 | N | NMe | Q1c | a bond | Me | a bond | NH | S | a bond | T3c | OH |
| 174 | N | NMe | Q1c | a bond | Me | a bond | NH | S | a bond | T3d | OH |
| 175 | N | NMe | Q1c | a bond | Me | a bond | NH | S | a bond | T3e | OH |
| 176 | N | NMe | Q1c | a bond | Me | a bond | NH | S | a bond | T3f | OH |
| 177 | N | NMe | Q1c | a bond | Me | a bond | NH | S | a bond | T3g | OH |
| 178 | N | NMe | Q1c | a bond | Me | a bond | NH | S | a bond | T3h | OH |
| 179 | N | NMe | Q1c | a bond | Me | a bond | NH | S | a bond | T3i | OH |
| 180 | N | NMe | Q1c | a bond | Me | a bond | NH | S | a bond | T3j | OH |
| 181 | N | NMe | Q1c | a bond | Me | a bond | NH | O | NH | T3a | OH |
| 182 | N | NMe | Q1c | a bond | Me | a bond | NH | O | NH | T3b | OH |
| 183 | N | NMe | Q1c | a bond | Me | a bond | NH | O | NH | T3c | OH |
| 184 | N | NMe | Q1c | a bond | Me | a bond | NH | O | NH | T3d | OH |
| 185 | N | NMe | Q1c | a bond | Me | a bond | NH | O | NH | T3e | OH |
| 186 | N | NMe | Q1c | a bond | Me | a bond | NH | O | NH | T3f | OH |
| 187 | N | NMe | Q1c | a bond | Me | a bond | NH | O | NH | T3g | OH |
| 188 | N | NMe | Q1c | a bond | Me | a bond | NH | O | NH | T3h | OH |
| 189 | N | NMe | Q1c | a bond | Me | a bond | NH | O | NH | T3i | OH |
| 190 | N | NMe | Q1c | a bond | Me | a bond | NH | O | NH | T3j | OH |
| 191 | N | NMe | Q1c | a bond | Me | a bond | NH | O | a bond | T3a | OH |
| 192 | N | NMe | Q1c | a bond | Me | a bond | NH | O | a bond | T3b | OH |
| 193 | N | NMe | Q1c | a bond | Me | a bond | NH | O | a bond | T3c | OH |
| 194 | N | NMe | Q1c | a bond | Me | a bond | NH | O | a bond | T3d | OH |
| 195 | N | NMe | Q1c | a bond | Me | a bond | NH | O | a bond | T3e | OH |
| 196 | N | NMe | Q1c | a bond | Me | a bond | NH | O | a bond | T3f | OH |
| 197 | N | NMe | Q1c | a bond | Me | a bond | NH | O | a bond | T3g | OH |
| 198 | N | NMe | Q1c | a bond | Me | a bond | NH | O | a bond | T3h | OH |
| 199 | N | NMe | Q1c | a bond | Me | a bond | NH | O | a bond | T3i | OH |
| 200 | N | NMe | Q1c | a bond | Me | a bond | NH | O | a bond | T3j | OH |
| 201 | N | NMe | Q1c | a bond | H | a bond | NH | S | NH | T3a | OH |
| 202 | N | NMe | Q1c | a bond | H | a bond | NH | S | NH | T3b | OH |
| 203 | N | NMe | Q1c | a bond | H | a bond | NH | S | NH | T3c | OH |
| 204 | N | NMe | Q1c | a bond | H | a bond | NH | S | NH | T3d | OH |
| 205 | N | NMe | Q1c | a bond | H | a bond | NH | S | NH | T3e | OH |
| 206 | N | NMe | Q1c | a bond | H | a bond | NH | S | NH | T3f | OH |
| 207 | N | NMe | Q1c | a bond | H | a bond | NH | S | NH | T3g | OH |
| 208 | N | NMe | Q1c | a bond | H | a bond | NH | S | NH | T3h | OH |
| 209 | N | NMe | Q1c | a bond | H | a bond | NH | S | NH | T3i | OH |
| 210 | N | NMe | Q1c | a bond | H | a bond | NH | S | NH | T3j | OH |
| 211 | N | NMe | Q1c | a bond | H | a bond | NH | S | a bond | T3a | OH |
| 212 | N | NMe | Q1c | a bond | H | a bond | NH | S | a bond | T3b | OH |
| 213 | N | NMe | Q1c | a bond | H | a bond | NH | S | a bond | T3c | OH |
| 214 | N | NMe | Q1c | a bond | H | a bond | NH | S | a bond | T3d | OH |
| 215 | N | NMe | Q1c | a bond | H | a bond | NH | S | a bond | T3e | OH |
| 216 | N | NMe | Q1c | a bond | H | a bond | NH | S | a bond | T3f | OH |
| 217 | N | NMe | Q1c | a bond | H | a bond | NH | S | a bond | T3g | OH |
| 218 | N | NMe | Q1c | a bond | H | a bond | NH | S | a bond | T3h | OH |
| 219 | N | NMe | Q1c | a bond | H | a bond | NH | S | a bond | T3i | OH |
| 220 | N | NMe | Q1c | a bond | H | a bond | NH | S | a bond | T3j | OH |
| 221 | N | NMe | Q1c | a bond | H | a bond | NH | O | NH | T3a | OH |
| 222 | N | NMe | Q1c | a bond | H | a bond | NH | O | NH | T3b | OH |
| 223 | N | NMe | Q1c | a bond | H | a bond | NH | O | NH | T3c | OH |
| 224 | N | NMe | Q1c | a bond | H | a bond | NH | O | NH | T3d | OH |
| 225 | N | NMe | Q1c | a bond | H | a bond | NH | O | NH | T3e | OH |
| 226 | N | NMe | Q1c | a bond | H | a bond | NH | O | NH | T3f | OH |
| 227 | N | NMe | Q1c | a bond | H | a bond | NH | O | NH | T3g | OH |
| 228 | N | NMe | Q1c | a bond | H | a bond | NH | O | NH | T3h | OH |
| 229 | N | NMe | Q1c | a bond | H | a bond | NH | O | NH | T3i | OH |
| 230 | N | NMe | Q1c | a bond | H | a bond | NH | O | NH | T3j | OH |
| 231 | N | NMe | Q1c | a bond | H | a bond | NH | O | a bond | T3a | OH |
| 232 | N | NMe | Q1c | a bond | H | a bond | NH | O | a bond | T3b | OH |
| 233 | N | NMe | Q1c | a bond | H | a bond | NH | O | a bond | T3c | OH |
| 234 | N | NMe | Q1c | a bond | H | a bond | NH | O | a bond | T3d | OH |
| 235 | N | NMe | Q1c | a bond | H | a bond | NH | O | a bond | T3e | OH |
| 236 | N | NMe | Q1c | a bond | H | a bond | NH | O | a bond | T3f | OH |
| 237 | N | NMe | Q1c | a bond | H | a bond | NH | O | a bond | T3g | OH |
| 238 | N | NMe | Q1c | a bond | H | a bond | NH | O | a bond | T3h | OH |
| 239 | N | NMe | Q1c | a bond | H | a bond | NH | O | a bond | T3i | OH |
| 240 | N | NMe | Q1c | a bond | H | a bond | NH | O | a bond | T3j | OH |
| 241 | N | NMe | Q1i | a bond | Me | a bond | NH | S | NH | T3a | OH |
| 242 | N | NMe | Q1i | a bond | Me | a bond | NH | S | NH | T3b | OH |
| 243 | N | NMe | Q1i | a bond | Me | a bond | NH | S | NH | T3c | OH |
| 244 | N | NMe | Q1i | a bond | Me | a bond | NH | S | NH | T3d | OH |
| 245 | N | NMe | Q1i | a bond | Me | a bond | NH | S | NH | T3e | OH |
| 246 | N | NMe | Q1i | a bond | Me | a bond | NH | S | NH | T3f | OH |
| 247 | N | NMe | Q1i | a bond | Me | a bond | NH | S | NH | T3g | OH |
| 248 | N | NMe | Q1i | a bond | Me | a bond | NH | S | NH | T3h | OH |
| 249 | N | NMe | Q1i | a bond | Me | a bond | NH | S | NH | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 250 | N | NMe | Q1i | a bond | Me | a bond | NH | S | NH | T3j | OH |
| 251 | N | NMe | Q1i | a bond | Me | a bond | NH | S | a bond | T3a | OH |
| 252 | N | NMe | Q1i | a bond | Me | a bond | NH | S | a bond | T3b | OH |
| 253 | N | NMe | Q1i | a bond | Me | a bond | NH | S | a bond | T3c | OH |
| 254 | N | NMe | Q1i | a bond | Me | a bond | NH | S | a bond | T3d | OH |
| 255 | N | NMe | Q1i | a bond | Me | a bond | NH | S | a bond | T3e | OH |
| 256 | N | NMe | Q1i | a bond | Me | a bond | NH | S | a bond | T3f | OH |
| 257 | N | NMe | Q1i | a bond | Me | a bond | NH | S | a bond | T3g | OH |
| 258 | N | NMe | Q1i | a bond | Me | a bond | NH | S | a bond | T3h | OH |
| 259 | N | NMe | Q1i | a bond | Me | a bond | NH | S | a bond | T3i | OH |
| 260 | N | NMe | Q1i | a bond | Me | a bond | NH | S | a bond | T3j | OH |
| 261 | N | NMe | Q1i | a bond | Me | a bond | NH | O | NH | T3a | OH |
| 262 | N | NMe | Q1i | a bond | Me | a bond | NH | O | NH | T3b | OH |
| 263 | N | NMe | Q1i | a bond | Me | a bond | NH | O | NH | T3c | OH |
| 264 | N | NMe | Q1i | a bond | Me | a bond | NH | O | NH | T3d | OH |
| 265 | N | NMe | Q1i | a bond | Me | a bond | NH | O | NH | T3e | OH |
| 266 | N | NMe | Q1i | a bond | Me | a bond | NH | O | NH | T3f | OH |
| 267 | N | NMe | Q1i | a bond | Me | a bond | NH | O | NH | T3g | OH |
| 268 | N | NMe | Q1i | a bond | Me | a bond | NH | O | NH | T3h | OH |
| 269 | N | NMe | Q1i | a bond | Me | a bond | NH | O | NH | T3i | OH |
| 270 | N | NMe | Q1i | a bond | Me | a bond | NH | O | NH | T3j | OH |
| 271 | N | NMe | Q1i | a bond | Me | a bond | NH | O | a bond | T3a | OH |
| 272 | N | NMe | Q1i | a bond | Me | a bond | NH | O | a bond | T3b | OH |
| 273 | N | NMe | Q1i | a bond | Me | a bond | NH | O | a bond | T3c | OH |
| 274 | N | NMe | Q1i | a bond | Me | a bond | NH | O | a bond | T3d | OH |
| 275 | N | NMe | Q1i | a bond | Me | a bond | NH | O | a bond | T3e | OH |
| 276 | N | NMe | Q1i | a bond | Me | a bond | NH | O | a bond | T3f | OH |
| 277 | N | NMe | Q1i | a bond | Me | a bond | NH | O | a bond | T3g | OH |
| 278 | N | NMe | Q1i | a bond | Me | a bond | NH | O | a bond | T3h | OH |
| 279 | N | NMe | Q1i | a bond | Me | a bond | NH | O | a bond | T3i | OH |
| 280 | N | NMe | Q1i | a bond | Me | a bond | NH | O | a bond | T3j | OH |
| 281 | N | NMe | Q1i | a bond | H | a bond | NH | S | NH | T3a | OH |
| 282 | N | NMe | Q1i | a bond | H | a bond | NH | S | NH | T3b | OH |
| 283 | N | NMe | Q1i | a bond | H | a bond | NH | S | NH | T3c | OH |
| 284 | N | NMe | Q1i | a bond | H | a bond | NH | S | NH | T3d | OH |
| 285 | N | NMe | Q1i | a bond | H | a bond | NH | S | NH | T3e | OH |
| 286 | N | NMe | Q1i | a bond | H | a bond | NH | S | NH | T3f | OH |
| 287 | N | NMe | Q1i | a bond | H | a bond | NH | S | NH | T3g | OH |
| 288 | N | NMe | Q1i | a bond | H | a bond | NH | S | NH | T3h | OH |
| 289 | N | NMe | Q1i | a bond | H | a bond | NH | S | NH | T3i | OH |
| 290 | N | NMe | Q1i | a bond | H | a bond | NH | S | NH | T3j | OH |
| 291 | N | NMe | Q1i | a bond | H | a bond | NH | S | a bond | T3a | OH |
| 292 | N | NMe | Q1i | a bond | H | a bond | NH | S | a bond | T3b | OH |
| 293 | N | NMe | Q1i | a bond | H | a bond | NH | S | a bond | T3c | OH |
| 294 | N | NMe | Q1i | a bond | H | a bond | NH | S | a bond | T3d | OH |
| 295 | N | NMe | Q1i | a bond | H | a bond | NH | S | a bond | T3e | OH |
| 296 | N | NMe | Q1i | a bond | H | a bond | NH | S | a bond | T3f | OH |
| 297 | N | NMe | Q1i | a bond | H | a bond | NH | S | a bond | T3g | OH |
| 298 | N | NMe | Q1i | a bond | H | a bond | NH | S | a bond | T3h | OH |
| 299 | N | NMe | Q1i | a bond | H | a bond | NH | S | a bond | T3i | OH |
| 300 | N | NMe | Q1i | a bond | H | a bond | NH | S | a bond | T3j | OH |
| 301 | N | NMe | Q1i | a bond | H | a bond | NH | O | NH | T3a | OH |
| 302 | N | NMe | Q1i | a bond | H | a bond | NH | O | NH | T3b | OH |
| 303 | N | NMe | Q1i | a bond | H | a bond | NH | O | NH | T3c | OH |
| 304 | N | NMe | Q1i | a bond | H | a bond | NH | O | NH | T3d | OH |
| 305 | N | NMe | Q1i | a bond | H | a bond | NH | O | NH | T3e | OH |
| 306 | N | NMe | Q1i | a bond | H | a bond | NH | O | NH | T3f | OH |
| 307 | N | NMe | Q1i | a bond | H | a bond | NH | O | NH | T3g | OH |
| 308 | N | NMe | Q1i | a bond | H | a bond | NH | O | NH | T3h | OH |
| 309 | N | NMe | Q1i | a bond | H | a bond | NH | O | NH | T3i | OH |
| 310 | N | NMe | Q1i | a bond | H | a bond | NH | O | NH | T3j | OH |
| 311 | N | NMe | Q1i | a bond | H | a bond | NH | O | a bond | T3a | OH |
| 312 | N | NMe | Q1i | a bond | H | a bond | NH | O | a bond | T3b | OH |
| 313 | N | NMe | Q1i | a bond | H | a bond | NH | O | a bond | T3c | OH |
| 314 | N | NMe | Q1i | a bond | H | a bond | NH | O | a bond | T3d | OH |
| 315 | N | NMe | Q1i | a bond | H | a bond | NH | O | a bond | T3e | OH |
| 316 | N | NMe | Q1i | a bond | H | a bond | NH | O | a bond | T3f | OH |
| 317 | N | NMe | Q1i | a bond | H | a bond | NH | O | a bond | T3g | OH |
| 318 | N | NMe | Q1i | a bond | H | a bond | NH | O | a bond | T3h | OH |
| 319 | N | NMe | Q1i | a bond | H | a bond | NH | O | a bond | T3i | OH |
| 320 | N | NMe | Q1i | a bond | H | a bond | NH | O | a bond | T3j | OH |
| 321 | N | NMe | Q1j | a bond | Me | a bond | NH | S | NH | T3a | OH |
| 322 | N | NMe | Q1j | a bond | Me | a bond | NH | S | NH | T3b | OH |
| 323 | N | NMe | Q1j | a bond | Me | a bond | NH | S | NH | T3c | OH |
| 324 | N | NMe | Q1j | a bond | Me | a bond | NH | S | NH | T3d | OH |
| 325 | N | NMe | Q1j | a bond | Me | a bond | NH | S | NH | T3e | OH |
| 326 | N | NMe | Q1j | a bond | Me | a bond | NH | S | NH | T3f | OH |
| 327 | N | NMe | Q1j | a bond | Me | a bond | NH | S | NH | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 328 | N | NMe | Q1j | a bond | Me | a bond | NH | S | NH | T3h | OH |
| 329 | N | NMe | Q1j | a bond | Me | a bond | NH | S | NH | T3i | OH |
| 330 | N | NMe | Q1j | a bond | Me | a bond | NH | S | NH | T3j | OH |
| 331 | N | NMe | Q1j | a bond | Me | a bond | NH | S | a bond | T3a | OH |
| 332 | N | NMe | Q1j | a bond | Me | a bond | NH | S | a bond | T3b | OH |
| 333 | N | NMe | Q1j | a bond | Me | a bond | NH | S | a bond | T3c | OH |
| 334 | N | NMe | Q1j | a bond | Me | a bond | NH | S | a bond | T3d | OH |
| 335 | N | NMe | Q1j | a bond | Me | a bond | NH | S | a bond | T3e | OH |
| 336 | N | NMe | Q1j | a bond | Me | a bond | NH | S | a bond | T3f | OH |
| 337 | N | NMe | Q1j | a bond | Me | a bond | NH | S | a bond | T3g | OH |
| 338 | N | NMe | Q1j | a bond | Me | a bond | NH | S | a bond | T3h | OH |
| 339 | N | NMe | Q1j | a bond | Me | a bond | NH | S | a bond | T3i | OH |
| 340 | N | NMe | Q1j | a bond | Me | a bond | NH | S | a bond | T3j | OH |
| 341 | N | NMe | Q1j | a bond | Me | a bond | NH | O | NH | T3a | OH |
| 342 | N | NMe | Q1j | a bond | Me | a bond | NH | O | NH | T3b | OH |
| 343 | N | NMe | Q1j | a bond | Me | a bond | NH | O | NH | T3c | OH |
| 344 | N | NMe | Q1j | a bond | Me | a bond | NH | O | NH | T3d | OH |
| 345 | N | NMe | Q1j | a bond | Me | a bond | NH | O | NH | T3e | OH |
| 346 | N | NMe | Q1j | a bond | Me | a bond | NH | O | NH | T3f | OH |
| 347 | N | NMe | Q1j | a bond | Me | a bond | NH | O | NH | T3g | OH |
| 348 | N | NMe | Q1j | a bond | Me | a bond | NH | O | NH | T3h | OH |
| 349 | N | NMe | Q1j | a bond | Me | a bond | NH | O | NH | T3i | OH |
| 350 | N | NMe | Q1j | a bond | Me | a bond | NH | O | NH | T3j | OH |
| 351 | N | NMe | Q1j | a bond | Me | a bond | NH | O | a bond | T3a | OH |
| 352 | N | NMe | Q1j | a bond | Me | a bond | NH | O | a bond | T3b | OH |
| 353 | N | NMe | Q1j | a bond | Me | a bond | NH | O | a bond | T3c | OH |
| 354 | N | NMe | Q1j | a bond | Me | a bond | NH | O | a bond | T3d | OH |
| 355 | N | NMe | Q1j | a bond | Me | a bond | NH | O | a bond | T3e | OH |
| 356 | N | NMe | Q1j | a bond | Me | a bond | NH | O | a bond | T3f | OH |
| 357 | N | NMe | Q1j | a bond | Me | a bond | NH | O | a bond | T3g | OH |
| 358 | N | NMe | Q1j | a bond | Me | a bond | NH | O | a bond | T3h | OH |
| 359 | N | NMe | Q1j | a bond | Me | a bond | NH | O | a bond | T3i | OH |
| 360 | N | NMe | Q1j | a bond | Me | a bond | NH | O | a bond | T3j | OH |
| 361 | N | NMe | Q1j | a bond | H | a bond | NH | S | NH | T3a | OH |
| 362 | N | NMe | Q1j | a bond | H | a bond | NH | S | NH | T3b | OH |
| 363 | N | NMe | Q1j | a bond | H | a bond | NH | S | NH | T3c | OH |
| 364 | N | NMe | Q1j | a bond | H | a bond | NH | S | NH | T3d | OH |
| 365 | N | NMe | Q1j | a bond | H | a bond | NH | S | NH | T3e | OH |
| 366 | N | NMe | Q1j | a bond | H | a bond | NH | S | NH | T3f | OH |
| 367 | N | NMe | Q1j | a bond | H | a bond | NH | S | NH | T3g | OH |
| 368 | N | NMe | Q1j | a bond | H | a bond | NH | S | NH | T3h | OH |
| 369 | N | NMe | Q1j | a bond | H | a bond | NH | S | NH | T3i | OH |
| 370 | N | NMe | Q1j | a bond | H | a bond | NH | S | NH | T3j | OH |
| 371 | N | NMe | Q1j | a bond | H | a bond | NH | S | a bond | T3a | OH |
| 372 | N | NMe | Q1j | a bond | H | a bond | NH | S | a bond | T3b | OH |
| 373 | N | NMe | Q1j | a bond | H | a bond | NH | S | a bond | T3c | OH |
| 374 | N | NMe | Q1j | a bond | H | a bond | NH | S | a bond | T3d | OH |
| 375 | N | NMe | Q1j | a bond | H | a bond | NH | S | a bond | T3e | OH |
| 376 | N | NMe | Q1j | a bond | H | a bond | NH | S | a bond | T3f | OH |
| 377 | N | NMe | Q1j | a bond | H | a bond | NH | S | a bond | T3g | OH |
| 378 | N | NMe | Q1j | a bond | H | a bond | NH | S | a bond | T3h | OH |
| 379 | N | NMe | Q1j | a bond | H | a bond | NH | S | a bond | T3i | OH |
| 380 | N | NMe | Q1j | a bond | H | a bond | NH | S | a bond | T3j | OH |
| 381 | N | NMe | Q1j | a bond | H | a bond | NH | O | NH | T3a | OH |
| 382 | N | NMe | Q1j | a bond | H | a bond | NH | O | NH | T3b | OH |
| 383 | N | NMe | Q1j | a bond | H | a bond | NH | O | NH | T3c | OH |
| 384 | N | NMe | Q1j | a bond | H | a bond | NH | O | NH | T3d | OH |
| 385 | N | NMe | Q1j | a bond | H | a bond | NH | O | NH | T3e | OH |
| 386 | N | NMe | Q1j | a bond | H | a bond | NH | O | NH | T3f | OH |
| 387 | N | NMe | Q1j | a bond | H | a bond | NH | O | NH | T3g | OH |
| 388 | N | NMe | Q1j | a bond | H | a bond | NH | O | NH | T3h | OH |
| 389 | N | NMe | Q1j | a bond | H | a bond | NH | O | NH | T3i | OH |
| 390 | N | NMe | Q1j | a bond | H | a bond | NH | O | NH | T3j | OH |
| 391 | N | NMe | Q1j | a bond | H | a bond | NH | O | a bond | T3a | OH |
| 392 | N | NMe | Q1j | a bond | H | a bond | NH | O | a bond | T3b | OH |
| 393 | N | NMe | Q1j | a bond | H | a bond | NH | O | a bond | T3c | OH |
| 394 | N | NMe | Q1j | a bond | H | a bond | NH | O | a bond | T3d | OH |
| 395 | N | NMe | Q1j | a bond | H | a bond | NH | O | a bond | T3e | OH |
| 396 | N | NMe | Q1j | a bond | H | a bond | NH | O | a bond | T3f | OH |
| 397 | N | NMe | Q1j | a bond | H | a bond | NH | O | a bond | T3g | OH |
| 398 | N | NMe | Q1j | a bond | H | a bond | NH | O | a bond | T3h | OH |
| 399 | N | NMe | Q1j | a bond | H | a bond | NH | O | a bond | T3i | OH |
| 400 | N | NMe | Q1j | a bond | H | a bond | NH | O | a bond | T3j | OH |
| 401 | N | S | Q1a | a bond | Me | a bond | NH | S | NH | T3a | OH |
| 402 | N | S | Q1a | a bond | Me | a bond | NH | S | NH | T3b | OH |
| 403 | N | S | Q1a | a bond | Me | a bond | NH | S | NH | T3c | OH |
| 404 | N | S | Q1a | a bond | Me | a bond | NH | S | NH | T3d | OH |
| 405 | N | S | Q1a | a bond | Me | a bond | NH | S | NH | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 406 | N | S | Q1a | a bond | Me | a bond | NH | S | NH | T3f | OH |
| 407 | N | S | Q1a | a bond | Me | a bond | NH | S | NH | T3g | OH |
| 408 | N | S | Q1a | a bond | Me | a bond | NH | S | NH | T3h | OH |
| 409 | N | S | Q1a | a bond | Me | a bond | NH | S | NH | T3i | OH |
| 410 | N | S | Q1a | a bond | Me | a bond | NH | S | NH | T3j | OH |
| 411 | N | S | Q1a | a bond | Me | a bond | NH | S | a bond | T3a | OH |
| 412 | N | S | Q1a | a bond | Me | a bond | NH | S | a bond | T3b | OH |
| 413 | N | S | Q1a | a bond | Me | a bond | NH | S | a bond | T3c | OH |
| 414 | N | S | Q1a | a bond | Me | a bond | NH | S | a bond | T3d | OH |
| 415 | N | S | Q1a | a bond | Me | a bond | NH | S | a bond | T3e | OH |
| 416 | N | S | Q1a | a bond | Me | a bond | NH | S | a bond | T3f | OH |
| 417 | N | S | Q1a | a bond | Me | a bond | NH | S | a bond | T3g | OH |
| 418 | N | S | Q1a | a bond | Me | a bond | NH | S | a bond | T3h | OH |
| 419 | N | S | Q1a | a bond | Me | a bond | NH | S | a bond | T3i | OH |
| 420 | N | S | Q1a | a bond | Me | a bond | NH | S | a bond | T3j | OH |
| 421 | N | S | Q1a | a bond | Me | a bond | NH | O | NH | T3a | OH |
| 422 | N | S | Q1a | a bond | Me | a bond | NH | O | NH | T3b | OH |
| 423 | N | S | Q1a | a bond | Me | a bond | NH | O | NH | T3c | OH |
| 424 | N | S | Q1a | a bond | Me | a bond | NH | O | NH | T3d | OH |
| 425 | N | S | Q1a | a bond | Me | a bond | NH | O | NH | T3e | OH |
| 426 | N | S | Q1a | a bond | Me | a bond | NH | O | NH | T3f | OH |
| 427 | N | S | Q1a | a bond | Me | a bond | NH | O | NH | T3g | OH |
| 428 | N | S | Q1a | a bond | Me | a bond | NH | O | NH | T3h | OH |
| 429 | N | S | Q1a | a bond | Me | a bond | NH | O | NH | T3i | OH |
| 430 | N | S | Q1a | a bond | Me | a bond | NH | O | NH | T3j | OH |
| 431 | N | S | Q1a | a bond | Me | a bond | NH | O | a bond | T3a | OH |
| 432 | N | S | Q1a | a bond | Me | a bond | NH | O | a bond | T3b | OH |
| 433 | N | S | Q1a | a bond | Me | a bond | NH | O | a bond | T3c | OH |
| 434 | N | S | Q1a | a bond | Me | a bond | NH | O | a bond | T3d | OH |
| 435 | N | S | Q1a | a bond | Me | a bond | NH | O | a bond | T3e | OH |
| 436 | N | S | Q1a | a bond | Me | a bond | NH | O | a bond | T3f | OH |
| 437 | N | S | Q1a | a bond | Me | a bond | NH | O | a bond | T3g | OH |
| 438 | N | S | Q1a | a bond | Me | a bond | NH | O | a bond | T3h | OH |
| 439 | N | S | Q1a | a bond | Me | a bond | NH | O | a bond | T3i | OH |
| 440 | N | S | Q1a | a bond | Me | a bond | NH | O | a bond | T3j | OH |
| 441 | N | S | Q1a | a bond | H | a bond | NH | S | NH | T3a | OH |
| 442 | N | S | Q1a | a bond | H | a bond | NH | S | NH | T3b | OH |
| 443 | N | S | Q1a | a bond | H | a bond | NH | S | NH | T3c | OH |
| 444 | N | S | Q1a | a bond | H | a bond | NH | S | NH | T3d | OH |
| 445 | N | S | Q1a | a bond | H | a bond | NH | S | NH | T3e | OH |
| 446 | N | S | Q1a | a bond | H | a bond | NH | S | NH | T3f | OH |
| 447 | N | S | Q1a | a bond | H | a bond | NH | S | NH | T3g | OH |
| 448 | N | S | Q1a | a bond | H | a bond | NH | S | NH | T3h | OH |
| 449 | N | S | Q1a | a bond | H | a bond | NH | S | NH | T3i | OH |
| 450 | N | S | Q1a | a bond | H | a bond | NH | S | NH | T3j | OH |
| 451 | N | S | Q1a | a bond | H | a bond | NH | S | a bond | T3a | OH |
| 452 | N | S | Q1a | a bond | H | a bond | NH | S | a bond | T3b | OH |
| 453 | N | S | Q1a | a bond | H | a bond | NH | S | a bond | T3c | OH |
| 454 | N | S | Q1a | a bond | H | a bond | NH | S | a bond | T3d | OH |
| 455 | N | S | Q1a | a bond | H | a bond | NH | S | a bond | T3e | OH |
| 456 | N | S | Q1a | a bond | H | a bond | NH | S | a bond | T3f | OH |
| 457 | N | S | Q1a | a bond | H | a bond | NH | S | a bond | T3g | OH |
| 458 | N | S | Q1a | a bond | H | a bond | NH | S | a bond | T3h | OH |
| 459 | N | S | Q1a | a bond | H | a bond | NH | S | a bond | T3i | OH |
| 460 | N | S | Q1a | a bond | H | a bond | NH | S | a bond | T3j | OH |
| 461 | N | S | Q1a | a bond | H | a bond | NH | O | NH | T3a | OH |
| 462 | N | S | Q1a | a bond | H | a bond | NH | O | NH | T3b | OH |
| 463 | N | S | Q1a | a bond | H | a bond | NH | O | NH | T3c | OH |
| 464 | N | S | Q1a | a bond | H | a bond | NH | O | NH | T3d | OH |
| 465 | N | S | Q1a | a bond | H | a bond | NH | O | NH | T3e | OH |
| 466 | N | S | Q1a | a bond | H | a bond | NH | O | NH | T3f | OH |
| 467 | N | S | Q1a | a bond | H | a bond | NH | O | NH | T3g | OH |
| 468 | N | S | Q1a | a bond | H | a bond | NH | O | NH | T3h | OH |
| 469 | N | S | Q1a | a bond | H | a bond | NH | O | NH | T3i | OH |
| 470 | N | S | Q1a | a bond | H | a bond | NH | O | NH | T3j | OH |
| 471 | N | S | Q1a | a bond | H | a bond | NH | O | a bond | T3a | OH |
| 472 | N | S | Q1a | a bond | H | a bond | NH | O | a bond | T3b | OH |
| 473 | N | S | Q1a | a bond | H | a bond | NH | O | a bond | T3c | OH |
| 474 | N | S | Q1a | a bond | H | a bond | NH | O | a bond | T3d | OH |
| 475 | N | S | Q1a | a bond | H | a bond | NH | O | a bond | T3e | OH |
| 476 | N | S | Q1a | a bond | H | a bond | NH | O | a bond | T3f | OH |
| 477 | N | S | Q1a | a bond | H | a bond | NH | O | a bond | T3g | OH |
| 478 | N | S | Q1a | a bond | H | a bond | NH | O | a bond | T3h | OH |
| 479 | N | S | Q1a | a bond | H | a bond | NH | O | a bond | T3i | OH |
| 480 | N | S | Q1a | a bond | H | a bond | NH | O | a bond | T3j | OH |
| 481 | N | S | Q1b | a bond | Me | a bond | NH | S | NH | T3a | OH |
| 482 | N | S | Q1b | a bond | Me | a bond | NH | S | NH | T3b | OH |
| 483 | N | S | Q1b | a bond | Me | a bond | NH | S | NH | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 484 | N | S | Q1b | a bond | Me | a bond | NH | S | NH | T3d | OH |
| 485 | N | S | Q1b | a bond | Me | a bond | NH | S | NH | T3e | OH |
| 486 | N | S | Q1b | a bond | Me | a bond | NH | S | NH | T3f | OH |
| 487 | N | S | Q1b | a bond | Me | a bond | NH | S | NH | T3g | OH |
| 488 | N | S | Q1b | a bond | Me | a bond | NH | S | NH | T3h | OH |
| 489 | N | S | Q1b | a bond | Me | a bond | NH | S | NH | T3i | OH |
| 490 | N | S | Q1b | a bond | Me | a bond | NH | S | NH | T3j | OH |
| 491 | N | S | Q1b | a bond | Me | a bond | NH | S | a bond | T3a | OH |
| 492 | N | S | Q1b | a bond | Me | a bond | NH | S | a bond | T3b | OH |
| 493 | N | S | Q1b | a bond | Me | a bond | NH | S | a bond | T3c | OH |
| 494 | N | S | Q1b | a bond | Me | a bond | NH | S | a bond | T3d | OH |
| 495 | N | S | Q1b | a bond | Me | a bond | NH | S | a bond | T3e | OH |
| 496 | N | S | Q1b | a bond | Me | a bond | NH | S | a bond | T3f | OH |
| 497 | N | S | Q1b | a bond | Me | a bond | NH | S | a bond | T3g | OH |
| 498 | N | S | Q1b | a bond | Me | a bond | NH | S | a bond | T3h | OH |
| 499 | N | S | Q1b | a bond | Me | a bond | NH | S | a bond | T3i | OH |
| 500 | N | S | Q1b | a bond | Me | a bond | NH | S | a bond | T3j | OH |
| 501 | N | S | Q1b | a bond | Me | a bond | NH | O | NH | T3a | OH |
| 502 | N | S | Q1b | a bond | Me | a bond | NH | O | NH | T3b | OH |
| 503 | N | S | Q1b | a bond | Me | a bond | NH | O | NH | T3c | OH |
| 504 | N | S | Q1b | a bond | Me | a bond | NH | O | NH | T3d | OH |
| 505 | N | S | Q1b | a bond | Me | a bond | NH | O | NH | T3e | OH |
| 506 | N | S | Q1b | a bond | Me | a bond | NH | O | NH | T3f | OH |
| 507 | N | S | Q1b | a bond | Me | a bond | NH | O | NH | T3g | OH |
| 508 | N | S | Q1b | a bond | Me | a bond | NH | O | NH | T3h | OH |
| 509 | N | S | Q1b | a bond | Me | a bond | NH | O | NH | T3i | OH |
| 510 | N | S | Q1b | a bond | Me | a bond | NH | O | NH | T3j | OH |
| 511 | N | S | Q1b | a bond | Me | a bond | NH | O | a bond | T3a | OH |
| 512 | N | S | Q1b | a bond | Me | a bond | NH | O | a bond | T3b | OH |
| 513 | N | S | Q1b | a bond | Me | a bond | NH | O | a bond | T3c | OH |
| 514 | N | S | Q1b | a bond | Me | a bond | NH | O | a bond | T3d | OH |
| 515 | N | S | Q1b | a bond | Me | a bond | NH | O | a bond | T3e | OH |
| 516 | N | S | Q1b | a bond | Me | a bond | NH | O | a bond | T3f | OH |
| 517 | N | S | Q1b | a bond | Me | a bond | NH | O | a bond | T3g | OH |
| 518 | N | S | Q1b | a bond | Me | a bond | NH | O | a bond | T3h | OH |
| 519 | N | S | Q1b | a bond | Me | a bond | NH | O | a bond | T3i | OH |
| 520 | N | S | Q1b | a bond | Me | a bond | NH | O | a bond | T3j | OH |
| 521 | N | S | Q1b | a bond | H | a bond | NH | S | NH | T3a | OH |
| 522 | N | S | Q1b | a bond | H | a bond | NH | S | NH | T3b | OH |
| 523 | N | S | Q1b | a bond | H | a bond | NH | S | NH | T3c | OH |
| 524 | N | S | Q1b | a bond | H | a bond | NH | S | NH | T3d | OH |
| 525 | N | S | Q1b | a bond | H | a bond | NH | S | NH | T3e | OH |
| 526 | N | S | Q1b | a bond | H | a bond | NH | S | NH | T3f | OH |
| 527 | N | S | Q1b | a bond | H | a bond | NH | S | NH | T3g | OH |
| 528 | N | S | Q1b | a bond | H | a bond | NH | S | NH | T3h | OH |
| 529 | N | S | Q1b | a bond | H | a bond | NH | S | NH | T3i | OH |
| 530 | N | S | Q1b | a bond | H | a bond | NH | S | NH | T3j | OH |
| 531 | N | S | Q1b | a bond | H | a bond | NH | S | a bond | T3a | OH |
| 532 | N | S | Q1b | a bond | H | a bond | NH | S | a bond | T3b | OH |
| 533 | N | S | Q1b | a bond | H | a bond | NH | S | a bond | T3c | OH |
| 534 | N | S | Q1b | a bond | H | a bond | NH | S | a bond | T3d | OH |
| 535 | N | S | Q1b | a bond | H | a bond | NH | S | a bond | T3e | OH |
| 536 | N | S | Q1b | a bond | H | a bond | NH | S | a bond | T3f | OH |
| 537 | N | S | Q1b | a bond | H | a bond | NH | S | a bond | T3g | OH |
| 538 | N | S | Q1b | a bond | H | a bond | NH | S | a bond | T3h | OH |
| 539 | N | S | Q1b | a bond | H | a bond | NH | S | a bond | T3i | OH |
| 540 | N | S | Q1b | a bond | H | a bond | NH | S | a bond | T3j | OH |
| 541 | N | S | Q1b | a bond | H | a bond | NH | O | NH | T3a | OH |
| 542 | N | S | Q1b | a bond | H | a bond | NH | O | NH | T3b | OH |
| 543 | N | S | Q1b | a bond | H | a bond | NH | O | NH | T3c | OH |
| 544 | N | S | Q1b | a bond | H | a bond | NH | O | NH | T3d | OH |
| 545 | N | S | Q1b | a bond | H | a bond | NH | O | NH | T3e | OH |
| 546 | N | S | Q1b | a bond | H | a bond | NH | O | NH | T3f | OH |
| 547 | N | S | Q1b | a bond | H | a bond | NH | O | NH | T3g | OH |
| 548 | N | S | Q1b | a bond | H | a bond | NH | O | NH | T3h | OH |
| 549 | N | S | Q1b | a bond | H | a bond | NH | O | NH | T3i | OH |
| 550 | N | S | Q1b | a bond | H | a bond | NH | O | NH | T3j | OH |
| 551 | N | S | Q1b | a bond | H | a bond | NH | O | a bond | T3a | OH |
| 552 | N | S | Q1b | a bond | H | a bond | NH | O | a bond | T3b | OH |
| 553 | N | S | Q1b | a bond | H | a bond | NH | O | a bond | T3c | OH |
| 554 | N | S | Q1b | a bond | H | a bond | NH | O | a bond | T3d | OH |
| 555 | N | S | Q1b | a bond | H | a bond | NH | O | a bond | T3e | OH |
| 556 | N | S | Q1b | a bond | H | a bond | NH | O | a bond | T3f | OH |
| 557 | N | S | Q1b | a bond | H | a bond | NH | O | a bond | T3g | OH |
| 558 | N | S | Q1b | a bond | H | a bond | NH | O | a bond | T3h | OH |
| 559 | N | S | Q1b | a bond | H | a bond | NH | O | a bond | T3i | OH |
| 560 | N | S | Q1b | a bond | H | a bond | NH | O | a bond | T3j | OH |
| 561 | N | S | Q1c | a bond | Me | a bond | NH | S | NH | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 562 | N | S | Q1c | a bond | Me | a bond | NH | S | NH | T3b | OH |
| 563 | N | S | Q1c | a bond | Me | a bond | NH | S | NH | T3c | OH |
| 564 | N | S | Q1c | a bond | Me | a bond | NH | S | NH | T3d | OH |
| 565 | N | S | Q1c | a bond | Me | a bond | NH | S | NH | T3e | OH |
| 566 | N | S | Q1c | a bond | Me | a bond | NH | S | NH | T3f | OH |
| 567 | N | S | Q1c | a bond | Me | a bond | NH | S | NH | T3g | OH |
| 568 | N | S | Q1c | a bond | Me | a bond | NH | S | NH | T3h | OH |
| 569 | N | S | Q1c | a bond | Me | a bond | NH | S | NH | T3i | OH |
| 570 | N | S | Q1c | a bond | Me | a bond | NH | S | NH | T3j | OH |
| 571 | N | S | Q1c | a bond | Me | a bond | NH | S | a bond | T3a | OH |
| 572 | N | S | Q1c | a bond | Me | a bond | NH | S | a bond | T3b | OH |
| 573 | N | S | Q1c | a bond | Me | a bond | NH | S | a bond | T3c | OH |
| 574 | N | S | Q1c | a bond | Me | a bond | NH | S | a bond | T3d | OH |
| 575 | N | S | Q1c | a bond | Me | a bond | NH | S | a bond | T3e | OH |
| 576 | N | S | Q1c | a bond | Me | a bond | NH | S | a bond | T3f | OH |
| 577 | N | S | Q1c | a bond | Me | a bond | NH | S | a bond | T3g | OH |
| 578 | N | S | Q1c | a bond | Me | a bond | NH | S | a bond | T3h | OH |
| 579 | N | S | Q1c | a bond | Me | a bond | NH | S | a bond | T3i | OH |
| 580 | N | S | Q1c | a bond | Me | a bond | NH | S | a bond | T3j | OH |
| 581 | N | S | Q1c | a bond | Me | a bond | NH | O | NH | T3a | OH |
| 582 | N | S | Q1c | a bond | Me | a bond | NH | O | NH | T3b | OH |
| 583 | N | S | Q1c | a bond | Me | a bond | NH | O | NH | T3c | OH |
| 584 | N | S | Q1c | a bond | Me | a bond | NH | O | NH | T3d | OH |
| 585 | N | S | Q1c | a bond | Me | a bond | NH | O | NH | T3e | OH |
| 586 | N | S | Q1c | a bond | Me | a bond | NH | O | NH | T3f | OH |
| 587 | N | S | Q1c | a bond | Me | a bond | NH | O | NH | T3g | OH |
| 588 | N | S | Q1c | a bond | Me | a bond | NH | O | NH | T3h | OH |
| 589 | N | S | Q1c | a bond | Me | a bond | NH | O | NH | T3i | OH |
| 590 | N | S | Q1c | a bond | Me | a bond | NH | O | NH | T3j | OH |
| 591 | N | S | Q1c | a bond | Me | a bond | NH | O | a bond | T3a | OH |
| 592 | N | S | Q1c | a bond | Me | a bond | NH | O | a bond | T3b | OH |
| 593 | N | S | Q1c | a bond | Me | a bond | NH | O | a bond | T3c | OH |
| 594 | N | S | Q1c | a bond | Me | a bond | NH | O | a bond | T3d | OH |
| 595 | N | S | Q1c | a bond | Me | a bond | NH | O | a bond | T3e | OH |
| 596 | N | S | Q1c | a bond | Me | a bond | NH | O | a bond | T3f | OH |
| 597 | N | S | Q1c | a bond | Me | a bond | NH | O | a bond | T3g | OH |
| 598 | N | S | Q1c | a bond | Me | a bond | NH | O | a bond | T3h | OH |
| 599 | N | S | Q1c | a bond | Me | a bond | NH | O | a bond | T3i | OH |
| 600 | N | S | Q1c | a bond | Me | a bond | NH | O | a bond | T3j | OH |
| 601 | N | S | Q1c | a bond | H | a bond | NH | S | NH | T3a | OH |
| 602 | N | S | Q1c | a bond | H | a bond | NH | S | NH | T3b | OH |
| 603 | N | S | Q1c | a bond | H | a bond | NH | S | NH | T3c | OH |
| 604 | N | S | Q1c | a bond | H | a bond | NH | S | NH | T3d | OH |
| 605 | N | S | Q1c | a bond | H | a bond | NH | S | NH | T3e | OH |
| 606 | N | S | Q1c | a bond | H | a bond | NH | S | NH | T3f | OH |
| 607 | N | S | Q1c | a bond | H | a bond | NH | S | NH | T3g | OH |
| 608 | N | S | Q1c | a bond | H | a bond | NH | S | NH | T3h | OH |
| 609 | N | S | Q1c | a bond | H | a bond | NH | S | NH | T3i | OH |
| 610 | N | S | Q1c | a bond | H | a bond | NH | S | NH | T3j | OH |
| 611 | N | S | Q1c | a bond | H | a bond | NH | S | a bond | T3a | OH |
| 612 | N | S | Q1c | a bond | H | a bond | NH | S | a bond | T3b | OH |
| 613 | N | S | Q1c | a bond | H | a bond | NH | S | a bond | T3c | OH |
| 614 | N | S | Q1c | a bond | H | a bond | NH | S | a bond | T3d | OH |
| 615 | N | S | Q1c | a bond | H | a bond | NH | S | a bond | T3e | OH |
| 616 | N | S | Q1c | a bond | H | a bond | NH | S | a bond | T3f | OH |
| 617 | N | S | Q1c | a bond | H | a bond | NH | S | a bond | T3g | OH |
| 618 | N | S | Q1c | a bond | H | a bond | NH | S | a bond | T3h | OH |
| 619 | N | S | Q1c | a bond | H | a bond | NH | S | a bond | T3i | OH |
| 620 | N | S | Q1c | a bond | H | a bond | NH | S | a bond | T3j | OH |
| 621 | N | S | Q1c | a bond | H | a bond | NH | O | NH | T3a | OH |
| 622 | N | S | Q1c | a bond | H | a bond | NH | O | NH | T3b | OH |
| 623 | N | S | Q1c | a bond | H | a bond | NH | O | NH | T3c | OH |
| 624 | N | S | Q1c | a bond | H | a bond | NH | O | NH | T3d | OH |
| 625 | N | S | Q1c | a bond | H | a bond | NH | O | NH | T3e | OH |
| 626 | N | S | Q1c | a bond | H | a bond | NH | O | NH | T3f | OH |
| 627 | N | S | Q1c | a bond | H | a bond | NH | O | NH | T3g | OH |
| 628 | N | S | Q1c | a bond | H | a bond | NH | O | NH | T3h | OH |
| 629 | N | S | Q1c | a bond | H | a bond | NH | O | NH | T3i | OH |
| 630 | N | S | Q1c | a bond | H | a bond | NH | O | NH | T3j | OH |
| 631 | N | S | Q1c | a bond | H | a bond | NH | O | a bond | T3a | OH |
| 632 | N | S | Q1c | a bond | H | a bond | NH | O | a bond | T3b | OH |
| 633 | N | S | Q1c | a bond | H | a bond | NH | O | a bond | T3c | OH |
| 634 | N | S | Q1c | a bond | H | a bond | NH | O | a bond | T3d | OH |
| 635 | N | S | Q1c | a bond | H | a bond | NH | O | a bond | T3e | OH |
| 636 | N | S | Q1c | a bond | H | a bond | NH | O | a bond | T3f | OH |
| 637 | N | S | Q1c | a bond | H | a bond | NH | O | a bond | T3g | OH |
| 638 | N | S | Q1c | a bond | H | a bond | NH | O | a bond | T3h | OH |
| 639 | N | S | Q1c | a bond | H | a bond | NH | O | a bond | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 640 | N | S | Q1c | a bond | H | a bond | NH | O | a bond | T3j | OH |
| 641 | N | S | Q1i | a bond | Me | a bond | NH | S | NH | T3a | OH |
| 642 | N | S | Q1i | a bond | Me | a bond | NH | S | NH | T3b | OH |
| 643 | N | S | Q1i | a bond | Me | a bond | NH | S | NH | T3c | OH |
| 644 | N | S | Q1i | a bond | Me | a bond | NH | S | NH | T3d | OH |
| 645 | N | S | Q1i | a bond | Me | a bond | NH | S | NH | T3e | OH |
| 646 | N | S | Q1i | a bond | Me | a bond | NH | S | NH | T3f | OH |
| 647 | N | S | Q1i | a bond | Me | a bond | NH | S | NH | T3g | OH |
| 648 | N | S | Q1i | a bond | Me | a bond | NH | S | NH | T3h | OH |
| 649 | N | S | Q1i | a bond | Me | a bond | NH | S | NH | T3i | OH |
| 650 | N | S | Q1i | a bond | Me | a bond | NH | S | NH | T3j | OH |
| 651 | N | S | Q1i | a bond | Me | a bond | NH | S | a bond | T3a | OH |
| 652 | N | S | Q1i | a bond | Me | a bond | NH | S | a bond | T3b | OH |
| 653 | N | S | Q1i | a bond | Me | a bond | NH | S | a bond | T3c | OH |
| 654 | N | S | Q1i | a bond | Me | a bond | NH | S | a bond | T3d | OH |
| 655 | N | S | Q1i | a bond | Me | a bond | NH | S | a bond | T3e | OH |
| 656 | N | S | Q1i | a bond | Me | a bond | NH | S | a bond | T3f | OH |
| 657 | N | S | Q1i | a bond | Me | a bond | NH | S | a bond | T3g | OH |
| 658 | N | S | Q1i | a bond | Me | a bond | NH | S | a bond | T3h | OH |
| 659 | N | S | Q1i | a bond | Me | a bond | NH | S | a bond | T3i | OH |
| 660 | N | S | Q1i | a bond | Me | a bond | NH | S | a bond | T3j | OH |
| 661 | N | S | Q1i | a bond | Me | a bond | NH | O | NH | T3a | OH |
| 662 | N | S | Q1i | a bond | Me | a bond | NH | O | NH | T3b | OH |
| 663 | N | S | Q1i | a bond | Me | a bond | NH | O | NH | T3c | OH |
| 664 | N | S | Q1i | a bond | Me | a bond | NH | O | NH | T3d | OH |
| 665 | N | S | Q1i | a bond | Me | a bond | NH | O | NH | T3e | OH |
| 666 | N | S | Q1i | a bond | Me | a bond | NH | O | NH | T3f | OH |
| 667 | N | S | Q1i | a bond | Me | a bond | NH | O | NH | T3g | OH |
| 668 | N | S | Q1i | a bond | Me | a bond | NH | O | NH | T3h | OH |
| 669 | N | S | Q1i | a bond | Me | a bond | NH | O | NH | T3i | OH |
| 670 | N | S | Q1i | a bond | Me | a bond | NH | O | NH | T3j | OH |
| 671 | N | S | Q1i | a bond | Me | a bond | NH | O | a bond | T3a | OH |
| 672 | N | S | Q1i | a bond | Me | a bond | NH | O | a bond | T3b | OH |
| 673 | N | S | Q1i | a bond | Me | a bond | NH | O | a bond | T3c | OH |
| 674 | N | S | Q1i | a bond | Me | a bond | NH | O | a bond | T3d | OH |
| 675 | N | S | Q1i | a bond | Me | a bond | NH | O | a bond | T3e | OH |
| 676 | N | S | Q1i | a bond | Me | a bond | NH | O | a bond | T3f | OH |
| 677 | N | S | Q1i | a bond | Me | a bond | NH | O | a bond | T3g | OH |
| 678 | N | S | Q1i | a bond | Me | a bond | NH | O | a bond | T3h | OH |
| 679 | N | S | Q1i | a bond | Me | a bond | NH | O | a bond | T3i | OH |
| 680 | N | S | Q1i | a bond | Me | a bond | NH | O | a bond | T3j | OH |
| 681 | N | S | Q1i | a bond | H | a bond | NH | S | NH | T3a | OH |
| 682 | N | S | Q1i | a bond | H | a bond | NH | S | NH | T3b | OH |
| 683 | N | S | Q1i | a bond | H | a bond | NH | S | NH | T3c | OH |
| 684 | N | S | Q1i | a bond | H | a bond | NH | S | NH | T3d | OH |
| 685 | N | S | Q1i | a bond | H | a bond | NH | S | NH | T3e | OH |
| 686 | N | S | Q1i | a bond | H | a bond | NH | S | NH | T3f | OH |
| 687 | N | S | Q1i | a bond | H | a bond | NH | S | NH | T3g | OH |
| 688 | N | S | Q1i | a bond | H | a bond | NH | S | NH | T3h | OH |
| 689 | N | S | Q1i | a bond | H | a bond | NH | S | NH | T3i | OH |
| 690 | N | S | Q1i | a bond | H | a bond | NH | S | NH | T3j | OH |
| 691 | N | S | Q1i | a bond | H | a bond | NH | S | a bond | T3a | OH |
| 692 | N | S | Q1i | a bond | H | a bond | NH | S | a bond | T3b | OH |
| 693 | N | S | Q1i | a bond | H | a bond | NH | S | a bond | T3c | OH |
| 694 | N | S | Q1i | a bond | H | a bond | NH | S | a bond | T3d | OH |
| 695 | N | S | Q1i | a bond | H | a bond | NH | S | a bond | T3e | OH |
| 696 | N | S | Q1i | a bond | H | a bond | NH | S | a bond | T3f | OH |
| 697 | N | S | Q1i | a bond | H | a bond | NH | S | a bond | T3g | OH |
| 698 | N | S | Q1i | a bond | H | a bond | NH | S | a bond | T3h | OH |
| 699 | N | S | Q1i | a bond | H | a bond | NH | S | a bond | T3i | OH |
| 700 | N | S | Q1i | a bond | H | a bond | NH | S | a bond | T3j | OH |
| 701 | N | S | Q1i | a bond | H | a bond | NH | O | NH | T3a | OH |
| 702 | N | S | Q1i | a bond | H | a bond | NH | O | NH | T3b | OH |
| 703 | N | S | Q1i | a bond | H | a bond | NH | O | NH | T3c | OH |
| 704 | N | S | Q1i | a bond | H | a bond | NH | O | NH | T3d | OH |
| 705 | N | S | Q1i | a bond | H | a bond | NH | O | NH | T3e | OH |
| 706 | N | S | Q1i | a bond | H | a bond | NH | O | NH | T3f | OH |
| 707 | N | S | Q1i | a bond | H | a bond | NH | O | NH | T3g | OH |
| 708 | N | S | Q1i | a bond | H | a bond | NH | O | NH | T3h | OH |
| 709 | N | S | Q1i | a bond | H | a bond | NH | O | NH | T3i | OH |
| 710 | N | S | Q1i | a bond | H | a bond | NH | O | NH | T3j | OH |
| 711 | N | S | Q1i | a bond | H | a bond | NH | O | a bond | T3a | OH |
| 712 | N | S | Q1i | a bond | H | a bond | NH | O | a bond | T3b | OH |
| 713 | N | S | Q1i | a bond | H | a bond | NH | O | a bond | T3c | OH |
| 714 | N | S | Q1i | a bond | H | a bond | NH | O | a bond | T3d | OH |
| 715 | N | S | Q1i | a bond | H | a bond | NH | O | a bond | T3e | OH |
| 716 | N | S | Q1i | a bond | H | a bond | NH | O | a bond | T3f | OH |
| 717 | N | S | Q1i | a bond | H | a bond | NH | O | a bond | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 718 | N | S | Q1i | a bond | H | a bond | NH | O | a bond | T3h | OH |
| 719 | N | S | Q1i | a bond | H | a bond | NH | O | a bond | T3i | OH |
| 720 | N | S | Q1i | a bond | H | a bond | NH | O | a bond | T3j | OH |
| 721 | N | S | Q1j | a bond | Me | a bond | NH | S | NH | T3a | OH |
| 722 | N | S | Q1j | a bond | Me | a bond | NH | S | NH | T3b | OH |
| 723 | N | S | Q1j | a bond | Me | a bond | NH | S | NH | T3c | OH |
| 724 | N | S | Q1j | a bond | Me | a bond | NH | S | NH | T3d | OH |
| 725 | N | S | Q1j | a bond | Me | a bond | NH | S | NH | T3e | OH |
| 726 | N | S | Q1j | a bond | Me | a bond | NH | S | NH | T3f | OH |
| 727 | N | S | Q1j | a bond | Me | a bond | NH | S | NH | T3g | OH |
| 728 | N | S | Q1j | a bond | Me | a bond | NH | S | NH | T3h | OH |
| 729 | N | S | Q1j | a bond | Me | a bond | NH | S | NH | T3i | OH |
| 730 | N | S | Q1j | a bond | Me | a bond | NH | S | NH | T3j | OH |
| 731 | N | S | Q1j | a bond | Me | a bond | NH | S | a bond | T3a | OH |
| 732 | N | S | Q1j | a bond | Me | a bond | NH | S | a bond | T3b | OH |
| 733 | N | S | Q1j | a bond | Me | a bond | NH | S | a bond | T3c | OH |
| 734 | N | S | Q1j | a bond | Me | a bond | NH | S | a bond | T3d | OH |
| 735 | N | S | Q1j | a bond | Me | a bond | NH | S | a bond | T3e | OH |
| 736 | N | S | Q1j | a bond | Me | a bond | NH | S | a bond | T3f | OH |
| 737 | N | S | Q1j | a bond | Me | a bond | NH | S | a bond | T3g | OH |
| 738 | N | S | Q1j | a bond | Me | a bond | NH | S | a bond | T3h | OH |
| 739 | N | S | Q1j | a bond | Me | a bond | NH | S | a bond | T3i | OH |
| 740 | N | S | Q1j | a bond | Me | a bond | NH | S | a bond | T3j | OH |
| 741 | N | S | Q1j | a bond | Me | a bond | NH | O | NH | T3a | OH |
| 742 | N | S | Q1j | a bond | Me | a bond | NH | O | NH | T3b | OH |
| 743 | N | S | Q1j | a bond | Me | a bond | NH | O | NH | T3c | OH |
| 744 | N | S | Q1j | a bond | Me | a bond | NH | O | NH | T3d | OH |
| 745 | N | S | Q1j | a bond | Me | a bond | NH | O | NH | T3e | OH |
| 746 | N | S | Q1j | a bond | Me | a bond | NH | O | NH | T3f | OH |
| 747 | N | S | Q1j | a bond | Me | a bond | NH | O | NH | T3g | OH |
| 748 | N | S | Q1j | a bond | Me | a bond | NH | O | NH | T3h | OH |
| 749 | N | S | Q1j | a bond | Me | a bond | NH | O | NH | T3i | OH |
| 750 | N | S | Q1j | a bond | Me | a bond | NH | O | NH | T3j | OH |
| 751 | N | S | Q1j | a bond | Me | a bond | NH | O | a bond | T3a | OH |
| 752 | N | S | Q1j | a bond | Me | a bond | NH | O | a bond | T3b | OH |
| 753 | N | S | Q1j | a bond | Me | a bond | NH | O | a bond | T3c | OH |
| 754 | N | S | Q1j | a bond | Me | a bond | NH | O | a bond | T3d | OH |
| 755 | N | S | Q1j | a bond | Me | a bond | NH | O | a bond | T3e | OH |
| 756 | N | S | Q1j | a bond | Me | a bond | NH | O | a bond | T3f | OH |
| 757 | N | S | Q1j | a bond | Me | a bond | NH | O | a bond | T3g | OH |
| 758 | N | S | Q1j | a bond | Me | a bond | NH | O | a bond | T3h | OH |
| 759 | N | S | Q1j | a bond | Me | a bond | NH | O | a bond | T3i | OH |
| 760 | N | S | Q1j | a bond | Me | a bond | NH | O | a bond | T3j | OH |
| 761 | N | S | Q1j | a bond | H | a bond | NH | S | NH | T3a | OH |
| 762 | N | S | Q1j | a bond | H | a bond | NH | S | NH | T3b | OH |
| 763 | N | S | Q1j | a bond | H | a bond | NH | S | NH | T3c | OH |
| 764 | N | S | Q1j | a bond | H | a bond | NH | S | NH | T3d | OH |
| 765 | N | S | Q1j | a bond | H | a bond | NH | S | NH | T3e | OH |
| 766 | N | S | Q1j | a bond | H | a bond | NH | S | NH | T3f | OH |
| 767 | N | S | Q1j | a bond | H | a bond | NH | S | NH | T3g | OH |
| 768 | N | S | Q1j | a bond | H | a bond | NH | S | NH | T3h | OH |
| 769 | N | S | Q1j | a bond | H | a bond | NH | S | NH | T3i | OH |
| 770 | N | S | Q1j | a bond | H | a bond | NH | S | NH | T3j | OH |
| 771 | N | S | Q1j | a bond | H | a bond | NH | S | a bond | T3a | OH |
| 772 | N | S | Q1j | a bond | H | a bond | NH | S | a bond | T3b | OH |
| 773 | N | S | Q1j | a bond | H | a bond | NH | S | a bond | T3c | OH |
| 774 | N | S | Q1j | a bond | H | a bond | NH | S | a bond | T3d | OH |
| 775 | N | S | Q1j | a bond | H | a bond | NH | S | a bond | T3e | OH |
| 776 | N | S | Q1j | a bond | H | a bond | NH | S | a bond | T3f | OH |
| 777 | N | S | Q1j | a bond | H | a bond | NH | S | a bond | T3g | OH |
| 778 | N | S | Q1j | a bond | H | a bond | NH | S | a bond | T3h | OH |
| 779 | N | S | Q1j | a bond | H | a bond | NH | S | a bond | T3i | OH |
| 780 | N | S | Q1j | a bond | H | a bond | NH | S | a bond | T3j | OH |
| 781 | N | S | Q1j | a bond | H | a bond | NH | O | NH | T3a | OH |
| 782 | N | S | Q1j | a bond | H | a bond | NH | O | NH | T3b | OH |
| 783 | N | S | Q1j | a bond | H | a bond | NH | O | NH | T3c | OH |
| 784 | N | S | Q1j | a bond | H | a bond | NH | O | NH | T3d | OH |
| 785 | N | S | Q1j | a bond | H | a bond | NH | O | NH | T3e | OH |
| 786 | N | S | Q1j | a bond | H | a bond | NH | O | NH | T3f | OH |
| 787 | N | S | Q1j | a bond | H | a bond | NH | O | NH | T3g | OH |
| 788 | N | S | Q1j | a bond | H | a bond | NH | O | NH | T3h | OH |
| 789 | N | S | Q1j | a bond | H | a bond | NH | O | NH | T3i | OH |
| 790 | N | S | Q1j | a bond | H | a bond | NH | O | NH | T3j | OH |
| 791 | N | S | Q1j | a bond | H | a bond | NH | O | a bond | T3a | OH |
| 792 | N | S | Q1j | a bond | H | a bond | NH | O | a bond | T3b | OH |
| 793 | N | S | Q1j | a bond | H | a bond | NH | O | a bond | T3c | OH |
| 794 | N | S | Q1j | a bond | H | a bond | NH | O | a bond | T3d | OH |
| 795 | N | S | Q1j | a bond | H | a bond | NH | O | a bond | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 796 | N | S | Q1j | a bond | H | a bond | NH | O | a bond | T3f | OH |
| 797 | N | S | Q1j | a bond | H | a bond | NH | O | a bond | T3g | OH |
| 798 | N | S | Q1j | a bond | H | a bond | NH | O | a bond | T3h | OH |
| 799 | N | S | Q1j | a bond | H | a bond | NH | O | a bond | T3i | OH |
| 800 | N | S | Q1j | a bond | H | a bond | NH | O | a bond | T3j | OH |
| 801 | N | O | Q1a | a bond | Me | a bond | NH | S | NH | T3a | OH |
| 802 | N | O | Q1a | a bond | Me | a bond | NH | S | NH | T3b | OH |
| 803 | N | O | Q1a | a bond | Me | a bond | NH | S | NH | T3c | OH |
| 804 | N | O | Q1a | a bond | Me | a bond | NH | S | NH | T3d | OH |
| 805 | N | O | Q1a | a bond | Me | a bond | NH | S | NH | T3e | OH |
| 806 | N | O | Q1a | a bond | Me | a bond | NH | S | NH | T3f | OH |
| 807 | N | O | Q1a | a bond | Me | a bond | NH | S | NH | T3g | OH |
| 808 | N | O | Q1a | a bond | Me | a bond | NH | S | NH | T3h | OH |
| 809 | N | O | Q1a | a bond | Me | a bond | NH | S | NH | T3i | OH |
| 810 | N | O | Q1a | a bond | Me | a bond | NH | S | NH | T3j | OH |
| 811 | N | O | Q1a | a bond | Me | a bond | NH | S | a bond | T3a | OH |
| 812 | N | O | Q1a | a bond | Me | a bond | NH | S | a bond | T3b | OH |
| 813 | N | O | Q1a | a bond | Me | a bond | NH | S | a bond | T3c | OH |
| 814 | N | O | Q1a | a bond | Me | a bond | NH | S | a bond | T3d | OH |
| 815 | N | O | Q1a | a bond | Me | a bond | NH | S | a bond | T3e | OH |
| 816 | N | O | Q1a | a bond | Me | a bond | NH | S | a bond | T3f | OH |
| 817 | N | O | Q1a | a bond | Me | a bond | NH | S | a bond | T3g | OH |
| 818 | N | O | Q1a | a bond | Me | a bond | NH | S | a bond | T3h | OH |
| 819 | N | O | Q1a | a bond | Me | a bond | NH | S | a bond | T3i | OH |
| 820 | N | O | Q1a | a bond | Me | a bond | NH | S | a bond | T3j | OH |
| 821 | N | O | Q1a | a bond | Me | a bond | NH | O | NH | T3a | OH |
| 822 | N | O | Q1a | a bond | Me | a bond | NH | O | NH | T3b | OH |
| 823 | N | O | Q1a | a bond | Me | a bond | NH | O | NH | T3c | OH |
| 824 | N | O | Q1a | a bond | Me | a bond | NH | O | NH | T3d | OH |
| 825 | N | O | Q1a | a bond | Me | a bond | NH | O | NH | T3e | OH |
| 826 | N | O | Q1a | a bond | Me | a bond | NH | O | NH | T3f | OH |
| 827 | N | O | Q1a | a bond | Me | a bond | NH | O | NH | T3g | OH |
| 828 | N | O | Q1a | a bond | Me | a bond | NH | O | NH | T3h | OH |
| 829 | N | O | Q1a | a bond | Me | a bond | NH | O | NH | T3i | OH |
| 830 | N | O | Q1a | a bond | Me | a bond | NH | O | NH | T3j | OH |
| 831 | N | O | Q1a | a bond | Me | a bond | NH | O | a bond | T3a | OH |
| 832 | N | O | Q1a | a bond | Me | a bond | NH | O | a bond | T3b | OH |
| 833 | N | O | Q1a | a bond | Me | a bond | NH | O | a bond | T3c | OH |
| 834 | N | O | Q1a | a bond | Me | a bond | NH | O | a bond | T3d | OH |
| 835 | N | O | Q1a | a bond | Me | a bond | NH | O | a bond | T3e | OH |
| 836 | N | O | Q1a | a bond | Me | a bond | NH | O | a bond | T3f | OH |
| 837 | N | O | Q1a | a bond | Me | a bond | NH | O | a bond | T3g | OH |
| 838 | N | O | Q1a | a bond | Me | a bond | NH | O | a bond | T3h | OH |
| 839 | N | O | Q1a | a bond | Me | a bond | NH | O | a bond | T3i | OH |
| 840 | N | O | Q1a | a bond | Me | a bond | NH | O | a bond | T3j | OH |
| 841 | N | O | Q1a | a bond | H | a bond | NH | S | NH | T3a | OH |
| 842 | N | O | Q1a | a bond | H | a bond | NH | S | NH | T3b | OH |
| 843 | N | O | Q1a | a bond | H | a bond | NH | S | NH | T3c | OH |
| 844 | N | O | Q1a | a bond | H | a bond | NH | S | NH | T3d | OH |
| 845 | N | O | Q1a | a bond | H | a bond | NH | S | NH | T3e | OH |
| 846 | N | O | Q1a | a bond | H | a bond | NH | S | NH | T3f | OH |
| 847 | N | O | Q1a | a bond | H | a bond | NH | S | NH | T3g | OH |
| 848 | N | O | Q1a | a bond | H | a bond | NH | S | NH | T3h | OH |
| 849 | N | O | Q1a | a bond | H | a bond | NH | S | NH | T3i | OH |
| 850 | N | O | Q1a | a bond | H | a bond | NH | S | NH | T3j | OH |
| 851 | N | O | Q1a | a bond | H | a bond | NH | S | a bond | T3a | OH |
| 852 | N | O | Q1a | a bond | H | a bond | NH | S | a bond | T3b | OH |
| 853 | N | O | Q1a | a bond | H | a bond | NH | S | a bond | T3c | OH |
| 854 | N | O | Q1a | a bond | H | a bond | NH | S | a bond | T3d | OH |
| 855 | N | O | Q1a | a bond | H | a bond | NH | S | a bond | T3e | OH |
| 856 | N | O | Q1a | a bond | H | a bond | NH | S | a bond | T3f | OH |
| 857 | N | O | Q1a | a bond | H | a bond | NH | S | a bond | T3g | OH |
| 858 | N | O | Q1a | a bond | H | a bond | NH | S | a bond | T3h | OH |
| 859 | N | O | Q1a | a bond | H | a bond | NH | S | a bond | T3i | OH |
| 860 | N | O | Q1a | a bond | H | a bond | NH | S | a bond | T3j | OH |
| 861 | N | O | Q1a | a bond | H | a bond | NH | O | NH | T3a | OH |
| 862 | N | O | Q1a | a bond | H | a bond | NH | O | NH | T3b | OH |
| 863 | N | O | Q1a | a bond | H | a bond | NH | O | NH | T3c | OH |
| 864 | N | O | Q1a | a bond | H | a bond | NH | O | NH | T3d | OH |
| 865 | N | O | Q1a | a bond | H | a bond | NH | O | NH | T3e | OH |
| 866 | N | O | Q1a | a bond | H | a bond | NH | O | NH | T3f | OH |
| 867 | N | O | Q1a | a bond | H | a bond | NH | O | NH | T3g | OH |
| 868 | N | O | Q1a | a bond | H | a bond | NH | O | NH | T3h | OH |
| 869 | N | O | Q1a | a bond | H | a bond | NH | O | NH | T3i | OH |
| 870 | N | O | Q1a | a bond | H | a bond | NH | O | NH | T3j | OH |
| 871 | N | O | Q1a | a bond | H | a bond | NH | O | a bond | T3a | OH |
| 872 | N | O | Q1a | a bond | H | a bond | NH | O | a bond | T3b | OH |
| 873 | N | O | Q1a | a bond | H | a bond | NH | O | a bond | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 874 | N | O | Q1a | a bond | H | a bond | NH | O | a bond | T3d | OH |
| 875 | N | O | Q1a | a bond | H | a bond | NH | O | a bond | T3e | OH |
| 876 | N | O | Q1a | a bond | H | a bond | NH | O | a bond | T3f | OH |
| 877 | N | O | Q1a | a bond | H | a bond | NH | O | a bond | T3g | OH |
| 878 | N | O | Q1a | a bond | H | a bond | NH | O | a bond | T3h | OH |
| 879 | N | O | Q1a | a bond | H | a bond | NH | O | a bond | T3i | OH |
| 880 | N | O | Q1a | a bond | H | a bond | NH | O | a bond | T3j | OH |
| 881 | N | O | Q1b | a bond | Me | a bond | NH | S | NH | T3a | OH |
| 882 | N | O | Q1b | a bond | Me | a bond | NH | S | NH | T3b | OH |
| 883 | N | O | Q1b | a bond | Me | a bond | NH | S | NH | T3c | OH |
| 884 | N | O | Q1b | a bond | Me | a bond | NH | S | NH | T3d | OH |
| 885 | N | O | Q1b | a bond | Me | a bond | NH | S | NH | T3e | OH |
| 886 | N | O | Q1b | a bond | Me | a bond | NH | S | NH | T3f | OH |
| 887 | N | O | Q1b | a bond | Me | a bond | NH | S | NH | T3g | OH |
| 888 | N | O | Q1b | a bond | Me | a bond | NH | S | NH | T3h | OH |
| 889 | N | O | Q1b | a bond | Me | a bond | NH | S | NH | T3i | OH |
| 890 | N | O | Q1b | a bond | Me | a bond | NH | S | NH | T3j | OH |
| 891 | N | O | Q1b | a bond | Me | a bond | NH | S | a bond | T3a | OH |
| 892 | N | O | Q1b | a bond | Me | a bond | NH | S | a bond | T3b | OH |
| 893 | N | O | Q1b | a bond | Me | a bond | NH | S | a bond | T3c | OH |
| 894 | N | O | Q1b | a bond | Me | a bond | NH | S | a bond | T3d | OH |
| 895 | N | O | Q1b | a bond | Me | a bond | NH | S | a bond | T3e | OH |
| 896 | N | O | Q1b | a bond | Me | a bond | NH | S | a bond | T3f | OH |
| 897 | N | O | Q1b | a bond | Me | a bond | NH | S | a bond | T3g | OH |
| 898 | N | O | Q1b | a bond | Me | a bond | NH | S | a bond | T3h | OH |
| 899 | N | O | Q1b | a bond | Me | a bond | NH | S | a bond | T3i | OH |
| 900 | N | O | Q1b | a bond | Me | a bond | NH | S | a bond | T3j | OH |
| 901 | N | O | Q1b | a bond | Me | a bond | NH | O | NH | T3a | OH |
| 902 | N | O | Q1b | a bond | Me | a bond | NH | O | NH | T3b | OH |
| 903 | N | O | Q1b | a bond | Me | a bond | NH | O | NH | T3c | OH |
| 904 | N | O | Q1b | a bond | Me | a bond | NH | O | NH | T3d | OH |
| 905 | N | O | Q1b | a bond | Me | a bond | NH | O | NH | T3e | OH |
| 906 | N | O | Q1b | a bond | Me | a bond | NH | O | NH | T3f | OH |
| 907 | N | O | Q1b | a bond | Me | a bond | NH | O | NH | T3g | OH |
| 908 | N | O | Q1b | a bond | Me | a bond | NH | O | NH | T3h | OH |
| 909 | N | O | Q1b | a bond | Me | a bond | NH | O | NH | T3i | OH |
| 910 | N | O | Q1b | a bond | Me | a bond | NH | O | NH | T3j | OH |
| 911 | N | O | Q1b | a bond | Me | a bond | NH | O | a bond | T3a | OH |
| 912 | N | O | Q1b | a bond | Me | a bond | NH | O | a bond | T3b | OH |
| 913 | N | O | Q1b | a bond | Me | a bond | NH | O | a bond | T3c | OH |
| 914 | N | O | Q1b | a bond | Me | a bond | NH | O | a bond | T3d | OH |
| 915 | N | O | Q1b | a bond | Me | a bond | NH | O | a bond | T3e | OH |
| 916 | N | O | Q1b | a bond | Me | a bond | NH | O | a bond | T3f | OH |
| 917 | N | O | Q1b | a bond | Me | a bond | NH | O | a bond | T3g | OH |
| 918 | N | O | Q1b | a bond | Me | a bond | NH | O | a bond | T3h | OH |
| 919 | N | O | Q1b | a bond | Me | a bond | NH | O | a bond | T3i | OH |
| 920 | N | O | Q1b | a bond | Me | a bond | NH | O | a bond | T3j | OH |
| 921 | N | O | Q1b | a bond | H | a bond | NH | S | NH | T3a | OH |
| 922 | N | O | Q1b | a bond | H | a bond | NH | S | NH | T3b | OH |
| 923 | N | O | Q1b | a bond | H | a bond | NH | S | NH | T3c | OH |
| 924 | N | O | Q1b | a bond | H | a bond | NH | S | NH | T3d | OH |
| 925 | N | O | Q1b | a bond | H | a bond | NH | S | NH | T3e | OH |
| 926 | N | O | Q1b | a bond | H | a bond | NH | S | NH | T3f | OH |
| 927 | N | O | Q1b | a bond | H | a bond | NH | S | NH | T3g | OH |
| 928 | N | O | Q1b | a bond | H | a bond | NH | S | NH | T3h | OH |
| 929 | N | O | Q1b | a bond | H | a bond | NH | S | NH | T3i | OH |
| 930 | N | O | Q1b | a bond | H | a bond | NH | S | NH | T3j | OH |
| 931 | N | O | Q1b | a bond | H | a bond | NH | S | a bond | T3a | OH |
| 932 | N | O | Q1b | a bond | H | a bond | NH | S | a bond | T3b | OH |
| 933 | N | O | Q1b | a bond | H | a bond | NH | S | a bond | T3c | OH |
| 934 | N | O | Q1b | a bond | H | a bond | NH | S | a bond | T3d | OH |
| 935 | N | O | Q1b | a bond | H | a bond | NH | S | a bond | T3e | OH |
| 936 | N | O | Q1b | a bond | H | a bond | NH | S | a bond | T3f | OH |
| 937 | N | O | Q1b | a bond | H | a bond | NH | S | a bond | T3g | OH |
| 938 | N | O | Q1b | a bond | H | a bond | NH | S | a bond | T3h | OH |
| 939 | N | O | Q1b | a bond | H | a bond | NH | S | a bond | T3i | OH |
| 940 | N | O | Q1b | a bond | H | a bond | NH | S | a bond | T3j | OH |
| 941 | N | O | Q1b | a bond | H | a bond | NH | O | NH | T3a | OH |
| 942 | N | O | Q1b | a bond | H | a bond | NH | O | NH | T3b | OH |
| 943 | N | O | Q1b | a bond | H | a bond | NH | O | NH | T3c | OH |
| 944 | N | O | Q1b | a bond | H | a bond | NH | O | NH | T3d | OH |
| 945 | N | O | Q1b | a bond | H | a bond | NH | O | NH | T3e | OH |
| 946 | N | O | Q1b | a bond | H | a bond | NH | O | NH | T3f | OH |
| 947 | N | O | Q1b | a bond | H | a bond | NH | O | NH | T3g | OH |
| 948 | N | O | Q1b | a bond | H | a bond | NH | O | NH | T3h | OH |
| 949 | N | O | Q1b | a bond | H | a bond | NH | O | NH | T3i | OH |
| 950 | N | O | Q1b | a bond | H | a bond | NH | O | NH | T3j | OH |
| 951 | N | O | Q1b | a bond | H | a bond | NH | O | a bond | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 952 | N | O | Q1b | a bond | H | a bond | NH | O | a bond | T3b | OH |
| 953 | N | O | Q1b | a bond | H | a bond | NH | O | a bond | T3c | OH |
| 954 | N | O | Q1b | a bond | H | a bond | NH | O | a bond | T3d | OH |
| 955 | N | O | Q1b | a bond | H | a bond | NH | O | a bond | T3e | OH |
| 956 | N | O | Q1b | a bond | H | a bond | NH | O | a bond | T3f | OH |
| 957 | N | O | Q1b | a bond | H | a bond | NH | O | a bond | T3g | OH |
| 958 | N | O | Q1b | a bond | H | a bond | NH | O | a bond | T3h | OH |
| 959 | N | O | Q1b | a bond | H | a bond | NH | O | a bond | T3i | OH |
| 960 | N | O | Q1b | a bond | H | a bond | NH | O | a bond | T3j | OH |
| 961 | N | O | Q1c | a bond | Me | a bond | NH | S | NH | T3a | OH |
| 962 | N | O | Q1c | a bond | Me | a bond | NH | S | NH | T3b | OH |
| 963 | N | O | Q1c | a bond | Me | a bond | NH | S | NH | T3c | OH |
| 964 | N | O | Q1c | a bond | Me | a bond | NH | S | NH | T3d | OH |
| 965 | N | O | Q1c | a bond | Me | a bond | NH | S | NH | T3e | OH |
| 966 | N | O | Q1c | a bond | Me | a bond | NH | S | NH | T3f | OH |
| 967 | N | O | Q1c | a bond | Me | a bond | NH | S | NH | T3g | OH |
| 968 | N | O | Q1c | a bond | Me | a bond | NH | S | NH | T3h | OH |
| 969 | N | O | Q1c | a bond | Me | a bond | NH | S | NH | T3i | OH |
| 970 | N | O | Q1c | a bond | Me | a bond | NH | S | NH | T3j | OH |
| 971 | N | O | Q1c | a bond | Me | a bond | NH | S | a bond | T3a | OH |
| 972 | N | O | Q1c | a bond | Me | a bond | NH | S | a bond | T3b | OH |
| 973 | N | O | Q1c | a bond | Me | a bond | NH | S | a bond | T3c | OH |
| 974 | N | O | Q1c | a bond | Me | a bond | NH | S | a bond | T3d | OH |
| 975 | N | O | Q1c | a bond | Me | a bond | NH | S | a bond | T3e | OH |
| 976 | N | O | Q1c | a bond | Me | a bond | NH | S | a bond | T3f | OH |
| 977 | N | O | Q1c | a bond | Me | a bond | NH | S | a bond | T3g | OH |
| 978 | N | O | Q1c | a bond | Me | a bond | NH | S | a bond | T3h | OH |
| 979 | N | O | Q1c | a bond | Me | a bond | NH | S | a bond | T3i | OH |
| 980 | N | O | Q1c | a bond | Me | a bond | NH | S | a bond | T3j | OH |
| 981 | N | O | Q1c | a bond | Me | a bond | NH | O | NH | T3a | OH |
| 982 | N | O | Q1c | a bond | Me | a bond | NH | O | NH | T3b | OH |
| 983 | N | O | Q1c | a bond | Me | a bond | NH | O | NH | T3c | OH |
| 984 | N | O | Q1c | a bond | Me | a bond | NH | O | NH | T3d | OH |
| 985 | N | O | Q1c | a bond | Me | a bond | NH | O | NH | T3e | OH |
| 986 | N | O | Q1c | a bond | Me | a bond | NH | O | NH | T3f | OH |
| 987 | N | O | Q1c | a bond | Me | a bond | NH | O | NH | T3g | OH |
| 988 | N | O | Q1c | a bond | Me | a bond | NH | O | NH | T3h | OH |
| 989 | N | O | Q1c | a bond | Me | a bond | NH | O | NH | T3i | OH |
| 990 | N | O | Q1c | a bond | Me | a bond | NH | O | NH | T3j | OH |
| 991 | N | O | Q1c | a bond | Me | a bond | NH | O | a bond | T3a | OH |
| 992 | N | O | Q1c | a bond | Me | a bond | NH | O | a bond | T3b | OH |
| 993 | N | O | Q1c | a bond | Me | a bond | NH | O | a bond | T3c | OH |
| 994 | N | O | Q1c | a bond | Me | a bond | NH | O | a bond | T3d | OH |
| 995 | N | O | Q1c | a bond | Me | a bond | NH | O | a bond | T3e | OH |
| 996 | N | O | Q1c | a bond | Me | a bond | NH | O | a bond | T3f | OH |
| 997 | N | O | Q1c | a bond | Me | a bond | NH | O | a bond | T3g | OH |
| 998 | N | O | Q1c | a bond | Me | a bond | NH | O | a bond | T3h | OH |
| 999 | N | O | Q1c | a bond | Me | a bond | NH | O | a bond | T3i | OH |
| 1000 | N | O | Q1c | a bond | Me | a bond | NH | O | a bond | T3j | OH |
| 1001 | N | O | Q1c | a bond | H | a bond | NH | S | NH | T3a | OH |
| 1002 | N | O | Q1c | a bond | H | a bond | NH | S | NH | T3b | OH |
| 1003 | N | O | Q1c | a bond | H | a bond | NH | S | NH | T3c | OH |
| 1004 | N | O | Q1c | a bond | H | a bond | NH | S | NH | T3d | OH |
| 1005 | N | O | Q1c | a bond | H | a bond | NH | S | NH | T3e | OH |
| 1006 | N | O | Q1c | a bond | H | a bond | NH | S | NH | T3f | OH |
| 1007 | N | O | Q1c | a bond | H | a bond | NH | S | NH | T3g | OH |
| 1008 | N | O | Q1c | a bond | H | a bond | NH | S | NH | T3h | OH |
| 1009 | N | O | Q1c | a bond | H | a bond | NH | S | NH | T3i | OH |
| 1010 | N | O | Q1c | a bond | H | a bond | NH | S | NH | T3j | OH |
| 1011 | N | O | Q1c | a bond | H | a bond | NH | S | a bond | T3a | OH |
| 1012 | N | O | Q1c | a bond | H | a bond | NH | S | a bond | T3b | OH |
| 1013 | N | O | Q1c | a bond | H | a bond | NH | S | a bond | T3c | OH |
| 1014 | N | O | Q1c | a bond | H | a bond | NH | S | a bond | T3d | OH |
| 1015 | N | O | Q1c | a bond | H | a bond | NH | S | a bond | T3e | OH |
| 1016 | N | O | Q1c | a bond | H | a bond | NH | S | a bond | T3f | OH |
| 1017 | N | O | Q1c | a bond | H | a bond | NH | S | a bond | T3g | OH |
| 1018 | N | O | Q1c | a bond | H | a bond | NH | S | a bond | T3h | OH |
| 1019 | N | O | Q1c | a bond | H | a bond | NH | S | a bond | T3i | OH |
| 1020 | N | O | Q1c | a bond | H | a bond | NH | S | a bond | T3j | OH |
| 1021 | N | O | Q1c | a bond | H | a bond | NH | O | NH | T3a | OH |
| 1022 | N | O | Q1c | a bond | H | a bond | NH | O | NH | T3b | OH |
| 1023 | N | O | Q1c | a bond | H | a bond | NH | O | NH | T3c | OH |
| 1024 | N | O | Q1c | a bond | H | a bond | NH | O | NH | T3d | OH |
| 1025 | N | O | Q1c | a bond | H | a bond | NH | O | NH | T3e | OH |
| 1026 | N | O | Q1c | a bond | H | a bond | NH | O | NH | T3f | OH |
| 1027 | N | O | Q1c | a bond | H | a bond | NH | O | NH | T3g | OH |
| 1028 | N | O | Q1c | a bond | H | a bond | NH | O | NH | T3h | OH |
| 1029 | N | O | Q1c | a bond | H | a bond | NH | O | NH | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 1030 | N | O | Q1c | a bond | H | a bond | NH | O | NH | T3j | OH |
| 1031 | N | O | Q1c | a bond | H | a bond | NH | O | a bond | T3a | OH |
| 1032 | N | O | Q1c | a bond | H | a bond | NH | O | a bond | T3b | OH |
| 1033 | N | O | Q1c | a bond | H | a bond | NH | O | a bond | T3c | OH |
| 1034 | N | O | Q1c | a bond | H | a bond | NH | O | a bond | T3d | OH |
| 1035 | N | O | Q1c | a bond | H | a bond | NH | O | a bond | T3e | OH |
| 1036 | N | O | Q1c | a bond | H | a bond | NH | O | a bond | T3f | OH |
| 1037 | N | O | Q1c | a bond | H | a bond | NH | O | a bond | T3g | OH |
| 1038 | N | O | Q1c | a bond | H | a bond | NH | O | a bond | T3h | OH |
| 1039 | N | O | Q1c | a bond | H | a bond | NH | O | a bond | T3i | OH |
| 1040 | N | O | Q1c | a bond | H | a bond | NH | O | a bond | T3j | OH |
| 1041 | N | O | Q1i | a bond | Me | a bond | NH | S | NH | T3a | OH |
| 1042 | N | O | Q1i | a bond | Me | a bond | NH | S | NH | T3b | OH |
| 1043 | N | O | Q1i | a bond | Me | a bond | NH | S | NH | T3c | OH |
| 1044 | N | O | Q1i | a bond | Me | a bond | NH | S | NH | T3d | OH |
| 1045 | N | O | Q1i | a bond | Me | a bond | NH | S | NH | T3e | OH |
| 1046 | N | O | Q1i | a bond | Me | a bond | NH | S | NH | T3f | OH |
| 1047 | N | O | Q1i | a bond | Me | a bond | NH | S | NH | T3g | OH |
| 1048 | N | O | Q1i | a bond | Me | a bond | NH | S | NH | T3h | OH |
| 1049 | N | O | Q1i | a bond | Me | a bond | NH | S | NH | T3i | OH |
| 1050 | N | O | Q1i | a bond | Me | a bond | NH | S | NH | T3j | OH |
| 1051 | N | O | Q1i | a bond | Me | a bond | NH | S | a bond | T3a | OH |
| 1052 | N | O | Q1i | a bond | Me | a bond | NH | S | a bond | T3b | OH |
| 1053 | N | O | Q1i | a bond | Me | a bond | NH | S | a bond | T3c | OH |
| 1054 | N | O | Q1i | a bond | Me | a bond | NH | S | a bond | T3d | OH |
| 1055 | N | O | Q1i | a bond | Me | a bond | NH | S | a bond | T3e | OH |
| 1056 | N | O | Q1i | a bond | Me | a bond | NH | S | a bond | T3f | OH |
| 1057 | N | O | Q1i | a bond | Me | a bond | NH | S | a bond | T3g | OH |
| 1058 | N | O | Q1i | a bond | Me | a bond | NH | S | a bond | T3h | OH |
| 1059 | N | O | Q1i | a bond | Me | a bond | NH | S | a bond | T3i | OH |
| 1060 | N | O | Q1i | a bond | Me | a bond | NH | S | a bond | T3j | OH |
| 1061 | N | O | Q1i | a bond | Me | a bond | NH | O | NH | T3a | OH |
| 1062 | N | O | Q1i | a bond | Me | a bond | NH | O | NH | T3b | OH |
| 1063 | N | O | Q1i | a bond | Me | a bond | NH | O | NH | T3c | OH |
| 1064 | N | O | Q1i | a bond | Me | a bond | NH | O | NH | T3d | OH |
| 1065 | N | O | Q1i | a bond | Me | a bond | NH | O | NH | T3e | OH |
| 1066 | N | O | Q1i | a bond | Me | a bond | NH | O | NH | T3f | OH |
| 1067 | N | O | Q1i | a bond | Me | a bond | NH | O | NH | T3g | OH |
| 1068 | N | O | Q1i | a bond | Me | a bond | NH | O | NH | T3h | OH |
| 1069 | N | O | Q1i | a bond | Me | a bond | NH | O | NH | T3i | OH |
| 1070 | N | O | Q1i | a bond | Me | a bond | NH | O | NH | T3j | OH |
| 1071 | N | O | Q1i | a bond | Me | a bond | NH | O | a bond | T3a | OH |
| 1072 | N | O | Q1i | a bond | Me | a bond | NH | O | a bond | T3b | OH |
| 1073 | N | O | Q1i | a bond | Me | a bond | NH | O | a bond | T3c | OH |
| 1074 | N | O | Q1i | a bond | Me | a bond | NH | O | a bond | T3d | OH |
| 1075 | N | O | Q1i | a bond | Me | a bond | NH | O | a bond | T3e | OH |
| 1076 | N | O | Q1i | a bond | Me | a bond | NH | O | a bond | T3f | OH |
| 1077 | N | O | Q1i | a bond | Me | a bond | NH | O | a bond | T3g | OH |
| 1078 | N | O | Q1i | a bond | Me | a bond | NH | O | a bond | T3h | OH |
| 1079 | N | O | Q1i | a bond | Me | a bond | NH | O | a bond | T3i | OH |
| 1080 | N | O | Q1i | a bond | Me | a bond | NH | O | a bond | T3j | OH |
| 1081 | N | O | Q1i | a bond | H | a bond | NH | S | NH | T3a | OH |
| 1082 | N | O | Q1i | a bond | H | a bond | NH | S | NH | T3b | OH |
| 1083 | N | O | Q1i | a bond | H | a bond | NH | S | NH | T3c | OH |
| 1084 | N | O | Q1i | a bond | H | a bond | NH | S | NH | T3d | OH |
| 1085 | N | O | Q1i | a bond | H | a bond | NH | S | NH | T3e | OH |
| 1086 | N | O | Q1i | a bond | H | a bond | NH | S | NH | T3f | OH |
| 1087 | N | O | Q1i | a bond | H | a bond | NH | S | NH | T3g | OH |
| 1088 | N | O | Q1i | a bond | H | a bond | NH | S | NH | T3h | OH |
| 1089 | N | O | Q1i | a bond | H | a bond | NH | S | NH | T3i | OH |
| 1090 | N | O | Q1i | a bond | H | a bond | NH | S | NH | T3j | OH |
| 1091 | N | O | Q1i | a bond | H | a bond | NH | S | a bond | T3a | OH |
| 1092 | N | O | Q1i | a bond | H | a bond | NH | S | a bond | T3b | OH |
| 1093 | N | O | Q1i | a bond | H | a bond | NH | S | a bond | T3c | OH |
| 1094 | N | O | Q1i | a bond | H | a bond | NH | S | a bond | T3d | OH |
| 1095 | N | O | Q1i | a bond | H | a bond | NH | S | a bond | T3e | OH |
| 1096 | N | O | Q1i | a bond | H | a bond | NH | S | a bond | T3f | OH |
| 1097 | N | O | Q1i | a bond | H | a bond | NH | S | a bond | T3g | OH |
| 1098 | N | O | Q1i | a bond | H | a bond | NH | S | a bond | T3h | OH |
| 1099 | N | O | Q1i | a bond | H | a bond | NH | S | a bond | T3i | OH |
| 1100 | N | O | Q1i | a bond | H | a bond | NH | S | a bond | T3j | OH |
| 1101 | N | O | Q1i | a bond | H | a bond | NH | O | NH | T3a | OH |
| 1102 | N | O | Q1i | a bond | H | a bond | NH | O | NH | T3b | OH |
| 1103 | N | O | Q1i | a bond | H | a bond | NH | O | NH | T3c | OH |
| 1104 | N | O | Q1i | a bond | H | a bond | NH | O | NH | T3d | OH |
| 1105 | N | O | Q1i | a bond | H | a bond | NH | O | NH | T3e | OH |
| 1106 | N | O | Q1i | a bond | H | a bond | NH | O | NH | T3f | OH |
| 1107 | N | O | Q1i | a bond | H | a bond | NH | O | NH | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 1108 | N | O | Q1i | a bond | H | a bond | NH | O | NH | T3h | OH |
| 1109 | N | O | Q1i | a bond | H | a bond | NH | O | NH | T3i | OH |
| 1110 | N | O | Q1i | a bond | H | a bond | NH | O | NH | T3j | OH |
| 1111 | N | O | Q1i | a bond | H | a bond | NH | O | a bond | T3a | OH |
| 1112 | N | O | Q1i | a bond | H | a bond | NH | O | a bond | T3b | OH |
| 1113 | N | O | Q1i | a bond | H | a bond | NH | O | a bond | T3c | OH |
| 1114 | N | O | Q1i | a bond | H | a bond | NH | O | a bond | T3d | OH |
| 1115 | N | O | Q1i | a bond | H | a bond | NH | O | a bond | T3e | OH |
| 1116 | N | O | Q1i | a bond | H | a bond | NH | O | a bond | T3f | OH |
| 1117 | N | O | Q1i | a bond | H | a bond | NH | O | a bond | T3g | OH |
| 1118 | N | O | Q1i | a bond | H | a bond | NH | O | a bond | T3h | OH |
| 1119 | N | O | Q1i | a bond | H | a bond | NH | O | a bond | T3i | OH |
| 1120 | N | O | Q1i | a bond | H | a bond | NH | O | a bond | T3j | OH |
| 1121 | N | O | Q1j | a bond | Me | a bond | NH | S | NH | T3a | OH |
| 1122 | N | O | Q1j | a bond | Me | a bond | NH | S | NH | T3b | OH |
| 1123 | N | O | Q1j | a bond | Me | a bond | NH | S | NH | T3c | OH |
| 1124 | N | O | Q1j | a bond | Me | a bond | NH | S | NH | T3d | OH |
| 1125 | N | O | Q1j | a bond | Me | a bond | NH | S | NH | T3e | OH |
| 1126 | N | O | Q1j | a bond | Me | a bond | NH | S | NH | T3f | OH |
| 1127 | N | O | Q1j | a bond | Me | a bond | NH | S | NH | T3g | OH |
| 1128 | N | O | Q1j | a bond | Me | a bond | NH | S | NH | T3h | OH |
| 1129 | N | O | Q1j | a bond | Me | a bond | NH | S | NH | T3i | OH |
| 1130 | N | O | Q1j | a bond | Me | a bond | NH | S | NH | T3j | OH |
| 1131 | N | O | Q1j | a bond | Me | a bond | NH | S | a bond | T3a | OH |
| 1132 | N | O | Q1j | a bond | Me | a bond | NH | S | a bond | T3b | OH |
| 1133 | N | O | Q1j | a bond | Me | a bond | NH | S | a bond | T3c | OH |
| 1134 | N | O | Q1j | a bond | Me | a bond | NH | S | a bond | T3d | OH |
| 1135 | N | O | Q1j | a bond | Me | a bond | NH | S | a bond | T3e | OH |
| 1136 | N | O | Q1j | a bond | Me | a bond | NH | S | a bond | T3f | OH |
| 1137 | N | O | Q1j | a bond | Me | a bond | NH | S | a bond | T3g | OH |
| 1138 | N | O | Q1j | a bond | Me | a bond | NH | S | a bond | T3h | OH |
| 1139 | N | O | Q1j | a bond | Me | a bond | NH | S | a bond | T3i | OH |
| 1140 | N | O | Q1j | a bond | Me | a bond | NH | S | a bond | T3j | OH |
| 1141 | N | O | Q1j | a bond | Me | a bond | NH | O | NH | T3a | OH |
| 1142 | N | O | Q1j | a bond | Me | a bond | NH | O | NH | T3b | OH |
| 1143 | N | O | Q1j | a bond | Me | a bond | NH | O | NH | T3c | OH |
| 1144 | N | O | Q1j | a bond | Me | a bond | NH | O | NH | T3d | OH |
| 1145 | N | O | Q1j | a bond | Me | a bond | NH | O | NH | T3e | OH |
| 1146 | N | O | Q1j | a bond | Me | a bond | NH | O | NH | T3f | OH |
| 1147 | N | O | Q1j | a bond | Me | a bond | NH | O | NH | T3g | OH |
| 1148 | N | O | Q1j | a bond | Me | a bond | NH | O | NH | T3h | OH |
| 1149 | N | O | Q1j | a bond | Me | a bond | NH | O | NH | T3i | OH |
| 1150 | N | O | Q1j | a bond | Me | a bond | NH | O | NH | T3j | OH |
| 1151 | N | O | Q1j | a bond | Me | a bond | NH | O | a bond | T3a | OH |
| 1152 | N | O | Q1j | a bond | Me | a bond | NH | O | a bond | T3b | OH |
| 1153 | N | O | Q1j | a bond | Me | a bond | NH | O | a bond | T3c | OH |
| 1154 | N | O | Q1j | a bond | Me | a bond | NH | O | a bond | T3d | OH |
| 1155 | N | O | Q1j | a bond | Me | a bond | NH | O | a bond | T3e | OH |
| 1156 | N | O | Q1j | a bond | Me | a bond | NH | O | a bond | T3f | OH |
| 1157 | N | O | Q1j | a bond | Me | a bond | NH | O | a bond | T3g | OH |
| 1158 | N | O | Q1j | a bond | Me | a bond | NH | O | a bond | T3h | OH |
| 1159 | N | O | Q1j | a bond | Me | a bond | NH | O | a bond | T3i | OH |
| 1160 | N | O | Q1j | a bond | Me | a bond | NH | O | a bond | T3j | OH |
| 1161 | N | O | Q1j | a bond | H | a bond | NH | S | NH | T3a | OH |
| 1162 | N | O | Q1j | a bond | H | a bond | NH | S | NH | T3b | OH |
| 1163 | N | O | Q1j | a bond | H | a bond | NH | S | NH | T3c | OH |
| 1164 | N | O | Q1j | a bond | H | a bond | NH | S | NH | T3d | OH |
| 1165 | N | O | Q1j | a bond | H | a bond | NH | S | NH | T3e | OH |
| 1166 | N | O | Q1j | a bond | H | a bond | NH | S | NH | T3f | OH |
| 1167 | N | O | Q1j | a bond | H | a bond | NH | S | NH | T3g | OH |
| 1168 | N | O | Q1j | a bond | H | a bond | NH | S | NH | T3h | OH |
| 1169 | N | O | Q1j | a bond | H | a bond | NH | S | NH | T3i | OH |
| 1170 | N | O | Q1j | a bond | H | a bond | NH | S | NH | T3j | OH |
| 1171 | N | O | Q1j | a bond | H | a bond | NH | S | a bond | T3a | OH |
| 1172 | N | O | Q1j | a bond | H | a bond | NH | S | a bond | T3b | OH |
| 1173 | N | O | Q1j | a bond | H | a bond | NH | S | a bond | T3c | OH |
| 1174 | N | O | Q1j | a bond | H | a bond | NH | S | a bond | T3d | OH |
| 1175 | N | O | Q1j | a bond | H | a bond | NH | S | a bond | T3e | OH |
| 1176 | N | O | Q1j | a bond | H | a bond | NH | S | a bond | T3f | OH |
| 1177 | N | O | Q1j | a bond | H | a bond | NH | S | a bond | T3g | OH |
| 1178 | N | O | Q1j | a bond | H | a bond | NH | S | a bond | T3h | OH |
| 1179 | N | O | Q1j | a bond | H | a bond | NH | S | a bond | T3i | OH |
| 1180 | N | O | Q1j | a bond | H | a bond | NH | S | a bond | T3j | OH |
| 1181 | N | O | Q1j | a bond | H | a bond | NH | O | NH | T3a | OH |
| 1182 | N | O | Q1j | a bond | H | a bond | NH | O | NH | T3b | OH |
| 1183 | N | O | Q1j | a bond | H | a bond | NH | O | NH | T3c | OH |
| 1184 | N | O | Q1j | a bond | H | a bond | NH | O | NH | T3d | OH |
| 1185 | N | O | Q1j | a bond | H | a bond | NH | O | NH | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 1186 | N | O | Q1j | a bond | H | a bond | NH | O | NH | T3f | OH |
| 1187 | N | O | Q1j | a bond | H | a bond | NH | O | NH | T3g | OH |
| 1188 | N | O | Q1j | a bond | H | a bond | NH | O | NH | T3h | OH |
| 1189 | N | O | Q1j | a bond | H | a bond | NH | O | NH | T3i | OH |
| 1190 | N | O | Q1j | a bond | H | a bond | NH | O | NH | T3j | OH |
| 1191 | N | O | Q1j | a bond | H | a bond | NH | O | a bond | T3a | OH |
| 1192 | N | O | Q1j | a bond | H | a bond | NH | O | a bond | T3b | OH |
| 1193 | N | O | Q1j | a bond | H | a bond | NH | O | a bond | T3c | OH |
| 1194 | N | O | Q1j | a bond | H | a bond | NH | O | a bond | T3d | OH |
| 1195 | N | O | Q1j | a bond | H | a bond | NH | O | a bond | T3e | OH |
| 1196 | N | O | Q1j | a bond | H | a bond | NH | O | a bond | T3f | OH |
| 1197 | N | O | Q1j | a bond | H | a bond | NH | O | a bond | T3g | OH |
| 1198 | N | O | Q1j | a bond | H | a bond | NH | O | a bond | T3h | OH |
| 1199 | N | O | Q1j | a bond | H | a bond | NH | O | a bond | T3i | OH |
| 1200 | N | O | Q1j | a bond | H | a bond | NH | O | a bond | T3j | OH |
| 1201 | CH | NMe | Q1a | a bond | Me | a bond | NH | S | NH | T3a | OH |
| 1202 | CH | NMe | Q1a | a bond | Me | a bond | NH | S | NH | T3b | OH |
| 1203 | CH | NMe | Q1a | a bond | Me | a bond | NH | S | NH | T3c | OH |
| 1204 | CH | NMe | Q1a | a bond | Me | a bond | NH | S | NH | T3d | OH |
| 1205 | CH | NMe | Q1a | a bond | Me | a bond | NH | S | NH | T3e | OH |
| 1206 | CH | NMe | Q1a | a bond | Me | a bond | NH | S | NH | T3f | OH |
| 1207 | CH | NMe | Q1a | a bond | Me | a bond | NH | S | NH | T3g | OH |
| 1208 | CH | NMe | Q1a | a bond | Me | a bond | NH | S | NH | T3h | OH |
| 1209 | CH | NMe | Q1a | a bond | Me | a bond | NH | S | NH | T3i | OH |
| 1210 | CH | NMe | Q1a | a bond | Me | a bond | NH | S | NH | T3j | OH |
| 1211 | CH | NMe | Q1a | a bond | Me | a bond | NH | S | a bond | T3a | OH |
| 1212 | CH | NMe | Q1a | a bond | Me | a bond | NH | S | a bond | T3b | OH |
| 1213 | CH | NMe | Q1a | a bond | Me | a bond | NH | S | a bond | T3c | OH |
| 1214 | CH | NMe | Q1a | a bond | Me | a bond | NH | S | a bond | T3d | OH |
| 1215 | CH | NMe | Q1a | a bond | Me | a bond | NH | S | a bond | T3e | OH |
| 1216 | CH | NMe | Q1a | a bond | Me | a bond | NH | S | a bond | T3f | OH |
| 1217 | CH | NMe | Q1a | a bond | Me | a bond | NH | S | a bond | T3g | OH |
| 1218 | CH | NMe | Q1a | a bond | Me | a bond | NH | S | a bond | T3h | OH |
| 1219 | CH | NMe | Q1a | a bond | Me | a bond | NH | S | a bond | T3i | OH |
| 1220 | CH | NMe | Q1a | a bond | Me | a bond | NH | S | a bond | T3j | OH |
| 1221 | CH | NMe | Q1a | a bond | Me | a bond | NH | O | NH | T3a | OH |
| 1222 | CH | NMe | Q1a | a bond | Me | a bond | NH | O | NH | T3b | OH |
| 1223 | CH | NMe | Q1a | a bond | Me | a bond | NH | O | NH | T3c | OH |
| 1224 | CH | NMe | Q1a | a bond | Me | a bond | NH | O | NH | T3d | OH |
| 1225 | CH | NMe | Q1a | a bond | Me | a bond | NH | O | NH | T3e | OH |
| 1226 | CH | NMe | Q1a | a bond | Me | a bond | NH | O | NH | T3f | OH |
| 1227 | CH | NMe | Q1a | a bond | Me | a bond | NH | O | NH | T3g | OH |
| 1228 | CH | NMe | Q1a | a bond | Me | a bond | NH | O | NH | T3h | OH |
| 1229 | CH | NMe | Q1a | a bond | Me | a bond | NH | O | NH | T3i | OH |
| 1230 | CH | NMe | Q1a | a bond | Me | a bond | NH | O | NH | T3j | OH |
| 1231 | CH | NMe | Q1a | a bond | Me | a bond | NH | O | a bond | T3a | OH |
| 1232 | CH | NMe | Q1a | a bond | Me | a bond | NH | O | a bond | T3b | OH |
| 1233 | CH | NMe | Q1a | a bond | Me | a bond | NH | O | a bond | T3c | OH |
| 1234 | CH | NMe | Q1a | a bond | Me | a bond | NH | O | a bond | T3d | OH |
| 1235 | CH | NMe | Q1a | a bond | Me | a bond | NH | O | a bond | T3e | OH |
| 1236 | CH | NMe | Q1a | a bond | Me | a bond | NH | O | a bond | T3f | OH |
| 1237 | CH | NMe | Q1a | a bond | Me | a bond | NH | O | a bond | T3g | OH |
| 1238 | CH | NMe | Q1a | a bond | Me | a bond | NH | O | a bond | T3h | OH |
| 1239 | CH | NMe | Q1a | a bond | Me | a bond | NH | O | a bond | T3i | OH |
| 1240 | CH | NMe | Q1a | a bond | Me | a bond | NH | O | a bond | T3j | OH |
| 1241 | CH | NMe | Q1a | a bond | H | a bond | NH | S | NH | T3a | OH |
| 1242 | CH | NMe | Q1a | a bond | H | a bond | NH | S | NH | T3b | OH |
| 1243 | CH | NMe | Q1a | a bond | H | a bond | NH | S | NH | T3c | OH |
| 1244 | CH | NMe | Q1a | a bond | H | a bond | NH | S | NH | T3d | OH |
| 1245 | CH | NMe | Q1a | a bond | H | a bond | NH | S | NH | T3e | OH |
| 1246 | CH | NMe | Q1a | a bond | H | a bond | NH | S | NH | T3f | OH |
| 1247 | CH | NMe | Q1a | a bond | H | a bond | NH | S | NH | T3g | OH |
| 1248 | CH | NMe | Q1a | a bond | H | a bond | NH | S | NH | T3h | OH |
| 1249 | CH | NMe | Q1a | a bond | H | a bond | NH | S | NH | T3i | OH |
| 1250 | CH | NMe | Q1a | a bond | H | a bond | NH | S | NH | T3j | OH |
| 1251 | CH | NMe | Q1a | a bond | H | a bond | NH | S | a bond | T3a | OH |
| 1252 | CH | NMe | Q1a | a bond | H | a bond | NH | S | a bond | T3b | OH |
| 1253 | CH | NMe | Q1a | a bond | H | a bond | NH | S | a bond | T3c | OH |
| 1254 | CH | NMe | Q1a | a bond | H | a bond | NH | S | a bond | T3d | OH |
| 1255 | CH | NMe | Q1a | a bond | H | a bond | NH | S | a bond | T3e | OH |
| 1256 | CH | NMe | Q1a | a bond | H | a bond | NH | S | a bond | T3f | OH |
| 1257 | CH | NMe | Q1a | a bond | H | a bond | NH | S | a bond | T3g | OH |
| 1258 | CH | NMe | Q1a | a bond | H | a bond | NH | S | a bond | T3h | OH |
| 1259 | CH | NMe | Q1a | a bond | H | a bond | NH | S | a bond | T3i | OH |
| 1260 | CH | NMe | Q1a | a bond | H | a bond | NH | S | a bond | T3j | OH |
| 1261 | CH | NMe | Q1a | a bond | H | a bond | NH | O | NH | T3a | OH |
| 1262 | CH | NMe | Q1a | a bond | H | a bond | NH | O | NH | T3b | OH |
| 1263 | CH | NMe | Q1a | a bond | H | a bond | NH | O | NH | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 1264 | CH | NMe | Q1a | a bond | H | a bond | NH | O | NH | T3d | OH |
| 1265 | CH | NMe | Q1a | a bond | H | a bond | NH | O | NH | T3e | OH |
| 1266 | CH | NMe | Q1a | a bond | H | a bond | NH | O | NH | T3f | OH |
| 1267 | CH | NMe | Q1a | a bond | H | a bond | NH | O | NH | T3g | OH |
| 1268 | CH | NMe | Q1a | a bond | H | a bond | NH | O | NH | T3h | OH |
| 1269 | CH | NMe | Q1a | a bond | H | a bond | NH | O | NH | T3i | OH |
| 1270 | CH | NMe | Q1a | a bond | H | a bond | NH | O | NH | T3j | OH |
| 1271 | CH | NMe | Q1a | a bond | H | a bond | NH | O | a bond | T3a | OH |
| 1272 | CH | NMe | Q1a | a bond | H | a bond | NH | O | a bond | T3b | OH |
| 1273 | CH | NMe | Q1a | a bond | H | a bond | NH | O | a bond | T3c | OH |
| 1274 | CH | NMe | Q1a | a bond | H | a bond | NH | O | a bond | T3d | OH |
| 1275 | CH | NMe | Q1a | a bond | H | a bond | NH | O | a bond | T3e | OH |
| 1276 | CH | NMe | Q1a | a bond | H | a bond | NH | O | a bond | T3f | OH |
| 1277 | CH | NMe | Q1a | a bond | H | a bond | NH | O | a bond | T3g | OH |
| 1278 | CH | NMe | Q1a | a bond | H | a bond | NH | O | a bond | T3h | OH |
| 1279 | CH | NMe | Q1a | a bond | H | a bond | NH | O | a bond | T3i | OH |
| 1280 | NH | NMe | Q1a | a bond | H | a bond | NH | O | a bond | T3j | OH |
| 1281 | CH | NMe | Q1b | a bond | Me | a bond | NH | S | NH | T3a | OH |
| 1282 | CH | NMe | Q1b | a bond | Me | a bond | NH | S | NH | T3b | OH |
| 1283 | CH | NMe | Q1b | a bond | Me | a bond | NH | S | NH | T3c | OH |
| 1284 | CH | NMe | Q1b | a bond | Me | a bond | NH | S | NH | T3d | OH |
| 1285 | CH | NMe | Q1b | a bond | Me | a bond | NH | S | NH | T3e | OH |
| 1286 | CH | NMe | Q1b | a bond | Me | a bond | NH | S | NH | T3f | OH |
| 1287 | CH | NMe | Q1b | a bond | Me | a bond | NH | S | NH | T3g | OH |
| 1288 | CH | NMe | Q1b | a bond | Me | a bond | NH | S | NH | T3h | OH |
| 1289 | CH | NMe | Q1b | a bond | Me | a bond | NH | S | NH | T3i | OH |
| 1290 | CH | NMe | Q1b | a bond | Me | a bond | NH | S | NH | T3j | OH |
| 1291 | CH | NMe | Q1b | a bond | Me | a bond | NH | S | a bond | T3a | OH |
| 1292 | CH | NMe | Q1b | a bond | Me | a bond | NH | S | a bond | T3b | OH |
| 1293 | CH | NMe | Q1b | a bond | Me | a bond | NH | S | a bond | T3c | OH |
| 1294 | CH | NMe | Q1b | a bond | Me | a bond | NH | S | a bond | T3d | OH |
| 1295 | CH | NMe | Q1b | a bond | Me | a bond | NH | S | a bond | T3e | OH |
| 1296 | CH | NMe | Q1b | a bond | Me | a bond | NH | S | a bond | T3f | OH |
| 1297 | CH | NMe | Q1b | a bond | Me | a bond | NH | S | a bond | T3g | OH |
| 1298 | CH | NMe | Q1b | a bond | Me | a bond | NH | S | a bond | T3h | OH |
| 1299 | CH | NMe | Q1b | a bond | Me | a bond | NH | S | a bond | T3i | OH |
| 1300 | CH | NMe | Q1b | a bond | Me | a bond | NH | S | a bond | T3j | OH |
| 1301 | CH | NMe | Q1b | a bond | Me | a bond | NH | O | NH | T3a | OH |
| 1302 | CH | NMe | Q1b | a bond | Me | a bond | NH | O | NH | T3b | OH |
| 1303 | CH | NMe | Q1b | a bond | Me | a bond | NH | O | NH | T3c | OH |
| 1304 | CH | NMe | Q1b | a bond | Me | a bond | NH | O | NH | T3d | OH |
| 1305 | CH | NMe | Q1b | a bond | Me | a bond | NH | O | NH | T3e | OH |
| 1306 | CH | NMe | Q1b | a bond | Me | a bond | NH | O | NH | T3f | OH |
| 1307 | CH | NMe | Q1b | a bond | Me | a bond | NH | O | NH | T3g | OH |
| 1308 | CH | NMe | Q1b | a bond | Me | a bond | NH | O | NH | T3h | OH |
| 1309 | CH | NMe | Q1b | a bond | Me | a bond | NH | O | NH | T3i | OH |
| 1310 | CH | NMe | Q1b | a bond | Me | a bond | NH | O | NH | T3j | OH |
| 1311 | CH | NMe | Q1b | a bond | Me | a bond | NH | O | a bond | T3a | OH |
| 1312 | CH | NMe | Q1b | a bond | Me | a bond | NH | O | a bond | T3b | OH |
| 1313 | CH | NMe | Q1b | a bond | Me | a bond | NH | O | a bond | T3c | OH |
| 1314 | CH | NMe | Q1b | a bond | Me | a bond | NH | O | a bond | T3d | OH |
| 1315 | CH | NMe | Q1b | a bond | Me | a bond | NH | O | a bond | T3e | OH |
| 1316 | CH | NMe | Q1b | a bond | Me | a bond | NH | O | a bond | T3f | OH |
| 1317 | CH | NMe | Q1b | a bond | Me | a bond | NH | O | a bond | T3g | OH |
| 1318 | CH | NMe | Q1b | a bond | Me | a bond | NH | O | a bond | T3h | OH |
| 1319 | CH | NMe | Q1b | a bond | Me | a bond | NH | O | a bond | T3i | OH |
| 1320 | CH | NMe | Q1b | a bond | Me | a bond | NH | O | a bond | T3j | OH |
| 1321 | CH | NMe | Q1b | a bond | H | a bond | NH | S | NH | T3a | OH |
| 1322 | CH | NMe | Q1b | a bond | H | a bond | NH | S | NH | T3b | OH |
| 1323 | CH | NMe | Q1b | a bond | H | a bond | NH | S | NH | T3c | OH |
| 1324 | CH | NMe | Q1b | a bond | H | a bond | NH | S | NH | T3d | OH |
| 1325 | CH | NMe | Q1b | a bond | H | a bond | NH | S | NH | T3e | OH |
| 1326 | CH | NMe | Q1b | a bond | H | a bond | NH | S | NH | T3f | OH |
| 1327 | CH | NMe | Q1b | a bond | H | a bond | NH | S | NH | T3g | OH |
| 1328 | CH | NMe | Q1b | a bond | H | a bond | NH | S | NH | T3h | OH |
| 1329 | CH | NMe | Q1b | a bond | H | a bond | NH | S | NH | T3i | OH |
| 1330 | CH | NMe | Q1b | a bond | H | a bond | NH | S | NH | T3j | OH |
| 1331 | CH | NMe | Q1b | a bond | H | a bond | NH | S | a bond | T3a | OH |
| 1332 | CH | NMe | Q1b | a bond | H | a bond | NH | S | a bond | T3b | OH |
| 1333 | CH | NMe | Q1b | a bond | H | a bond | NH | S | a bond | T3c | OH |
| 1334 | CH | NMe | Q1b | a bond | H | a bond | NH | S | a bond | T3d | OH |
| 1335 | CH | NMe | Q1b | a bond | H | a bond | NH | S | a bond | T3e | OH |
| 1336 | CH | NMe | Q1b | a bond | H | a bond | NH | S | a bond | T3f | OH |
| 1337 | CH | NMe | Q1b | a bond | H | a bond | NH | S | a bond | T3g | OH |
| 1338 | CH | NMe | Q1b | a bond | H | a bond | NH | S | a bond | T3h | OH |
| 1339 | CH | NMe | Q1b | a bond | H | a bond | NH | S | a bond | T3i | OH |
| 1340 | CH | NMe | Q1b | a bond | H | a bond | NH | S | a bond | T3j | OH |
| 1341 | CH | NMe | Q1b | a bond | H | a bond | NH | O | NH | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 1342 | CH | NMe | Q1b | a bond | H | a bond | NH | O | NH | T3b | OH |
| 1343 | CH | NMe | Q1b | a bond | H | a bond | NH | O | NH | T3c | OH |
| 1344 | CH | NMe | Q1b | a bond | H | a bond | NH | O | NH | T3d | OH |
| 1345 | CH | NMe | Q1b | a bond | H | a bond | NH | O | NH | T3e | OH |
| 1346 | CH | NMe | Q1b | a bond | H | a bond | NH | O | NH | T3f | OH |
| 1347 | CH | NMe | Q1b | a bond | H | a bond | NH | O | NH | T3g | OH |
| 1348 | CH | NMe | Q1b | a bond | H | a bond | NH | O | NH | T3h | OH |
| 1349 | CH | NMe | Q1b | a bond | H | a bond | NH | O | NH | T3i | OH |
| 1350 | CH | NMe | Q1b | a bond | H | a bond | NH | O | NH | T3j | OH |
| 1351 | CH | NMe | Q1b | a bond | H | a bond | NH | O | a bond | T3a | OH |
| 1352 | CH | NMe | Q1b | a bond | H | a bond | NH | O | a bond | T3b | OH |
| 1353 | CH | NMe | Q1b | a bond | H | a bond | NH | O | a bond | T3c | OH |
| 1354 | CH | NMe | Q1b | a bond | H | a bond | NH | O | a bond | T3d | OH |
| 1355 | CH | NMe | Q1b | a bond | H | a bond | NH | O | a bond | T3e | OH |
| 1356 | CH | NMe | Q1b | a bond | H | a bond | NH | O | a bond | T3f | OH |
| 1357 | CH | NMe | Q1b | a bond | H | a bond | NH | O | a bond | T3g | OH |
| 1358 | CH | NMe | Q1b | a bond | H | a bond | NH | O | a bond | T3h | OH |
| 1359 | CH | NMe | Q1b | a bond | H | a bond | NH | O | a bond | T3i | OH |
| 1360 | CH | NMe | Q1b | a bond | H | a bond | NH | O | a bond | T3j | OH |
| 1361 | CH | NMe | Q1c | a bond | Me | a bond | NH | S | NH | T3a | OH |
| 1362 | CH | NMe | Q1c | a bond | Me | a bond | NH | S | NH | T3b | OH |
| 1363 | CH | NMe | Q1c | a bond | Me | a bond | NH | S | NH | T3c | OH |
| 1364 | CH | NMe | Q1c | a bond | Me | a bond | NH | S | NH | T3d | OH |
| 1365 | CH | NMe | Q1c | a bond | Me | a bond | NH | S | NH | T3e | OH |
| 1366 | CH | NMe | Q1c | a bond | Me | a bond | NH | S | NH | T3f | OH |
| 1367 | CH | NMe | Q1c | a bond | Me | a bond | NH | S | NH | T3g | OH |
| 1368 | CH | NMe | Q1c | a bond | Me | a bond | NH | S | NH | T3h | OH |
| 1369 | CH | NMe | Q1c | a bond | Me | a bond | NH | S | NH | T3i | OH |
| 1370 | CH | NMe | Q1c | a bond | Me | a bond | NH | S | NH | T3j | OH |
| 1371 | CH | NMe | Q1c | a bond | Me | a bond | NH | S | a bond | T3a | OH |
| 1372 | CH | NMe | Q1c | a bond | Me | a bond | NH | S | a bond | T3b | OH |
| 1373 | CH | NMe | Q1c | a bond | Me | a bond | NH | S | a bond | T3c | OH |
| 1374 | CH | NMe | Q1c | a bond | Me | a bond | NH | S | a bond | T3d | OH |
| 1375 | CH | NMe | Q1c | a bond | Me | a bond | NH | S | a bond | T3e | OH |
| 1376 | CH | NMe | Q1c | a bond | Me | a bond | NH | S | a bond | T3f | OH |
| 1377 | CH | NMe | Q1c | a bond | Me | a bond | NH | S | a bond | T3g | OH |
| 1378 | CH | NMe | Q1c | a bond | Me | a bond | NH | S | a bond | T3h | OH |
| 1379 | CH | NMe | Q1c | a bond | Me | a bond | NH | S | a bond | T3i | OH |
| 1380 | CH | NMe | Q1c | a bond | Me | a bond | NH | S | a bond | T3j | OH |
| 1381 | CH | NMe | Q1c | a bond | Me | a bond | NH | O | NH | T3a | OH |
| 1382 | CH | NMe | Q1c | a bond | Me | a bond | NH | O | NH | T3b | OH |
| 1383 | CH | NMe | Q1c | a bond | Me | a bond | NH | O | NH | T3c | OH |
| 1384 | CH | NMe | Q1c | a bond | Me | a bond | NH | O | NH | T3d | OH |
| 1385 | CH | NMe | Q1c | a bond | Me | a bond | NH | O | NH | T3e | OH |
| 1386 | CH | NMe | Q1c | a bond | Me | a bond | NH | O | NH | T3f | OH |
| 1387 | CH | NMe | Q1c | a bond | Me | a bond | NH | O | NH | T3g | OH |
| 1388 | CH | NMe | Q1c | a bond | Me | a bond | NH | O | NH | T3h | OH |
| 1389 | CH | NMe | Q1c | a bond | Me | a bond | NH | O | NH | T3i | OH |
| 1390 | CH | NMe | Q1c | a bond | Me | a bond | NH | O | NH | T3j | OH |
| 1391 | CH | NMe | Q1c | a bond | Me | a bond | NH | O | a bond | T3a | OH |
| 1392 | CH | NMe | Q1c | a bond | Me | a bond | NH | O | a bond | T3b | OH |
| 1393 | CH | NMe | Q1c | a bond | Me | a bond | NH | O | a bond | T3c | OH |
| 1394 | CH | NMe | Q1c | a bond | Me | a bond | NH | O | a bond | T3d | OH |
| 1395 | CH | NMe | Q1c | a bond | Me | a bond | NH | O | a bond | T3e | OH |
| 1396 | CH | NMe | Q1c | a bond | Me | a bond | NH | O | a bond | T3f | OH |
| 1397 | CH | NMe | Q1c | a bond | Me | a bond | NH | O | a bond | T3g | OH |
| 1398 | CH | NMe | Q1c | a bond | Me | a bond | NH | O | a bond | T3h | OH |
| 1399 | CH | NMe | Q1c | a bond | Me | a bond | NH | O | a bond | T3i | OH |
| 1400 | CH | NMe | Q1c | a bond | Me | a bond | NH | O | a bond | T3j | OH |
| 1401 | CH | NMe | Q1c | a bond | H | a bond | NH | S | NH | T3a | OH |
| 1402 | CH | NMe | Q1c | a bond | H | a bond | NH | S | NH | T3b | OH |
| 1403 | CH | NMe | Q1c | a bond | H | a bond | NH | S | NH | T3c | OH |
| 1404 | CH | NMe | Q1c | a bond | H | a bond | NH | S | NH | T3d | OH |
| 1405 | CH | NMe | Q1c | a bond | H | a bond | NH | S | NH | T3e | OH |
| 1406 | CH | NMe | Q1c | a bond | H | a bond | NH | S | NH | T3f | OH |
| 1407 | CH | NMe | Q1c | a bond | H | a bond | NH | S | NH | T3g | OH |
| 1408 | CH | NMe | Q1c | a bond | H | a bond | NH | S | NH | T3h | OH |
| 1409 | CH | NMe | Q1c | a bond | H | a bond | NH | S | NH | T3i | OH |
| 1410 | CH | NMe | Q1c | a bond | H | a bond | NH | S | NH | T3j | OH |
| 1411 | CH | NMe | Q1c | a bond | H | a bond | NH | S | a bond | T3a | OH |
| 1412 | CH | NMe | Q1c | a bond | H | a bond | NH | S | a bond | T3b | OH |
| 1413 | CH | NMe | Q1c | a bond | H | a bond | NH | S | a bond | T3c | OH |
| 1414 | CH | NMe | Q1c | a bond | H | a bond | NH | S | a bond | T3d | OH |
| 1415 | CH | NMe | Q1c | a bond | H | a bond | NH | S | a bond | T3e | OH |
| 1416 | CH | NMe | Q1c | a bond | H | a bond | NH | S | a bond | T3f | OH |
| 1417 | CH | NMe | Q1c | a bond | H | a bond | NH | S | a bond | T3g | OH |
| 1418 | CH | NMe | Q1c | a bond | H | a bond | NH | S | a bond | T3h | OH |
| 1419 | CH | NMe | Q1c | a bond | H | a bond | NH | S | a bond | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 1420 | CH | NMe | Q1c | a bond | H | a bond | NH | S | a bond | T3j | OH |
| 1421 | CH | NMe | Q1c | a bond | H | a bond | NH | O | NH | T3a | OH |
| 1422 | CH | NMe | Q1c | a bond | H | a bond | NH | O | NH | T3b | OH |
| 1423 | CH | NMe | Q1c | a bond | H | a bond | NH | O | NH | T3c | OH |
| 1424 | CH | NMe | Q1c | a bond | H | a bond | NH | O | NH | T3d | OH |
| 1425 | CH | NMe | Q1c | a bond | H | a bond | NH | O | NH | T3e | OH |
| 1426 | CH | NMe | Q1c | a bond | H | a bond | NH | O | NH | T3f | OH |
| 1427 | CH | NMe | Q1c | a bond | H | a bond | NH | O | NH | T3g | OH |
| 1428 | CH | NMe | Q1c | a bond | H | a bond | NH | O | NH | T3h | OH |
| 1429 | CH | NMe | Q1c | a bond | H | a bond | NH | O | NH | T3i | OH |
| 1430 | CH | NMe | Q1c | a bond | H | a bond | NH | O | NH | T3j | OH |
| 1431 | CH | NMe | Q1c | a bond | H | a bond | NH | O | a bond | T3a | OH |
| 1432 | CH | NMe | Q1c | a bond | H | a bond | NH | O | a bond | T3b | OH |
| 1433 | CH | NMe | Q1c | a bond | H | a bond | NH | O | a bond | T3c | OH |
| 1434 | CH | NMe | Q1c | a bond | H | a bond | NH | O | a bond | T3d | OH |
| 1435 | CH | NMe | Q1c | a bond | H | a bond | NH | O | a bond | T3e | OH |
| 1436 | CH | NMe | Q1c | a bond | H | a bond | NH | O | a bond | T3f | OH |
| 1437 | CH | NMe | Q1c | a bond | H | a bond | NH | O | a bond | T3g | OH |
| 1438 | CH | NMe | Q1c | a bond | H | a bond | NH | O | a bond | T3h | OH |
| 1439 | CH | NMe | Q1c | a bond | H | a bond | NH | O | a bond | T3i | OH |
| 1440 | CH | NMe | Q1c | a bond | H | a bond | NH | O | a bond | T3j | OH |
| 1441 | CH | NMe | Q1i | a bond | Me | a bond | NH | S | NH | T3a | OH |
| 1442 | CH | NMe | Q1i | a bond | Me | a bond | NH | S | NH | T3b | OH |
| 1443 | CH | NMe | Q1i | a bond | Me | a bond | NH | S | NH | T3c | OH |
| 1444 | CH | NMe | Q1i | a bond | Me | a bond | NH | S | NH | T3d | OH |
| 1445 | CH | NMe | Q1i | a bond | Me | a bond | NH | S | NH | T3e | OH |
| 1446 | CH | NMe | Q1i | a bond | Me | a bond | NH | S | NH | T3f | OH |
| 1447 | CH | NMe | Q1i | a bond | Me | a bond | NH | S | NH | T3g | OH |
| 1448 | CH | NMe | Q1i | a bond | Me | a bond | NH | S | NH | T3h | OH |
| 1449 | CH | NMe | Q1i | a bond | Me | a bond | NH | S | NH | T3i | OH |
| 1450 | CH | NMe | Q1i | a bond | Me | a bond | NH | S | NH | T3j | OH |
| 1451 | CH | NMe | Q1i | a bond | Me | a bond | NH | S | a bond | T3a | OH |
| 1452 | CH | NMe | Q1i | a bond | Me | a bond | NH | S | a bond | T3b | OH |
| 1453 | CH | NMe | Q1i | a bond | Me | a bond | NH | S | a bond | T3c | OH |
| 1454 | CH | NMe | Q1i | a bond | Me | a bond | NH | S | a bond | T3d | OH |
| 1455 | CH | NMe | Q1i | a bond | Me | a bond | NH | S | a bond | T3e | OH |
| 1456 | CH | NMe | Q1i | a bond | Me | a bond | NH | S | a bond | T3f | OH |
| 1457 | CH | NMe | Q1i | a bond | Me | a bond | NH | S | a bond | T3g | OH |
| 1458 | CH | NMe | Q1i | a bond | Me | a bond | NH | S | a bond | T3h | OH |
| 1459 | CH | NMe | Q1i | a bond | Me | a bond | NH | S | a bond | T3i | OH |
| 1460 | CH | NMe | Q1i | a bond | Me | a bond | NH | S | a bond | T3j | OH |
| 1461 | CH | NMe | Q1i | a bond | Me | a bond | NH | O | NH | T3a | OH |
| 1462 | CH | NMe | Q1i | a bond | Me | a bond | NH | O | NH | T3b | OH |
| 1463 | CH | NMe | Q1i | a bond | Me | a bond | NH | O | NH | T3c | OH |
| 1464 | CH | NMe | Q1i | a bond | Me | a bond | NH | O | NH | T3d | OH |
| 1465 | CH | NMe | Q1i | a bond | Me | a bond | NH | O | NH | T3e | OH |
| 1466 | CH | NMe | Q1i | a bond | Me | a bond | NH | O | NH | T3f | OH |
| 1467 | CH | NMe | Q1i | a bond | Me | a bond | NH | O | NH | T3g | OH |
| 1468 | CH | NMe | Q1i | a bond | Me | a bond | NH | O | NH | T3h | OH |
| 1469 | CH | NMe | Q1i | a bond | Me | a bond | NH | O | NH | T3i | OH |
| 1470 | CH | NMe | Q1i | a bond | Me | a bond | NH | O | NH | T3j | OH |
| 1471 | CH | NMe | Q1i | a bond | Me | a bond | NH | O | a bond | T3a | OH |
| 1472 | CH | NMe | Q1i | a bond | Me | a bond | NH | O | a bond | T3b | OH |
| 1473 | CH | NMe | Q1i | a bond | Me | a bond | NH | O | a bond | T3c | OH |
| 1474 | CH | NMe | Q1i | a bond | Me | a bond | NH | O | a bond | T3d | OH |
| 1475 | CH | NMe | Q1i | a bond | Me | a bond | NH | O | a bond | T3e | OH |
| 1476 | CH | NMe | Q1i | a bond | Me | a bond | NH | O | a bond | T3f | OH |
| 1477 | CH | NMe | Q1i | a bond | Me | a bond | NH | O | a bond | T3g | OH |
| 1478 | CH | NMe | Q1i | a bond | Me | a bond | NH | O | a bond | T3h | OH |
| 1479 | CH | NMe | Q1i | a bond | Me | a bond | NH | O | a bond | T3i | OH |
| 1480 | CH | NMe | Q1i | a bond | Me | a bond | NH | O | a bond | T3j | OH |
| 1481 | CH | NMe | Q1i | a bond | H | a bond | NH | S | NH | T3a | OH |
| 1482 | CH | NMe | Q1i | a bond | H | a bond | NH | S | NH | T3b | OH |
| 1483 | CH | NMe | Q1i | a bond | H | a bond | NH | S | NH | T3c | OH |
| 1484 | CH | NMe | Q1i | a bond | H | a bond | NH | S | NH | T3d | OH |
| 1485 | CH | NMe | Q1i | a bond | N | a bond | NH | S | NH | T3e | OH |
| 1486 | CH | NMe | Q1i | a bond | H | a bond | NH | S | NH | T3f | OH |
| 1487 | CH | NMe | Q1i | a bond | H | a bond | NH | S | NH | T3g | OH |
| 1488 | CH | NMe | Q1i | a bond | H | a bond | NH | S | NH | T3h | OH |
| 1489 | CH | NMe | Q1i | a bond | H | a bond | NH | S | NH | T3i | OH |
| 1490 | CH | NMe | Q1i | a bond | H | a bond | NH | S | NH | T3j | OH |
| 1491 | CH | NMe | Q1i | a bond | H | a bond | NH | S | a bond | T3a | OH |
| 1492 | CH | NMe | Q1i | a bond | H | a bond | NH | S | a bond | T3b | OH |
| 1493 | CH | NMe | Q1i | a bond | H | a bond | NH | S | a bond | T3c | OH |
| 1494 | CH | NMe | Q1i | a bond | H | a bond | NH | S | a bond | T3d | OH |
| 1495 | CH | NMe | Q1i | a bond | H | a bond | NH | S | a bond | T3e | OH |
| 1496 | CH | NMe | Q1i | a bond | H | a bond | NH | S | a bond | T3f | OH |
| 1497 | CH | NMe | Q1i | a bond | H | a bond | NH | S | a bond | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 1498 | CH | NMe | Q1i | a bond | H | a bond | NH | S | a bond | T3h | OH |
| 1499 | CH | NMe | Q1i | a bond | H | a bond | NH | S | a bond | T3i | OH |
| 1500 | CH | NMe | Q1i | a bond | H | a bond | NH | S | a bond | T3j | OH |
| 1501 | CH | NMe | Q1i | a bond | H | a bond | NH | O | NH | T3a | OH |
| 1502 | CH | NMe | Q1i | a bond | H | a bond | NH | O | NH | T3b | OH |
| 1503 | CH | NMe | Q1i | a bond | H | a bond | NH | O | NH | T3c | OH |
| 1504 | CH | NMe | Q1i | a bond | H | a bond | NH | O | NH | T3d | OH |
| 1505 | CH | NMe | Q1i | a bond | H | a bond | NH | O | NH | T3e | OH |
| 1506 | CH | NMe | Q1i | a bond | H | a bond | NH | O | NH | T3f | OH |
| 1507 | CH | NMe | Q1i | a bond | H | a bond | NH | O | NH | T3g | OH |
| 1508 | CH | NMe | Q1i | a bond | H | a bond | NH | O | NH | T3h | OH |
| 1509 | CH | NMe | Q1i | a bond | H | a bond | NH | O | NH | T3i | OH |
| 1510 | CH | NMe | Q1i | a bond | H | a bond | NH | O | NH | T3j | OH |
| 1511 | CH | NMe | Q1i | a bond | H | a bond | NH | O | a bond | T3a | OH |
| 1512 | CH | NMe | Q1i | a bond | H | a bond | NH | O | a bond | T3b | OH |
| 1513 | CH | NMe | Q1i | a bond | H | a bond | NH | O | a bond | T3c | OH |
| 1514 | CH | NMe | Q1i | a bond | H | a bond | NH | O | a bond | T3d | OH |
| 1515 | CH | NMe | Q1i | a bond | H | a bond | NH | O | a bond | T3e | OH |
| 1516 | CH | NMe | Q1i | a bond | H | a bond | NH | O | a bond | T3f | OH |
| 1517 | CH | NMe | Q1i | a bond | H | a bond | NH | O | a bond | T3g | OH |
| 1518 | CH | NMe | Q1i | a bond | H | a bond | NH | O | a bond | T3h | OH |
| 1519 | CH | NMe | Q1i | a bond | H | a bond | NH | O | a bond | T3i | OH |
| 1520 | CH | NMe | Q1i | a bond | H | a bond | NH | O | a bond | T3j | OH |
| 1521 | CH | NMe | Q1j | a bond | Me | a bond | NH | S | NH | T3a | OH |
| 1522 | CH | NMe | Q1j | a bond | Me | a bond | NH | S | NH | T3b | OH |
| 1523 | CH | NMe | Q1j | a bond | Me | a bond | NH | S | NH | T3c | OH |
| 1524 | CH | NMe | Q1j | a bond | Me | a bond | NH | S | NH | T3d | OH |
| 1525 | CH | NMe | Q1j | a bond | Me | a bond | NH | S | NH | T3e | OH |
| 1526 | CH | NMe | Q1j | a bond | Me | a bond | NH | S | NH | T3f | OH |
| 1527 | CH | NMe | Q1j | a bond | Me | a bond | NH | S | NH | T3g | OH |
| 1528 | CH | NMe | Q1j | a bond | Me | a bond | NH | S | NH | T3h | OH |
| 1529 | CH | NMe | Q1j | a bond | Me | a bond | NH | S | NH | T3i | OH |
| 1530 | CH | NMe | Q1j | a bond | Me | a bond | NH | S | NH | T3j | OH |
| 1531 | CH | NMe | Q1j | a bond | Me | a bond | NH | S | a bond | T3a | OH |
| 1532 | CH | NMe | Q1j | a bond | Me | a bond | NH | S | a bond | T3b | OH |
| 1533 | CH | NMe | Q1j | a bond | Me | a bond | NH | S | a bond | T3c | OH |
| 1534 | CH | NMe | Q1j | a bond | Me | a bond | NH | S | a bond | T3d | OH |
| 1535 | CH | NMe | Q1j | a bond | Me | a bond | NH | S | a bond | T3e | OH |
| 1536 | CH | NMe | Q1j | a bond | Me | a bond | NH | S | a bond | T3f | OH |
| 1537 | CH | NMe | Q1j | a bond | Me | a bond | NH | S | a bond | T3g | OH |
| 1538 | CH | NMe | Q1j | a bond | Me | a bond | NH | S | a bond | T3h | OH |
| 1539 | CH | NMe | Q1j | a bond | Me | a bond | NH | S | a bond | T3i | OH |
| 1540 | CH | NMe | Q1j | a bond | Me | a bond | NH | S | a bond | T3j | OH |
| 1541 | CH | NMe | Q1j | a bond | Me | a bond | NH | O | NH | T3a | OH |
| 1542 | CH | NMe | Q1j | a bond | Me | a bond | NH | O | NH | T3b | OH |
| 1543 | CH | NMe | Q1j | a bond | Me | a bond | NH | O | NH | T3c | OH |
| 1544 | CH | NMe | Q1j | a bond | Me | a bond | NH | O | NH | T3d | OH |
| 1545 | CH | NMe | Q1j | a bond | Me | a bond | NH | O | NH | T3e | OH |
| 1546 | CH | NMe | Q1j | a bond | Me | a bond | NH | O | NH | T3f | OH |
| 1547 | CH | NMe | Q1j | a bond | Me | a bond | NH | O | NH | T3g | OH |
| 1548 | CH | NMe | Q1j | a bond | Me | a bond | NH | O | NH | T3h | OH |
| 1549 | CH | NMe | Q1j | a bond | Me | a bond | NH | O | NH | T3i | OH |
| 1550 | CH | NMe | Q1j | a bond | Me | a bond | NH | O | NH | T3j | OH |
| 1551 | CH | NMe | Q1j | a bond | Me | a bond | NH | O | a bond | T3a | OH |
| 1552 | CH | NMe | Q1j | a bond | Me | a bond | NH | O | a bond | T3b | OH |
| 1553 | CH | NMe | Q1j | a bond | Me | a bond | NH | O | a bond | T3c | OH |
| 1554 | CH | NMe | Q1j | a bond | Me | a bond | NH | O | a bond | T3d | OH |
| 1555 | CH | NMe | Q1j | a bond | Me | a bond | NH | O | a bond | T3e | OH |
| 1556 | CH | NMe | Q1j | a bond | Me | a bond | NH | O | a bond | T3f | OH |
| 1557 | CH | NMe | Q1j | a bond | Me | a bond | NH | O | a bond | T3g | OH |
| 1558 | CH | NMe | Q1j | a bond | Me | a bond | NH | O | a bond | T3h | OH |
| 1559 | CH | NMe | Q1j | a bond | Me | a bond | NH | O | a bond | T3i | OH |
| 1560 | CH | NMe | Q1j | a bond | Me | a bond | NH | O | a bond | T3j | OH |
| 1561 | CH | NMe | Q1j | a bond | H | a bond | NH | S | NH | T3a | OH |
| 1562 | CH | NMe | Q1j | a bond | H | a bond | NH | S | NH | T3b | OH |
| 1563 | CH | NMe | Q1j | a bond | H | a bond | NH | S | NH | T3c | OH |
| 1564 | CH | NMe | Q1j | a bond | H | a bond | NH | S | NH | T3d | OH |
| 1565 | CH | NMe | Q1j | a bond | H | a bond | NH | S | NH | T3e | OH |
| 1566 | CH | NMe | Q1j | a bond | H | a bond | NH | S | NH | T3f | OH |
| 1567 | CH | NMe | Q1j | a bond | H | a bond | NH | S | NH | T3g | OH |
| 1568 | CH | NMe | Q1j | a bond | H | a bond | NH | S | NH | T3h | OH |
| 1569 | CH | NMe | Q1j | a bond | H | a bond | NH | S | NH | T3i | OH |
| 1570 | CH | NMe | Q1j | a bond | H | a bond | NH | S | NH | T3j | OH |
| 1571 | CH | NMe | Q1j | a bond | H | a bond | NH | S | a bond | T3a | OH |
| 1572 | CH | NMe | Q1j | a bond | H | a bond | NH | S | a bond | T3b | OH |
| 1573 | CH | NMe | Q1j | a bond | H | a bond | NH | S | a bond | T3c | OH |
| 1574 | CH | NMe | Q1j | a bond | H | a bond | NH | S | a bond | T3d | OH |
| 1575 | CH | NMe | Q1j | a bond | H | a bond | NH | S | a bond | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 1576 | CH | NMe | Q1j | a bond | H | a bond | NH | S | a bond | T3f | OH |
| 1577 | CH | NMe | Q1j | a bond | H | a bond | NH | S | a bond | T3g | OH |
| 1578 | CH | NMe | Q1j | a bond | H | a bond | NH | S | a bond | T3h | OH |
| 1579 | CH | NMe | Q1j | a bond | H | a bond | NH | S | a bond | T3i | OH |
| 1580 | CH | NMe | Q1j | a bond | H | a bond | NH | S | a bond | T3j | OH |
| 1581 | CH | NMe | Q1j | a bond | H | a bond | NH | O | NH | T3a | OH |
| 1582 | CH | NMe | Q1j | a bond | H | a bond | NH | O | NH | T3b | OH |
| 1583 | CH | NMe | Q1j | a bond | H | a bond | NH | O | NH | T3c | OH |
| 1584 | CH | NMe | Q1j | a bond | H | a bond | NH | O | NH | T3d | OH |
| 1585 | CH | NMe | Q1j | a bond | H | a bond | NH | O | NH | T3e | OH |
| 1586 | CH | NMe | Q1j | a bond | H | a bond | NH | O | NH | T3f | OH |
| 1587 | CH | NMe | Q1j | a bond | H | a bond | NH | O | NH | T3g | OH |
| 1588 | CH | NMe | Q1j | a bond | H | a bond | NH | O | NH | T3h | OH |
| 1589 | CH | NMe | Q1j | a bond | H | a bond | NH | O | NH | T3i | OH |
| 1590 | CH | NMe | Q1j | a bond | H | a bond | NH | O | NH | T3j | OH |
| 1591 | CH | NMe | Q1j | a bond | H | a bond | NH | O | a bond | T3a | OH |
| 1592 | CH | NMe | Q1j | a bond | H | a bond | NH | O | a bond | T3b | OH |
| 1593 | CH | NMe | Q1j | a bond | H | a bond | NH | O | a bond | T3c | OH |
| 1594 | CH | NMe | Q1j | a bond | H | a bond | NH | O | a bond | T3d | OH |
| 1595 | CH | NMe | Q1j | a bond | H | a bond | NH | O | a bond | T3e | OH |
| 1596 | CH | NMe | Q1j | a bond | H | a bond | NH | O | a bond | T3f | OH |
| 1597 | CH | NMe | Q1j | a bond | H | a bond | NH | O | a bond | T3g | OH |
| 1598 | CH | NMe | Q1j | a bond | H | a bond | NH | O | a bond | T3h | OH |
| 1599 | CH | NMe | Q1j | a bond | H | a bond | NH | O | a bond | T3i | OH |
| 1600 | CH | NMe | Q1j | a bond | H | a bond | NH | O | a bond | T3j | OH |
| 1601 | CH | S | Q1a | a bond | Me | a bond | NH | S | NH | T3a | OH |
| 1602 | CH | S | Q1a | a bond | Me | a bond | NH | S | NH | T3b | OH |
| 1603 | CH | S | Q1a | a bond | Me | a bond | NH | S | NH | T3c | OH |
| 1604 | CH | S | Q1a | a bond | Me | a bond | NH | S | NH | T3d | OH |
| 1605 | CH | S | Q1a | a bond | Me | a bond | NH | S | NH | T3e | OH |
| 1606 | CH | S | Q1a | a bond | Me | a bond | NH | S | NH | T3f | OH |
| 1607 | CH | S | Q1a | a bond | Me | a bond | NH | S | NH | T3g | OH |
| 1608 | CH | S | Q1a | a bond | Me | a bond | NH | S | NH | T3h | OH |
| 1609 | CH | S | Q1a | a bond | Me | a bond | NH | S | NH | T3i | OH |
| 1610 | CH | S | Q1a | a bond | Me | a bond | NH | S | NH | T3j | OH |
| 1611 | CH | S | Q1a | a bond | Me | a bond | NH | S | a bond | T3a | OH |
| 1612 | CH | S | Q1a | a bond | Me | a bond | NH | S | a bond | T3b | OH |
| 1613 | CH | S | Q1a | a bond | Me | a bond | NH | S | a bond | T3c | OH |
| 1614 | CH | S | Q1a | a bond | Me | a bond | NH | S | a bond | T3d | OH |
| 1615 | CH | S | Q1a | a bond | Me | a bond | NH | S | a bond | T3e | OH |
| 1616 | CH | S | Q1a | a bond | Me | a bond | NH | S | a bond | T3f | OH |
| 1617 | CH | S | Q1a | a bond | Me | a bond | NH | S | a bond | T3g | OH |
| 1618 | CH | S | Q1a | a bond | Me | a bond | NH | S | a bond | T3h | OH |
| 1619 | CH | S | Q1a | a bond | Me | a bond | NH | S | a bond | T3i | OH |
| 1620 | CH | S | Q1a | a bond | Me | a bond | NH | S | a bond | T3j | OH |
| 1621 | CH | S | Q1a | a bond | Me | a bond | NH | O | NH | T3a | OH |
| 1622 | CH | S | Q1a | a bond | Me | a bond | NH | O | NH | T3b | OH |
| 1623 | CH | S | Q1a | a bond | Me | a bond | NH | O | NH | T3c | OH |
| 1624 | CH | S | Q1a | a bond | Me | a bond | NH | O | NH | T3d | OH |
| 1625 | CH | S | Q1a | a bond | Me | a bond | NH | O | NH | T3e | OH |
| 1626 | CH | S | Q1a | a bond | Me | a bond | NH | O | NH | T3f | OH |
| 1627 | CH | S | Q1a | a bond | Me | a bond | NH | O | NH | T3g | OH |
| 1628 | CH | S | Q1a | a bond | Me | a bond | NH | O | NH | T3h | OH |
| 1629 | CH | S | Q1a | a bond | Me | a bond | NH | O | NH | T3i | OH |
| 1630 | CH | S | Q1a | a bond | Me | a bond | NH | O | NH | T3j | OH |
| 1631 | CH | S | Q1a | a bond | Me | a bond | NH | O | a bond | T3a | OH |
| 1632 | CH | S | Q1a | a bond | Me | a bond | NH | O | a bond | T3b | OH |
| 1633 | CH | S | Q1a | a bond | Me | a bond | NH | O | a bond | T3c | OH |
| 1634 | CH | S | Q1a | a bond | Me | a bond | NH | O | a bond | T3d | OH |
| 1635 | CH | S | Q1a | a bond | Me | a bond | NH | O | a bond | T3e | OH |
| 1636 | CH | S | Q1a | a bond | Me | a bond | NH | O | a bond | T3f | OH |
| 1637 | CH | S | Q1a | a bond | Me | a bond | NH | O | a bond | T3g | OH |
| 1638 | CH | S | Q1a | a bond | Me | a bond | NH | O | a bond | T3h | OH |
| 1639 | CH | S | Q1a | a bond | Me | a bond | NH | O | a bond | T3i | OH |
| 1640 | CH | S | Q1a | a bond | Me | a bond | NH | O | a bond | T3j | OH |
| 1641 | CH | S | Q1a | a bond | H | a bond | NH | S | NH | T3a | OH |
| 1642 | CH | S | Q1a | a bond | H | a bond | NH | S | NH | T3b | OH |
| 1643 | CH | S | Q1a | a bond | H | a bond | NH | S | NH | T3c | OH |
| 1644 | CH | S | Q1a | a bond | H | a bond | NH | S | NH | T3d | OH |
| 1645 | CH | S | Q1a | a bond | H | a bond | NH | S | NH | T3e | OH |
| 1646 | CH | S | Q1a | a bond | H | a bond | NH | S | NH | T3f | OH |
| 1647 | CH | S | Q1a | a bond | H | a bond | NH | S | NH | T3g | OH |
| 1648 | CH | S | Q1a | a bond | H | a bond | NH | S | NH | T3h | OH |
| 1649 | CH | S | Q1a | a bond | H | a bond | NH | S | NH | T3i | OH |
| 1650 | CH | S | Q1a | a bond | H | a bond | NH | S | NH | T3j | OH |
| 1651 | CH | S | Q1a | a bond | H | a bond | NH | S | a bond | T3a | OH |
| 1652 | CH | S | Q1a | a bond | H | a bond | NH | S | a bond | T3b | OH |
| 1653 | CH | S | Q1a | a bond | H | a bond | NH | S | a bond | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 1654 | CH | S | Q1a | a bond | H | a bond | NH | S | a bond | T3d | OH |
| 1655 | CH | S | Q1a | a bond | H | a bond | NH | S | a bond | T3e | OH |
| 1656 | CH | S | Q1a | a bond | H | a bond | NH | S | a bond | T3f | OH |
| 1657 | CH | S | Q1a | a bond | H | a bond | NH | S | a bond | T3g | OH |
| 1658 | CH | S | Q1a | a bond | H | a bond | NH | S | a bond | T3h | OH |
| 1659 | CH | S | Q1a | a bond | H | a bond | NH | S | a bond | T3i | OH |
| 1660 | CH | S | Q1a | a bond | H | a bond | NH | S | a bond | T3j | OH |
| 1661 | CH | S | Q1a | a bond | H | a bond | NH | O | NH | T3a | OH |
| 1662 | CH | S | Q1a | a bond | H | a bond | NH | O | NH | T3b | OH |
| 1663 | CH | S | Q1a | a bond | H | a bond | NH | O | NH | T3c | OH |
| 1664 | CH | S | Q1a | a bond | H | a bond | NH | O | NH | T3d | OH |
| 1665 | CH | S | Q1a | a bond | H | a bond | NH | O | NH | T3e | OH |
| 1666 | CH | S | Q1a | a bond | H | a bond | NH | O | NH | T3f | OH |
| 1667 | CH | S | Q1a | a bond | H | a bond | NH | O | NH | T3g | OH |
| 1668 | CH | S | Q1a | a bond | H | a bond | NH | O | NH | T3h | OH |
| 1669 | CH | S | Q1a | a bond | H | a bond | NH | O | NH | T3i | OH |
| 1670 | CH | S | Q1a | a bond | H | a bond | NH | O | NH | T3j | OH |
| 1671 | CH | S | Q1a | a bond | H | a bond | NH | O | a bond | T3a | OH |
| 1672 | CH | S | Q1a | a bond | H | a bond | NH | O | a bond | T3b | OH |
| 1673 | CH | S | Q1a | a bond | H | a bond | NH | O | a bond | T3c | OH |
| 1674 | CH | S | Q1a | a bond | H | a bond | NH | O | a bond | T3d | OH |
| 1675 | CH | S | Q1a | a bond | H | a bond | NH | O | a bond | T3e | OH |
| 1676 | CH | S | Q1a | a bond | H | a bond | NH | O | a bond | T3f | OH |
| 1677 | CH | S | Q1a | a bond | H | a bond | NH | O | a bond | T3g | OH |
| 1678 | CH | S | Q1a | a bond | H | a bond | NH | O | a bond | T3h | OH |
| 1679 | CH | S | Q1a | a bond | H | a bond | NH | O | a bond | T3i | OH |
| 1680 | CH | S | Q1a | a bond | H | a bond | NH | O | a bond | T3j | OH |
| 1681 | CH | S | Q1b | a bond | Me | a bond | NH | S | NH | T3a | OH |
| 1682 | CH | S | Q1b | a bond | Me | a bond | NH | S | NH | T3b | OH |
| 1683 | CH | S | Q1b | a bond | Me | a bond | NH | S | NH | T3c | OH |
| 1684 | CH | S | Q1b | a bond | Me | a bond | NH | S | NH | T3d | OH |
| 1685 | CH | S | Q1b | a bond | Me | a bond | NH | S | NH | T3e | OH |
| 1686 | CH | S | Q1b | a bond | Me | a bond | NH | S | NH | T3f | OH |
| 1687 | CH | S | Q1b | a bond | Me | a bond | NH | S | NH | T3g | OH |
| 1688 | CH | S | Q1b | a bond | Me | a bond | NH | S | NH | T3h | OH |
| 1689 | CH | S | Q1b | a bond | Me | a bond | NH | S | NH | T3i | OH |
| 1690 | CH | S | Q1b | a bond | Me | a bond | NH | S | NH | T3j | OH |
| 1691 | CH | S | Q1b | a bond | Me | a bond | NH | S | a bond | T3a | OH |
| 1692 | CH | S | Q1b | a bond | Me | a bond | NH | S | a bond | T3b | OH |
| 1693 | CH | S | Q1b | a bond | Me | a bond | NH | S | a bond | T3c | OH |
| 1694 | CH | S | Q1b | a bond | Me | a bond | NH | S | a bond | T3d | OH |
| 1695 | CH | S | Q1b | a bond | Me | a bond | NH | S | a bond | T3e | OH |
| 1696 | CH | S | Q1b | a bond | Me | a bond | NH | S | a bond | T3f | OH |
| 1697 | CH | S | Q1b | a bond | Me | a bond | NH | S | a bond | T3g | OH |
| 1698 | CH | S | Q1b | a bond | Me | a bond | NH | S | a bond | T3h | OH |
| 1699 | CH | S | Q1b | a bond | Me | a bond | NH | S | a bond | T3i | OH |
| 1700 | CH | S | Q1b | a bond | Me | a bond | NH | S | a bond | T3j | OH |
| 1701 | CH | S | Q1b | a bond | Me | a bond | NH | O | NH | T3a | OH |
| 1702 | CH | S | Q1b | a bond | Me | a bond | NH | O | NH | T3b | OH |
| 1703 | CH | S | Q1b | a bond | Me | a bond | NH | O | NH | T3c | OH |
| 1704 | CH | S | Q1b | a bond | Me | a bond | NH | O | NH | T3d | OH |
| 1705 | CH | S | Q1b | a bond | Me | a bond | NH | O | NH | T3e | OH |
| 1706 | CH | S | Q1b | a bond | Me | a bond | NH | O | NH | T3f | OH |
| 1707 | CH | S | Q1b | a bond | Me | a bond | NH | O | NH | T3g | OH |
| 1708 | CH | S | Q1b | a bond | Me | a bond | NH | O | NH | T3h | OH |
| 1709 | CH | S | Q1b | a bond | Me | a bond | NH | O | NH | T3i | OH |
| 1710 | CH | S | Q1b | a bond | Me | a bond | NH | O | NH | T3j | OH |
| 1711 | CH | S | Q1b | a bond | Me | a bond | NH | O | a bond | T3a | OH |
| 1712 | CH | S | Q1b | a bond | Me | a bond | NH | O | a bond | T3b | OH |
| 1713 | CH | S | Q1b | a bond | Me | a bond | NH | O | a bond | T3c | OH |
| 1714 | CH | S | Q1b | a bond | Me | a bond | NH | O | a bond | T3d | OH |
| 1715 | CH | S | Q1b | a bond | Me | a bond | NH | O | a bond | T3e | OH |
| 1716 | CH | S | Q1b | a bond | Me | a bond | NH | O | a bond | T3f | OH |
| 1717 | CH | S | Q1b | a bond | Me | a bond | NH | O | a bond | T3g | OH |
| 1718 | CH | S | Q1b | a bond | Me | a bond | NH | O | a bond | T3h | OH |
| 1719 | CH | S | Q1b | a bond | Me | a bond | NH | O | a bond | T3i | OH |
| 1720 | CH | S | Q1b | a bond | Me | a bond | NH | O | a bond | T3j | OH |
| 1721 | CH | S | Q1b | a bond | H | a bond | NH | S | NH | T3a | OH |
| 1722 | CH | S | Q1b | a bond | H | a bond | NH | S | NH | T3b | OH |
| 1723 | CH | S | Q1b | a bond | H | a bond | NH | S | NH | T3c | OH |
| 1724 | CH | S | Q1b | a bond | H | a bond | NH | S | NH | T3d | OH |
| 1725 | CH | S | Q1b | a bond | H | a bond | NH | S | NH | T3e | OH |
| 1726 | CH | S | Q1b | a bond | H | a bond | NH | S | NH | T3f | OH |
| 1727 | CH | S | Q1b | a bond | H | a bond | NH | S | NH | T3g | OH |
| 1728 | CH | S | Q1b | a bond | H | a bond | NH | S | NH | T3h | OH |
| 1729 | CH | S | Q1b | a bond | H | a bond | NH | S | NH | T3i | OH |
| 1730 | CH | S | Q1b | a bond | H | a bond | NH | S | NH | T3j | OH |
| 1731 | CH | S | Q1b | a bond | H | a bond | NH | S | a bond | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 1732 | CH | S | Q1b | a bond | H | a bond | NH | S | a bond | T3b | OH |
| 1733 | CH | S | Q1b | a bond | H | a bond | NH | S | a bond | T3c | OH |
| 1734 | CH | S | Q1b | a bond | H | a bond | NH | S | a bond | T3d | OH |
| 1735 | CH | S | Q1b | a bond | H | a bond | NH | S | a bond | T3e | OH |
| 1736 | CH | S | Q1b | a bond | H | a bond | NH | S | a bond | T3f | OH |
| 1737 | CH | S | Q1b | a bond | H | a bond | NH | S | a bond | T3g | OH |
| 1738 | CH | S | Q1b | a bond | H | a bond | NH | S | a bond | T3h | OH |
| 1739 | CH | S | Q1b | a bond | H | a bond | NH | S | a bond | T3i | OH |
| 1740 | CH | S | Q1b | a bond | H | a bond | NH | S | a bond | T3j | OH |
| 1741 | CH | S | Q1b | a bond | H | a bond | NH | O | NH | T3a | OH |
| 1742 | CH | S | Q1b | a bond | H | a bond | NH | O | NH | T3b | OH |
| 1743 | CH | S | Q1b | a bond | H | a bond | NH | O | NH | T3c | OH |
| 1744 | CH | S | Q1b | a bond | H | a bond | NH | O | NH | T3d | OH |
| 1745 | CH | S | Q1b | a bond | H | a bond | NH | O | NH | T3e | OH |
| 1746 | CH | S | Q1b | a bond | H | a bond | NH | O | NH | T3f | OH |
| 1747 | CH | S | Q1b | a bond | H | a bond | NH | O | NH | T3g | OH |
| 1748 | CH | S | Q1b | a bond | H | a bond | NH | O | NH | T3h | OH |
| 1749 | CH | S | Q1b | a bond | H | a bond | NH | O | NH | T3i | OH |
| 1750 | CH | S | Q1b | a bond | H | a bond | NH | O | NH | T3j | OH |
| 1751 | CH | S | Q1b | a bond | H | a bond | NH | O | a bond | T3a | OH |
| 1752 | CH | S | Q1b | a bond | H | a bond | NH | O | a bond | T3b | OH |
| 1753 | CH | S | Q1b | a bond | H | a bond | NH | O | a bond | T3c | OH |
| 1754 | CH | S | Q1b | a bond | H | a bond | NH | O | a bond | T3d | OH |
| 1755 | CH | S | Q1b | a bond | H | a bond | NH | O | a bond | T3e | OH |
| 1756 | CH | S | Q1b | a bond | H | a bond | NH | O | a bond | T3f | OH |
| 1757 | CH | S | Q1b | a bond | H | a bond | NH | O | a bond | T3g | OH |
| 1758 | CH | S | Q1b | a bond | H | a bond | NH | O | a bond | T3h | OH |
| 1759 | CH | S | Q1b | a bond | H | a bond | NH | O | a bond | T3i | OH |
| 1760 | CH | S | Q1b | a bond | H | a bond | NH | O | a bond | T3j | OH |
| 1761 | CH | S | Q1c | a bond | Me | a bond | NH | S | NH | T3a | OH |
| 1762 | CH | S | Q1c | a bond | Me | a bond | NH | S | NH | T3b | OH |
| 1763 | CH | S | Q1c | a bond | Me | a bond | NH | S | NH | T3c | OH |
| 1764 | CH | S | Q1c | a bond | Me | a bond | NH | S | NH | T3d | OH |
| 1765 | CH | S | Q1c | a bond | Me | a bond | NH | S | NH | T3e | OH |
| 1766 | CH | S | Q1c | a bond | Me | a bond | NH | S | NH | T3f | OH |
| 1767 | CH | S | Q1c | a bond | Me | a bond | NH | S | NH | T3g | OH |
| 1768 | CH | S | Q1c | a bond | Me | a bond | NH | S | NH | T3h | OH |
| 1769 | CH | S | Q1c | a bond | Me | a bond | NH | S | NH | T3i | OH |
| 1770 | CH | S | Q1c | a bond | Me | a bond | NH | S | NH | T3j | OH |
| 1771 | CH | S | Q1c | a bond | Me | a bond | NH | S | a bond | T3a | OH |
| 1772 | CH | S | Q1c | a bond | Me | a bond | NH | S | a bond | T3b | OH |
| 1773 | CH | S | Q1c | a bond | Me | a bond | NH | S | a bond | T3c | OH |
| 1774 | CH | S | Q1c | a bond | Me | a bond | NH | S | a bond | T3d | OH |
| 1775 | CH | S | Q1c | a bond | Me | a bond | NH | S | a bond | T3e | OH |
| 1776 | CH | S | Q1c | a bond | Me | a bond | NH | S | a bond | T3f | OH |
| 1777 | CH | S | Q1c | a bond | Me | a bond | NH | S | a bond | T3g | OH |
| 1778 | CH | S | Q1c | a bond | Me | a bond | NH | S | a bond | T3h | OH |
| 1779 | CH | S | Q1c | a bond | Me | a bond | NH | S | a bond | T3i | OH |
| 1780 | CH | S | Q1c | a bond | Me | a bond | NH | S | a bond | T3j | OH |
| 1781 | CH | S | Q1c | a bond | Me | a bond | NH | O | NH | T3a | OH |
| 1782 | CH | S | Q1c | a bond | Me | a bond | NH | O | NH | T3b | OH |
| 1783 | CH | S | Q1c | a bond | Me | a bond | NH | O | NH | T3c | OH |
| 1784 | CH | S | Q1c | a bond | Me | a bond | NH | O | NH | T3d | OH |
| 1785 | CH | S | Q1c | a bond | Me | a bond | NH | O | NH | T3e | OH |
| 1786 | CH | S | Q1c | a bond | Me | a bond | NH | O | NH | T3f | OH |
| 1787 | CH | S | Q1c | a bond | Me | a bond | NH | O | NH | T3g | OH |
| 1788 | CH | S | Q1c | a bond | Me | a bond | NH | O | NH | T3h | OH |
| 1789 | CH | S | Q1c | a bond | Me | a bond | NH | O | NH | T3i | OH |
| 1790 | CH | S | Q1c | a bond | Me | a bond | NH | O | NH | T3j | OH |
| 1791 | CH | S | Q1c | a bond | Me | a bond | NH | O | a bond | T3a | OH |
| 1792 | CH | S | Q1c | a bond | Me | a bond | NH | O | a bond | T3b | OH |
| 1793 | CH | S | Q1c | a bond | Me | a bond | NH | O | a bond | T3c | OH |
| 1794 | CH | S | Q1c | a bond | Me | a bond | NH | O | a bond | T3d | OH |
| 1795 | CH | S | Q1c | a bond | Me | a bond | NH | O | a bond | T3e | OH |
| 1796 | CH | S | Q1c | a bond | Me | a bond | NH | O | a bond | T3f | OH |
| 1797 | CH | S | Q1c | a bond | Me | a bond | NH | O | a bond | T3g | OH |
| 1798 | CH | S | Q1c | a bond | Me | a bond | NH | O | a bond | T3h | OH |
| 1799 | CH | S | Q1c | a bond | Me | a bond | NH | O | a bond | T3i | OH |
| 1800 | CH | S | Q1c | a bond | Me | a bond | NH | O | a bond | T3j | OH |
| 1801 | CH | S | Q1c | a bond | H | a bond | NH | S | NH | T3a | OH |
| 1802 | CH | S | Q1c | a bond | H | a bond | NH | S | NH | T3b | OH |
| 1803 | CH | S | Q1c | a bond | H | a bond | NH | S | NH | T3c | OH |
| 1804 | CH | S | Q1c | a bond | H | a bond | NH | S | NH | T3d | OH |
| 1805 | CH | S | Q1c | a bond | H | a bond | NH | S | NH | T3e | OH |
| 1806 | CH | S | Q1c | a bond | H | a bond | NH | S | NH | T3f | OH |
| 1807 | CH | S | Q1c | a bond | H | a bond | NH | S | NH | T3g | OH |
| 1808 | CH | S | Q1c | a bond | H | a bond | NH | S | NH | T3h | OH |
| 1809 | CH | S | Q1c | a bond | H | a bond | NH | S | NH | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 1810 | CH | S | Q1c | a bond | H | a bond | NH | S | NH | T3j | OH |
| 1811 | CH | S | Q1c | a bond | H | a bond | NH | S | a bond | T3a | OH |
| 1812 | CH | S | Q1c | a bond | H | a bond | NH | S | a bond | T3b | OH |
| 1813 | CH | S | Q1c | a bond | H | a bond | NH | S | a bond | T3c | OH |
| 1814 | CH | S | Q1c | a bond | H | a bond | NH | S | a bond | T3d | OH |
| 1815 | CH | S | Q1c | a bond | H | a bond | NH | S | a bond | T3e | OH |
| 1816 | CH | S | Q1c | a bond | H | a bond | NH | S | a bond | T3f | OH |
| 1817 | CH | S | Q1c | a bond | H | a bond | NH | S | a bond | T3g | OH |
| 1818 | CH | S | Q1c | a bond | H | a bond | NH | S | a bond | T3h | OH |
| 1819 | CH | S | Q1c | a bond | H | a bond | NH | S | a bond | T3i | OH |
| 1820 | CH | S | Q1c | a bond | H | a bond | NH | S | a bond | T3j | OH |
| 1821 | CH | S | Q1c | a bond | H | a bond | NH | O | NH | T3a | OH |
| 1822 | CH | S | Q1c | a bond | H | a bond | NH | O | NH | T3b | OH |
| 1823 | CH | S | Q1c | a bond | H | a bond | NH | O | NH | T3c | OH |
| 1824 | CH | S | Q1c | a bond | H | a bond | NH | O | NH | T3d | OH |
| 1825 | CH | S | Q1c | a bond | H | a bond | NH | O | NH | T3e | OH |
| 1826 | CH | S | Q1c | a bond | H | a bond | NH | O | NH | T3f | OH |
| 1827 | CH | S | Q1c | a bond | H | a bond | NH | O | NH | T3g | OH |
| 1828 | CH | S | Q1c | a bond | H | a bond | NH | O | NH | T3h | OH |
| 1829 | CH | S | Q1c | a bond | H | a bond | NH | O | NH | T3i | OH |
| 1830 | CH | S | Q1c | a bond | H | a bond | NH | O | NH | T3j | OH |
| 1831 | CH | S | Q1c | a bond | H | a bond | NH | O | a bond | T3a | OH |
| 1832 | CH | S | Q1c | a bond | H | a bond | NH | O | a bond | T3b | OH |
| 1833 | CH | S | Q1c | a bond | H | a bond | NH | O | a bond | T3c | OH |
| 1834 | CH | S | Q1c | a bond | H | a bond | NH | O | a bond | T3d | OH |
| 1835 | CH | S | Q1c | a bond | H | a bond | NH | O | a bond | T3e | OH |
| 1836 | CH | S | Q1c | a bond | H | a bond | NH | O | a bond | T3f | OH |
| 1837 | CH | S | Q1c | a bond | H | a bond | NH | O | a bond | T3g | OH |
| 1838 | CH | S | Q1c | a bond | H | a bond | NH | O | a bond | T3h | OH |
| 1839 | CH | S | Q1c | a bond | H | a bond | NH | O | a bond | T3i | OH |
| 1840 | CH | S | Q1c | a bond | H | a bond | NH | O | a bond | T3j | OH |
| 1841 | CH | S | Q1i | a bond | Me | a bond | NH | S | NH | T3a | OH |
| 1842 | CH | S | Q1i | a bond | Me | a bond | NH | S | NH | T3b | OH |
| 1843 | CH | S | Q1i | a bond | Me | a bond | NH | S | NH | T3c | OH |
| 1844 | CH | S | Q1i | a bond | Me | a bond | NH | S | NH | T3d | OH |
| 1845 | CH | S | Q1i | a bond | Me | a bond | NH | S | NH | T3e | OH |
| 1846 | CH | S | Q1i | a bond | Me | a bond | NH | S | NH | T3f | OH |
| 1847 | CH | S | Q1i | a bond | Me | a bond | NH | S | NH | T3g | OH |
| 1848 | CH | S | Q1i | a bond | Me | a bond | NH | S | NH | T3h | OH |
| 1849 | CH | S | Q1i | a bond | Me | a bond | NH | S | NH | T3i | OH |
| 1850 | CH | S | Q1i | a bond | Me | a bond | NH | S | NH | T3j | OH |
| 1851 | CH | S | Q1i | a bond | Me | a bond | NH | S | a bond | T3a | OH |
| 1852 | CH | S | Q1i | a bond | Me | a bond | NH | S | a bond | T3b | OH |
| 1853 | CH | S | Q1i | a bond | Me | a bond | NH | S | a bond | T3c | OH |
| 1854 | CH | S | Q1i | a bond | Me | a bond | NH | S | a bond | T3d | OH |
| 1855 | CH | S | Q1i | a bond | Me | a bond | NH | S | a bond | T3e | OH |
| 1856 | CH | S | Q1i | a bond | Me | a bond | NH | S | a bond | T3f | OH |
| 1857 | CH | S | Q1i | a bond | Me | a bond | NH | S | a bond | T3g | OH |
| 1858 | CH | S | Q1i | a bond | Me | a bond | NH | S | a bond | T3h | OH |
| 1859 | CH | S | Q1i | a bond | Me | a bond | NH | S | a bond | T3i | OH |
| 1860 | CH | S | Q1i | a bond | Me | a bond | NH | S | a bond | T3j | OH |
| 1861 | CH | S | Q1i | a bond | Me | a bond | NH | O | NH | T3a | OH |
| 1862 | CH | S | Q1i | a bond | Me | a bond | NH | O | NH | T3b | OH |
| 1863 | CH | S | Q1i | a bond | Me | a bond | NH | O | NH | T3c | OH |
| 1864 | CH | S | Q1i | a bond | Me | a bond | NH | O | NH | T3d | OH |
| 1865 | CH | S | Q1i | a bond | Me | a bond | NH | O | NH | T3e | OH |
| 1866 | CH | S | Q1i | a bond | Me | a bond | NH | O | NH | T3f | OH |
| 1867 | CH | S | Q1i | a bond | Me | a bond | NH | O | NH | T3g | OH |
| 1868 | CH | S | Q1i | a bond | Me | a bond | NH | O | NH | T3h | OH |
| 1869 | CH | S | Q1i | a bond | Me | a bond | NH | O | NH | T3i | OH |
| 1870 | CH | S | Q1i | a bond | Me | a bond | NH | O | NH | T3j | OH |
| 1871 | CH | S | Q1i | a bond | Me | a bond | NH | O | a bond | T3a | OH |
| 1872 | CH | S | Q1i | a bond | Me | a bond | NH | O | a bond | T3b | OH |
| 1873 | CH | S | Q1i | a bond | Me | a bond | NH | O | a bond | T3c | OH |
| 1874 | CH | S | Q1i | a bond | Me | a bond | NH | O | a bond | T3d | OH |
| 1875 | CH | S | Q1i | a bond | Me | a bond | NH | O | a bond | T3e | OH |
| 1876 | CH | S | Q1i | a bond | Me | a bond | NH | O | a bond | T3f | OH |
| 1877 | CH | S | Q1i | a bond | Me | a bond | NH | O | a bond | T3g | OH |
| 1878 | CH | S | Q1i | a bond | Me | a bond | NH | O | a bond | T3h | OH |
| 1879 | CH | S | Q1i | a bond | Me | a bond | NH | O | a bond | T3i | OH |
| 1880 | CH | S | Q1i | a bond | Me | a bond | NH | O | a bond | T3j | OH |
| 1881 | CH | S | Q1i | a bond | H | a bond | NH | S | NH | T3a | OH |
| 1882 | CH | S | Q1i | a bond | H | a bond | NH | S | NH | T3b | OH |
| 1883 | CH | S | Q1i | a bond | H | a bond | NH | S | NH | T3c | OH |
| 1884 | CH | S | Q1i | a bond | H | a bond | NH | S | NH | T3d | OH |
| 1885 | CH | S | Q1i | a bond | H | a bond | NH | S | NH | T3e | OH |
| 1886 | CH | S | Q1i | a bond | H | a bond | NH | S | NH | T3f | OH |
| 1887 | CH | S | Q1i | a bond | H | a bond | NH | S | NH | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 1888 | CH | S | Q1i | a bond | H | a bond | NH | S | NH | T3h | OH |
| 1889 | CH | S | Q1i | a bond | H | a bond | NH | S | NH | T3i | OH |
| 1890 | CH | S | Q1i | a bond | H | a bond | NH | S | NH | T3j | OH |
| 1891 | CH | S | Q1i | a bond | H | a bond | NH | S | a bond | T3a | OH |
| 1892 | CH | S | Q1i | a bond | H | a bond | NH | S | a bond | T3b | OH |
| 1893 | CH | S | Q1i | a bond | H | a bond | NH | S | a bond | T3c | OH |
| 1894 | CH | S | Q1i | a bond | H | a bond | NH | S | a bond | T3d | OH |
| 1895 | CH | S | Q1i | a bond | H | a bond | NH | S | a bond | T3e | OH |
| 1896 | CH | S | Q1i | a bond | H | a bond | NH | S | a bond | T3f | OH |
| 1897 | CH | S | Q1i | a bond | H | a bond | NH | S | a bond | T3g | OH |
| 1898 | CH | S | Q1i | a bond | H | a bond | NH | S | a bond | T3h | OH |
| 1899 | CH | S | Q1i | a bond | H | a bond | NH | S | a bond | T3i | OH |
| 1900 | CH | S | Q1i | a bond | H | a bond | NH | S | a bond | T3j | OH |
| 1901 | CH | S | Q1i | a bond | H | a bond | NH | O | NH | T3a | OH |
| 1902 | CH | S | Q1i | a bond | H | a bond | NH | O | NH | T3b | OH |
| 1903 | CH | S | Q1i | a bond | H | a bond | NH | O | NH | T3c | OH |
| 1904 | CH | S | Q1i | a bond | H | a bond | NH | O | NH | T3d | OH |
| 1905 | CH | S | Q1i | a bond | H | a bond | NH | O | NH | T3e | OH |
| 1906 | CH | S | Q1i | a bond | H | a bond | NH | O | NH | T3f | OH |
| 1907 | CH | S | Q1i | a bond | H | a bond | NH | O | NH | T3g | OH |
| 1908 | CH | S | Q1i | a bond | H | a bond | NH | O | NH | T3h | OH |
| 1909 | CH | S | Q1i | a bond | H | a bond | NH | O | NH | T3i | OH |
| 1910 | CH | S | Q1i | a bond | H | a bond | NH | O | NH | T3j | OH |
| 1911 | CH | S | Q1i | a bond | H | a bond | NH | O | a bond | T3a | OH |
| 1912 | CH | S | Q1i | a bond | H | a bond | NH | O | a bond | T3b | OH |
| 1913 | CH | S | Q1i | a bond | H | a bond | NH | O | a bond | T3c | OH |
| 1914 | CH | S | Q1i | a bond | H | a bond | NH | O | a bond | T3d | OH |
| 1915 | CH | S | Q1i | a bond | H | a bond | NH | O | a bond | T3e | OH |
| 1916 | CH | S | Q1i | a bond | H | a bond | NH | O | a bond | T3f | OH |
| 1917 | CH | S | Q1i | a bond | H | a bond | NH | O | a bond | T3g | OH |
| 1918 | CH | S | Q1i | a bond | H | a bond | NH | O | a bond | T3h | OH |
| 1919 | CH | S | Q1i | a bond | H | a bond | NH | O | a bond | T3i | OH |
| 1920 | CH | S | Q1i | a bond | H | a bond | NH | O | a bond | T3j | OH |
| 1921 | CH | S | Q1j | a bond | Me | a bond | NH | S | NH | T3a | OH |
| 1922 | CH | S | Q1j | a bond | Me | a bond | NH | S | NH | T3b | OH |
| 1923 | CH | S | Q1j | a bond | Me | a bond | NH | S | NH | T3c | OH |
| 1924 | CH | S | Q1j | a bond | Me | a bond | NH | S | NH | T3d | OH |
| 1925 | CH | S | Q1j | a bond | Me | a bond | NH | S | NH | T3e | OH |
| 1926 | CH | S | Q1j | a bond | Me | a bond | NH | S | NH | T3f | OH |
| 1927 | CH | S | Q1j | a bond | Me | a bond | NH | S | NH | T3g | OH |
| 1928 | CH | S | Q1j | a bond | Me | a bond | NH | S | NH | T3h | OH |
| 1929 | CH | S | Q1j | a bond | Me | a bond | NH | S | NH | T3i | OH |
| 1930 | CH | S | Q1j | a bond | Me | a bond | NH | S | NH | T3j | OH |
| 1931 | CH | S | Q1j | a bond | Me | a bond | NH | S | a bond | T3a | OH |
| 1932 | CH | S | Q1j | a bond | Me | a bond | NH | S | a bond | T3b | OH |
| 1933 | CH | S | Q1j | a bond | Me | a bond | NH | S | a bond | T3c | OH |
| 1934 | CH | S | Q1j | a bond | Me | a bond | NH | S | a bond | T3d | OH |
| 1935 | CH | S | Q1j | a bond | Me | a bond | NH | S | a bond | T3e | OH |
| 1936 | CH | S | Q1j | a bond | Me | a bond | NH | S | a bond | T3f | OH |
| 1937 | CH | S | Q1j | a bond | Me | a bond | NH | S | a bond | T3g | OH |
| 1938 | CH | S | Q1j | a bond | Me | a bond | NH | S | a bond | T3h | OH |
| 1939 | CH | S | Q1j | a bond | Me | a bond | NH | S | a bond | T3i | OH |
| 1940 | CH | S | Q1j | a bond | Me | a bond | NH | S | a bond | T3j | OH |
| 1941 | CH | S | Q1j | a bond | Me | a bond | NH | O | NH | T3a | OH |
| 1942 | CH | S | Q1j | a bond | Me | a bond | NH | O | NH | T3b | OH |
| 1943 | CH | S | Q1j | a bond | Me | a bond | NH | O | NH | T3c | OH |
| 1944 | CH | S | Q1j | a bond | Me | a bond | NH | O | NH | T3d | OH |
| 1945 | CH | S | Q1j | a bond | Me | a bond | NH | O | NH | T3e | OH |
| 1946 | CH | S | Q1j | a bond | Me | a bond | NH | O | NH | T3f | OH |
| 1947 | CH | S | Q1j | a bond | Me | a bond | NH | O | NH | T3g | OH |
| 1948 | CH | S | Q1j | a bond | Me | a bond | NH | O | NH | T3h | OH |
| 1949 | CH | S | Q1j | a bond | Me | a bond | NH | O | NH | T3i | OH |
| 1950 | CH | S | Q1j | a bond | Me | a bond | NH | O | NH | T3j | OH |
| 1951 | CH | S | Q1j | a bond | Me | a bond | NH | O | a bond | T3a | OH |
| 1952 | CH | S | Q1j | a bond | Me | a bond | NH | O | a bond | T3b | OH |
| 1953 | CH | S | Q1j | a bond | Me | a bond | NH | O | a bond | T3c | OH |
| 1954 | CH | S | Q1j | a bond | Me | a bond | NH | O | a bond | T3d | OH |
| 1955 | CH | S | Q1j | a bond | Me | a bond | NH | O | a bond | T3e | OH |
| 1956 | CH | S | Q1j | a bond | Me | a bond | NH | O | a bond | T3f | OH |
| 1957 | CH | S | Q1j | a bond | Me | a bond | NH | O | a bond | T3g | OH |
| 1958 | CH | S | Q1j | a bond | Me | a bond | NH | O | a bond | T3h | OH |
| 1959 | CH | S | Q1j | a bond | Me | a bond | NH | O | a bond | T3i | OH |
| 1960 | CH | S | Q1j | a bond | Me | a bond | NH | O | a bond | T3j | OH |
| 1961 | CH | S | Q1j | a bond | H | a bond | NH | S | NH | T3a | OH |
| 1962 | CH | S | Q1j | a bond | H | a bond | NH | S | NH | T3b | OH |
| 1963 | CH | S | Q1j | a bond | H | a bond | NH | S | NH | T3c | OH |
| 1964 | CH | S | Q1j | a bond | H | a bond | NH | S | NH | T3d | OH |
| 1965 | CH | S | Q1j | a bond | H | a bond | NH | S | NH | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 1966 | CH | S | Q1j | a bond | H | a bond | NH | S | NH | T3f | OH |
| 1967 | CH | S | Q1j | a bond | H | a bond | NH | S | NH | T3g | OH |
| 1968 | CH | S | Q1j | a bond | H | a bond | NH | S | NH | T3h | OH |
| 1969 | CH | S | Q1j | a bond | H | a bond | NH | S | NH | T3i | OH |
| 1970 | CH | S | Q1j | a bond | H | a bond | NH | S | NH | T3j | OH |
| 1971 | CH | S | Q1j | a bond | H | a bond | NH | S | a bond | T3a | OH |
| 1972 | CH | S | Q1j | a bond | H | a bond | NH | S | a bond | T3b | OH |
| 1973 | CH | S | Q1j | a bond | H | a bond | NH | S | a bond | T3c | OH |
| 1974 | CH | S | Q1j | a bond | H | a bond | NH | S | a bond | T3d | OH |
| 1975 | CH | S | Q1j | a bond | H | a bond | NH | S | a bond | T3e | OH |
| 1976 | CH | S | Q1j | a bond | H | a bond | NH | S | a bond | T3f | OH |
| 1977 | CH | S | Q1j | a bond | H | a bond | NH | S | a bond | T3g | OH |
| 1978 | CH | S | Q1j | a bond | H | a bond | NH | S | a bond | T3h | OH |
| 1979 | CH | S | Q1j | a bond | H | a bond | NH | S | a bond | T3i | OH |
| 1980 | CH | S | Q1j | a bond | H | a bond | NH | S | a bond | T3j | OH |
| 1981 | CH | S | Q1j | a bond | H | a bond | NH | O | NH | T3a | OH |
| 1982 | CH | S | Q1j | a bond | H | a bond | NH | O | NH | T3b | OH |
| 1983 | CH | S | Q1j | a bond | H | a bond | NH | O | NH | T3c | OH |
| 1984 | CH | S | Q1j | a bond | H | a bond | NH | O | NH | T3d | OH |
| 1985 | CH | S | Q1j | a bond | H | a bond | NH | O | NH | T3e | OH |
| 1986 | CH | S | Q1j | a bond | H | a bond | NH | O | NH | T3f | OH |
| 1987 | CH | S | Q1j | a bond | H | a bond | NH | O | NH | T3g | OH |
| 1988 | CH | S | Q1j | a bond | H | a bond | NH | O | NH | T3h | OH |
| 1989 | CH | S | Q1j | a bond | H | a bond | NH | O | NH | T3i | OH |
| 1990 | CH | S | Q1j | a bond | H | a bond | NH | O | NH | T3j | OH |
| 1991 | CH | S | Q1j | a bond | H | a bond | NH | O | a bond | T3a | OH |
| 1992 | CH | S | Q1j | a bond | H | a bond | NH | O | a bond | T3b | OH |
| 1993 | CH | S | Q1j | a bond | H | a bond | NH | O | a bond | T3c | OH |
| 1994 | CH | S | Q1j | a bond | H | a bond | NH | O | a bond | T3d | OH |
| 1995 | CH | S | Q1j | a bond | H | a bond | NH | O | a bond | T3e | OH |
| 1996 | CH | S | Q1j | a bond | H | a bond | NH | O | a bond | T3f | OH |
| 1997 | CH | S | Q1j | a bond | H | a bond | NH | O | a bond | T3g | OH |
| 1998 | CH | S | Q1j | a bond | H | a bond | NH | O | a bond | T3h | OH |
| 1999 | CH | S | Q1j | a bond | H | a bond | NH | O | a bond | T3i | OH |
| 2000 | CH | S | Q1j | a bond | H | a bond | NH | O | a bond | T3j | OH |
| 2001 | CH | O | Q1a | a bond | Me | a bond | NH | S | NH | T3a | OH |
| 2002 | CH | O | Q1a | a bond | Me | a bond | NH | S | NH | T3b | OH |
| 2003 | CH | O | Q1a | a bond | Me | a bond | NH | S | NH | T3c | OH |
| 2004 | CH | O | Q1a | a bond | Me | a bond | NH | S | NH | T3d | OH |
| 2005 | CH | O | Q1a | a bond | Me | a bond | NH | S | NH | T3e | OH |
| 2006 | CH | O | Q1a | a bond | Me | a bond | NH | S | NH | T3f | OH |
| 2007 | CH | O | Q1a | a bond | Me | a bond | NH | S | NH | T3g | OH |
| 2008 | CH | O | Q1a | a bond | Me | a bond | NH | S | NH | T3h | OH |
| 2009 | CH | O | Q1a | a bond | Me | a bond | NH | S | NH | T3i | OH |
| 2010 | CH | O | Q1a | a bond | Me | a bond | NH | S | NH | T3j | OH |
| 2011 | CH | O | Q1a | a bond | Me | a bond | NH | S | a bond | T3a | OH |
| 2012 | CH | O | Q1a | a bond | Me | a bond | NH | S | a bond | T3b | OH |
| 2013 | CH | O | Q1a | a bond | Me | a bond | NH | S | a bond | T3c | OH |
| 2014 | CH | O | Q1a | a bond | Me | a bond | NH | S | a bond | T3d | OH |
| 2015 | CH | O | Q1a | a bond | Me | a bond | NH | S | a bond | T3e | OH |
| 2016 | CH | O | Q1a | a bond | Me | a bond | NH | S | a bond | T3f | OH |
| 2017 | CH | O | Q1a | a bond | Me | a bond | NH | S | a bond | T3g | OH |
| 2018 | CH | O | Q1a | a bond | Me | a bond | NH | S | a bond | T3h | OH |
| 2019 | CH | O | Q1a | a bond | Me | a bond | NH | S | a bond | T3i | OH |
| 2020 | CH | O | Q1a | a bond | Me | a bond | NH | S | a bond | T3j | OH |
| 2021 | CH | O | Q1a | a bond | Me | a bond | NH | O | NH | T3a | OH |
| 2022 | CH | O | Q1a | a bond | Me | a bond | NH | O | NH | T3b | OH |
| 2023 | CH | O | Q1a | a bond | Me | a bond | NH | O | NH | T3c | OH |
| 2024 | CH | O | Q1a | a bond | Me | a bond | NH | O | NH | T3d | OH |
| 2025 | CH | O | Q1a | a bond | Me | a bond | NH | O | NH | T3e | OH |
| 2026 | CH | O | Q1a | a bond | Me | a bond | NH | O | NH | T3f | OH |
| 2027 | CH | O | Q1a | a bond | Me | a bond | NH | O | NH | T3g | OH |
| 2028 | CH | O | Q1a | a bond | Me | a bond | NH | O | NH | T3h | OH |
| 2029 | CH | O | Q1a | a bond | Me | a bond | NH | O | NH | T3i | OH |
| 2030 | CH | O | Q1a | a bond | Me | a bond | NH | O | NH | T3j | OH |
| 2031 | CH | O | Q1a | a bond | Me | a bond | NH | O | a bond | T3a | OH |
| 2032 | CH | O | Q1a | a bond | Me | a bond | NH | O | a bond | T3b | OH |
| 2033 | CH | O | Q1a | a bond | Me | a bond | NH | O | a bond | T3c | OH |
| 2034 | CH | O | Q1a | a bond | Me | a bond | NH | O | a bond | T3d | OH |
| 2035 | CH | O | Q1a | a bond | Me | a bond | NH | O | a bond | T3e | OH |
| 2036 | CH | O | Q1a | a bond | Me | a bond | NH | O | a bond | T3f | OH |
| 2037 | CH | O | Q1a | a bond | Me | a bond | NH | O | a bond | T3g | OH |
| 2038 | CH | O | Q1a | a bond | Me | a bond | NH | O | a bond | T3h | OH |
| 2039 | CH | O | Q1a | a bond | Me | a bond | NH | O | a bond | T3i | OH |
| 2040 | CH | O | Q1a | a bond | Me | a bond | NH | O | a bond | T3j | OH |
| 2041 | CH | O | Q1a | a bond | H | a bond | NH | S | NH | T3a | OH |
| 2042 | CH | O | Q1a | a bond | H | a bond | NH | S | NH | T3b | OH |
| 2043 | CH | O | Q1a | a bond | H | a bond | NH | S | NH | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 2044 | CH | O | Q1a | a bond | H | a bond | NH | S | NH | T3d | OH |
| 2045 | CH | O | Q1a | a bond | H | a bond | NH | S | NH | T3e | OH |
| 2046 | CH | O | Q1a | a bond | H | a bond | NH | S | NH | T3f | OH |
| 2047 | CH | O | Q1a | a bond | H | a bond | NH | S | NH | T3g | OH |
| 2048 | CH | O | Q1a | a bond | H | a bond | NH | S | NH | T3h | OH |
| 2049 | CH | O | Q1a | a bond | H | a bond | NH | S | NH | T3i | OH |
| 2050 | CH | O | Q1a | a bond | H | a bond | NH | S | NH | T3j | OH |
| 2051 | CH | O | Q1a | a bond | H | a bond | NH | S | a bond | T3a | OH |
| 2052 | CH | O | Q1a | a bond | H | a bond | NH | S | a bond | T3b | OH |
| 2053 | CH | O | Q1a | a bond | H | a bond | NH | S | a bond | T3c | OH |
| 2054 | CH | O | Q1a | a bond | H | a bond | NH | S | a bond | T3d | OH |
| 2055 | CH | O | Q1a | a bond | H | a bond | NH | S | a bond | T3e | OH |
| 2056 | CH | O | Q1a | a bond | H | a bond | NH | S | a bond | T3f | OH |
| 2057 | CH | O | Q1a | a bond | H | a bond | NH | S | a bond | T3g | OH |
| 2058 | CH | O | Q1a | a bond | H | a bond | NH | S | a bond | T3h | OH |
| 2059 | CH | O | Q1a | a bond | H | a bond | NH | S | a bond | T3i | OH |
| 2060 | CH | O | Q1a | a bond | H | a bond | NH | S | a bond | T3j | OH |
| 2061 | CH | O | Q1a | a bond | H | a bond | NH | O | NH | T3a | OH |
| 2062 | CH | O | Q1a | a bond | H | a bond | NH | O | NH | T3b | OH |
| 2063 | CH | O | Q1a | a bond | H | a bond | NH | O | NH | T3c | OH |
| 2064 | CH | O | Q1a | a bond | H | a bond | NH | O | NH | T3d | OH |
| 2065 | CH | O | Q1a | a bond | H | a bond | NH | O | NH | T3e | OH |
| 2066 | CH | O | Q1a | a bond | H | a bond | NH | O | NH | T3f | OH |
| 2067 | CH | O | Q1a | a bond | H | a bond | NH | O | NH | T3g | OH |
| 2068 | CH | O | Q1a | a bond | H | a bond | NH | O | NH | T3h | OH |
| 2069 | CH | O | Q1a | a bond | H | a bond | NH | O | NH | T3i | OH |
| 2070 | CH | O | Q1a | a bond | H | a bond | NH | O | NH | T3j | OH |
| 2071 | CH | O | Q1a | a bond | H | a bond | NH | O | a bond | T3a | OH |
| 2072 | CH | O | Q1a | a bond | H | a bond | NH | O | a bond | T3b | OH |
| 2073 | CH | O | Q1a | a bond | H | a bond | NH | O | a bond | T3c | OH |
| 2074 | CH | O | Q1a | a bond | H | a bond | NH | O | a bond | T3d | OH |
| 2075 | CH | O | Q1a | a bond | H | a bond | NH | O | a bond | T3e | OH |
| 2076 | CH | O | Q1a | a bond | H | a bond | NH | O | a bond | T3f | OH |
| 2077 | CH | O | Q1a | a bond | H | a bond | NH | O | a bond | T3g | OH |
| 2078 | CH | O | Q1a | a bond | H | a bond | NH | O | a bond | T3h | OH |
| 2079 | CH | O | Q1a | a bond | H | a bond | NH | O | a bond | T3i | OH |
| 2080 | CH | O | Q1a | a bond | H | a bond | NH | O | a bond | T3j | OH |
| 2081 | CH | O | Q1b | a bond | Me | a bond | NH | S | NH | T3a | OH |
| 2082 | CH | O | Q1b | a bond | Me | a bond | NH | S | NH | T3b | OH |
| 2083 | CH | O | Q1b | a bond | Me | a bond | NH | S | NH | T3c | OH |
| 2084 | CH | O | Q1b | a bond | Me | a bond | NH | S | NH | T3d | OH |
| 2085 | CH | O | Q1b | a bond | Me | a bond | NH | S | NH | T3e | OH |
| 2086 | CH | O | Q1b | a bond | Me | a bond | NH | S | NH | T3f | OH |
| 2087 | CH | O | Q1b | a bond | Me | a bond | NH | S | NH | T3g | OH |
| 2088 | CH | O | Q1b | a bond | Me | a bond | NH | S | NH | T3h | OH |
| 2089 | CH | O | Q1b | a bond | Me | a bond | NH | S | NH | T3i | OH |
| 2090 | CH | O | Q1b | a bond | Me | a bond | NH | S | NH | T3j | OH |
| 2091 | CH | O | Q1b | a bond | Me | a bond | NH | S | a bond | T3a | OH |
| 2092 | CH | O | Q1b | a bond | Me | a bond | NH | S | a bond | T3b | OH |
| 2093 | CH | O | Q1b | a bond | Me | a bond | NH | S | a bond | T3c | OH |
| 2094 | CH | O | Q1b | a bond | Me | a bond | NH | S | a bond | T3d | OH |
| 2095 | CH | O | Q1b | a bond | Me | a bond | NH | S | a bond | T3e | OH |
| 2096 | CH | O | Q1b | a bond | Me | a bond | NH | S | a bond | T3f | OH |
| 2097 | CH | O | Q1b | a bond | Me | a bond | NH | S | a bond | T3g | OH |
| 2098 | CH | O | Q1b | a bond | Me | a bond | NH | S | a bond | T3h | OH |
| 2099 | CH | O | Q1b | a bond | Me | a bond | NH | S | a bond | T3i | OH |
| 2100 | CH | O | Q1b | a bond | Me | a bond | NH | S | a bond | T3j | OH |
| 2101 | CH | O | Q1b | a bond | Me | a bond | NH | O | NH | T3a | OH |
| 2102 | CH | O | Q1b | a bond | Me | a bond | NH | O | NH | T3b | OH |
| 2103 | CH | O | Q1b | a bond | Me | a bond | NH | O | NH | T3c | OH |
| 2104 | CH | O | Q1b | a bond | Me | a bond | NH | O | NH | T3d | OH |
| 2105 | CH | O | Q1b | a bond | Me | a bond | NH | O | NH | T3e | OH |
| 2106 | CH | O | Q1b | a bond | Me | a bond | NH | O | NH | T3f | OH |
| 2107 | CH | O | Q1b | a bond | Me | a bond | NH | O | NH | T3g | OH |
| 2108 | CH | O | Q1b | a bond | Me | a bond | NH | O | NH | T3h | OH |
| 2109 | CH | O | Q1b | a bond | Me | a bond | NH | O | NH | T3i | OH |
| 2110 | CH | O | Q1b | a bond | Me | a bond | NH | O | NH | T3j | OH |
| 2111 | CH | O | Q1b | a bond | Me | a bond | NH | O | a bond | T3a | OH |
| 2112 | CH | O | Q1b | a bond | Me | a bond | NH | O | a bond | T3b | OH |
| 2113 | CH | O | Q1b | a bond | Me | a bond | NH | O | a bond | T3c | OH |
| 2114 | CH | O | Q1b | a bond | Me | a bond | NH | O | a bond | T3d | OH |
| 2115 | CH | O | Q1b | a bond | Me | a bond | NH | O | a bond | T3e | OH |
| 2116 | CH | O | Q1b | a bond | Me | a bond | NH | O | a bond | T3f | OH |
| 2117 | CH | O | Q1b | a bond | Me | a bond | NH | O | a bond | T3g | OH |
| 2118 | CH | O | Q1b | a bond | Me | a bond | NH | O | a bond | T3h | OH |
| 2119 | CH | O | Q1b | a bond | Me | a bond | NH | O | a bond | T3i | OH |
| 2120 | CH | O | Q1b | a bond | Me | a bond | NH | O | a bond | T3j | OH |
| 2121 | CH | O | Q1b | a bond | H | a bond | NH | S | NH | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 2122 | CH | O | Q1b | a bond | H | a bond | NH | S | NH | T3b | OH |
| 2123 | CH | O | Q1b | a bond | H | a bond | NH | S | NH | T3c | OH |
| 2124 | CH | O | Q1b | a bond | H | a bond | NH | S | NH | T3d | OH |
| 2125 | CH | O | Q1b | a bond | H | a bond | NH | S | NH | T3e | OH |
| 2126 | CH | O | Q1b | a bond | H | a bond | NH | S | NH | T3f | OH |
| 2127 | CH | O | Q1b | a bond | H | a bond | NH | S | NH | T3g | OH |
| 2128 | CH | O | Q1b | a bond | H | a bond | NH | S | NH | T3h | OH |
| 2129 | CH | O | Q1b | a bond | H | a bond | NH | S | NH | T3i | OH |
| 2130 | CH | O | Q1b | a bond | H | a bond | NH | S | NH | T3j | OH |
| 2131 | CH | O | Q1b | a bond | H | a bond | NH | S | a bond | T3a | OH |
| 2132 | CH | O | Q1b | a bond | H | a bond | NH | S | a bond | T3b | OH |
| 2133 | CH | O | Q1b | a bond | H | a bond | NH | S | a bond | T3c | OH |
| 2134 | CH | O | Q1b | a bond | H | a bond | NH | S | a bond | T3d | OH |
| 2135 | CH | O | Q1b | a bond | H | a bond | NH | S | a bond | T3e | OH |
| 2136 | CH | O | Q1b | a bond | H | a bond | NH | S | a bond | T3f | OH |
| 2137 | CH | O | Q1b | a bond | H | a bond | NH | S | a bond | T3g | OH |
| 2138 | CH | O | Q1b | a bond | H | a bond | NH | S | a bond | T3h | OH |
| 2139 | CH | O | Q1b | a bond | H | a bond | NH | S | a bond | T3i | OH |
| 2140 | CH | O | Q1b | a bond | H | a bond | NH | S | a bond | T3j | OH |
| 2141 | CH | O | Q1b | a bond | H | a bond | NH | O | NH | T3a | OH |
| 2142 | CH | O | Q1b | a bond | H | a bond | NH | O | NH | T3b | OH |
| 2143 | CH | O | Q1b | a bond | H | a bond | NH | O | NH | T3c | OH |
| 2144 | CH | O | Q1b | a bond | H | a bond | NH | O | NH | T3d | OH |
| 2145 | CH | O | Q1b | a bond | H | a bond | NH | O | NH | T3e | OH |
| 2146 | CH | O | Q1b | a bond | H | a bond | NH | O | NH | T3f | OH |
| 2147 | CH | O | Q1b | a bond | H | a bond | NH | O | NH | T3g | OH |
| 2148 | CH | O | Q1b | a bond | H | a bond | NH | O | NH | T3h | OH |
| 2149 | CH | O | Q1b | a bond | H | a bond | NH | O | NH | T3i | OH |
| 2150 | CH | O | Q1b | a bond | H | a bond | NH | O | NH | T3j | OH |
| 2151 | CH | O | Q1b | a bond | H | a bond | NH | O | a bond | T3a | OH |
| 2152 | CH | O | Q1b | a bond | H | a bond | NH | O | a bond | T3b | OH |
| 2153 | CH | O | Q1b | a bond | H | a bond | NH | O | a bond | T3c | OH |
| 2154 | CH | O | Q1b | a bond | H | a bond | NH | O | a bond | T3d | OH |
| 2155 | CH | O | Q1b | a bond | H | a bond | NH | O | a bond | T3e | OH |
| 2156 | CH | O | Q1b | a bond | H | a bond | NH | O | a bond | T3f | OH |
| 2157 | CH | O | Q1b | a bond | H | a bond | NH | O | a bond | T3g | OH |
| 2158 | CH | O | Q1b | a bond | H | a bond | NH | O | a bond | T3h | OH |
| 2159 | CH | O | Q1b | a bond | H | a bond | NH | O | a bond | T3i | OH |
| 2160 | CH | O | Q1b | a bond | H | a bond | NH | O | a bond | T3j | OH |
| 2161 | CH | O | Q1c | a bond | Me | a bond | NH | S | NH | T3a | OH |
| 2162 | CH | O | Q1c | a bond | Me | a bond | NH | S | NH | T3b | OH |
| 2163 | CH | O | Q1c | a bond | Me | a bond | NH | S | NH | T3c | OH |
| 2164 | CH | O | Q1c | a bond | Me | a bond | NH | S | NH | T3d | OH |
| 2165 | CH | O | Q1c | a bond | Me | a bond | NH | S | NH | T3e | OH |
| 2166 | CH | O | Q1c | a bond | Me | a bond | NH | S | NH | T3f | OH |
| 2167 | CH | O | Q1c | a bond | Me | a bond | NH | S | NH | T3g | OH |
| 2168 | CH | O | Q1c | a bond | Me | a bond | NH | S | NH | T3h | OH |
| 2169 | CH | O | Q1c | a bond | Me | a bond | NH | S | NH | T3i | OH |
| 2170 | CH | O | Q1c | a bond | Me | a bond | NH | S | NH | T3j | OH |
| 2171 | CH | O | Q1c | a bond | Me | a bond | NH | S | a bond | T3a | OH |
| 2172 | CH | O | Q1c | a bond | Me | a bond | NH | S | a bond | T3b | OH |
| 2173 | CH | O | Q1c | a bond | Me | a bond | NH | S | a bond | T3c | OH |
| 2174 | CH | O | Q1c | a bond | Me | a bond | NH | S | a bond | T3d | OH |
| 2175 | CH | O | Q1c | a bond | Me | a bond | NH | S | a bond | T3e | OH |
| 2176 | CH | O | Q1c | a bond | Me | a bond | NH | S | a bond | T3f | OH |
| 2177 | CH | O | Q1c | a bond | Me | a bond | NH | S | a bond | T3g | OH |
| 2178 | CH | O | Q1c | a bond | Me | a bond | NH | S | a bond | T3h | OH |
| 2179 | CH | O | Q1c | a bond | Me | a bond | NH | S | a bond | T3i | OH |
| 2180 | CH | O | Q1c | a bond | Me | a bond | NH | S | a bond | T3j | OH |
| 2181 | CH | O | Q1c | a bond | Me | a bond | NH | O | NH | T3a | OH |
| 2182 | CH | O | Q1c | a bond | Me | a bond | NH | O | NH | T3b | OH |
| 2183 | CH | O | Q1c | a bond | Me | a bond | NH | O | NH | T3c | OH |
| 2184 | CH | O | Q1c | a bond | Me | a bond | NH | O | NH | T3d | OH |
| 2185 | CH | O | Q1c | a bond | Me | a bond | NH | O | NH | T3e | OH |
| 2186 | CH | O | Q1c | a bond | Me | a bond | NH | O | NH | T3f | OH |
| 2187 | CH | O | Q1c | a bond | Me | a bond | NH | O | NH | T3g | OH |
| 2188 | CH | O | Q1c | a bond | Me | a bond | NH | O | NH | T3h | OH |
| 2189 | CH | O | Q1c | a bond | Me | a bond | NH | O | NH | T3i | OH |
| 2190 | CH | O | Q1c | a bond | Me | a bond | NH | O | NH | T3j | OH |
| 2191 | CH | O | Q1c | a bond | Me | a bond | NH | O | a bond | T3a | OH |
| 2192 | CH | O | Q1c | a bond | Me | a bond | NH | O | a bond | T3b | OH |
| 2193 | CH | O | Q1c | a bond | Me | a bond | NH | O | a bond | T3c | OH |
| 2194 | CH | O | Q1c | a bond | Me | a bond | NH | O | a bond | T3d | OH |
| 2195 | CH | O | Q1c | a bond | Me | a bond | NH | O | a bond | T3e | OH |
| 2196 | CH | O | Q1c | a bond | Me | a bond | NH | O | a bond | T3f | OH |
| 2197 | CH | O | Q1c | a bond | Me | a bond | NH | O | a bond | T3g | OH |
| 2198 | CH | O | Q1c | a bond | Me | a bond | NH | O | a bond | T3h | OH |
| 2199 | CH | O | Q1c | a bond | Me | a bond | NH | O | a bond | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 2200 | CH | O | Q1c | a bond | Me | a bond | NH | O | a bond | T3j | OH |
| 2201 | CH | O | Q1c | a bond | H | a bond | NH | S | NH | T3a | OH |
| 2202 | CH | O | Q1c | a bond | H | a bond | NH | S | NH | T3b | OH |
| 2203 | CH | O | Q1c | a bond | H | a bond | NH | S | NH | T3c | OH |
| 2204 | CH | O | Q1c | a bond | H | a bond | NH | S | NH | T3d | OH |
| 2205 | CH | O | Q1c | a bond | H | a bond | NH | S | NH | T3e | OH |
| 2206 | CH | O | Q1c | a bond | H | a bond | NH | S | NH | T3f | OH |
| 2207 | CH | O | Q1c | a bond | H | a bond | NH | S | NH | T3g | OH |
| 2208 | CH | O | Q1c | a bond | H | a bond | NH | S | NH | T3h | OH |
| 2209 | CH | O | Q1c | a bond | H | a bond | NH | S | NH | T3i | OH |
| 2210 | CH | O | Q1c | a bond | H | a bond | NH | S | NH | T3j | OH |
| 2211 | CH | O | Q1c | a bond | H | a bond | NH | S | a bond | T3a | OH |
| 2212 | CH | O | Q1c | a bond | H | a bond | NH | S | a bond | T3b | OH |
| 2213 | CH | O | Q1c | a bond | H | a bond | NH | S | a bond | T3c | OH |
| 2214 | CH | O | Q1c | a bond | H | a bond | NH | S | a bond | T3d | OH |
| 2215 | CH | O | Q1c | a bond | H | a bond | NH | S | a bond | T3e | OH |
| 2216 | CH | O | Q1c | a bond | H | a bond | NH | S | a bond | T3f | OH |
| 2217 | CH | O | Q1c | a bond | H | a bond | NH | S | a bond | T3g | OH |
| 2218 | CH | O | Q1c | a bond | H | a bond | NH | S | a bond | T3h | OH |
| 2219 | CH | O | Q1c | a bond | H | a bond | NH | S | a bond | T3i | OH |
| 2220 | CH | O | Q1c | a bond | H | a bond | NH | S | a bond | T3j | OH |
| 2221 | CH | O | Q1c | a bond | H | a bond | NH | O | NH | T3a | OH |
| 2222 | CH | O | Q1c | a bond | H | a bond | NH | O | NH | T3b | OH |
| 2223 | CH | O | Q1c | a bond | H | a bond | NH | O | NH | T3c | OH |
| 2224 | CH | O | Q1c | a bond | H | a bond | NH | O | NH | T3d | OH |
| 2225 | CH | O | Q1c | a bond | H | a bond | NH | O | NH | T3e | OH |
| 2226 | CH | O | Q1c | a bond | H | a bond | NH | O | NH | T3f | OH |
| 2227 | CH | O | Q1c | a bond | H | a bond | NH | O | NH | T3g | OH |
| 2228 | CH | O | Q1c | a bond | H | a bond | NH | O | NH | T3h | OH |
| 2229 | CH | O | Q1c | a bond | H | a bond | NH | O | NH | T3i | OH |
| 2230 | CH | O | Q1c | a bond | H | a bond | NH | O | NH | T3j | OH |
| 2231 | CH | O | Q1c | a bond | H | a bond | NH | O | a bond | T3a | OH |
| 2232 | CH | O | Q1c | a bond | H | a bond | NH | O | a bond | T3b | OH |
| 2233 | CH | O | Q1c | a bond | H | a bond | NH | O | a bond | T3c | OH |
| 2234 | CH | O | Q1c | a bond | H | a bond | NH | O | a bond | T3d | OH |
| 2235 | CH | O | Q1c | a bond | H | a bond | NH | O | a bond | T3e | OH |
| 2236 | CH | O | Q1c | a bond | H | a bond | NH | O | a bond | T3f | OH |
| 2237 | CH | O | Q1c | a bond | H | a bond | NH | O | a bond | T3g | OH |
| 2238 | CH | O | Q1c | a bond | H | a bond | NH | O | a bond | T3h | OH |
| 2239 | CH | O | Q1c | a bond | H | a bond | NH | O | a bond | T3i | OH |
| 2240 | CH | O | Q1c | a bond | H | a bond | NH | O | a bond | T3j | OH |
| 2241 | CH | O | Q1i | a bond | Me | a bond | NH | S | NH | T3a | OH |
| 2242 | CH | O | Q1i | a bond | Me | a bond | NH | S | NH | T3b | OH |
| 2243 | CH | O | Q1i | a bond | Me | a bond | NH | S | NH | T3c | OH |
| 2244 | CH | O | Q1i | a bond | Me | a bond | NH | S | NH | T3d | OH |
| 2245 | CH | O | Q1i | a bond | Me | a bond | NH | S | NH | T3e | OH |
| 2246 | CH | O | Q1i | a bond | Me | a bond | NH | S | NH | T3f | OH |
| 2247 | CH | O | Q1i | a bond | Me | a bond | NH | S | NH | T3g | OH |
| 2248 | CH | O | Q1i | a bond | Me | a bond | NH | S | NH | T3h | OH |
| 2249 | CH | O | Q1i | a bond | Me | a bond | NH | S | NH | T3i | OH |
| 2250 | CH | O | Q1i | a bond | Me | a bond | NH | S | NH | T3j | OH |
| 2251 | CH | O | Q1i | a bond | Me | a bond | NH | S | a bond | T3a | OH |
| 2252 | CH | O | Q1i | a bond | Me | a bond | NH | S | a bond | T3b | OH |
| 2253 | CH | O | Q1i | a bond | Me | a bond | NH | S | a bond | T3c | OH |
| 2254 | CH | O | Q1i | a bond | Me | a bond | NH | S | a bond | T3d | OH |
| 2255 | CH | O | Q1i | a bond | Me | a bond | NH | S | a bond | T3e | OH |
| 2256 | CH | O | Q1i | a bond | Me | a bond | NH | S | a bond | T3f | OH |
| 2257 | CH | O | Q1i | a bond | Me | a bond | NH | S | a bond | T3g | OH |
| 2258 | CH | O | Q1i | a bond | Me | a bond | NH | S | a bond | T3h | OH |
| 2259 | CH | O | Q1i | a bond | Me | a bond | NH | S | a bond | T3i | OH |
| 2260 | CH | O | Q1i | a bond | Me | a bond | NH | S | a bond | T3j | OH |
| 2261 | CH | O | Q1i | a bond | Me | a bond | NH | O | NH | T3a | OH |
| 2262 | CH | O | Q1i | a bond | Me | a bond | NH | O | NH | T3b | OH |
| 2263 | CH | O | Q1i | a bond | Me | a bond | NH | O | NH | T3c | OH |
| 2264 | CH | O | Q1i | a bond | Me | a bond | NH | O | NH | T3d | OH |
| 2265 | CH | O | Q1i | a bond | Me | a bond | NH | O | NH | T3e | OH |
| 2266 | CH | O | Q1i | a bond | Me | a bond | NH | O | NH | T3f | OH |
| 2267 | CH | O | Q1i | a bond | Me | a bond | NH | O | NH | T3g | OH |
| 2268 | CH | O | Q1i | a bond | Me | a bond | NH | O | NH | T3h | OH |
| 2269 | CH | O | Q1i | a bond | Me | a bond | NH | O | NH | T3i | OH |
| 2270 | CH | O | Q1i | a bond | Me | a bond | NH | O | NH | T3j | OH |
| 2271 | CH | O | Q1i | a bond | Me | a bond | NH | O | a bond | T3a | OH |
| 2272 | CH | O | Q1i | a bond | Me | a bond | NH | O | a bond | T3b | OH |
| 2273 | CH | O | Q1i | a bond | Me | a bond | NH | O | a bond | T3c | OH |
| 2274 | CH | O | Q1i | a bond | Me | a bond | NH | O | a bond | T3d | OH |
| 2275 | CH | O | Q1i | a bond | Me | a bond | NH | O | a bond | T3e | OH |
| 2276 | CH | O | Q1i | a bond | Me | a bond | NH | O | a bond | T3f | OH |
| 2277 | CH | O | Q1i | a bond | Me | a bond | NH | O | a bond | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 2278 | CH | O | Q1i | a bond | Me | a bond | NH | O | a bond | T3h | OH |
| 2279 | CH | O | Q1i | a bond | Me | a bond | NH | O | a bond | T3i | OH |
| 2280 | CH | O | Q1i | a bond | Me | a bond | NH | O | a bond | T3j | OH |
| 2281 | CH | O | Q1i | a bond | H | a bond | NH | S | NH | T3a | OH |
| 2282 | CH | O | Q1i | a bond | H | a bond | NH | S | NH | T3b | OH |
| 2283 | CH | O | Q1i | a bond | H | a bond | NH | S | NH | T3c | OH |
| 2284 | CH | O | Q1i | a bond | H | a bond | NH | S | NH | T3d | OH |
| 2285 | CH | O | Q1i | a bond | H | a bond | NH | S | NH | T3e | OH |
| 2286 | CH | O | Q1i | a bond | H | a bond | NH | S | NH | T3f | OH |
| 2287 | CH | O | Q1i | a bond | H | a bond | NH | S | NH | T3g | OH |
| 2288 | CH | O | Q1i | a bond | H | a bond | NH | S | NH | T3h | OH |
| 2289 | CH | O | Q1i | a bond | H | a bond | NH | S | NH | T3i | OH |
| 2290 | CH | O | Q1i | a bond | H | a bond | NH | S | NH | T3j | OH |
| 2291 | CH | O | Q1i | a bond | H | a bond | NH | S | a bond | T3a | OH |
| 2292 | CH | O | Q1i | a bond | H | a bond | NH | S | a bond | T3b | OH |
| 2293 | CH | O | Q1i | a bond | H | a bond | NH | S | a bond | T3c | OH |
| 2294 | CH | O | Q1i | a bond | H | a bond | NH | S | a bond | T3d | OH |
| 2295 | CH | O | Q1i | a bond | H | a bond | NH | S | a bond | T3e | OH |
| 2296 | CH | O | Q1i | a bond | H | a bond | NH | S | a bond | T3f | OH |
| 2297 | CH | O | Q1i | a bond | H | a bond | NH | S | a bond | T3g | OH |
| 2298 | CH | O | Q1i | a bond | H | a bond | NH | S | a bond | T3h | OH |
| 2299 | CH | O | Q1i | a bond | H | a bond | NH | S | a bond | T3i | OH |
| 2300 | CH | O | Q1i | a bond | H | a bond | NH | S | a bond | T3j | OH |
| 2301 | CH | O | Q1i | a bond | H | a bond | NH | O | NH | T3a | OH |
| 2302 | CH | O | Q1i | a bond | H | a bond | NH | O | NH | T3b | OH |
| 2303 | CH | O | Q1i | a bond | H | a bond | NH | O | NH | T3c | OH |
| 2304 | CH | O | Q1i | a bond | H | a bond | NH | O | NH | T3d | OH |
| 2305 | CH | O | Q1i | a bond | H | a bond | NH | O | NH | T3e | OH |
| 2306 | CH | O | Q1i | a bond | H | a bond | NH | O | NH | T3f | OH |
| 2307 | CH | O | Q1i | a bond | H | a bond | NH | O | NH | T3g | OH |
| 2308 | CH | O | Q1i | a bond | H | a bond | NH | O | NH | T3h | OH |
| 2309 | CH | O | Q1i | a bond | H | a bond | NH | O | NH | T3i | OH |
| 2310 | CH | O | Q1i | a bond | H | a bond | NH | O | NH | T3j | OH |
| 2311 | CH | O | Q1i | a bond | H | a bond | NH | O | a bond | T3a | OH |
| 2312 | CH | O | Q1i | a bond | H | a bond | NH | O | a bond | T3b | OH |
| 2313 | CH | O | Q1i | a bond | H | a bond | NH | O | a bond | T3c | OH |
| 2314 | CH | O | Q1i | a bond | H | a bond | NH | O | a bond | T3d | OH |
| 2315 | CH | O | Q1i | a bond | H | a bond | NH | O | a bond | T3e | OH |
| 2316 | CH | O | Q1i | a bond | H | a bond | NH | O | a bond | T3f | OH |
| 2317 | CH | O | Q1i | a bond | H | a bond | NH | O | a bond | T3g | OH |
| 2318 | CH | O | Q1i | a bond | H | a bond | NH | O | a bond | T3h | OH |
| 2319 | CH | O | Q1i | a bond | H | a bond | NH | O | a bond | T3i | OH |
| 2320 | CH | O | Q1i | a bond | H | a bond | NH | O | a bond | T3j | OH |
| 2321 | CH | O | Q1j | a bond | Me | a bond | NH | S | NH | T3a | OH |
| 2322 | CH | O | Q1j | a bond | Me | a bond | NH | S | NH | T3b | OH |
| 2323 | CH | O | Q1j | a bond | Me | a bond | NH | S | NH | T3c | OH |
| 2324 | CH | O | Q1j | a bond | Me | a bond | NH | S | NH | T3d | OH |
| 2325 | CH | O | Q1j | a bond | Me | a bond | NH | S | NH | T3e | OH |
| 2326 | CH | O | Q1j | a bond | Me | a bond | NH | S | NH | T3f | OH |
| 2327 | CH | O | Q1j | a bond | Me | a bond | NH | S | NH | T3g | OH |
| 2328 | CH | O | Q1j | a bond | Me | a bond | NH | S | NH | T3h | OH |
| 2329 | CH | O | Q1j | a bond | Me | a bond | NH | S | NH | T3i | OH |
| 2330 | CH | O | Q1j | a bond | Me | a bond | NH | S | NH | T3j | OH |
| 2331 | CH | O | Q1j | a bond | Me | a bond | NH | S | a bond | T3a | OH |
| 2332 | CH | O | Q1j | a bond | Me | a bond | NH | S | a bond | T3b | OH |
| 2333 | CH | O | Q1j | a bond | Me | a bond | NH | S | a bond | T3c | OH |
| 2334 | CH | O | Q1j | a bond | Me | a bond | NH | S | a bond | T3d | OH |
| 2335 | CH | O | Q1j | a bond | Me | a bond | NH | S | a bond | T3e | OH |
| 2336 | CH | O | Q1j | a bond | Me | a bond | NH | S | a bond | T3f | OH |
| 2337 | CH | O | Q1j | a bond | Me | a bond | NH | S | a bond | T3g | OH |
| 2338 | CH | O | Q1j | a bond | Me | a bond | NH | S | a bond | T3h | OH |
| 2339 | CH | O | Q1j | a bond | Me | a bond | NH | S | a bond | T3i | OH |
| 2340 | CH | O | Q1j | a bond | Me | a bond | NH | S | a bond | T3j | OH |
| 2341 | CH | O | Q1j | a bond | Me | a bond | NH | O | NH | T3a | OH |
| 2342 | CH | O | Q1j | a bond | Me | a bond | NH | O | NH | T3b | OH |
| 2343 | CH | O | Q1j | a bond | Me | a bond | NH | O | NH | T3c | OH |
| 2344 | CH | O | Q1j | a bond | Me | a bond | NH | O | NH | T3d | OH |
| 2345 | CH | O | Q1j | a bond | Me | a bond | NH | O | NH | T3e | OH |
| 2346 | CH | O | Q1j | a bond | Me | a bond | NH | O | NH | T3f | OH |
| 2347 | CH | O | Q1j | a bond | Me | a bond | NH | O | NH | T3g | OH |
| 2348 | CH | O | Q1j | a bond | Me | a bond | NH | O | NH | T3h | OH |
| 2349 | CH | O | Q1j | a bond | Me | a bond | NH | O | NH | T3i | OH |
| 2350 | CH | O | Q1j | a bond | Me | a bond | NH | O | NH | T3j | OH |
| 2351 | CH | O | Q1j | a bond | Me | a bond | NH | O | a bond | T3a | OH |
| 2352 | CH | O | Q1j | a bond | Me | a bond | NH | O | a bond | T3b | OH |
| 2353 | CH | O | Q1j | a bond | Me | a bond | NH | O | a bond | T3c | OH |
| 2354 | CH | O | Q1j | a bond | Me | a bond | NH | O | a bond | T3d | OH |
| 2355 | CH | O | Q1j | a bond | Me | a bond | NH | O | a bond | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 2356 | CH | O | Q1j | a bond | Me | a bond | NH | O | a bond | T3f | OH |
| 2357 | CH | O | Q1j | a bond | Me | a bond | NH | O | a bond | T3g | OH |
| 2358 | CH | O | Q1j | a bond | Me | a bond | NH | O | a bond | T3h | OH |
| 2359 | CH | O | Q1j | a bond | Me | a bond | NH | O | a bond | T3i | OH |
| 2360 | CH | O | Q1j | a bond | Me | a bond | NH | O | a bond | T3j | OH |
| 2361 | CH | O | Q1j | a bond | H | a bond | NH | S | NH | T3a | OH |
| 2362 | CH | O | Q1j | a bond | H | a bond | NH | S | NH | T3b | OH |
| 2363 | CH | O | Q1j | a bond | H | a bond | NH | S | NH | T3c | OH |
| 2364 | CH | O | Q1j | a bond | H | a bond | NH | S | NH | T3d | OH |
| 2365 | CH | O | Q1j | a bond | H | a bond | NH | S | NH | T3e | OH |
| 2366 | CH | O | Q1j | a bond | H | a bond | NH | S | NH | T3f | OH |
| 2367 | CH | O | Q1j | a bond | H | a bond | NH | S | NH | T3g | OH |
| 2368 | CH | O | Q1j | a bond | H | a bond | NH | S | NH | T3h | OH |
| 2369 | CH | O | Q1j | a bond | H | a bond | NH | S | NH | T3i | OH |
| 2370 | CH | O | Q1j | a bond | H | a bond | NH | S | NH | T3j | OH |
| 2371 | CH | O | Q1j | a bond | H | a bond | NH | S | a bond | T3a | OH |
| 2372 | CH | O | Q1j | a bond | H | a bond | NH | S | a bond | T3b | OH |
| 2373 | CH | O | Q1j | a bond | H | a bond | NH | S | a bond | T3c | OH |
| 2374 | CH | O | Q1j | a bond | H | a bond | NH | S | a bond | T3d | OH |
| 2375 | CH | O | Q1j | a bond | H | a bond | NH | S | a bond | T3e | OH |
| 2376 | CH | O | Q1j | a bond | H | a bond | NH | S | a bond | T3f | OH |
| 2377 | CH | O | Q1j | a bond | H | a bond | NH | S | a bond | T3g | OH |
| 2378 | CH | O | Q1j | a bond | H | a bond | NH | S | a bond | T3h | OH |
| 2379 | CH | O | Q1j | a bond | H | a bond | NH | S | a bond | T3i | OH |
| 2380 | CH | O | Q1j | a bond | H | a bond | NH | S | a bond | T3j | OH |
| 2381 | CH | O | Q1j | a bond | H | a bond | NH | O | NH | T3a | OH |
| 2382 | CH | O | Q1j | a bond | H | a bond | NH | O | NH | T3b | OH |
| 2383 | CH | O | Q1j | a bond | H | a bond | NH | O | NH | T3c | OH |
| 2384 | CH | O | Q1j | a bond | H | a bond | NH | O | NH | T3d | OH |
| 2385 | CH | O | Q1j | a bond | H | a bond | NH | O | NH | T3e | OH |
| 2386 | CH | O | Q1j | a bond | H | a bond | NH | O | NH | T3f | OH |
| 2387 | CH | O | Q1j | a bond | H | a bond | NH | O | NH | T3g | OH |
| 2388 | CH | O | Q1j | a bond | H | a bond | NH | O | NH | T3h | OH |
| 2389 | CH | O | Q1j | a bond | H | a bond | NH | O | NH | T3i | OH |
| 2390 | CH | O | Q1j | a bond | H | a bond | NH | O | NH | T3j | OH |
| 2391 | CH | O | Q1j | a bond | H | a bond | NH | O | a bond | T3a | OH |
| 2392 | CH | O | Q1j | a bond | H | a bond | NH | O | a bond | T3b | OH |
| 2393 | CH | O | Q1j | a bond | H | a bond | NH | O | a bond | T3c | OH |
| 2394 | CH | O | Q1j | a bond | H | a bond | NH | O | a bond | T3d | OH |
| 2395 | CH | O | Q1j | a bond | H | a bond | NH | O | a bond | T3e | OH |
| 2396 | CH | O | Q1j | a bond | H | a bond | NH | O | a bond | T3f | OH |
| 2397 | CH | O | Q1j | a bond | H | a bond | NH | O | a bond | T3g | OH |
| 2398 | CH | O | Q1j | a bond | H | a bond | NH | O | a bond | T3h | OH |
| 2399 | CH | O | Q1j | a bond | H | a bond | NH | O | a bond | T3i | OH |
| 2400 | CH | O | Q1j | a bond | H | a bond | NH | O | a bond | T3j | OH |
| 2401 | CMe | NMe | Q1a | a bond | Me | a bond | NH | S | NH | T3a | OH |
| 2402 | CMe | NMe | Q1a | a bond | Me | a bond | NH | S | NH | T3b | OH |
| 2403 | CMe | NMe | Q1a | a bond | Me | a bond | NH | S | NH | T3c | OH |
| 2404 | CMe | NMe | Q1a | a bond | Me | a bond | NH | S | NH | T3d | OH |
| 2405 | CMe | NMe | Q1a | a bond | Me | a bond | NH | S | NH | T3e | OH |
| 2406 | CMe | NMe | Q1a | a bond | Me | a bond | NH | S | NH | T3f | OH |
| 2407 | CMe | NMe | Q1a | a bond | Me | a bond | NH | S | NH | T3g | OH |
| 2408 | CMe | NMe | Q1a | a bond | Me | a bond | NH | S | NH | T3h | OH |
| 2409 | CMe | NMe | Q1a | a bond | Me | a bond | NH | S | NH | T3i | OH |
| 2410 | CMe | NMe | Q1a | a bond | Me | a bond | NH | S | NH | T3j | OH |
| 2411 | CMe | NMe | Q1a | a bond | Me | a bond | NH | S | a bond | T3a | OH |
| 2412 | CMe | NMe | Q1a | a bond | Me | a bond | NH | S | a bond | T3b | OH |
| 2413 | CMe | NMe | Q1a | a bond | Me | a bond | NH | S | a bond | T3c | OH |
| 2414 | CMe | NMe | Q1a | a bond | Me | a bond | NH | S | a bond | T3d | OH |
| 2415 | CMe | NMe | Q1a | a bond | Me | a bond | NH | S | a bond | T3e | OH |
| 2416 | CMe | NMe | Q1a | a bond | Me | a bond | NH | S | a bond | T3f | OH |
| 2417 | CMe | NMe | Q1a | a bond | Me | a bond | NH | S | a bond | T3g | OH |
| 2418 | CMe | NMe | Q1a | a bond | Me | a bond | NH | S | a bond | T3h | OH |
| 2419 | CMe | NMe | Q1a | a bond | Me | a bond | NH | S | a bond | T3i | OH |
| 2420 | CMe | NMe | Q1a | a bond | Me | a bond | NH | S | a bond | T3j | OH |
| 2421 | CMe | NMe | Q1a | a bond | Me | a bond | NH | O | NH | T3a | OH |
| 2422 | CMe | NMe | Q1a | a bond | Me | a bond | NH | O | NH | T3b | OH |
| 2423 | CMe | NMe | Q1a | a bond | Me | a bond | NH | O | NH | T3c | OH |
| 2424 | CMe | NMe | Q1a | a bond | Me | a bond | NH | O | NH | T3d | OH |
| 2425 | CMe | NMe | Q1a | a bond | Me | a bond | NH | O | NH | T3e | OH |
| 2426 | CMe | NMe | Q1a | a bond | Me | a bond | NH | O | NH | T3f | OH |
| 2427 | CMe | NMe | Q1a | a bond | Me | a bond | NH | O | NH | T3g | OH |
| 2428 | CMe | NMe | Q1a | a bond | Me | a bond | NH | O | NH | T3h | OH |
| 2429 | CMe | NMe | Q1a | a bond | Me | a bond | NH | O | NH | T3i | OH |
| 2430 | CMe | NMe | Q1a | a bond | Me | a bond | NH | O | NH | T3j | OH |
| 2431 | CMe | NMe | Q1a | a bond | Me | a bond | NH | O | a bond | T3a | OH |
| 2432 | CMe | NMe | Q1a | a bond | Me | a bond | NH | O | a bond | T3b | OH |
| 2433 | CMe | NMe | Q1a | a bond | Me | a bond | NH | O | a bond | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 2434 | CMe | NMe | Q1a | a bond | Me | a bond | NH | O | a bond | T3d | OH |
| 2435 | CMe | NMe | Q1a | a bond | Me | a bond | NH | O | a bond | T3e | OH |
| 2436 | CMe | NMe | Q1a | a bond | Me | a bond | NH | O | a bond | T3f | OH |
| 2437 | CMe | NMe | Q1a | a bond | Me | a bond | NH | O | a bond | T3g | OH |
| 2438 | CMe | NMe | Q1a | a bond | Me | a bond | NH | O | a bond | T3h | OH |
| 2439 | CMe | NMe | Q1a | a bond | Me | a bond | NH | O | a bond | T3i | OH |
| 2440 | CMe | NMe | Q1a | a bond | Me | a bond | NH | O | a bond | T3j | OH |
| 2441 | CMe | NMe | Q1a | a bond | H | a bond | NH | S | NH | T3a | OH |
| 2442 | CMe | NMe | Q1a | a bond | H | a bond | NH | S | NH | T3b | OH |
| 2443 | CMe | NMe | Q1a | a bond | H | a bond | NH | S | NH | T3c | OH |
| 2444 | CMe | NMe | Q1a | a bond | H | a bond | NH | S | NH | T3d | OH |
| 2445 | CMe | NMe | Q1a | a bond | H | a bond | NH | S | NH | T3e | OH |
| 2446 | CMe | NMe | Q1a | a bond | H | a bond | NH | S | NH | T3f | OH |
| 2447 | CMe | NMe | Q1a | a bond | H | a bond | NH | S | NH | T3g | OH |
| 2448 | CMe | NMe | Q1a | a bond | H | a bond | NH | S | NH | T3h | OH |
| 2449 | CMe | NMe | Q1a | a bond | H | a bond | NH | S | NH | T3i | OH |
| 2450 | CMe | NMe | Q1a | a bond | H | a bond | NH | S | NH | T3j | OH |
| 2451 | CMe | NMe | Q1a | a bond | H | a bond | NH | S | a bond | T3a | OH |
| 2452 | CMe | NMe | Q1a | a bond | H | a bond | NH | S | a bond | T3b | OH |
| 2453 | CMe | NMe | Q1a | a bond | H | a bond | NH | S | a bond | T3c | OH |
| 2454 | CMe | NMe | Q1a | a bond | H | a bond | NH | S | a bond | T3d | OH |
| 2455 | CMe | NMe | Q1a | a bond | H | a bond | NH | S | a bond | T3e | OH |
| 2456 | CMe | NMe | Q1a | a bond | H | a bond | NH | S | a bond | T3f | OH |
| 2457 | CMe | NMe | Q1a | a bond | H | a bond | NH | S | a bond | T3g | OH |
| 2458 | CMe | NMe | Q1a | a bond | H | a bond | NH | S | a bond | T3h | OH |
| 2459 | CMe | NMe | Q1a | a bond | H | a bond | NH | S | a bond | T3i | OH |
| 2460 | CMe | NMe | Q1a | a bond | H | a bond | NH | S | a bond | T3j | OH |
| 2461 | CMe | NMe | Q1a | a bond | H | a bond | NH | O | NH | T3a | OH |
| 2462 | CMe | NMe | Q1a | a bond | H | a bond | NH | O | NH | T3b | OH |
| 2463 | CMe | NMe | Q1a | a bond | H | a bond | NH | O | NH | T3c | OH |
| 2464 | CMe | NMe | Q1a | a bond | H | a bond | NH | O | NH | T3d | OH |
| 2465 | CMe | NMe | Q1a | a bond | H | a bond | NH | O | NH | T3e | OH |
| 2466 | CMe | NMe | Q1a | a bond | H | a bond | NH | O | NH | T3f | OH |
| 2467 | CMe | NMe | Q1a | a bond | H | a bond | NH | O | NH | T3g | OH |
| 2468 | CMe | NMe | Q1a | a bond | H | a bond | NH | O | NH | T3h | OH |
| 2469 | CMe | NMe | Q1a | a bond | H | a bond | NH | O | NH | T3i | OH |
| 2470 | CMe | NMe | Q1a | a bond | H | a bond | NH | O | NH | T3j | OH |
| 2471 | CMe | NMe | Q1a | a bond | H | a bond | NH | O | a bond | T3a | OH |
| 2472 | CMe | NMe | Q1a | a bond | H | a bond | NH | O | a bond | T3b | OH |
| 2473 | CMe | NMe | Q1a | a bond | H | a bond | NH | O | a bond | T3c | OH |
| 2474 | CMe | NMe | Q1a | a bond | H | a bond | NH | O | a bond | T3d | OH |
| 2475 | CMe | NMe | Q1a | a bond | H | a bond | NH | O | a bond | T3e | OH |
| 2476 | CMe | NMe | Q1a | a bond | H | a bond | NH | O | a bond | T3f | OH |
| 2477 | CMe | NMe | Q1a | a bond | H | a bond | NH | O | a bond | T3g | OH |
| 2478 | CMe | NMe | Q1a | a bond | H | a bond | NH | O | a bond | T3h | OH |
| 2479 | CMe | NMe | Q1a | a bond | H | a bond | NH | O | a bond | T3i | OH |
| 2480 | CMe | NMe | Q1a | a bond | H | a bond | NH | O | a bond | T3j | OH |
| 2481 | CMe | NMe | Q1a | a bond | Me | a bond | NH | S | NH | T3a | OH |
| 2482 | CMe | NMe | Q1b | a bond | Me | a bond | NH | S | NH | T3b | OH |
| 2483 | CMe | NMe | Q1b | a bond | Me | a bond | NH | S | NH | T3c | OH |
| 2484 | CMe | NMe | Q1b | a bond | Me | a bond | NH | S | NH | T3d | OH |
| 2485 | CMe | NMe | Q1b | a bond | Me | a bond | NH | S | NH | T3e | OH |
| 2486 | CMe | NMe | Q1b | a bond | Me | a bond | NH | S | NH | T3f | OH |
| 2487 | CMe | NMe | Q1b | a bond | Me | a bond | NH | S | NH | T3g | OH |
| 2488 | CMe | NMe | Q1b | a bond | Me | a bond | NH | S | NH | T3h | OH |
| 2489 | CMe | NMe | Q1b | a bond | Me | a bond | NH | S | NH | T3i | OH |
| 2490 | CMe | NMe | Q1b | a bond | Me | a bond | NH | S | NH | T3j | OH |
| 2491 | CMe | NMe | Q1b | a bond | Me | a bond | NH | S | a bond | T3a | OH |
| 2492 | CMe | NMe | Q1b | a bond | Me | a bond | NH | S | a bond | T3b | OH |
| 2493 | CMe | NMe | Q1b | a bond | Me | a bond | NH | S | a bond | T3c | OH |
| 2494 | CMe | NMe | Q1b | a bond | Me | a bond | NH | S | a bond | T3d | OH |
| 2495 | CMe | NMe | Q1b | a bond | Me | a bond | NH | S | a bond | T3e | OH |
| 2496 | CMe | NMe | Q1b | a bond | Me | a bond | NH | S | a bond | T3f | OH |
| 2497 | CMe | NMe | Q1b | a bond | Me | a bond | NH | S | a bond | T3g | OH |
| 2498 | CMe | NMe | Q1b | a bond | Me | a bond | NH | S | a bond | T3h | OH |
| 2499 | CMe | NMe | Q1b | a bond | Me | a bond | NH | S | a bond | T3i | OH |
| 2500 | CMe | NMe | Q1b | a bond | Me | a bond | NH | S | a bond | T3j | OH |
| 2501 | CMe | NMe | Q1b | a bond | Me | a bond | NH | O | NH | T3a | OH |
| 2502 | CMe | NMe | Q1b | a bond | Me | a bond | NH | O | NH | T3b | OH |
| 2503 | CMe | NMe | Q1b | a bond | Me | a bond | NH | O | NH | T3c | OH |
| 2504 | CMe | NMe | Q1b | a bond | Me | a bond | NH | O | NH | T3d | OH |
| 2505 | CMe | NMe | Q1b | a bond | Me | a bond | NH | O | NH | T3e | OH |
| 2506 | CMe | NMe | Q1b | a bond | Me | a bond | NH | O | NH | T3f | OH |
| 2507 | CMe | NMe | Q1b | a bond | Me | a bond | NH | O | NH | T3g | OH |
| 2508 | CMe | NMe | Q1b | a bond | Me | a bond | NH | O | NH | T3h | OH |
| 2509 | CMe | NMe | Q1b | a bond | Me | a bond | NH | O | NH | T3i | OH |
| 2510 | CMe | NMe | Q1b | a bond | Me | a bond | NH | O | NH | T3j | OH |
| 2511 | CMe | NMe | Q1b | a bond | Me | a bond | NH | O | a bond | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 2512 | CMe | NMe | Q1b | a bond | Me | a bond | NH | O | a bond | T3b | OH |
| 2513 | CMe | NMe | Q1b | a bond | Me | a bond | NH | O | a bond | T3c | OH |
| 2514 | CMe | NMe | Q1b | a bond | Me | a bond | NH | O | a bond | T3d | OH |
| 2515 | CMe | NMe | Q1b | a bond | Me | a bond | NH | O | a bond | T3e | OH |
| 2516 | CMe | NMe | Q1b | a bond | Me | a bond | NH | O | a bond | T3f | OH |
| 2517 | CMe | NMe | Q1b | a bond | Me | a bond | NH | O | a bond | T3g | OH |
| 2518 | CMe | NMe | Q1b | a bond | Me | a bond | NH | O | a bond | T3h | OH |
| 2519 | CMe | NMe | Q1b | a bond | Me | a bond | NH | O | a bond | T3i | OH |
| 2520 | CMe | NMe | Q1b | a bond | Me | a bond | NH | O | a bond | T3j | OH |
| 2521 | CMe | NMe | Q1b | a bond | H | a bond | NH | S | NH | T3a | OH |
| 2522 | CMe | NMe | Q1b | a bond | H | a bond | NH | S | NH | T3b | OH |
| 2523 | CMe | NMe | Q1b | a bond | H | a bond | NH | S | NH | T3c | OH |
| 2524 | CMe | NMe | Q1b | a bond | H | a bond | NH | S | NH | T3d | OH |
| 2525 | CMe | NMe | Q1b | a bond | H | a bond | NH | S | NH | T3e | OH |
| 2526 | CMe | NMe | Q1b | a bond | H | a bond | NH | S | NH | T3f | OH |
| 2527 | CMe | NMe | Q1b | a bond | H | a bond | NH | S | NH | T3g | OH |
| 2528 | CMe | NMe | Q1b | a bond | H | a bond | NH | S | NH | T3h | OH |
| 2529 | CMe | NMe | Q1b | a bond | H | a bond | NH | S | NH | T3i | OH |
| 2530 | CMe | NMe | Q1b | a bond | H | a bond | NH | S | NH | T3j | OH |
| 2531 | CMe | NMe | Q1b | a bond | H | a bond | NH | S | a bond | T3a | OH |
| 2532 | CMe | NMe | Q1b | a bond | H | a bond | NH | S | a bond | T3b | OH |
| 2533 | CMe | NMe | Q1b | a bond | H | a bond | NH | S | a bond | T3c | OH |
| 2534 | CMe | NMe | Q1b | a bond | H | a bond | NH | S | a bond | T3d | OH |
| 2535 | CMe | NMe | Q1b | a bond | H | a bond | NH | S | a bond | T3e | OH |
| 2536 | CMe | NMe | Q1b | a bond | H | a bond | NH | S | a bond | T3f | OH |
| 2537 | CMe | NMe | Q1b | a bond | H | a bond | NH | S | a bond | T3g | OH |
| 2538 | CMe | NMe | Q1b | a bond | H | a bond | NH | S | a bond | T3h | OH |
| 2539 | CMe | NMe | Q1b | a bond | H | a bond | NH | S | a bond | T3i | OH |
| 2540 | CMe | NMe | Q1b | a bond | H | a bond | NH | S | a bond | T3j | OH |
| 2541 | CMe | NMe | Q1b | a bond | H | a bond | NH | O | NH | T3a | OH |
| 2542 | CMe | NMe | Q1b | a bond | H | a bond | NH | O | NH | T3b | OH |
| 2543 | CMe | NMe | Q1b | a bond | H | a bond | NH | O | NH | T3c | OH |
| 2544 | CMe | NMe | Q1b | a bond | H | a bond | NH | O | NH | T3d | OH |
| 2545 | CMe | NMe | Q1b | a bond | H | a bond | NH | O | NH | T3e | OH |
| 2546 | CMe | NMe | Q1b | a bond | H | a bond | NH | O | NH | T3f | OH |
| 2547 | CMe | NMe | Q1b | a bond | H | a bond | NH | O | NH | T3g | OH |
| 2548 | CMe | NMe | Q1b | a bond | H | a bond | NH | O | NH | T3h | OH |
| 2549 | CMe | NMe | Q1b | a bond | H | a bond | NH | O | NH | T3i | OH |
| 2550 | CMe | NMe | Q1b | a bond | H | a bond | NH | O | NH | T3j | OH |
| 2551 | CMe | NMe | Q1b | a bond | H | a bond | NH | O | a bond | T3a | OH |
| 2552 | CMe | NMe | Q1b | a bond | H | a bond | NH | O | a bond | T3b | OH |
| 2553 | CMe | NMe | Q1b | a bond | H | a bond | NH | O | a bond | T3c | OH |
| 2554 | CMe | NMe | Q1b | a bond | H | a bond | NH | O | a bond | T3d | OH |
| 2555 | CMe | NMe | Q1b | a bond | H | a bond | NH | O | a bond | T3e | OH |
| 2556 | CMe | NMe | Q1b | a bond | H | a bond | NH | O | a bond | T3f | OH |
| 2557 | CMe | NMe | Q1b | a bond | H | a bond | NH | O | a bond | T3g | OH |
| 2558 | CMe | NMe | Q1b | a bond | H | a bond | NH | O | a bond | T3h | OH |
| 2559 | CMe | NMe | Q1b | a bond | H | a bond | NH | O | a bond | T3i | OH |
| 2560 | CMe | NMe | Q1b | a bond | H | a bond | NH | O | a bond | T3j | OH |
| 2561 | CMe | NMe | Q1c | a bond | Me | a bond | NH | S | NH | T3a | OH |
| 2562 | CMe | NMe | Q1c | a bond | Me | a bond | NH | S | NH | T3b | OH |
| 2563 | CMe | NMe | Q1c | a bond | Me | a bond | NH | S | NH | T3c | OH |
| 2564 | CMe | NMe | Q1c | a bond | Me | a bond | NH | S | NH | T3d | OH |
| 2565 | CMe | NMe | Q1c | a bond | Me | a bond | NH | S | NH | T3e | OH |
| 2566 | CMe | NMe | Q1c | a bond | Me | a bond | NH | S | NH | T3f | OH |
| 2567 | CMe | NMe | Q1c | a bond | Me | a bond | NH | S | NH | T3g | OH |
| 2568 | CMe | NMe | Q1c | a bond | Me | a bond | NH | S | NH | T3h | OH |
| 2569 | CMe | NMe | Q1c | a bond | Me | a bond | NH | S | NH | T3i | OH |
| 2570 | CMe | NMe | Q1c | a bond | Me | a bond | NH | S | NH | T3j | OH |
| 2571 | CMe | NMe | Q1c | a bond | Me | a bond | NH | S | a bond | T3a | OH |
| 2572 | CMe | NMe | Q1c | a bond | Me | a bond | NH | S | a bond | T3b | OH |
| 2573 | CMe | NMe | Q1c | a bond | Me | a bond | NH | S | a bond | T3c | OH |
| 2574 | CMe | NMe | Q1c | a bond | Me | a bond | NH | S | a bond | T3d | OH |
| 2575 | CMe | NMe | Q1c | a bond | Me | a bond | NH | S | a bond | T3e | OH |
| 2576 | CMe | NMe | Q1c | a bond | Me | a bond | NH | S | a bond | T3f | OH |
| 2577 | CMe | NMe | Q1c | a bond | Me | a bond | NH | S | a bond | T3g | OH |
| 2578 | CMe | NMe | Q1c | a bond | Me | a bond | NH | S | a bond | T3h | OH |
| 2579 | CMe | NMe | Q1c | a bond | Me | a bond | NH | S | a bond | T3i | OH |
| 2580 | CMe | NMe | Q1c | a bond | Me | a bond | NH | S | a bond | T3j | OH |
| 2581 | CMe | NMe | Q1c | a bond | Me | a bond | NH | O | NH | T3a | OH |
| 2582 | CMe | NMe | Q1c | a bond | Me | a bond | NH | O | NH | T3b | OH |
| 2583 | CMe | NMe | Q1c | a bond | Me | a bond | NH | O | NH | T3c | OH |
| 2584 | CMe | NMe | Q1c | a bond | Me | a bond | NH | O | NH | T3d | OH |
| 2585 | CMe | NMe | Q1c | a bond | Me | a bond | NH | O | NH | T3e | OH |
| 2586 | CMe | NMe | Q1c | a bond | Me | a bond | NH | O | NH | T3f | OH |
| 2587 | CMe | NMe | Q1c | a bond | Me | a bond | NH | O | NH | T3g | OH |
| 2588 | CMe | NMe | Q1c | a bond | Me | a bond | NH | O | NH | T3h | OH |
| 2589 | CMe | NMe | Q1c | a bond | Me | a bond | NH | O | NH | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 2590 | CMe | NMe | Q1c | a bond | Me | a bond | NH | O | NH | T3j | OH |
| 2591 | CMe | NMe | Q1c | a bond | Me | a bond | NH | O | a bond | T3a | OH |
| 2592 | CMe | NMe | Q1c | a bond | Me | a bond | NH | O | a bond | T3b | OH |
| 2593 | CMe | NMe | Q1c | a bond | Me | a bond | NH | O | a bond | T3c | OH |
| 2594 | CMe | NMe | Q1c | a bond | Me | a bond | NH | O | a bond | T3d | OH |
| 2595 | CMe | NMe | Q1c | a bond | Me | a bond | NH | O | a bond | T3e | OH |
| 2596 | CMe | NMe | Q1c | a bond | Me | a bond | NH | O | a bond | T3f | OH |
| 2597 | CMe | NMe | Q1c | a bond | Me | a bond | NH | O | a bond | T3g | OH |
| 2598 | CMe | NMe | Q1c | a bond | Me | a bond | NH | O | a bond | T3h | OH |
| 2599 | CMe | NMe | Q1c | a bond | Me | a bond | NH | O | a bond | T3i | OH |
| 2600 | CMe | NMe | Q1c | a bond | Me | a bond | NH | O | a bond | T3j | OH |
| 2601 | CMe | NMe | Q1c | a bond | H | a bond | NH | S | NH | T3a | OH |
| 2602 | CMe | NMe | Q1c | a bond | H | a bond | NH | S | NH | T3b | OH |
| 2603 | CMe | NMe | Q1c | a bond | H | a bond | NH | S | NH | T3c | OH |
| 2604 | CMe | NMe | Q1c | a bond | H | a bond | NH | S | NH | T3d | OH |
| 2605 | CMe | NMe | Q1c | a bond | H | a bond | NH | S | NH | T3e | OH |
| 2606 | CMe | NMe | Q1c | a bond | H | a bond | NH | S | NH | T3f | OH |
| 2607 | CMe | NMe | Q1c | a bond | H | a bond | NH | S | NH | T3g | OH |
| 2608 | CMe | NMe | Q1c | a bond | H | a bond | NH | S | NH | T3h | OH |
| 2609 | CMe | NMe | Q1c | a bond | H | a bond | NH | S | NH | T3i | OH |
| 2610 | CMe | NMe | Q1c | a bond | H | a bond | NH | S | NH | T3j | OH |
| 2611 | CMe | NMe | Q1c | a bond | H | a bond | NH | S | a bond | T3a | OH |
| 2612 | CMe | NMe | Q1c | a bond | H | a bond | NH | S | a bond | T3b | OH |
| 2613 | CMe | NMe | Q1c | a bond | H | a bond | NH | S | a bond | T3c | OH |
| 2614 | CMe | NMe | Q1c | a bond | H | a bond | NH | S | a bond | T3d | OH |
| 2615 | CMe | NMe | Q1c | a bond | H | a bond | NH | S | a bond | T3e | OH |
| 2616 | CMe | NMe | Q1c | a bond | H | a bond | NH | S | a bond | T3f | OH |
| 2617 | CMe | NMe | Q1c | a bond | H | a bond | NH | S | a bond | T3g | OH |
| 2618 | CMe | NMe | Q1c | a bond | H | a bond | NH | S | a bond | T3h | OH |
| 2619 | CMe | NMe | Q1c | a bond | H | a bond | NH | S | a bond | T3i | OH |
| 2620 | CMe | NMe | Q1c | a bond | H | a bond | NH | S | a bond | T3j | OH |
| 2621 | CMe | NMe | Q1c | a bond | H | a bond | NH | O | NH | T3a | OH |
| 2622 | CMe | NMe | Q1c | a bond | H | a bond | NH | O | NH | T3b | OH |
| 2623 | CMe | NMe | Q1c | a bond | H | a bond | NH | O | NH | T3c | OH |
| 2624 | CMe | NMe | Q1c | a bond | H | a bond | NH | O | NH | T3d | OH |
| 2625 | CMe | NMe | Q1c | a bond | H | a bond | NH | O | NH | T3e | OH |
| 2626 | CMe | NMe | Q1c | a bond | H | a bond | NH | O | NH | T3f | OH |
| 2627 | CMe | NMe | Q1c | a bond | H | a bond | NH | O | NH | T3g | OH |
| 2628 | CMe | NMe | Q1c | a bond | H | a bond | NH | O | NH | T3h | OH |
| 2629 | CMe | NMe | Q1c | a bond | H | a bond | NH | O | NH | T3i | OH |
| 2630 | CMe | NMe | Q1c | a bond | H | a bond | NH | O | NH | T3j | OH |
| 2631 | CMe | NMe | Q1c | a bond | H | a bond | NH | O | a bond | T3a | OH |
| 2632 | CMe | NMe | Q1c | a bond | H | a bond | NH | O | a bond | T3b | OH |
| 2633 | CMe | NMe | Q1c | a bond | H | a bond | NH | O | a bond | T3c | OH |
| 2634 | CMe | NMe | Q1c | a bond | H | a bond | NH | O | a bond | T3d | OH |
| 2635 | CMe | NMe | Q1c | a bond | H | a bond | NH | O | a bond | T3e | OH |
| 2636 | CMe | NMe | Q1c | a bond | H | a bond | NH | O | a bond | T3f | OH |
| 2637 | CMe | NMe | Q1c | a bond | H | a bond | NH | O | a bond | T3g | OH |
| 2638 | CMe | NMe | Q1c | a bond | H | a bond | NH | O | a bond | T3h | OH |
| 2639 | CMe | NMe | Q1c | a bond | H | a bond | NH | O | a bond | T3i | OH |
| 2640 | CMe | NMe | Q1c | a bond | H | a bond | NH | O | a bond | T3j | OH |
| 2641 | CMe | NMe | Q1i | a bond | Me | a bond | NH | S | NH | T3a | OH |
| 2642 | CMe | NMe | Q1i | a bond | Me | a bond | NH | S | NH | T3b | OH |
| 2643 | CMe | NMe | Q1i | a bond | Me | a bond | NH | S | NH | T3c | OH |
| 2644 | CMe | NMe | Q1i | a bond | Me | a bond | NH | S | NH | T3d | OH |
| 2645 | CMe | NMe | Q1i | a bond | Me | a bond | NH | S | NH | T3e | OH |
| 2646 | CMe | NMe | Q1i | a bond | Me | a bond | NH | S | NH | T3f | OH |
| 2647 | CMe | NMe | Q1i | a bond | Me | a bond | NH | S | NH | T3g | OH |
| 2648 | CMe | NMe | Q1i | a bond | Me | a bond | NH | S | NH | T3h | OH |
| 2649 | CMe | NMe | Q1i | a bond | Me | a bond | NH | S | NH | T3i | OH |
| 2650 | CMe | NMe | Q1i | a bond | Me | a bond | NH | S | NH | T3j | OH |
| 2651 | CMe | NMe | Q1i | a bond | Me | a bond | NH | S | a bond | T3a | OH |
| 2652 | CMe | NMe | Q1i | a bond | Me | a bond | NH | S | a bond | T3b | OH |
| 2653 | CMe | NMe | Q1i | a bond | Me | a bond | NH | S | a bond | T3c | OH |
| 2654 | CMe | NMe | Q1i | a bond | Me | a bond | NH | S | a bond | T3d | OH |
| 2655 | CMe | NMe | Q1i | a bond | Me | a bond | NH | S | a bond | T3e | OH |
| 2656 | CMe | NMe | Q1i | a bond | Me | a bond | NH | S | a bond | T3f | OH |
| 2657 | CMe | NMe | Q1i | a bond | Me | a bond | NH | S | a bond | T3g | OH |
| 2658 | CMe | NMe | Q1i | a bond | Me | a bond | NH | S | a bond | T3h | OH |
| 2659 | CMe | NMe | Q1i | a bond | Me | a bond | NH | S | a bond | T3i | OH |
| 2660 | CMe | NMe | Q1i | a bond | Me | a bond | NH | S | a bond | T3j | OH |
| 2661 | CMe | NMe | Q1i | a bond | Me | a bond | NH | O | NH | T3a | OH |
| 2662 | CMe | NMe | Q1i | a bond | Me | a bond | NH | O | NH | T3b | OH |
| 2663 | CMe | NMe | Q1i | a bond | Me | a bond | NH | O | NH | T3c | OH |
| 2664 | CMe | NMe | Q1i | a bond | Me | a bond | NH | O | NH | T3d | OH |
| 2665 | CMe | NMe | Q1i | a bond | Me | a bond | NH | O | NH | T3e | OH |
| 2666 | CMe | NMe | Q1i | a bond | Me | a bond | NH | O | NH | T3f | OH |
| 2667 | CMe | NMe | Q1i | a bond | Me | a bond | NH | O | NH | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 2668 | CMe | NMe | Q1i | a bond | Me | a bond | NH | O | NH | T3h | OH |
| 2669 | CMe | NMe | Q1i | a bond | Me | a bond | NH | O | NH | T3i | OH |
| 2670 | CMe | NMe | Q1i | a bond | Me | a bond | NH | O | NH | T3j | OH |
| 2671 | CMe | NMe | Q1i | a bond | Me | a bond | NH | O | a bond | T3a | OH |
| 2672 | CMe | NMe | Q1i | a bond | Me | a bond | NH | O | a bond | T3b | OH |
| 2673 | CMe | NMe | Q1i | a bond | Me | a bond | NH | O | a bond | T3c | OH |
| 2674 | CMe | NMe | Q1i | a bond | Me | a bond | NH | O | a bond | T3d | OH |
| 2675 | CMe | NMe | Q1i | a bond | Me | a bond | NH | O | a bond | T3e | OH |
| 2676 | CMe | NMe | Q1i | a bond | Me | a bond | NH | O | a bond | T3f | OH |
| 2677 | CMe | NMe | Q1i | a bond | Me | a bond | NH | O | a bond | T3g | OH |
| 2678 | CMe | NMe | Q1i | a bond | Me | a bond | NH | O | a bond | T3h | OH |
| 2679 | CMe | NMe | Q1i | a bond | Me | a bond | NH | O | a bond | T3i | OH |
| 2680 | CMe | NMe | Q1i | a bond | Me | a bond | NH | O | a bond | T3j | OH |
| 2681 | CMe | NMe | Q1i | a bond | H | a bond | NH | S | NH | T3a | OH |
| 2682 | CMe | NMe | Q1i | a bond | H | a bond | NH | S | NH | T3b | OH |
| 2683 | CMe | NMe | Q1i | a bond | H | a bond | NH | S | NH | T3c | OH |
| 2684 | CMe | NMe | Q1i | a bond | H | a bond | NH | S | NH | T3d | OH |
| 2685 | CMe | NMe | Q1i | a bond | H | a bond | NH | S | NH | T3e | OH |
| 2686 | CMe | NMe | Q1i | a bond | H | a bond | NH | S | NH | T3f | OH |
| 2687 | CMe | NMe | Q1i | a bond | H | a bond | NH | S | NH | T3g | OH |
| 2688 | CMe | NMe | Q1i | a bond | H | a bond | NH | S | NH | T3h | OH |
| 2689 | CMe | NMe | Q1i | a bond | H | a bond | NH | S | NH | T3i | OH |
| 2690 | CMe | NMe | Q1i | a bond | H | a bond | NH | S | NH | T3j | OH |
| 2691 | CMe | NMe | Q1i | a bond | H | a bond | NH | S | a bond | T3a | OH |
| 2692 | CMe | NMe | Q1i | a bond | H | a bond | NH | S | a bond | T3b | OH |
| 2693 | CMe | NMe | Q1i | a bond | H | a bond | NH | S | a bond | T3c | OH |
| 2694 | CMe | NMe | Q1i | a bond | H | a bond | NH | S | a bond | T3d | OH |
| 2695 | CMe | NMe | Q1i | a bond | H | a bond | NH | S | a bond | T3e | OH |
| 2696 | CMe | NMe | Q1i | a bond | H | a bond | NH | S | a bond | T3f | OH |
| 2697 | CMe | NMe | Q1i | a bond | H | a bond | NH | S | a bond | T3g | OH |
| 2698 | CMe | NMe | Q1i | a bond | H | a bond | NH | S | a bond | T3h | OH |
| 2699 | CMe | NMe | Q1i | a bond | H | a bond | NH | S | a bond | T3i | OH |
| 2700 | CMe | NMe | Q1i | a bond | H | a bond | NH | S | a bond | T3j | OH |
| 2701 | CMe | NMe | Q1i | a bond | H | a bond | NH | O | NH | T3a | OH |
| 2702 | CMe | NMe | Q1i | a bond | H | a bond | NH | O | NH | T3b | OH |
| 2703 | CMe | NMe | Q1i | a bond | H | a bond | NH | O | NH | T3c | OH |
| 2704 | CMe | NMe | Q1i | a bond | H | a bond | NH | O | NH | T3d | OH |
| 2705 | CMe | NMe | Q1i | a bond | H | a bond | NH | O | NH | T3e | OH |
| 2706 | CMe | NMe | Q1i | a bond | H | a bond | NH | O | NH | T3f | OH |
| 2707 | CMe | NMe | Q1i | a bond | H | a bond | NH | O | NH | T3g | OH |
| 2708 | CMe | NMe | Q1i | a bond | H | a bond | NH | O | NH | T3h | OH |
| 2709 | CMe | NMe | Q1i | a bond | H | a bond | NH | O | NH | T3i | OH |
| 2710 | CMe | NMe | Q1i | a bond | H | a bond | NH | O | NH | T3j | OH |
| 2711 | CMe | NMe | Q1i | a bond | H | a bond | NH | O | a bond | T3a | OH |
| 2712 | CMe | NMe | Q1i | a bond | H | a bond | NH | O | a bond | T3b | OH |
| 2713 | CMe | NMe | Q1i | a bond | H | a bond | NH | O | a bond | T3c | OH |
| 2714 | CMe | NMe | Q1i | a bond | H | a bond | NH | O | a bond | T3d | OH |
| 2715 | CMe | NMe | Q1i | a bond | H | a bond | NH | O | a bond | T3e | OH |
| 2716 | CMe | NMe | Q1i | a bond | H | a bond | NH | O | a bond | T3f | OH |
| 2717 | CMe | NMe | Q1i | a bond | H | a bond | NH | O | a bond | T3g | OH |
| 2718 | CMe | NMe | Q1i | a bond | H | a bond | NH | O | a bond | T3h | OH |
| 2719 | CMe | NMe | Q1i | a bond | H | a bond | NH | O | a bond | T3i | OH |
| 2720 | CMe | NMe | Q1i | a bond | H | a bond | NH | O | a bond | T3j | OH |
| 2721 | CMe | NMe | Q1j | a bond | Me | a bond | NH | S | NH | T3a | OH |
| 2722 | CMe | NMe | Q1j | a bond | Me | a bond | NH | S | NH | T3b | OH |
| 2723 | CMe | NMe | Q1j | a bond | Me | a bond | NH | S | NH | T3c | OH |
| 2724 | CMe | NMe | Q1j | a bond | Me | a bond | NH | S | NH | T3d | OH |
| 2725 | CMe | NMe | Q1j | a bond | Me | a bond | NH | S | NH | T3e | OH |
| 2726 | CMe | NMe | Q1j | a bond | Me | a bond | NH | S | NH | T3f | OH |
| 2727 | CMe | NMe | Q1j | a bond | Me | a bond | NH | S | NH | T3g | OH |
| 2728 | CMe | NMe | Q1j | a bond | Me | a bond | NH | S | NH | T3h | OH |
| 2729 | CMe | NMe | Q1j | a bond | Me | a bond | NH | S | NH | T3i | OH |
| 2730 | CMe | NMe | Q1j | a bond | Me | a bond | NH | S | NH | T3j | OH |
| 2731 | CMe | NMe | Q1j | a bond | Me | a bond | NH | S | a bond | T3a | OH |
| 2732 | CMe | NMe | Q1j | a bond | Me | a bond | NH | S | a bond | T3b | OH |
| 2733 | CMe | NMe | Q1j | a bond | Me | a bond | NH | S | a bond | T3c | OH |
| 2734 | CMe | NMe | Q1j | a bond | Me | a bond | NH | S | a bond | T3d | OH |
| 2735 | CMe | NMe | Q1j | a bond | Me | a bond | NH | S | a bond | T3e | OH |
| 2736 | CMe | NMe | Q1j | a bond | Me | a bond | NH | S | a bond | T3f | OH |
| 2737 | CMe | NMe | Q1j | a bond | Me | a bond | NH | S | a bond | T3g | OH |
| 2738 | CMe | NMe | Q1j | a bond | Me | a bond | NH | S | a bond | T3h | OH |
| 2739 | CMe | NMe | Q1j | a bond | Me | a bond | NH | S | a bond | T3i | OH |
| 2740 | CMe | NMe | Q1j | a bond | Me | a bond | NH | S | a bond | T3j | OH |
| 2741 | CMe | NMe | Q1j | a bond | Me | a bond | NH | O | NH | T3a | OH |
| 2742 | CMe | NMe | Q1j | a bond | Me | a bond | NH | O | NH | T3b | OH |
| 2743 | CMe | NMe | Q1j | a bond | Me | a bond | NH | O | NH | T3c | OH |
| 2744 | CMe | NMe | Q1j | a bond | Me | a bond | NH | O | NH | T3d | OH |
| 2745 | CMe | NMe | Q1j | a bond | Me | a bond | NH | O | NH | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 2746 | CMe | NMe | Q1j | a bond | Me | a bond | NH | O | NH | T3f | OH |
| 2747 | CMe | NMe | Q1j | a bond | Me | a bond | NH | O | NH | T3g | OH |
| 2748 | CMe | NMe | Q1j | a bond | Me | a bond | NH | O | NH | T3h | OH |
| 2749 | CMe | NMe | Q1j | a bond | Me | a bond | NH | O | NH | T3i | OH |
| 2750 | CMe | NMe | Q1j | a bond | Me | a bond | NH | O | NH | T3j | OH |
| 2751 | CMe | NMe | Q1j | a bond | Me | a bond | NH | O | a bond | T3a | OH |
| 2752 | CMe | NMe | Q1j | a bond | Me | a bond | NH | O | a bond | T3b | OH |
| 2753 | CMe | NMe | Q1j | a bond | Me | a bond | NH | O | a bond | T3c | OH |
| 2754 | CMe | NMe | Q1j | a bond | Me | a bond | NH | O | a bond | T3d | OH |
| 2755 | CMe | NMe | Q1j | a bond | Me | a bond | NH | O | a bond | T3e | OH |
| 2756 | CMe | NMe | Q1j | a bond | Me | a bond | NH | O | a bond | T3f | OH |
| 2757 | CMe | NMe | Q1j | a bond | Me | a bond | NH | O | a bond | T3g | OH |
| 2758 | CMe | NMe | Q1j | a bond | Me | a bond | NH | O | a bond | T3h | OH |
| 2759 | CMe | NMe | Q1j | a bond | Me | a bond | NH | O | a bond | T3i | OH |
| 2760 | CMe | NMe | Q1j | a bond | Me | a bond | NH | O | a bond | T3j | OH |
| 2761 | CMe | NMe | Q1j | a bond | H | a bond | NH | S | NH | T3a | OH |
| 2762 | CMe | NMe | Q1j | a bond | H | a bond | NH | S | NH | T3b | OH |
| 2763 | CMe | NMe | Q1j | a bond | H | a bond | NH | S | NH | T3c | OH |
| 2764 | CMe | NMe | Q1j | a bond | H | a bond | NH | S | NH | T3d | OH |
| 2765 | CMe | NMe | Q1j | a bond | H | a bond | NH | S | NH | T3e | OH |
| 2766 | CMe | NMe | Q1j | a bond | H | a bond | NH | S | NH | T3f | OH |
| 2767 | CMe | NMe | Q1j | a bond | H | a bond | NH | S | NH | T3g | OH |
| 2768 | CMe | NMe | Q1j | a bond | H | a bond | NH | S | NH | T3h | OH |
| 2769 | CMe | NMe | Q1j | a bond | H | a bond | NH | S | NH | T3i | OH |
| 2770 | CMe | NMe | Q1j | a bond | H | a bond | NH | S | NH | T3j | OH |
| 2771 | CMe | NMe | Q1j | a bond | H | a bond | NH | S | a bond | T3a | OH |
| 2772 | CMe | NMe | Q1j | a bond | H | a bond | NH | S | a bond | T3b | OH |
| 2773 | CMe | NMe | Q1j | a bond | H | a bond | NH | S | a bond | T3c | OH |
| 2774 | CMe | NMe | Q1j | a bond | H | a bond | NH | S | a bond | T3d | OH |
| 2775 | CMe | NMe | Q1j | a bond | H | a bond | NH | S | a bond | T3e | OH |
| 2776 | CMe | NMe | Q1j | a bond | H | a bond | NH | S | a bond | T3f | OH |
| 2777 | CMe | NMe | Q1j | a bond | H | a bond | NH | S | a bond | T3g | OH |
| 2778 | CMe | NMe | Q1j | a bond | H | a bond | NH | S | a bond | T3h | OH |
| 2779 | CMe | NMe | Q1j | a bond | H | a bond | NH | S | a bond | T3i | OH |
| 2780 | CMe | NMe | Q1j | a bond | H | a bond | NH | S | a bond | T3j | OH |
| 2781 | CMe | NMe | Q1j | a bond | H | a bond | NH | O | NH | T3a | OH |
| 2782 | CMe | NMe | Q1j | a bond | H | a bond | NH | O | NH | T3b | OH |
| 2783 | CMe | NMe | Q1j | a bond | H | a bond | NH | O | NH | T3c | OH |
| 2784 | CMe | NMe | Q1j | a bond | H | a bond | NH | O | NH | T3d | OH |
| 2785 | CMe | NMe | Q1j | a bond | H | a bond | NH | O | NH | T3e | OH |
| 2786 | CMe | NMe | Q1j | a bond | H | a bond | NH | O | NH | T3f | OH |
| 2787 | CMe | NMe | Q1j | a bond | H | a bond | NH | O | NH | T3g | OH |
| 2788 | CMe | NMe | Q1j | a bond | H | a bond | NH | O | NH | T3h | OH |
| 2789 | CMe | NMe | Q1j | a bond | H | a bond | NH | O | NH | T3i | OH |
| 2790 | CMe | NMe | Q1j | a bond | H | a bond | NH | O | NH | T3j | OH |
| 2791 | CMe | NMe | Q1j | a bond | H | a bond | NH | O | a bond | T3a | OH |
| 2792 | CMe | NMe | Q1j | a bond | H | a bond | NH | O | a bond | T3b | OH |
| 2793 | CMe | NMe | Q1j | a bond | H | a bond | NH | O | a bond | T3c | OH |
| 2794 | CMe | NMe | Q1j | a bond | H | a bond | NH | O | a bond | T3d | OH |
| 2795 | CMe | NMe | Q1j | a bond | H | a bond | NH | O | a bond | T3e | OH |
| 2796 | CMe | NMe | Q1j | a bond | H | a bond | NH | O | a bond | T3f | OH |
| 2797 | CMe | NMe | Q1j | a bond | H | a bond | NH | O | a bond | T3g | OH |
| 2798 | CMe | NMe | Q1j | a bond | H | a bond | NH | O | a bond | T3h | OH |
| 2799 | CMe | NMe | Q1j | a bond | H | a bond | NH | O | a bond | T3i | OH |
| 2800 | CMe | NMe | Q1j | a bond | H | a bond | NH | O | a bond | T3j | OH |
| 2801 | CMe | S | Q1a | a bond | Me | a bond | NH | S | NH | T3a | OH |
| 2802 | CMe | S | Q1a | a bond | Me | a bond | NH | S | NH | T3b | OH |
| 2803 | CMe | S | Q1a | a bond | Me | a bond | NH | S | NH | T3c | OH |
| 2804 | CMe | S | Q1a | a bond | Me | a bond | NH | S | NH | T3d | OH |
| 2805 | CMe | S | Q1a | a bond | Me | a bond | NH | S | NH | T3e | OH |
| 2806 | CMe | S | Q1a | a bond | Me | a bond | NH | S | NH | T3f | OH |
| 2807 | CMe | S | Q1a | a bond | Me | a bond | NH | S | NH | T3g | OH |
| 2808 | CMe | S | Q1a | a bond | Me | a bond | NH | S | NH | T3h | OH |
| 2809 | CMe | S | Q1a | a bond | Me | a bond | NH | S | NH | T3i | OH |
| 2810 | CMe | S | Q1a | a bond | Me | a bond | NH | S | NH | T3j | OH |
| 2811 | CMe | S | Q1a | a bond | Me | a bond | NH | S | a bond | T3a | OH |
| 2812 | CMe | S | Q1a | a bond | Me | a bond | NH | S | a bond | T3b | OH |
| 2813 | CMe | S | Q1a | a bond | Me | a bond | NH | S | a bond | T3c | OH |
| 2814 | CMe | S | Q1a | a bond | Me | a bond | NH | S | a bond | T3d | OH |
| 2815 | CMe | S | Q1a | a bond | Me | a bond | NH | S | a bond | T3e | OH |
| 2816 | CMe | S | Q1a | a bond | Me | a bond | NH | S | a bond | T3f | OH |
| 2817 | CMe | S | Q1a | a bond | Me | a bond | NH | S | a bond | T3g | OH |
| 2818 | CMe | S | Q1a | a bond | Me | a bond | NH | S | a bond | T3h | OH |
| 2819 | CMe | S | Q1a | a bond | Me | a bond | NH | S | a bond | T3i | OH |
| 2820 | CMe | S | Q1a | a bond | Me | a bond | NH | S | a bond | T3j | OH |
| 2821 | CMe | S | Q1a | a bond | Me | a bond | NH | O | NH | T3a | OH |
| 2822 | CMe | S | Q1a | a bond | Me | a bond | NH | O | NH | T3b | OH |
| 2823 | CMe | S | Q1a | a bond | Me | a bond | NH | O | NH | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 2824 | CMe | S | Q1a | a bond | Me | a bond | NH | O | NH | T3d | OH |
| 2825 | CMe | S | Q1a | a bond | Me | a bond | NH | O | NH | T3e | OH |
| 2826 | CMe | S | Q1a | a bond | Me | a bond | NH | O | NH | T3f | OH |
| 2827 | CMe | S | Q1a | a bond | Me | a bond | NH | O | NH | T3g | OH |
| 2828 | CMe | S | Q1a | a bond | Me | a bond | NH | O | NH | T3h | OH |
| 2829 | CMe | S | Q1a | a bond | Me | a bond | NH | O | NH | T3i | OH |
| 2830 | CMe | S | Q1a | a bond | Me | a bond | NH | O | NH | T3j | OH |
| 2831 | CMe | S | Q1a | a bond | Me | a bond | NH | O | a bond | T3a | OH |
| 2832 | CMe | S | Q1a | a bond | Me | a bond | NH | O | a bond | T3b | OH |
| 2833 | CMe | S | Q1a | a bond | Me | a bond | NH | O | a bond | T3c | OH |
| 2834 | CMe | S | Q1a | a bond | Me | a bond | NH | O | a bond | T3d | OH |
| 2835 | CMe | S | Q1a | a bond | Me | a bond | NH | O | a bond | T3e | OH |
| 2836 | CMe | S | Q1a | a bond | Me | a bond | NH | O | a bond | T3f | OH |
| 2837 | CMe | S | Q1a | a bond | Me | a bond | NH | O | a bond | T3g | OH |
| 2838 | CMe | S | Q1a | a bond | Me | a bond | NH | O | a bond | T3h | OH |
| 2839 | CMe | S | Q1a | a bond | Me | a bond | NH | O | a bond | T3i | OH |
| 2840 | CMe | S | Q1a | a bond | Me | a bond | NH | O | a bond | T3j | OH |
| 2841 | CMe | S | Q1a | a bond | H | a bond | NH | S | NH | T3a | OH |
| 2842 | CMe | S | Q1a | a bond | H | a bond | NH | S | NH | T3b | OH |
| 2843 | CMe | S | Q1a | a bond | H | a bond | NH | S | NH | T3c | OH |
| 2844 | CMe | S | Q1a | a bond | H | a bond | NH | S | NH | T3d | OH |
| 2845 | CMe | S | Q1a | a bond | H | a bond | NH | S | NH | T3e | OH |
| 2846 | CMe | S | Q1a | a bond | H | a bond | NH | S | NH | T3f | OH |
| 2847 | CMe | S | Q1a | a bond | H | a bond | NH | S | NH | T3g | OH |
| 2848 | CMe | S | Q1a | a bond | H | a bond | NH | S | NH | T3h | OH |
| 2849 | CMe | S | Q1a | a bond | H | a bond | NH | S | NH | T3i | OH |
| 2850 | CMe | S | Q1a | a bond | H | a bond | NH | S | NH | T3j | OH |
| 2851 | CMe | S | Q1a | a bond | H | a bond | NH | S | a bond | T3a | OH |
| 2852 | CMe | S | Q1a | a bond | H | a bond | NH | S | a bond | T3b | OH |
| 2853 | CMe | S | Q1a | a bond | H | a bond | NH | S | a bond | T3c | OH |
| 2854 | CMe | S | Q1a | a bond | H | a bond | NH | S | a bond | T3d | OH |
| 2855 | CMe | S | Q1a | a bond | H | a bond | NH | S | a bond | T3e | OH |
| 2856 | CMe | S | Q1a | a bond | H | a bond | NH | S | a bond | T3f | OH |
| 2857 | CMe | S | Q1a | a bond | H | a bond | NH | S | a bond | T3g | OH |
| 2858 | CMe | S | Q1a | a bond | H | a bond | NH | S | a bond | T3h | OH |
| 2859 | CMe | S | Q1a | a bond | H | a bond | NH | S | a bond | T3i | OH |
| 2860 | CMe | S | Q1a | a bond | H | a bond | NH | S | a bond | T3j | OH |
| 2861 | CMe | S | Q1a | a bond | H | a bond | NH | O | NH | T3a | OH |
| 2862 | CMe | S | Q1a | a bond | H | a bond | NH | O | NH | T3b | OH |
| 2863 | CMe | S | Q1a | a bond | H | a bond | NH | O | NH | T3c | OH |
| 2864 | CMe | S | Q1a | a bond | H | a bond | NH | O | NH | T3d | OH |
| 2865 | CMe | S | Q1a | a bond | H | a bond | NH | O | NH | T3e | OH |
| 2866 | CMe | S | Q1a | a bond | H | a bond | NH | O | NH | T3f | OH |
| 2867 | CMe | S | Q1a | a bond | H | a bond | NH | O | NH | T3g | OH |
| 2868 | CMe | S | Q1a | a bond | H | a bond | NH | O | NH | T3h | OH |
| 2869 | CMe | S | Q1a | a bond | H | a bond | NH | O | NH | T3i | OH |
| 2870 | CMe | S | Q1a | a bond | H | a bond | NH | O | NH | T3j | OH |
| 2871 | CMe | S | Q1a | a bond | H | a bond | NH | O | a bond | T3a | OH |
| 2872 | CMe | S | Q1a | a bond | H | a bond | NH | O | a bond | T3b | OH |
| 2873 | CMe | S | Q1a | a bond | H | a bond | NH | O | a bond | T3c | OH |
| 2874 | CMe | S | Q1a | a bond | H | a bond | NH | O | a bond | T3d | OH |
| 2875 | CMe | S | Q1a | a bond | H | a bond | NH | O | a bond | T3e | OH |
| 2876 | CMe | S | Q1a | a bond | H | a bond | NH | O | a bond | T3f | OH |
| 2877 | CMe | S | Q1a | a bond | H | a bond | NH | O | a bond | T3g | OH |
| 2878 | CMe | S | Q1a | a bond | H | a bond | NH | O | a bond | T3h | OH |
| 2879 | CMe | S | Q1a | a bond | H | a bond | NH | O | a bond | T3i | OH |
| 2880 | CMe | S | Q1a | a bond | H | a bond | NH | O | a bond | T3j | OH |
| 2881 | CMe | S | Q1b | a bond | Me | a bond | NH | S | NH | T3a | OH |
| 2882 | CMe | S | Q1b | a bond | Me | a bond | NH | S | NH | T3b | OH |
| 2883 | CMe | S | Q1b | a bond | Me | a bond | NH | S | NH | T3c | OH |
| 2884 | CMe | S | Q1b | a bond | Me | a bond | NH | S | NH | T3d | OH |
| 2885 | CMe | S | Q1b | a bond | Me | a bond | NH | S | NH | T3e | OH |
| 2886 | CMe | S | Q1b | a bond | Me | a bond | NH | S | NH | T3f | OH |
| 2887 | CMe | S | Q1b | a bond | Me | a bond | NH | S | NH | T3g | OH |
| 2888 | CMe | S | Q1b | a bond | Me | a bond | NH | S | NH | T3h | OH |
| 2889 | CMe | S | Q1b | a bond | Me | a bond | NH | S | NH | T3i | OH |
| 2890 | CMe | S | Q1b | a bond | Me | a bond | NH | S | NH | T3j | OH |
| 2891 | CMe | S | Q1b | a bond | Me | a bond | NH | S | a bond | T3a | OH |
| 2892 | CMe | S | Q1b | a bond | Me | a bond | NH | S | a bond | T3b | OH |
| 2893 | CMe | S | Q1b | a bond | Me | a bond | NH | S | a bond | T3c | OH |
| 2894 | CMe | S | Q1b | a bond | Me | a bond | NH | S | a bond | T3d | OH |
| 2895 | CMe | S | Q1b | a bond | Me | a bond | NH | S | a bond | T3e | OH |
| 2896 | CMe | S | Q1b | a bond | Me | a bond | NH | S | a bond | T3f | OH |
| 2897 | CMe | S | Q1b | a bond | Me | a bond | NH | S | a bond | T3g | OH |
| 2898 | CMe | S | Q1b | a bond | Me | a bond | NH | S | a bond | T3h | OH |
| 2899 | CMe | S | Q1b | a bond | Me | a bond | NH | S | a bond | T3i | OH |
| 2900 | CMe | S | Q1b | a bond | Me | a bond | NH | S | a bond | T3j | OH |
| 2901 | CMe | S | Q1b | a bond | Me | a bond | NH | O | NH | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 2902 | CMe | S | Q1b | a bond | Me | a bond | NH | O | NH | T3b | OH |
| 2903 | CMe | S | Q1b | a bond | Me | a bond | NH | O | NH | T3c | OH |
| 2904 | CMe | S | Q1b | a bond | Me | a bond | NH | O | NH | T3d | OH |
| 2905 | CMe | S | Q1b | a bond | Me | a bond | NH | O | NH | T3e | OH |
| 2906 | CMe | S | Q1b | a bond | Me | a bond | NH | O | NH | T3f | OH |
| 2907 | CMe | S | Q1b | a bond | Me | a bond | NH | O | NH | T3g | OH |
| 2908 | CMe | S | Q1b | a bond | Me | a bond | NH | O | NH | T3h | OH |
| 2909 | CMe | S | Q1b | a bond | Me | a bond | NH | O | NH | T3i | OH |
| 2910 | CMe | S | Q1b | a bond | Me | a bond | NH | O | NH | T3j | OH |
| 2911 | CMe | S | Q1b | a bond | Me | a bond | NH | O | a bond | T3a | OH |
| 2912 | CMe | S | Q1b | a bond | Me | a bond | NH | O | a bond | T3b | OH |
| 2913 | CMe | S | Q1b | a bond | Me | a bond | NH | O | a bond | T3c | OH |
| 2914 | CMe | S | Q1b | a bond | Me | a bond | NH | O | a bond | T3d | OH |
| 2915 | CMe | S | Q1b | a bond | Me | a bond | NH | O | a bond | T3e | OH |
| 2916 | CMe | S | Q1b | a bond | Me | a bond | NH | O | a bond | T3f | OH |
| 2917 | CMe | S | Q1b | a bond | Me | a bond | NH | O | a bond | T3g | OH |
| 2918 | CMe | S | Q1b | a bond | Me | a bond | NH | O | a bond | T3h | OH |
| 2919 | CMe | S | Q1b | a bond | Me | a bond | NH | O | a bond | T3i | OH |
| 2920 | CMe | S | Q1b | a bond | Me | a bond | NH | O | a bond | T3j | OH |
| 2921 | CMe | S | Q1b | a bond | H | a bond | NH | S | NH | T3a | OH |
| 2922 | CMe | S | Q1b | a bond | H | a bond | NH | S | NH | T3b | OH |
| 2923 | CMe | S | Q1b | a bond | H | a bond | NH | S | NH | T3c | OH |
| 2924 | CMe | S | Q1b | a bond | H | a bond | NH | S | NH | T3d | OH |
| 2925 | CMe | S | Q1b | a bond | H | a bond | NH | S | NH | T3e | OH |
| 2926 | CMe | S | Q1b | a bond | H | a bond | NH | S | NH | T3f | OH |
| 2927 | CMe | S | Q1b | a bond | H | a bond | NH | S | NH | T3g | OH |
| 2928 | CMe | S | Q1b | a bond | H | a bond | NH | S | NH | T3h | OH |
| 2929 | CMe | S | Q1b | a bond | H | a bond | NH | S | NH | T3i | OH |
| 2930 | CMe | S | Q1b | a bond | H | a bond | NH | S | NH | T3j | OH |
| 2931 | CMe | S | Q1b | a bond | H | a bond | NH | S | a bond | T3a | OH |
| 2932 | CMe | S | Q1b | a bond | H | a bond | NH | S | a bond | T3b | OH |
| 2933 | CMe | S | Q1b | a bond | H | a bond | NH | S | a bond | T3c | OH |
| 2934 | CMe | S | Q1b | a bond | H | a bond | NH | S | a bond | T3d | OH |
| 2935 | CMe | S | Q1b | a bond | H | a bond | NH | S | a bond | T3e | OH |
| 2936 | CMe | S | Q1b | a bond | H | a bond | NH | S | a bond | T3f | OH |
| 2937 | CMe | S | Q1b | a bond | H | a bond | NH | S | a bond | T3g | OH |
| 2938 | CMe | S | Q1b | a bond | H | a bond | NH | S | a bond | T3h | OH |
| 2939 | CMe | S | Q1b | a bond | H | a bond | NH | S | a bond | T3i | OH |
| 2940 | CMe | S | Q1b | a bond | H | a bond | NH | S | a bond | T3j | OH |
| 2941 | CMe | S | Q1b | a bond | H | a bond | NH | O | NH | T3a | OH |
| 2942 | CMe | S | Q1b | a bond | H | a bond | NH | O | NH | T3b | OH |
| 2943 | CMe | S | Q1b | a bond | H | a bond | NH | O | NH | T3c | OH |
| 2944 | CMe | S | Q1b | a bond | H | a bond | NH | O | NH | T3d | OH |
| 2945 | CMe | S | Q1b | a bond | H | a bond | NH | O | NH | T3e | OH |
| 2946 | CMe | S | Q1b | a bond | H | a bond | NH | O | NH | T3f | OH |
| 2947 | CMe | S | Q1b | a bond | H | a bond | NH | O | NH | T3g | OH |
| 2948 | CMe | S | Q1b | a bond | H | a bond | NH | O | NH | T3h | OH |
| 2949 | CMe | S | Q1b | a bond | H | a bond | NH | O | NH | T3i | OH |
| 2950 | CMe | S | Q1b | a bond | H | a bond | NH | O | NH | T3j | OH |
| 2951 | CMe | S | Q1b | a bond | H | a bond | NH | O | a bond | T3a | OH |
| 2952 | CMe | S | Q1b | a bond | H | a bond | NH | O | a bond | T3b | OH |
| 2953 | CMe | S | Q1b | a bond | H | a bond | NH | O | a bond | T3c | OH |
| 2954 | CMe | S | Q1b | a bond | H | a bond | NH | O | a bond | T3d | OH |
| 2955 | CMe | S | Q1b | a bond | H | a bond | NH | O | a bond | T3e | OH |
| 2956 | CMe | S | Q1b | a bond | H | a bond | NH | O | a bond | T3f | OH |
| 2957 | CMe | S | Q1b | a bond | H | a bond | NH | O | a bond | T3g | OH |
| 2958 | CMe | S | Q1b | a bond | H | a bond | NH | O | a bond | T3h | OH |
| 2959 | CMe | S | Q1b | a bond | H | a bond | NH | O | a bond | T3i | OH |
| 2960 | CMe | S | Q1b | a bond | H | a bond | NH | O | a bond | T3j | OH |
| 2961 | CMe | S | Q1c | a bond | Me | a bond | NH | S | NH | T3a | OH |
| 2962 | CMe | S | Q1c | a bond | Me | a bond | NH | S | NH | T3b | OH |
| 2963 | CMe | S | Q1c | a bond | Me | a bond | NH | S | NH | T3c | OH |
| 2964 | CMe | S | Q1c | a bond | Me | a bond | NH | S | NH | T3d | OH |
| 2965 | CMe | S | Q1c | a bond | Me | a bond | NH | S | NH | T3e | OH |
| 2966 | CMe | S | Q1c | a bond | Me | a bond | NH | S | NH | T3f | OH |
| 2967 | CMe | S | Q1c | a bond | Me | a bond | NH | S | NH | T3g | OH |
| 2968 | CMe | S | Q1c | a bond | Me | a bond | NH | S | NH | T3h | OH |
| 2969 | CMe | S | Q1c | a bond | Me | a bond | NH | S | NH | T3i | OH |
| 2970 | CMe | S | Q1c | a bond | Me | a bond | NH | S | NH | T3j | OH |
| 2971 | CMe | S | Q1c | a bond | Me | a bond | NH | S | a bond | T3a | OH |
| 2972 | CMe | S | Q1c | a bond | Me | a bond | NH | S | a bond | T3b | OH |
| 2973 | CMe | S | Q1c | a bond | Me | a bond | NH | S | a bond | T3c | OH |
| 2974 | CMe | S | Q1c | a bond | Me | a bond | NH | S | a bond | T3d | OH |
| 2975 | CMe | S | Q1c | a bond | Me | a bond | NH | S | a bond | T3e | OH |
| 2976 | CMe | S | Q1c | a bond | Me | a bond | NH | S | a bond | T3f | OH |
| 2977 | CMe | S | Q1c | a bond | Me | a bond | NH | S | a bond | T3g | OH |
| 2978 | CMe | S | Q1c | a bond | Me | a bond | NH | S | a bond | T3h | OH |
| 2979 | CMe | S | Q1c | a bond | Me | a bond | NH | S | a bond | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 2980 | CMe | S | Q1c | a bond | Me | a bond | NH | S | a bond | T3j | OH |
| 2981 | CMe | S | Q1c | a bond | Me | a bond | NH | O | NH | T3a | OH |
| 2982 | CMe | S | Q1c | a bond | Me | a bond | NH | O | NH | T3b | OH |
| 2983 | CMe | S | Q1c | a bond | Me | a bond | NH | O | NH | T3c | OH |
| 2984 | CMe | S | Q1c | a bond | Me | a bond | NH | O | NH | T3d | OH |
| 2985 | CMe | S | Q1c | a bond | Me | a bond | NH | O | NH | T3e | OH |
| 2986 | CMe | S | Q1c | a bond | Me | a bond | NH | O | NH | T3f | OH |
| 2987 | CMe | S | Q1c | a bond | Me | a bond | NH | O | NH | T3g | OH |
| 2988 | CMe | S | Q1c | a bond | Me | a bond | NH | O | NH | T3h | OH |
| 2989 | CMe | S | Q1c | a bond | Me | a bond | NH | O | NH | T3i | OH |
| 2990 | CMe | S | Q1c | a bond | Me | a bond | NH | O | NH | T3j | OH |
| 2991 | CMe | S | Q1c | a bond | Me | a bond | NH | O | a bond | T3a | OH |
| 2992 | CMe | S | Q1c | a bond | Me | a bond | NH | O | a bond | T3b | OH |
| 2993 | CMe | S | Q1c | a bond | Me | a bond | NH | O | a bond | T3c | OH |
| 2994 | CMe | S | Q1c | a bond | Me | a bond | NH | O | a bond | T3d | OH |
| 2995 | CMe | S | Q1c | a bond | Me | a bond | NH | O | a bond | T3e | OH |
| 2996 | CMe | S | Q1c | a bond | Me | a bond | NH | O | a bond | T3f | OH |
| 2997 | CMe | S | Q1c | a bond | Me | a bond | NH | O | a bond | T3g | OH |
| 2998 | CMe | S | Q1c | a bond | Me | a bond | NH | O | a bond | T3h | OH |
| 2999 | CMe | S | Q1c | a bond | Me | a bond | NH | O | a bond | T3i | OH |
| 3000 | CMe | S | Q1c | a bond | Me | a bond | NH | O | a bond | T3j | OH |
| 3001 | CMe | S | Q1c | a bond | H | a bond | NH | S | NH | T3a | OH |
| 3002 | CMe | S | Q1c | a bond | H | a bond | NH | S | NH | T3b | OH |
| 3003 | CMe | S | Q1c | a bond | H | a bond | NH | S | NH | T3c | OH |
| 3004 | CMe | S | Q1c | a bond | H | a bond | NH | S | NH | T3d | OH |
| 3005 | CMe | S | Q1c | a bond | H | a bond | NH | S | NH | T3e | OH |
| 3006 | CMe | S | Q1c | a bond | H | a bond | NH | S | NH | T3f | OH |
| 3007 | CMe | S | Q1c | a bond | H | a bond | NH | S | NH | T3g | OH |
| 3008 | CMe | S | Q1c | a bond | H | a bond | NH | S | NH | T3h | OH |
| 3009 | CMe | S | Q1c | a bond | H | a bond | NH | S | NH | T3i | OH |
| 3010 | CMe | S | Q1c | a bond | H | a bond | NH | S | NH | T3j | OH |
| 3011 | CMe | S | Q1c | a bond | H | a bond | NH | S | a bond | T3a | OH |
| 3012 | CMe | S | Q1c | a bond | H | a bond | NH | S | a bond | T3b | OH |
| 3013 | CMe | S | Q1c | a bond | H | a bond | NH | S | a bond | T3c | OH |
| 3014 | CMe | S | Q1c | a bond | H | a bond | NH | S | a bond | T3d | OH |
| 3015 | CMe | S | Q1c | a bond | H | a bond | NH | S | a bond | T3e | OH |
| 3016 | CMe | S | Q1c | a bond | H | a bond | NH | S | a bond | T3f | OH |
| 3017 | CMe | S | Q1c | a bond | H | a bond | NH | S | a bond | T3g | OH |
| 3018 | CMe | S | Q1c | a bond | H | a bond | NH | S | a bond | T3h | OH |
| 3019 | CMe | S | Q1c | a bond | H | a bond | NH | S | a bond | T3i | OH |
| 3020 | CMe | S | Q1c | a bond | H | a bond | NH | S | a bond | T3j | OH |
| 3021 | CMe | S | Q1c | a bond | H | a bond | NH | O | NH | T3a | OH |
| 3022 | CMe | S | Q1c | a bond | H | a bond | NH | O | NH | T3b | OH |
| 3023 | CMe | S | Q1c | a bond | H | a bond | NH | O | NH | T3c | OH |
| 3024 | CMe | S | Q1c | a bond | H | a bond | NH | O | NH | T3d | OH |
| 3025 | CMe | S | Q1c | a bond | H | a bond | NH | O | NH | T3e | OH |
| 3026 | CMe | S | Q1c | a bond | H | a bond | NH | O | NH | T3f | OH |
| 3027 | CMe | S | Q1c | a bond | H | a bond | NH | O | NH | T3g | OH |
| 3028 | CMe | S | Q1c | a bond | H | a bond | NH | O | NH | T3h | OH |
| 3029 | CMe | S | Q1c | a bond | H | a bond | NH | O | NH | T3i | OH |
| 3030 | CMe | S | Q1c | a bond | H | a bond | NH | O | NH | T3j | OH |
| 3031 | CMe | S | Q1c | a bond | H | a bond | NH | O | a bond | T3a | OH |
| 3032 | CMe | S | Q1c | a bond | H | a bond | NH | O | a bond | T3b | OH |
| 3033 | CMe | S | Q1c | a bond | H | a bond | NH | O | a bond | T3c | OH |
| 3034 | CMe | S | Q1c | a bond | H | a bond | NH | O | a bond | T3d | OH |
| 3035 | CMe | S | Q1c | a bond | H | a bond | NH | O | a bond | T3e | OH |
| 3036 | CMe | S | Q1c | a bond | H | a bond | NH | O | a bond | T3f | OH |
| 3037 | CMe | S | Q1c | a bond | H | a bond | NH | O | a bond | T3g | OH |
| 3038 | CMe | S | Q1c | a bond | H | a bond | NH | O | a bond | T3h | OH |
| 3039 | CMe | S | Q1c | a bond | H | a bond | NH | O | a bond | T3i | OH |
| 3040 | CMe | S | Q1c | a bond | H | a bond | NH | O | a bond | T3j | OH |
| 3041 | CMe | S | Q1i | a bond | Me | a bond | NH | S | NH | T3a | OH |
| 3042 | CMe | S | Q1i | a bond | Me | a bond | NH | S | NH | T3b | OH |
| 3043 | CMe | S | Q1i | a bond | Me | a bond | NH | S | NH | T3c | OH |
| 3044 | CMe | S | Q1i | a bond | Me | a bond | NH | S | NH | T3d | OH |
| 3045 | CMe | S | Q1i | a bond | Me | a bond | NH | S | NH | T3e | OH |
| 3046 | CMe | S | Q1i | a bond | Me | a bond | NH | S | NH | T3f | OH |
| 3047 | CMe | S | Q1i | a bond | Me | a bond | NH | S | NH | T3g | OH |
| 3048 | CMe | S | Q1i | a bond | Me | a bond | NH | S | NH | T3h | OH |
| 3049 | CMe | S | Q1i | a bond | Me | a bond | NH | S | NH | T3i | OH |
| 3050 | CMe | S | Q1i | a bond | Me | a bond | NH | S | NH | T3j | OH |
| 3051 | CMe | S | Q1i | a bond | Me | a bond | NH | S | a bond | T3a | OH |
| 3052 | CMe | S | Q1i | a bond | Me | a bond | NH | S | a bond | T3b | OH |
| 3053 | CMe | S | Q1i | a bond | Me | a bond | NH | S | a bond | T3c | OH |
| 3054 | CMe | S | Q1i | a bond | Me | a bond | NH | S | a bond | T3d | OH |
| 3055 | CMe | S | Q1i | a bond | Me | a bond | NH | S | a bond | T3e | OH |
| 3056 | CMe | S | Q1i | a bond | Me | a bond | NH | S | a bond | T3f | OH |
| 3057 | CMe | S | Q1i | a bond | Me | a bond | NH | S | a bond | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 3058 | CMe | S | Q1i | a bond | Me | a bond | NH | S | a bond | T3h | OH |
| 3059 | CMe | S | Q1i | a bond | Me | a bond | NH | S | a bond | T3i | OH |
| 3060 | CMe | S | Q1i | a bond | Me | a bond | NH | S | a bond | T3j | OH |
| 3061 | CMe | S | Q1i | a bond | Me | a bond | NH | O | NH | T3a | OH |
| 3062 | CMe | S | Q1i | a bond | Me | a bond | NH | O | NH | T3b | OH |
| 3063 | CMe | S | Q1i | a bond | Me | a bond | NH | O | NH | T3c | OH |
| 3064 | CMe | S | Q1i | a bond | Me | a bond | NH | O | NH | T3d | OH |
| 3065 | CMe | S | Q1i | a bond | Me | a bond | NH | O | NH | T3e | OH |
| 3066 | CMe | S | Q1i | a bond | Me | a bond | NH | O | NH | T3f | OH |
| 3067 | CMe | S | Q1i | a bond | Me | a bond | NH | O | NH | T3g | OH |
| 3068 | CMe | S | Q1i | a bond | Me | a bond | NH | O | NH | T3h | OH |
| 3069 | CMe | S | Q1i | a bond | Me | a bond | NH | O | NH | T3i | OH |
| 3070 | CMe | S | Q1i | a bond | Me | a bond | NH | O | NH | T3j | OH |
| 3071 | CMe | S | Q1i | a bond | Me | a bond | NH | O | a bond | T3a | OH |
| 3072 | CMe | S | Q1i | a bond | Me | a bond | NH | O | a bond | T3b | OH |
| 3073 | CMe | S | Q1i | a bond | Me | a bond | NH | O | a bond | T3c | OH |
| 3074 | CMe | S | Q1i | a bond | Me | a bond | NH | O | a bond | T3d | OH |
| 3075 | CMe | S | Q1i | a bond | Me | a bond | NH | O | a bond | T3e | OH |
| 3076 | CMe | S | Q1i | a bond | Me | a bond | NH | O | a bond | T3f | OH |
| 3077 | CMe | S | Q1i | a bond | Me | a bond | NH | O | a bond | T3g | OH |
| 3078 | CMe | S | Q1i | a bond | Me | a bond | NH | O | a bond | T3h | OH |
| 3079 | CMe | S | Q1i | a bond | Me | a bond | NH | O | a bond | T3i | OH |
| 3080 | CMe | S | Q1i | a bond | Me | a bond | NH | O | a bond | T3j | OH |
| 3081 | CMe | S | Q1i | a bond | H | a bond | NH | S | NH | T3a | OH |
| 3082 | CMe | S | Q1i | a bond | H | a bond | NH | S | NH | T3b | OH |
| 3083 | CMe | S | Q1i | a bond | H | a bond | NH | S | NH | T3c | OH |
| 3084 | CMe | S | Q1i | a bond | H | a bond | NH | S | NH | T3d | OH |
| 3085 | CMe | S | Q1i | a bond | H | a bond | NH | S | NH | T3e | OH |
| 3086 | CMe | S | Q1i | a bond | H | a bond | NH | S | NH | T3f | OH |
| 3087 | CMe | S | Q1i | a bond | H | a bond | NH | S | NH | T3g | OH |
| 3088 | CMe | S | Q1i | a bond | H | a bond | NH | S | NH | T3h | OH |
| 3089 | CMe | S | Q1i | a bond | H | a bond | NH | S | NH | T3i | OH |
| 3090 | CMe | S | Q1i | a bond | H | a bond | NH | S | NH | T3j | OH |
| 3091 | CMe | S | Q1i | a bond | H | a bond | NH | S | a bond | T3a | OH |
| 3092 | CMe | S | Q1i | a bond | H | a bond | NH | S | a bond | T3b | OH |
| 3093 | CMe | S | Q1i | a bond | H | a bond | NH | S | a bond | T3c | OH |
| 3094 | CMe | S | Q1i | a bond | H | a bond | NH | S | a bond | T3d | OH |
| 3095 | CMe | S | Q1i | a bond | H | a bond | NH | S | a bond | T3e | OH |
| 3096 | CMe | S | Q1i | a bond | H | a bond | NH | S | a bond | T3f | OH |
| 3097 | CMe | S | Q1i | a bond | H | a bond | NH | S | a bond | T3g | OH |
| 3098 | CMe | S | Q1i | a bond | H | a bond | NH | S | a bond | T3h | OH |
| 3099 | CMe | S | Q1i | a bond | H | a bond | NH | S | a bond | T3i | OH |
| 3100 | CMe | S | Q1i | a bond | H | a bond | NH | S | a bond | T3j | OH |
| 3101 | CMe | S | Q1i | a bond | H | a bond | NH | O | NH | T3a | OH |
| 3102 | CMe | S | Q1i | a bond | H | a bond | NH | O | NH | T3b | OH |
| 3103 | CMe | S | Q1i | a bond | H | a bond | NH | O | NH | T3c | OH |
| 3104 | CMe | S | Q1i | a bond | H | a bond | NH | O | NH | T3d | OH |
| 3105 | CMe | S | Q1i | a bond | H | a bond | NH | O | NH | T3e | OH |
| 3106 | CMe | S | Q1i | a bond | H | a bond | NH | O | NH | T3f | OH |
| 3107 | CMe | S | Q1i | a bond | H | a bond | NH | O | NH | T3g | OH |
| 3108 | CMe | S | Q1i | a bond | H | a bond | NH | O | NH | T3h | OH |
| 3109 | CMe | S | Q1i | a bond | H | a bond | NH | O | NH | T3i | OH |
| 3110 | CMe | S | Q1i | a bond | H | a bond | NH | O | NH | T3j | OH |
| 3111 | CMe | S | Q1i | a bond | H | a bond | NH | O | a bond | T3a | OH |
| 3112 | CMe | S | Q1i | a bond | H | a bond | NH | O | a bond | T3b | OH |
| 3113 | CMe | S | Q1i | a bond | H | a bond | NH | O | a bond | T3c | OH |
| 3114 | CMe | S | Q1i | a bond | H | a bond | NH | O | a bond | T3d | OH |
| 3115 | CMe | S | Q1i | a bond | H | a bond | NH | O | a bond | T3e | OH |
| 3116 | CMe | S | Q1i | a bond | H | a bond | NH | O | a bond | T3f | OH |
| 3117 | CMe | S | Q1i | a bond | H | a bond | NH | O | a bond | T3g | OH |
| 3118 | CMe | S | Q1i | a bond | H | a bond | NH | O | a bond | T3h | OH |
| 3119 | CMe | S | Q1i | a bond | H | a bond | NH | O | a bond | T3i | OH |
| 3120 | CMe | S | Q1i | a bond | H | a bond | NH | O | a bond | T3j | OH |
| 3121 | CMe | S | Q1j | a bond | Me | a bond | NH | S | NH | T3a | OH |
| 3122 | CMe | S | Q1j | a bond | Me | a bond | NH | S | NH | T3b | OH |
| 3123 | CMe | S | Q1j | a bond | Me | a bond | NH | S | NH | T3c | OH |
| 3124 | CMe | S | Q1j | a bond | Me | a bond | NH | S | NH | T3d | OH |
| 3125 | CMe | S | Q1j | a bond | Me | a bond | NH | S | NH | T3e | OH |
| 3126 | CMe | S | Q1j | a bond | Me | a bond | NH | S | NH | T3f | OH |
| 3127 | CMe | S | Q1j | a bond | Me | a bond | NH | S | NH | T3g | OH |
| 3128 | CMe | S | Q1j | a bond | Me | a bond | NH | S | NH | T3h | OH |
| 3129 | CMe | S | Q1j | a bond | Me | a bond | NH | S | NH | T3i | OH |
| 3130 | CMe | S | Q1j | a bond | Me | a bond | NH | S | NH | T3j | OH |
| 3131 | CMe | S | Q1j | a bond | Me | a bond | NH | S | a bond | T3a | OH |
| 3132 | CMe | S | Q1j | a bond | Me | a bond | NH | S | a bond | T3b | OH |
| 3133 | CMe | S | Q1j | a bond | Me | a bond | NH | S | a bond | T3c | OH |
| 3134 | CMe | S | Q1j | a bond | Me | a bond | NH | S | a bond | T3d | OH |
| 3135 | CMe | S | Q1j | a bond | Me | a bond | NH | S | a bond | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 3136 | CMe | S | Q1j | a bond | Me | a bond | NH | S | a bond | T3f | OH |
| 3137 | CMe | S | Q1j | a bond | Me | a bond | NH | S | a bond | T3g | OH |
| 3138 | CMe | S | Q1j | a bond | Me | a bond | NH | S | a bond | T3h | OH |
| 3139 | CMe | S | Q1j | a bond | Me | a bond | NH | S | a bond | T3i | OH |
| 3140 | CMe | S | Q1j | a bond | Me | a bond | NH | S | a bond | T3j | OH |
| 3141 | CMe | S | Q1j | a bond | Me | a bond | NH | O | NH | T3a | OH |
| 3142 | CMe | S | Q1j | a bond | Me | a bond | NH | O | NH | T3b | OH |
| 3143 | CMe | S | Q1j | a bond | Me | a bond | NH | O | NH | T3c | OH |
| 3144 | CMe | S | Q1j | a bond | Me | a bond | NH | O | NH | T3d | OH |
| 3145 | CMe | S | Q1j | a bond | Me | a bond | NH | O | NH | T3e | OH |
| 3146 | CMe | S | Q1j | a bond | Me | a bond | NH | O | NH | T3f | OH |
| 3147 | CMe | S | Q1j | a bond | Me | a bond | NH | O | NH | T3g | OH |
| 3148 | CMe | S | Q1j | a bond | Me | a bond | NH | O | NH | T3h | OH |
| 3149 | CMe | S | Q1j | a bond | Me | a bond | NH | O | NH | T3i | OH |
| 3150 | CMe | S | Q1j | a bond | Me | a bond | NH | O | NH | T3j | OH |
| 3151 | CMe | S | Q1j | a bond | Me | a bond | NH | O | a bond | T3a | OH |
| 3152 | CMe | S | Q1j | a bond | Me | a bond | NH | O | a bond | T3b | OH |
| 3153 | CMe | S | Q1j | a bond | Me | a bond | NH | O | a bond | T3c | OH |
| 3154 | CMe | S | Q1j | a bond | Me | a bond | NH | O | a bond | T3d | OH |
| 3155 | CMe | S | Q1j | a bond | Me | a bond | NH | O | a bond | T3e | OH |
| 3156 | CMe | S | Q1j | a bond | Me | a bond | NH | O | a bond | T3f | OH |
| 3157 | CMe | S | Q1j | a bond | Me | a bond | NH | O | a bond | T3g | OH |
| 3158 | CMe | S | Q1j | a bond | Me | a bond | NH | O | a bond | T3h | OH |
| 3159 | CMe | S | Q1j | a bond | Me | a bond | NH | O | a bond | T3i | OH |
| 3160 | CMe | S | Q1j | a bond | Me | a bond | NH | O | a bond | T3j | OH |
| 3161 | CMe | S | Q1j | a bond | H | a bond | NH | S | NH | T3a | OH |
| 3162 | CMe | S | Q1j | a bond | H | a bond | NH | S | NH | T3b | OH |
| 3163 | CMe | S | Q1j | a bond | H | a bond | NH | S | NH | T3c | OH |
| 3164 | CMe | S | Q1j | a bond | H | a bond | NH | S | NH | T3d | OH |
| 3165 | CMe | S | Q1j | a bond | H | a bond | NH | S | NH | T3e | OH |
| 3166 | CMe | S | Q1j | a bond | H | a bond | NH | S | NH | T3f | OH |
| 3167 | CMe | S | Q1j | a bond | H | a bond | NH | S | NH | T3g | OH |
| 3168 | CMe | S | Q1j | a bond | H | a bond | NH | S | NH | T3h | OH |
| 3169 | CMe | S | Q1j | a bond | H | a bond | NH | S | NH | T3i | OH |
| 3170 | CMe | S | Q1j | a bond | H | a bond | NH | S | NH | T3j | OH |
| 3171 | CMe | S | Q1j | a bond | H | a bond | NH | S | a bond | T3a | OH |
| 3172 | CMe | S | Q1j | a bond | H | a bond | NH | S | a bond | T3b | OH |
| 3173 | CMe | S | Q1j | a bond | H | a bond | NH | S | a bond | T3c | OH |
| 3174 | CMe | S | Q1j | a bond | H | a bond | NH | S | a bond | T3d | OH |
| 3175 | CMe | S | Q1j | a bond | H | a bond | NH | S | a bond | T3e | OH |
| 3176 | CMe | S | Q1j | a bond | H | a bond | NH | S | a bond | T3f | OH |
| 3177 | CMe | S | Q1j | a bond | H | a bond | NH | S | a bond | T3g | OH |
| 3178 | CMe | S | Q1j | a bond | H | a bond | NH | S | a bond | T3h | OH |
| 3179 | CMe | S | Q1j | a bond | H | a bond | NH | S | a bond | T3i | OH |
| 3180 | CMe | S | Q1j | a bond | H | a bond | NH | S | a bond | T3j | OH |
| 3181 | CMe | S | Q1j | a bond | H | a bond | NH | O | NH | T3a | OH |
| 3182 | CMe | S | Q1j | a bond | H | a bond | NH | O | NH | T3b | OH |
| 3183 | CMe | S | Q1j | a bond | H | a bond | NH | O | NH | T3c | OH |
| 3184 | CMe | S | Q1j | a bond | H | a bond | NH | O | NH | T3d | OH |
| 3185 | CMe | S | Q1j | a bond | H | a bond | NH | O | NH | T3e | OH |
| 3186 | CMe | S | Q1j | a bond | H | a bond | NH | O | NH | T3f | OH |
| 3187 | CMe | S | Q1j | a bond | H | a bond | NH | O | NH | T3g | OH |
| 3188 | CMe | S | Q1j | a bond | H | a bond | NH | O | NH | T3h | OH |
| 3189 | CMe | S | Q1j | a bond | H | a bond | NH | O | NH | T3i | OH |
| 3190 | CMe | S | Q1j | a bond | H | a bond | NH | O | NH | T3j | OH |
| 3191 | CMe | S | Q1j | a bond | H | a bond | NH | O | a bond | T3a | OH |
| 3192 | CMe | S | Q1j | a bond | H | a bond | NH | O | a bond | T3b | OH |
| 3193 | CMe | S | Q1j | a bond | H | a bond | NH | O | a bond | T3c | OH |
| 3194 | CMe | S | Q1j | a bond | H | a bond | NH | O | a bond | T3d | OH |
| 3195 | CMe | S | Q1j | a bond | H | a bond | NH | O | a bond | T3e | OH |
| 3196 | CMe | S | Q1j | a bond | H | a bond | NH | O | a bond | T3f | OH |
| 3197 | CMe | S | Q1j | a bond | H | a bond | NH | O | a bond | T3g | OH |
| 3198 | CMe | S | Q1j | a bond | H | a bond | NH | O | a bond | T3h | OH |
| 3199 | CMe | S | Q1j | a bond | H | a bond | NH | O | a bond | T3i | OH |
| 3200 | CMe | S | Q1j | a bond | H | a bond | NH | O | a bond | T3j | OH |
| 3201 | CMe | O | Q1a | a bond | Me | a bond | NH | S | NH | T3a | OH |
| 3202 | CMe | O | Q1a | a bond | Me | a bond | NH | S | NH | T3b | OH |
| 3203 | CMe | O | Q1a | a bond | Me | a bond | NH | S | NH | T3c | OH |
| 3204 | CMe | O | Q1a | a bond | Me | a bond | NH | S | NH | T3d | OH |
| 3205 | CMe | O | Q1a | a bond | Me | a bond | NH | S | NH | T3e | OH |
| 3206 | CMe | O | Q1a | a bond | Me | a bond | NH | S | NH | T3f | OH |
| 3207 | CMe | O | Q1a | a bond | Me | a bond | NH | S | NH | T3g | OH |
| 3208 | CMe | O | Q1a | a bond | Me | a bond | NH | S | NH | T3h | OH |
| 3209 | CMe | O | Q1a | a bond | Me | a bond | NH | S | NH | T3i | OH |
| 3210 | CMe | O | Q1a | a bond | Me | a bond | NH | S | NH | T3j | OH |
| 3211 | CMe | O | Q1a | a bond | Me | a bond | NH | S | a bond | T3a | OH |
| 3212 | CMe | O | Q1a | a bond | Me | a bond | NH | S | a bond | T3b | OH |
| 3213 | CMe | O | Q1a | a bond | Me | a bond | NH | S | a bond | T3c | OH |

TABLE 1-continued

| No | A | B | R¹ | L¹ | R² | L² | L³ | Y | L⁴ | R³ | X |
|---|---|---|---|---|---|---|---|---|---|---|---|
| 3214 | CMe | O | Q1a | a bond | Me | a bond | NH | S | a bond | T3d | OH |
| 3215 | CMe | O | Q1a | a bond | Me | a bond | NH | S | a bond | T3e | OH |
| 3216 | CMe | O | Q1a | a bond | Me | a bond | NH | S | a bond | T3f | OH |
| 3217 | CMe | O | Q1a | a bond | Me | a bond | NH | S | a bond | T3g | OH |
| 3218 | CMe | O | Q1a | a bond | Me | a bond | NH | S | a bond | T3h | OH |
| 3219 | CMe | O | Q1a | a bond | Me | a bond | NH | S | a bond | T3i | OH |
| 3220 | CMe | O | Q1a | a bond | Me | a bond | NH | S | a bond | T3j | OH |
| 3221 | CMe | O | Q1a | a bond | Me | a bond | NH | O | NH | T3a | OH |
| 3222 | CMe | O | Q1a | a bond | Me | a bond | NH | O | NH | T3b | OH |
| 3223 | CMe | O | Q1a | a bond | Me | a bond | NH | O | NH | T3c | OH |
| 3224 | CMe | O | Q1a | a bond | Me | a bond | NH | O | NH | T3d | OH |
| 3225 | CMe | O | Q1a | a bond | Me | a bond | NH | O | NH | T3e | OH |
| 3226 | CMe | O | Q1a | a bond | Me | a bond | NH | O | NH | T3f | OH |
| 3227 | CMe | O | Q1a | a bond | Me | a bond | NH | O | NH | T3g | OH |
| 3228 | CMe | O | Q1a | a bond | Me | a bond | NH | O | NH | T3h | OH |
| 3229 | CMe | O | Q1a | a bond | Me | a bond | NH | O | NH | T3i | OH |
| 3230 | CMe | O | Q1a | a bond | Me | a bond | NH | O | NH | T3j | OH |
| 3231 | CMe | O | Q1a | a bond | Me | a bond | NH | O | a bond | T3a | OH |
| 3232 | CMe | O | Q1a | a bond | Me | a bond | NH | O | a bond | T3b | OH |
| 3233 | CMe | O | Q1a | a bond | Me | a bond | NH | O | a bond | T3c | OH |
| 3234 | CMe | O | Q1a | a bond | Me | a bond | NH | O | a bond | T3d | OH |
| 3235 | CMe | O | Q1a | a bond | Me | a bond | NH | O | a bond | T3e | OH |
| 3236 | CMe | O | Q1a | a bond | Me | a bond | NH | O | a bond | T3f | OH |
| 3237 | CMe | O | Q1a | a bond | Me | a bond | NH | O | a bond | T3g | OH |
| 3238 | CMe | O | Q1a | a bond | Me | a bond | NH | O | a bond | T3h | OH |
| 3239 | CMe | O | Q1a | a bond | Me | a bond | NH | O | a bond | T3i | OH |
| 3240 | CMe | O | Q1a | a bond | Me | a bond | NH | O | a bond | T3j | OH |
| 3241 | CMe | O | Q1a | a bond | H | a bond | NH | S | NH | T3a | OH |
| 3242 | CMe | O | Q1a | a bond | H | a bond | NH | S | NH | T3b | OH |
| 3243 | CMe | O | Q1a | a bond | H | a bond | NH | S | NH | T3c | OH |
| 3244 | CMe | O | Q1a | a bond | H | a bond | NH | S | NH | T3d | OH |
| 3245 | CMe | O | Q1a | a bond | H | a bond | NH | S | NH | T3e | OH |
| 3246 | CMe | O | Q1a | a bond | H | a bond | NH | S | NH | T3f | OH |
| 3247 | CMe | O | Q1a | a bond | H | a bond | NH | S | NH | T3g | OH |
| 3248 | CMe | O | Q1a | a bond | H | a bond | NH | S | NH | T3h | OH |
| 3249 | CMe | O | Q1a | a bond | H | a bond | NH | S | NH | T3i | OH |
| 3250 | CMe | O | Q1a | a bond | H | a bond | NH | S | NH | T3j | OH |
| 3251 | CMe | O | Q1a | a bond | H | a bond | NH | S | a bond | T3a | OH |
| 3252 | CMe | O | Q1a | a bond | H | a bond | NH | S | a bond | T3b | OH |
| 3253 | CMe | O | Q1a | a bond | H | a bond | NH | S | a bond | T3c | OH |
| 3254 | CMe | O | Q1a | a bond | H | a bond | NH | S | a bond | T3d | OH |
| 3255 | CMe | O | Q1a | a bond | H | a bond | NH | S | a bond | T3e | OH |
| 3256 | CMe | O | Q1a | a bond | H | a bond | NH | S | a bond | T3f | OH |
| 3257 | CMe | O | Q1a | a bond | H | a bond | NH | S | a bond | T3g | OH |
| 3258 | CMe | O | Q1a | a bond | H | a bond | NH | S | a bond | T3h | OH |
| 3259 | CMe | O | Q1a | a bond | H | a bond | NH | S | a bond | T3i | OH |
| 3260 | CMe | O | Q1a | a bond | H | a bond | NH | S | a bond | T3j | OH |
| 3261 | CMe | O | Q1a | a bond | H | a bond | NH | O | NH | T3a | OH |
| 3262 | CMe | O | Q1a | a bond | H | a bond | NH | O | NH | T3b | OH |
| 3263 | CMe | O | Q1a | a bond | H | a bond | NH | O | NH | T3c | OH |
| 3264 | CMe | O | Q1a | a bond | H | a bond | NH | O | NH | T3d | OH |
| 3265 | CMe | O | Q1a | a bond | H | a bond | NH | O | NH | T3e | OH |
| 3266 | CMe | O | Q1a | a bond | H | a bond | NH | O | NH | T3f | OH |
| 3267 | CMe | O | Q1a | a bond | H | a bond | NH | O | NH | T3g | OH |
| 3268 | CMe | O | Q1a | a bond | H | a bond | NH | O | NH | T3h | OH |
| 3269 | CMe | O | Q1a | a bond | H | a bond | NH | O | NH | T3i | OH |
| 3270 | CMe | O | Q1a | a bond | H | a bond | NH | O | NH | T3j | OH |
| 3271 | CMe | O | Q1a | a bond | H | a bond | NH | O | a bond | T3a | OH |
| 3272 | CMe | O | Q1a | a bond | H | a bond | NH | O | a bond | T3b | OH |
| 3273 | CMe | O | Q1a | a bond | H | a bond | NH | O | a bond | T3c | OH |
| 3274 | CMe | O | Q1a | a bond | H | a bond | NH | O | a bond | T3d | OH |
| 3275 | CMe | O | Q1a | a bond | H | a bond | NH | O | a bond | T3e | OH |
| 3276 | CMe | O | Q1a | a bond | H | a bond | NH | O | a bond | T3f | OH |
| 3277 | CMe | O | Q1a | a bond | H | a bond | NH | O | a bond | T3g | OH |
| 3278 | CMe | O | Q1a | a bond | H | a bond | NH | O | a bond | T3h | OH |
| 3279 | CMe | O | Q1a | a bond | H | a bond | NH | O | a bond | T3i | OH |
| 3280 | CMe | O | Q1a | a bond | H | a bond | NH | O | a bond | T3j | OH |
| 3281 | CMe | O | Q1b | a bond | Me | a bond | NH | S | NH | T3a | OH |
| 3282 | CMe | O | Q1b | a bond | Me | a bond | NH | S | NH | T3b | OH |
| 3283 | CMe | O | Q1b | a bond | Me | a bond | NH | S | NH | T3c | OH |
| 3284 | CMe | O | Q1b | a bond | Me | a bond | NH | S | NH | T3d | OH |
| 3285 | CMe | O | Q1b | a bond | Me | a bond | NH | S | NH | T3e | OH |
| 3286 | CMe | O | Q1b | a bond | Me | a bond | NH | S | NH | T3f | OH |
| 3287 | CMe | O | Q1b | a bond | Me | a bond | NH | S | NH | T3g | OH |
| 3288 | CMe | O | Q1b | a bond | Me | a bond | NH | S | NH | 73h | OH |
| 3289 | CMe | O | Q1b | a bond | Me | a bond | NH | S | NH | T3i | OH |
| 3290 | CMe | O | Q1b | a bond | Me | a bond | NH | S | NH | T3j | OH |
| 3291 | CMe | O | Q1b | a bond | Me | a bond | NH | S | a bond | T3a | OH |

TABLE 1-continued

| No | A | B | R¹ | L¹ | R² | L² | L³ | Y | L⁴ | R³ | X |
|---|---|---|---|---|---|---|---|---|---|---|---|
| 3292 | CMe | O | Q1b | a bond | Me | a bond | NH | S | a bond | T3b | OH |
| 3293 | CMe | O | Q1b | a bond | Me | a bond | NH | S | a bond | T3c | OH |
| 3294 | CMe | O | Q1b | a bond | Me | a bond | NH | S | a bond | T3d | OH |
| 3295 | CMe | O | Q1b | a bond | Me | a bond | NH | S | a bond | T3e | OH |
| 3296 | CMe | O | Q1b | a bond | Me | a bond | NH | S | a bond | T3f | OH |
| 3297 | CMe | O | Q1b | a bond | Me | a bond | NH | S | a bond | T3g | OH |
| 3298 | CMe | O | Q1b | a bond | Me | a bond | NH | S | a bond | T3h | OH |
| 3299 | CMe | O | Q1b | a bond | Me | a bond | NH | S | a bond | T3i | OH |
| 3300 | CMe | O | Q1b | a bond | Me | a bond | NH | S | a bond | T3j | OH |
| 3301 | CMe | O | Q1b | a bond | Me | a bond | NH | O | NH | T3a | OH |
| 3302 | CMe | O | Q1b | a bond | Me | a bond | NH | O | NH | T3b | OH |
| 3303 | CMe | O | Q1b | a bond | Me | a bond | NH | O | NH | T3c | OH |
| 3304 | CMe | O | Q1b | a bond | Me | a bond | NH | O | NH | T3d | OH |
| 3305 | CMe | O | Q1b | a bond | Me | a bond | NH | O | NH | T3e | OH |
| 3306 | CMe | O | Q1b | a bond | Me | a bond | NH | O | NH | T3f | OH |
| 3307 | CMe | O | Q1b | a bond | Me | a bond | NH | O | NH | T3g | OH |
| 3308 | CMe | O | Q1b | a bond | Me | a bond | NH | O | NH | T3h | OH |
| 3309 | CMe | O | Q1b | a bond | Me | a bond | NH | O | NH | T3i | OH |
| 3310 | CMe | O | Q1b | a bond | Me | a bond | NH | O | NH | T3j | OH |
| 3311 | CMe | O | Q1b | a bond | Me | a bond | NH | O | a bond | T3a | OH |
| 3312 | CMe | O | Q1b | a bond | Me | a bond | NH | O | a bond | T3b | OH |
| 3313 | CMe | O | Q1b | a bond | Me | a bond | NH | O | a bond | T3c | OH |
| 3314 | CMe | O | Q1b | a bond | Me | a bond | NH | O | a bond | T3d | OH |
| 3315 | CMe | O | Q1b | a bond | Me | a bond | NH | O | a bond | T3e | OH |
| 3316 | CMe | O | Q1b | a bond | Me | a bond | NH | O | a bond | T3f | OH |
| 3317 | CMe | O | Q1b | a bond | Me | a bond | NH | O | a bond | T3g | OH |
| 3318 | CMe | O | Q1b | a bond | Me | a bond | NH | O | a bond | T3h | OH |
| 3319 | CMe | O | Q1b | a bond | Me | a bond | NH | O | a bond | T3i | OH |
| 3320 | CMe | O | Q1b | a bond | Me | a bond | NH | O | a bond | T3j | OH |
| 3321 | CMe | O | Q1b | a bond | H | a bond | NH | S | NH | T3a | OH |
| 3322 | CMe | O | Q1b | a bond | H | a bond | NH | S | NH | T3b | OH |
| 3323 | CMe | O | Q1b | a bond | H | a bond | NH | S | NH | T3c | OH |
| 3324 | CMe | O | Q1b | a bond | H | a bond | NH | S | NH | T3d | OH |
| 3325 | CMe | O | Q1b | a bond | H | a bond | NH | S | NH | T3e | OH |
| 3326 | CMe | O | Q1b | a bond | H | a bond | NH | S | NH | T3f | OH |
| 3327 | CMe | O | Q1b | a bond | H | a bond | NH | S | NH | T3g | OH |
| 3328 | CMe | O | Q1b | a bond | H | a bond | NH | S | NH | 73h | OH |
| 3329 | CMe | O | Q1b | a bond | H | a bond | NH | S | NH | T3i | OH |
| 3330 | CMe | O | Q1b | a bond | H | a bond | NH | S | NH | T3j | OH |
| 3331 | CMe | O | Q1b | a bond | H | a bond | NH | S | a bond | T3a | OH |
| 3332 | CMe | O | Q1b | a bond | H | a bond | NH | S | a bond | T3b | OH |
| 3333 | CMe | O | Q1b | a bond | H | a bond | NH | S | a bond | T3c | OH |
| 3334 | CMe | O | Q1b | a bond | H | a bond | NH | S | a bond | T3d | OH |
| 3335 | CMe | O | Q1b | a bond | H | a bond | NH | S | a bond | T3e | OH |
| 3336 | CMe | O | Q1b | a bond | H | a bond | NH | S | a bond | T3f | OH |
| 3337 | CMe | O | Q1b | a bond | H | a bond | NH | S | a bond | T3g | OH |
| 3338 | CMe | O | Q1b | a bond | H | a bond | NH | S | a bond | T3h | OH |
| 3339 | CMe | O | Q1b | a bond | H | a bond | NH | S | a bond | T3i | OH |
| 3340 | CMe | O | Q1b | a bond | H | a bond | NH | S | a bond | T3j | OH |
| 3341 | CMe | O | Q1b | a bond | H | a bond | NH | O | NH | T3a | OH |
| 3342 | CMe | O | Q1b | a bond | H | a bond | NH | O | NH | T3b | OH |
| 3343 | CMe | O | Q1b | a bond | H | a bond | NH | O | NH | T3c | OH |
| 3344 | CMe | O | Q1b | a bond | H | a bond | NH | O | NH | T3d | OH |
| 3345 | CMe | O | Q1b | a bond | H | a bond | NH | O | NH | T3e | OH |
| 3346 | CMe | O | Q1b | a bond | H | a bond | NH | O | NH | T3f | OH |
| 3347 | CMe | O | Q1b | a bond | H | a bond | NH | O | NH | T3g | OH |
| 3348 | CMe | O | Q1b | a bond | H | a bond | NH | O | NH | T3h | OH |
| 3349 | CMe | O | Q1b | a bond | H | a bond | NH | O | NH | T3i | OH |
| 3350 | CMe | O | Q1b | a bond | H | a bond | NH | O | NH | T3j | OH |
| 3351 | CMe | O | Q1b | a bond | H | a bond | NH | O | a bond | T3a | OH |
| 3352 | CMe | O | Q1b | a bond | H | a bond | NH | O | a bond | T3b | OH |
| 3353 | CMe | O | Q1b | a bond | H | a bond | NH | O | a bond | T3c | OH |
| 3354 | CMe | O | Q1b | a bond | H | a bond | NH | O | a bond | T3d | OH |
| 3355 | CMe | O | Q1b | a bond | H | a bond | NH | O | a bond | T3e | OH |
| 3356 | CMe | O | Q1b | a bond | H | a bond | NH | O | a bond | T3f | OH |
| 3357 | CMe | O | Q1b | a bond | H | a bond | NH | O | a bond | T3g | OH |
| 3358 | CMe | O | Q1b | a bond | H | a bond | NH | O | a bond | T3h | OH |
| 3359 | CMe | O | Q1b | a bond | H | a bond | NH | O | a bond | T3i | OH |
| 3360 | CMe | O | Q1b | a bond | H | a bond | NH | O | a bond | T3j | OH |
| 3361 | CMe | O | Q1c | a bond | Me | a bond | NH | S | NH | T3a | OH |
| 3362 | CMe | O | Q1c | a bond | Me | a bond | NH | S | NH | T3b | OH |
| 3363 | CMe | O | Q1c | a bond | Me | a bond | NH | S | NH | T3c | OH |
| 3364 | CMe | O | Q1c | a bond | Me | a bond | NH | S | NH | T3d | OH |
| 3365 | CMe | O | Q1c | a bond | Me | a bond | NH | S | NH | T3e | OH |
| 3366 | CMe | O | Q1c | a bond | Me | a bond | NH | S | NH | T3f | OH |
| 3367 | CMe | O | Q1c | a bond | Me | a bond | NH | S | NH | T3g | OH |
| 3368 | CMe | O | Q1c | a bond | Me | a bond | NH | S | NH | T3h | OH |
| 3369 | CMe | O | Q1c | a bond | Me | a bond | NH | S | NH | T3i | OH |

TABLE 1-continued

| No | A | B | R¹ | L¹ | R² | L² | L³ | Y | L⁴ | R³ | X |
|---|---|---|---|---|---|---|---|---|---|---|---|
| 3370 | CMe | O | Q1c | a bond | Me | a bond | NH | S | NH | T3j | OH |
| 3371 | CMe | O | Q1c | a bond | Me | a bond | NH | S | a bond | T3a | OH |
| 3372 | CMe | O | Q1c | a bond | Me | a bond | NH | S | a bond | T3b | OH |
| 3373 | CMe | O | Q1c | a bond | Me | a bond | NH | S | a bond | T3c | OH |
| 3374 | CMe | O | Q1c | a bond | Me | a bond | NH | S | a bond | T3d | OH |
| 3375 | CMe | O | Q1c | a bond | Me | a bond | NH | S | a bond | T3e | OH |
| 3376 | CMe | O | Q1c | a bond | Me | a bond | NH | S | a bond | T3f | OH |
| 3377 | CMe | O | Q1c | a bond | Me | a bond | NH | S | a bond | T3g | OH |
| 3378 | CMe | O | Q1c | a bond | Me | a bond | NH | S | a bond | T3h | OH |
| 3379 | CMe | O | Q1c | a bond | Me | a bond | NH | S | a bond | T3i | OH |
| 3380 | CMe | O | Q1c | a bond | Me | a bond | NH | S | a bond | T3j | OH |
| 3381 | CMe | O | Q1c | a bond | Me | a bond | NH | O | NH | T3a | OH |
| 3382 | CMe | O | Q1c | a bond | Me | a bond | NH | O | NH | T3b | OH |
| 3383 | CMe | O | Q1c | a bond | Me | a bond | NH | O | NH | T3c | OH |
| 3384 | CMe | O | Q1c | a bond | Me | a bond | NH | O | NH | T3d | OH |
| 3385 | CMe | O | Q1c | a bond | Me | a bond | NH | O | NH | T3e | OH |
| 3386 | CMe | O | Q1c | a bond | Me | a bond | NH | O | NH | T3f | OH |
| 3387 | CMe | O | Q1c | a bond | Me | a bond | NH | O | NH | T3g | OH |
| 3388 | CMe | O | Q1c | a bond | Me | a bond | NH | O | NH | T3h | OH |
| 3389 | CMe | O | Q1c | a bond | Me | a bond | NH | O | NH | T3i | OH |
| 3390 | CMe | O | Q1c | a bond | Me | a bond | NH | O | NH | T3j | OH |
| 3391 | CMe | O | Q1c | a bond | Me | a bond | NH | O | a bond | T3a | OH |
| 3392 | CMe | O | Q1c | a bond | Me | a bond | NH | O | a bond | T3b | OH |
| 3393 | CMe | O | Q1c | a bond | Me | a bond | NH | O | a bond | T3c | OH |
| 3394 | CMe | O | Q1c | a bond | Me | a bond | NH | O | a bond | T3d | OH |
| 3395 | CMe | O | Q1c | a bond | Me | a bond | NH | O | a bond | T3e | OH |
| 3396 | CMe | O | Q1c | a bond | Me | a bond | NH | O | a bond | T3f | OH |
| 3397 | CMe | O | Q1c | a bond | Me | a bond | NH | O | a bond | T3g | OH |
| 3398 | CMe | O | Q1c | a bond | Me | a bond | NH | O | a bond | T3h | OH |
| 3399 | CMe | O | Q1c | a bond | Me | a bond | NH | O | a bond | T3i | OH |
| 3400 | CMe | O | Q1c | a bond | Me | a bond | NH | O | a bond | T3j | OH |
| 3401 | CMe | O | Q1c | a bond | H | a bond | NH | S | NH | T3a | OH |
| 3402 | CMe | O | Q1c | a bond | H | a bond | NH | S | NH | T3b | OH |
| 3403 | CMe | O | Q1c | a bond | H | a bond | NH | S | NH | T3c | OH |
| 3404 | CMe | O | Q1c | a bond | H | a bond | NH | S | NH | T3d | OH |
| 3405 | CMe | O | Q1c | a bond | H | a bond | NH | S | NH | T3e | OH |
| 3406 | CMe | O | Q1c | a bond | H | a bond | NH | S | NH | T3f | OH |
| 3407 | CMe | O | Q1c | a bond | H | a bond | NH | S | NH | T3g | OH |
| 3408 | CMe | O | Q1c | a bond | H | a bond | NH | S | NH | T3h | OH |
| 3409 | CMe | O | Q1c | a bond | H | a bond | NH | S | NH | T3i | OH |
| 3410 | CMe | O | Q1c | a bond | H | a bond | NH | S | NH | T3j | OH |
| 3411 | CMe | O | Q1c | a bond | H | a bond | NH | S | a bond | T3a | OH |
| 3412 | CMe | O | Q1c | a bond | H | a bond | NH | S | a bond | T3b | OH |
| 3413 | CMe | O | Q1c | a bond | H | a bond | NH | S | a bond | T3c | OH |
| 3414 | CMe | O | Q1c | a bond | H | a bond | NH | S | a bond | T3d | OH |
| 3415 | CMe | O | Q1c | a bond | H | a bond | NH | S | a bond | T3e | OH |
| 3416 | CMe | O | Q1c | a bond | H | a bond | NH | S | a bond | T3f | OH |
| 3417 | CMe | O | Q1c | a bond | H | a bond | NH | S | a bond | T3g | OH |
| 3418 | CMe | O | Q1c | a bond | H | a bond | NH | S | a bond | T3h | OH |
| 3419 | CMe | O | Q1c | a bond | H | a bond | NH | S | a bond | T3i | OH |
| 3420 | CMe | O | Q1c | a bond | H | a bond | NH | S | a bond | T3j | OH |
| 3421 | CMe | O | Q1c | a bond | H | a bond | NH | O | NH | T3a | OH |
| 3422 | CMe | O | Q1c | a bond | H | a bond | NH | O | NH | T3b | OH |
| 3423 | CMe | O | Q1c | a bond | H | a bond | NH | O | NH | T3c | OH |
| 3424 | CMe | O | Q1c | a bond | H | a bond | NH | O | NH | T3d | OH |
| 3425 | CMe | O | Q1c | a bond | H | a bond | NH | O | NH | T3e | OH |
| 3426 | CMe | O | Q1c | a bond | H | a bond | NH | O | NH | T3f | OH |
| 3427 | CMe | O | Q1c | a bond | H | a bond | NH | O | NH | T3g | OH |
| 3428 | CMe | O | Q1c | a bond | H | a bond | NH | O | NH | T3h | OH |
| 3429 | CMe | O | Q1c | a bond | H | a bond | NH | O | NH | T3i | OH |
| 3430 | CMe | O | Q1c | a bond | H | a bond | NH | O | NH | T3j | OH |
| 3431 | CMe | O | Q1c | a bond | H | a bond | NH | O | a bond | T3a | OH |
| 3432 | CMe | O | Q1c | a bond | H | a bond | NH | O | a bond | T3b | OH |
| 3433 | CMe | O | Q1c | a bond | H | a bond | NH | O | a bond | T3c | OH |
| 3434 | CMe | O | Q1c | a bond | H | a bond | NH | O | a bond | T3d | OH |
| 3435 | CMe | O | Q1c | a bond | H | a bond | NH | O | a bond | T3e | OH |
| 3436 | CMe | O | Q1c | a bond | H | a bond | NH | O | a bond | T3f | OH |
| 3437 | CMe | O | Q1c | a bond | H | a bond | NH | O | a bond | T3g | OH |
| 3438 | CMe | O | Q1c | a bond | H | a bond | NH | O | a bond | T3h | OH |
| 3439 | CMe | O | Q1c | a bond | H | a bond | NH | O | a bond | T3i | OH |
| 3440 | CMe | O | Q1c | a bond | H | a bond | NH | O | a bond | T3j | OH |
| 3441 | CMe | O | Q1i | a bond | Me | a bond | NH | S | NH | T3a | OH |
| 3442 | CMe | O | Q1i | a bond | Me | a bond | NH | S | NH | T3b | OH |
| 3443 | CMe | O | Q1i | a bond | Me | a bond | NH | S | NH | T3c | OH |
| 3444 | CMe | O | Q1i | a bond | Me | a bond | NH | S | NH | T3d | OH |
| 3445 | CMe | O | Q1i | a bond | Me | a bond | NH | S | NH | T3e | OH |
| 3446 | CMe | O | Q1i | a bond | Me | a bond | NH | S | NH | T3f | OH |
| 3447 | CMe | O | Q1i | a bond | Me | a bond | NH | S | NH | T3g | OH |

TABLE 1-continued

| No | A | B | R¹ | L¹ | R² | L² | L³ | Y | L⁴ | R³ | X |
|---|---|---|---|---|---|---|---|---|---|---|---|
| 3448 | CMe | O | Q1i | a bond | Me | a bond | NH | S | NH | T3h | OH |
| 3449 | CMe | O | Q1i | a bond | Me | a bond | NH | S | NH | T3i | OH |
| 3450 | CMe | O | Q1i | a bond | Me | a bond | NH | S | NH | T3j | OH |
| 3451 | CMe | O | Q1i | a bond | Me | a bond | NH | S | a bond | T3a | OH |
| 3452 | CMe | O | Q1i | a bond | Me | a bond | NH | S | a bond | T3b | OH |
| 3453 | CMe | O | Q1i | a bond | Me | a bond | NH | S | a bond | T3c | OH |
| 3454 | CMe | O | Q1i | a bond | Me | a bond | NH | S | a bond | T3d | OH |
| 3455 | CMe | O | Q1i | a bond | Me | a bond | NH | S | a bond | T3e | OH |
| 3456 | CMe | O | Q1i | a bond | Me | a bond | NH | S | a bond | T3f | OH |
| 3457 | CMe | O | Q1i | a bond | Me | a bond | NH | S | a bond | T3g | OH |
| 3458 | CMe | O | Q1i | a bond | Me | a bond | NH | S | a bond | T3h | OH |
| 3459 | CMe | O | Q1i | a bond | Me | a bond | NH | S | a bond | T3i | OH |
| 3460 | CMe | O | Q1i | a bond | Me | a bond | NH | S | a bond | T3j | OH |
| 3461 | CMe | O | Q1i | a bond | Me | a bond | NH | O | NH | T3a | OH |
| 3462 | CMe | O | Q1i | a bond | Me | a bond | NH | O | NH | T3b | OH |
| 3463 | CMe | O | Q1i | a bond | Me | a bond | NH | O | NH | T3c | OH |
| 3464 | CMe | O | Q1i | a bond | Me | a bond | NH | O | NH | T3d | OH |
| 3465 | CMe | O | Q1i | a bond | Me | a bond | NH | O | NH | T3e | OH |
| 3466 | CMe | O | Q1i | a bond | Me | a bond | NH | O | NH | T3f | OH |
| 3467 | CMe | O | Q1i | a bond | Me | a bond | NH | O | NH | T3g | OH |
| 3468 | CMe | O | Q1i | a bond | Me | a bond | NH | O | NH | T3h | OH |
| 3469 | CMe | O | Q1i | a bond | Me | a bond | NH | O | NH | T3i | OH |
| 3470 | CMe | O | Q1i | a bond | Me | a bond | NH | O | NH | T3j | OH |
| 3471 | CMe | O | Q1i | a bond | Me | a bond | NH | O | a bond | T3a | OH |
| 3472 | CMe | O | Q1i | a bond | Me | a bond | NH | O | a bond | T3b | OH |
| 3473 | CMe | O | Q1i | a bond | Me | a bond | NH | O | a bond | T3c | OH |
| 3474 | CMe | O | Q1i | a bond | Me | a bond | NH | O | a bond | T3d | OH |
| 3475 | CMe | O | Q1i | a bond | Me | a bond | NH | O | a bond | T3e | OH |
| 3476 | CMe | O | Q1i | a bond | Me | a bond | NH | O | a bond | T3f | OH |
| 3477 | CMe | O | Q1i | a bond | Me | a bond | NH | O | a bond | T3g | OH |
| 3478 | CMe | O | Q1i | a bond | Me | a bond | NH | O | a bond | T3h | OH |
| 3479 | CMe | O | Q1i | a bond | Me | a bond | NH | O | a bond | T3i | OH |
| 3480 | CMe | O | Q1i | a bond | Me | a bond | NH | O | a bond | T3j | OH |
| 3481 | CMe | O | Q1i | a bond | H | a bond | NH | S | NH | T3a | OH |
| 3482 | CMe | O | Q1i | a bond | H | a bond | NH | S | NH | T3b | OH |
| 3483 | CMe | O | Q1i | a bond | H | a bond | NH | S | NH | T3c | OH |
| 3484 | CMe | O | Q1i | a bond | H | a bond | NH | S | NH | T3d | OH |
| 3485 | CMe | O | Q1i | a bond | H | a bond | NH | S | NH | T3e | OH |
| 3486 | CMe | O | Q1i | a bond | H | a bond | NH | S | NH | T3f | OH |
| 3487 | CMe | O | Q1i | a bond | H | a bond | NH | S | NH | T3g | OH |
| 3488 | CMe | O | Q1i | a bond | H | a bond | NH | S | NH | T3h | OH |
| 3489 | CMe | O | Q1i | a bond | H | a bond | NH | S | NH | T3i | OH |
| 3490 | CMe | O | Q1i | a bond | H | a bond | NH | S | NH | T3j | OH |
| 3491 | CMe | O | Q1i | a bond | H | a bond | NH | S | a bond | T3a | OH |
| 3492 | CMe | O | Q1i | a bond | H | a bond | NH | S | a bond | T3b | OH |
| 3493 | CMe | O | Q1i | a bond | H | a bond | NH | S | a bond | T3c | OH |
| 3494 | CMe | O | Q1i | a bond | H | a bond | NH | S | a bond | T3d | OH |
| 3495 | CMe | O | Q1i | a bond | H | a bond | NH | S | a bond | T3e | OH |
| 3496 | CMe | O | Q1i | a bond | H | a bond | NH | S | a bond | T3f | OH |
| 3497 | CMe | O | Q1i | a bond | H | a bond | NH | S | a bond | T3g | OH |
| 3498 | CMe | O | Q1i | a bond | H | a bond | NH | S | a bond | T3h | OH |
| 3499 | CMe | O | Q1i | a bond | H | a bond | NH | S | a bond | T3i | OH |
| 3500 | CMe | O | Q1i | a bond | H | a bond | NH | S | a bond | T3j | OH |
| 3501 | CMe | O | Q1i | a bond | H | a bond | NH | O | NH | T3a | OH |
| 3502 | CMe | O | Q1i | a bond | H | a bond | NH | O | NH | T3b | OH |
| 3503 | CMe | O | Q1i | a bond | H | a bond | NH | O | NH | T3c | OH |
| 3504 | CMe | O | Q1i | a bond | H | a bond | NH | O | NH | T3d | OH |
| 3505 | CMe | O | Q1i | a bond | H | a bond | NH | O | NH | T3e | OH |
| 3506 | CMe | O | Q1i | a bond | H | a bond | NH | O | NH | T3f | OH |
| 3507 | CMe | O | Q1i | a bond | H | a bond | NH | O | NH | T3g | OH |
| 3508 | CMe | O | Q1i | a bond | H | a bond | NH | O | NH | T3h | OH |
| 3509 | CMe | O | Q1i | a bond | H | a bond | NH | O | NH | T3i | OH |
| 3510 | CMe | O | Q1i | a bond | H | a bond | NH | O | NH | T3j | OH |
| 3511 | CMe | O | Q1i | a bond | H | a bond | NH | O | a bond | T3a | OH |
| 3512 | CMe | O | Q1i | a bond | H | a bond | NH | O | a bond | T3b | OH |
| 3513 | CMe | O | Q1i | a bond | H | a bond | NH | O | a bond | T3c | OH |
| 3514 | CMe | O | Q1i | a bond | H | a bond | NH | O | a bond | T3d | OH |
| 3515 | CMe | O | Q1i | a bond | H | a bond | NH | O | a bond | T3e | OH |
| 3516 | CMe | O | Q1i | a bond | H | a bond | NH | O | a bond | T3f | OH |
| 3517 | CMe | O | Q1i | a bond | H | a bond | NH | O | a bond | T3g | OH |
| 3518 | CMe | O | Q1i | a bond | H | a bond | NH | O | a bond | T3h | OH |
| 3519 | CMe | O | Q1i | a bond | H | a bond | NH | O | a bond | T3i | OH |
| 3520 | CMe | O | Q1i | a bond | H | a bond | NH | O | a bond | T3j | OH |
| 3521 | CMe | O | Q1j | a bond | Me | a bond | NH | S | NH | T3a | OH |
| 3522 | CMe | O | Q1j | a bond | Me | a bond | NH | S | NH | T3b | OH |
| 3523 | CMe | O | Q1j | a bond | Me | a bond | NH | S | NH | T3c | OH |
| 3524 | CMe | O | Q1j | a bond | Me | a bond | NH | S | NH | T3d | OH |
| 3525 | CMe | O | Q1j | a bond | Me | a bond | NH | S | NH | T3e | OH |

TABLE 1-continued

| No | A | B | R¹ | L¹ | R² | L² | L³ | Y | L⁴ | R³ | X |
|---|---|---|---|---|---|---|---|---|---|---|---|
| 3526 | CMe | O | Q1j | a bond | Me | a bond | NH | S | NH | T3f | OH |
| 3527 | CMe | O | Q1j | a bond | Me | a bond | NH | S | NH | T3g | OH |
| 3528 | CMe | O | Q1j | a bond | Me | a bond | NH | S | NH | T3h | OH |
| 3529 | CMe | O | Q1j | a bond | Me | a bond | NH | S | NH | T3i | OH |
| 3530 | CMe | O | Q1j | a bond | Me | a bond | NH | S | NH | T3j | OH |
| 3531 | CMe | O | Q1j | a bond | Me | a bond | NH | S | a bond | T3a | OH |
| 3532 | CMe | O | Q1j | a bond | Me | a bond | NH | S | a bond | T3b | OH |
| 3533 | CMe | O | Q1j | a bond | Me | a bond | NH | S | a bond | T3c | OH |
| 3534 | CMe | O | Q1j | a bond | Me | a bond | NH | S | a bond | T3d | OH |
| 3535 | CMe | O | Q1j | a bond | Me | a bond | NH | S | a bond | T3e | OH |
| 3536 | CMe | O | Q1j | a bond | Me | a bond | NH | S | a bond | T3f | OH |
| 3537 | CMe | O | Q1j | a bond | Me | a bond | NH | S | a bond | T3g | OH |
| 3538 | CMe | O | Q1j | a bond | Me | a bond | NH | S | a bond | T3h | OH |
| 3539 | CMe | O | Q1j | a bond | Me | a bond | NH | S | a bond | T3i | OH |
| 3540 | CMe | O | Q1j | a bond | Me | a bond | NH | S | a bond | T3j | OH |
| 3541 | CMe | O | Q1j | a bond | Me | a bond | NH | O | NH | T3a | OH |
| 3542 | CMe | O | Q1j | a bond | Me | a bond | NH | O | NH | T3b | OH |
| 3543 | CMe | O | Q1j | a bond | Me | a bond | NH | O | NH | T3c | OH |
| 3544 | CMe | O | Q1j | a bond | Me | a bond | NH | O | NH | T3d | OH |
| 3545 | CMe | O | Q1j | a bond | Me | a bond | NH | O | NH | T3e | OH |
| 3546 | CMe | O | Q1j | a bond | Me | a bond | NH | O | NH | T3f | OH |
| 3547 | CMe | O | Q1j | a bond | Me | a bond | NH | O | NH | T3g | OH |
| 3548 | CMe | O | Q1j | a bond | Me | a bond | NH | O | NH | T3h | OH |
| 3549 | CMe | O | Q1j | a bond | Me | a bond | NH | O | NH | T3i | OH |
| 3550 | CMe | O | Q1j | a bond | Me | a bond | NH | O | NH | T3j | OH |
| 3551 | CMe | O | Q1j | a bond | Me | a bond | NH | O | a bond | T3a | OH |
| 3552 | CMe | O | Q1j | a bond | Me | a bond | NH | O | a bond | T3b | OH |
| 3553 | CMe | O | Q1j | a bond | Me | a bond | NH | O | a bond | T3c | OH |
| 3554 | CMe | O | Q1j | a bond | Me | a bond | NH | O | a bond | T3d | OH |
| 3555 | CMe | O | Q1j | a bond | Me | a bond | NH | O | a bond | T3e | OH |
| 3556 | CMe | O | Q1j | a bond | Me | a bond | NH | O | a bond | T3f | OH |
| 3557 | CMe | O | Q1j | a bond | Me | a bond | NH | O | a bond | T3g | OH |
| 3558 | CMe | O | Q1j | a bond | Me | a bond | NH | O | a bond | T3h | OH |
| 3559 | CMe | O | Q1j | a bond | Me | a bond | NH | O | a bond | T3i | OH |
| 3560 | CMe | O | Q1j | a bond | Me | a bond | NH | O | a bond | T3j | OH |
| 3561 | CMe | O | Q1j | a bond | H | a bond | NH | S | NH | T3a | OH |
| 3562 | CMe | O | Q1j | a bond | H | a bond | NH | S | NH | T3b | OH |
| 3563 | CMe | O | Q1j | a bond | H | a bond | NH | S | NH | T3c | OH |
| 3564 | CMe | O | Q1j | a bond | H | a bond | NH | S | NH | T3d | OH |
| 3565 | CMe | O | Q1j | a bond | H | a bond | NH | S | NH | T3e | OH |
| 3566 | CMe | O | Q1j | a bond | H | a bond | NH | S | NH | T3f | OH |
| 3567 | CMe | O | Q1j | a bond | H | a bond | NH | S | NH | T3g | OH |
| 3568 | CMe | O | Q1j | a bond | H | a bond | NH | S | NH | T3h | OH |
| 3569 | CMe | O | Q1j | a bond | H | a bond | NH | S | NH | T3i | OH |
| 3570 | CMe | O | Q1j | a bond | H | a bond | NH | S | NH | T3j | OH |
| 3571 | CMe | O | Q1j | a bond | H | a bond | NH | S | a bond | T3a | OH |
| 3572 | CMe | O | Q1j | a bond | H | a bond | NH | S | a bond | T3b | OH |
| 3573 | CMe | O | Q1j | a bond | H | a bond | NH | S | a bond | T3c | OH |
| 3574 | CMe | O | Q1j | a bond | H | a bond | NH | S | a bond | T3d | OH |
| 3575 | CMe | O | Q1j | a bond | H | a bond | NH | S | a bond | T3e | OH |
| 3576 | CMe | O | Q1j | a bond | H | a bond | NH | S | a bond | T3f | OH |
| 3577 | CMe | O | Q1j | a bond | H | a bond | NH | S | a bond | T3g | OH |
| 3578 | CMe | O | Q1j | a bond | H | a bond | NH | S | a bond | T3h | OH |
| 3579 | CMe | O | Q1j | a bond | H | a bond | NH | S | a bond | T3i | OH |
| 3580 | CMe | O | Q1j | a bond | H | a bond | NH | S | a bond | T3j | OH |
| 3581 | CMe | O | Q1j | a bond | H | a bond | NH | O | NH | T3a | OH |
| 3582 | CMe | O | Q1j | a bond | H | a bond | NH | O | NH | T3b | OH |
| 3583 | CMe | O | Q1j | a bond | H | a bond | NH | O | NH | T3c | OH |
| 3584 | CMe | O | Q1j | a bond | H | a bond | NH | O | NH | T3d | OH |
| 3585 | CMe | O | Q1j | a bond | H | a bond | NH | O | NH | T3e | OH |
| 3586 | CMe | O | Q1j | a bond | H | a bond | NH | O | NH | T3f | OH |
| 3587 | CMe | O | Q1j | a bond | H | a bond | NH | O | NH | T3g | OH |
| 3588 | CMe | O | Q1j | a bond | H | a bond | NH | O | NH | T3h | OH |
| 3589 | CMe | O | Q1j | a bond | H | a bond | NH | O | NH | T3i | OH |
| 3590 | CMe | O | Q1j | a bond | H | a bond | NH | O | NH | T3j | OH |
| 3591 | CMe | O | Q1j | a bond | H | a bond | NH | O | a bond | T3a | OH |
| 3592 | CMe | O | Q1j | a bond | H | a bond | NH | O | a bond | T3b | OH |
| 3593 | CMe | O | Q1j | a bond | H | a bond | NH | O | a bond | T3c | OH |
| 3594 | CMe | O | Q1j | a bond | H | a bond | NH | O | a bond | T3d | OH |
| 3595 | CMe | O | Q1j | a bond | H | a bond | NH | O | a bond | T3e | OH |
| 3596 | CMe | O | Q1j | a bond | H | a bond | NH | O | a bond | T3f | OH |
| 3597 | CMe | O | Q1j | a bond | H | a bond | NH | O | a bond | T3g | OH |
| 3598 | CMe | O | Q1j | a bond | H | a bond | NH | O | a bond | T3h | OH |
| 3599 | CMe | O | Q1j | a bond | H | a bond | NH | O | a bond | T3i | OH |
| 3600 | CMe | O | Q1j | a bond | H | a bond | NH | O | a bond | T3j | OH |
| 3601 | N | NMe | Q1i | a bond | Me | a bond | NH | S | NH | Q3e | OH |
| 3602 | N | NMe | Q1i | a bond | Me | a bond | NH | S | a bond | Q3e | OH |
| 3603 | N | NMe | Q1i | a bond | Me | a bond | NH | O | NH | Q3e | OH |

TABLE 1-continued

| No | A | B | R¹ | L¹ | R² | L² | L³ | Y | L⁴ | R³ | X |
|---|---|---|---|---|---|---|---|---|---|---|---|
| 3604 | N | NMe | Q1i | a bond | Me | a bond | NH | O | a bond | Q3e | OH |
| 3605 | N | NMe | Q1i | a bond | H | a bond | NH | S | NH | Q3e | OH |
| 3606 | N | NMe | Q1i | a bond | H | a bond | NH | S | a bond | Q3e | OH |
| 3607 | N | NMe | Q1i | a bond | H | a bond | NH | O | NH | Q3e | OH |
| 3608 | N | NMe | Q1i | a bond | H | a bond | NH | O | a bond | Q3e | OH |
| 3609 | N | NMe | Q1j | a bond | Me | a bond | NH | S | NH | Q3e | OH |
| 3610 | N | NMe | Q1j | a bond | Me | a bond | NH | S | a bond | Q3e | OH |
| 3611 | N | NMe | Q1j | a bond | Me | a bond | NH | O | NH | Q3e | OH |
| 3612 | N | NMe | Q1j | a bond | Me | a bond | NH | O | a bond | Q3e | OH |
| 3613 | N | NMe | Q1j | a bond | H | a bond | NH | S | NH | Q3e | OH |
| 3614 | N | NMe | Q1j | a bond | H | a bond | NH | S | a bond | Q3e | OH |
| 3615 | N | NMe | Q1j | a bond | H | a bond | NH | O | NH | Q3e | OH |
| 3616 | N | NMe | Q1j | a bond | H | a bond | NH | O | a bond | Q3e | OH |
| 3617 | N | S | Q1i | a bond | Me | a bond | NH | S | NH | Q3e | OH |
| 3618 | N | S | Q1i | a bond | Me | a bond | NH | S | a bond | Q3e | OH |
| 3619 | N | S | Q1i | a bond | Me | a bond | NH | O | NH | Q3e | OH |
| 3620 | N | S | Q1i | a bond | Me | a bond | NH | O | a bond | Q3e | OH |
| 3621 | N | S | Q1i | a bond | H | a bond | NH | S | NH | Q3e | OH |
| 3622 | N | S | Q1i | a bond | H | a bond | NH | S | a bond | Q3e | OH |
| 3623 | N | S | Q1i | a bond | H | a bond | NH | O | NH | Q3e | OH |
| 3624 | N | S | Q1i | a bond | H | a bond | NH | O | a bond | Q3e | OH |
| 3625 | N | S | Q1j | a bond | Me | a bond | NH | S | NH | Q3e | OH |
| 3626 | N | S | Q1j | a bond | Me | a bond | NH | S | a bond | Q3e | OH |
| 3627 | N | S | Q1j | a bond | Me | a bond | NH | O | NH | Q3e | OH |
| 3628 | N | S | Q1j | a bond | Me | a bond | NH | O | a bond | Q3e | OH |
| 3629 | N | S | Q1j | a bond | H | a bond | NH | S | NH | Q3e | OH |
| 3630 | N | S | Q1j | a bond | H | a bond | NH | S | a bond | Q3e | OH |
| 3631 | N | S | Q1j | a bond | H | a bond | NH | O | NH | Q3e | OH |
| 3632 | N | S | Q1j | a bond | H | a bond | NH | O | a bond | Q3e | OH |
| 3633 | N | O | Q1i | a bond | Me | a bond | NH | S | NH | Q3e | OH |
| 3634 | N | O | Q1i | a bond | Me | a bond | NH | S | a bond | Q3e | OH |
| 3635 | N | O | Q1i | a bond | Me | a bond | NH | O | NH | Q3e | OH |
| 3636 | N | O | Q1i | a bond | Me | a bond | NH | O | a bond | Q3e | OH |
| 3637 | N | O | Q1i | a bond | H | a bond | NH | S | NH | Q3e | OH |
| 3638 | N | O | Q1i | a bond | H | a bond | NH | S | a bond | Q3e | OH |
| 3639 | N | O | Q1i | a bond | H | a bond | NH | O | NH | Q3e | OH |
| 3640 | N | O | Q1i | a bond | H | a bond | NH | O | a bond | Q3e | OH |
| 3641 | N | O | Q1j | a bond | Me | a bond | NH | S | NH | Q3e | OH |
| 3642 | N | O | Q1j | a bond | Me | a bond | NH | S | a bond | Q3e | OH |
| 3643 | N | O | Q1j | a bond | Me | a bond | NH | O | NH | Q3e | OH |
| 3644 | N | O | Q1j | a bond | Me | a bond | NH | O | a bond | Q3e | OH |
| 3645 | N | O | Q1j | a bond | H | a bond | NH | S | NH | Q3e | OH |
| 3646 | N | O | Q1j | a bond | H | a bond | NH | S | a bond | Q3e | OH |
| 3647 | N | O | Q1j | a bond | H | a bond | NH | O | NH | Q3e | OH |
| 3648 | N | O | Q1j | a bond | H | a bond | NH | O | a bond | Q3e | OH |
| 3649 | CH | NMe | Q1i | a bond | Me | a bond | NH | S | NH | Q3e | OH |
| 3650 | CH | NMe | Q1i | a bond | Me | a bond | NH | S | a bond | Q3e | OH |
| 3651 | CH | NMe | Q1i | a bond | Me | a bond | NH | O | NH | Q3e | OH |
| 3652 | CH | NMe | Q1i | a bond | Me | a bond | NH | O | a bond | Q3e | OH |
| 3653 | CH | NMe | Q1i | a bond | H | a bond | NH | S | NH | Q3e | OH |
| 3654 | CH | NMe | Q1i | a bond | H | a bond | NH | S | a bond | Q3e | OH |
| 3655 | CH | NMe | Q1i | a bond | H | a bond | NH | O | NH | Q3e | OH |
| 3656 | CH | NMe | Q1i | a bond | H | a bond | NH | O | a bond | Q3e | OH |
| 3657 | CH | NMe | Q1j | a bond | Me | a bond | NH | S | NH | Q3e | OH |
| 3658 | CH | NMe | Q1j | a bond | Me | a bond | NH | S | a bond | Q3e | OH |
| 3659 | CH | NMe | Q1j | a bond | Me | a bond | NH | O | NH | Q3e | OH |
| 3660 | CH | NMe | Q1j | a bond | Me | a bond | NH | O | a bond | Q3e | OH |
| 3661 | CH | NMe | Q1j | a bond | H | a bond | NH | S | NH | Q3e | OH |
| 3662 | CH | NMe | Q1j | a bond | H | a bond | NH | S | a bond | Q3e | OH |
| 3663 | CH | NMe | Q1j | a bond | H | a bond | NH | O | NH | Q3e | OH |
| 3664 | CH | NMe | Q1j | a bond | H | a bond | NH | O | a bond | Q3e | OH |
| 3665 | CH | S | Q1i | a bond | Me | a bond | NH | S | NH | Q3e | OH |
| 3666 | CH | S | Q1i | a bond | Me | a bond | NH | S | a bond | Q3e | OH |
| 3667 | CH | S | Q1i | a bond | Me | a bond | NH | O | NH | Q3e | OH |
| 3668 | CH | S | Q1i | a bond | Me | a bond | NH | O | a bond | Q3e | OH |
| 3669 | CH | S | Q1i | a bond | H | a bond | NH | S | NH | Q3e | OH |
| 3670 | CH | S | Q1i | a bond | H | a bond | NH | S | a bond | Q3e | OH |
| 3671 | CH | S | Q1i | a bond | H | a bond | NH | O | NH | Q3e | OH |
| 3672 | CH | S | Q1i | a bond | H | a bond | NH | O | a bond | Q3e | OH |
| 3673 | CH | S | Q1j | a bond | Me | a bond | NH | S | NH | Q3e | OH |
| 3674 | CH | S | Q1j | a bond | Me | a bond | NH | S | a bond | Q3e | OH |
| 3675 | CH | S | Q1j | a bond | Me | a bond | NH | O | NH | Q3e | OH |
| 3676 | CH | S | Q1j | a bond | Me | a bond | NH | O | a bond | Q3e | OH |
| 3677 | CH | S | Q1j | a bond | H | a bond | NH | S | NH | Q3e | OH |
| 3678 | CH | S | Q1j | a bond | H | a bond | NH | S | a bond | Q3e | OH |
| 3679 | CH | S | Q1j | a bond | H | a bond | NH | O | NH | Q3e | OH |
| 3680 | CH | S | Q1j | a bond | H | a bond | NH | O | a bond | Q3e | OH |
| 3681 | CH | O | Q1i | a bond | Me | a bond | NH | S | NH | Q3e | OH |

TABLE 1-continued

| No | A | B | R¹ | L¹ | R² | L² | L³ | Y | L⁴ | R³ | X |
|---|---|---|---|---|---|---|---|---|---|---|---|
| 3682 | CH | O | Q1i | a bond | Me | a bond | NH | S | a bond | Q3e | OH |
| 3683 | CH | O | Q1i | a bond | Me | a bond | NH | O | NH | Q3e | OH |
| 3684 | CH | O | Q1i | a bond | Me | a bond | NH | O | a bond | Q3e | OH |
| 3685 | CH | O | Q1i | a bond | H | a bond | NH | S | NH | Q3e | OH |
| 3686 | CH | O | Q1i | a bond | H | a bond | NH | S | a bond | Q3e | OH |
| 3687 | CH | O | Q1i | a bond | H | a bond | NH | O | NH | Q3e | OH |
| 3688 | CH | O | Q1i | a bond | H | a bond | NH | O | a bond | Q3e | OH |
| 3689 | CH | O | Q1j | a bond | Me | a bond | NH | S | NH | Q3e | OH |
| 3690 | CH | O | Q1j | a bond | Me | a bond | NH | S | a bond | Q3e | OH |
| 3691 | CH | O | Q1j | a bond | Me | a bond | NH | O | NH | Q3e | OH |
| 3692 | CH | O | Q1j | a bond | Me | a bond | NH | O | a bond | Q3e | OH |
| 3693 | CH | O | Q1j | a bond | H | a bond | NH | S | NH | Q3e | OH |
| 3694 | CH | O | Q1j | a bond | H | a bond | NH | S | a bond | Q3e | OH |
| 3695 | CH | O | Q1j | a bond | H | a bond | NH | O | NH | Q3e | OH |
| 3696 | CH | O | Q1j | a bond | H | a bond | NH | O | a bond | Q3e | OH |
| 3697 | CMe | NMe | Q1i | a bond | Me | a bond | NH | S | NH | Q3e | OH |
| 3698 | CMe | NMe | Q1i | a bond | Me | a bond | NH | S | a bond | Q3e | OH |
| 3699 | CMe | NMe | Q1i | a bond | Me | a bond | NH | O | NH | Q3e | OH |
| 3700 | CMe | NMe | Q1i | a bond | Me | a bond | NH | O | a bond | Q3e | OH |
| 3701 | CMe | NMe | Q1i | a bond | H | a bond | NH | S | NH | Q3e | OH |
| 3702 | CMe | NMe | Q1i | a bond | H | a bond | NH | S | a bond | Q3e | OH |
| 3703 | CMe | NMe | Q1i | a bond | H | a bond | NH | O | NH | Q3e | OH |
| 3704 | CMe | NMe | Q1i | a bond | H | a bond | NH | O | a bond | Q3e | OH |
| 3705 | CMe | NMe | Q1j | a bond | Me | a bond | NH | S | NH | Q3e | OH |
| 3706 | CMe | NMe | Q1j | a bond | Me | a bond | NH | S | a bond | Q3e | OH |
| 3707 | CMe | NMe | Q1j | a bond | Me | a bond | NH | O | NH | Q3e | OH |
| 3708 | CMe | NMe | Q1j | a bond | Me | a bond | NH | O | a bond | Q3e | OH |
| 3709 | CMe | NMe | Q1j | a bond | H | a bond | NH | S | NH | Q3e | OH |
| 3710 | CMe | NMe | Q1j | a bond | H | a bond | NH | S | a bond | Q3e | OH |
| 3711 | CMe | NMe | Q1j | a bond | H | a bond | NH | O | NH | Q3e | OH |
| 3712 | CMe | NMe | Q1j | a bond | H | a bond | NH | O | a bond | Q3e | OH |
| 3713 | CMe | S | Q1i | a bond | Me | a bond | NH | S | NH | Q3e | OH |
| 3714 | CMe | S | Q1i | a bond | Me | a bond | NH | S | a bond | Q3e | OH |
| 3715 | CMe | S | Q1i | a bond | Me | a bond | NH | O | NH | Q3e | OH |
| 3716 | CMe | S | Q1i | a bond | Me | a bond | NH | O | a bond | Q3e | OH |
| 3717 | CMe | S | Q1i | a bond | H | a bond | NH | S | NH | Q3e | OH |
| 3718 | CMe | S | Q1i | a bond | H | a bond | NH | S | a bond | Q3e | OH |
| 3719 | CMe | S | Q1i | a bond | H | a bond | NH | O | NH | Q3e | OH |
| 3720 | CMe | S | Q1i | a bond | H | a bond | NH | O | a bond | Q3e | OH |
| 3721 | CMe | S | Q1j | a bond | Me | a bond | NH | S | NH | Q3e | OH |
| 3722 | CMe | S | Q1j | a bond | Me | a bond | NH | S | a bond | Q3e | OH |
| 3723 | CMe | S | Q1j | a bond | Me | a bond | NH | O | NH | Q3e | OH |
| 3724 | CMe | S | Q1j | a bond | Me | a bond | NH | O | a bond | Q3e | OH |
| 3725 | CMe | S | Q1j | a bond | H | a bond | NH | S | NH | Q3e | OH |
| 3726 | CMe | S | Q1j | a bond | H | a bond | NH | S | a bond | Q3e | OH |
| 3727 | CMe | S | Q1j | a bond | H | a bond | NH | O | NH | Q3e | OH |
| 3728 | CMe | S | Q1j | a bond | H | a bond | NH | O | a bond | Q3e | OH |
| 3729 | CMe | O | Q1i | a bond | Me | a bond | NH | S | NH | Q3e | OH |
| 3730 | CMe | O | Q1i | a bond | Me | a bond | NH | S | a bond | Q3e | OH |
| 3731 | CMe | O | Q1i | a bond | Me | a bond | NH | O | NH | Q3e | OH |
| 3732 | CMe | O | Q1i | a bond | Me | a bond | NH | O | a bond | Q3e | OH |
| 3733 | CMe | O | Q1i | a bond | H | a bond | NH | S | NH | Q3e | OH |
| 3734 | CMe | O | Q1i | a bond | H | a bond | NH | S | a bond | Q3e | OH |
| 3735 | CMe | O | Q1i | a bond | H | a bond | NH | O | NH | Q3e | OH |
| 3736 | CMe | O | Q1i | a bond | H | a bond | NH | O | a bond | Q3e | OH |
| 3737 | CMe | O | Q1j | a bond | Me | a bond | NH | S | NH | Q3e | OH |
| 3738 | CMe | O | Q1j | a bond | Me | a bond | NH | S | a bond | Q3e | OH |
| 3739 | CMe | O | Q1j | a bond | Me | a bond | NH | O | NH | Q3e | OH |
| 3740 | CMe | O | Q1j | a bond | Me | a bond | NH | O | a bond | Q3e | OH |
| 3741 | CMe | O | Q1j | a bond | H | a bond | NH | S | NH | Q3e | OH |
| 3742 | CMe | O | Q1j | a bond | H | a bond | NH | S | a bond | Q3e | OH |
| 3743 | CMe | O | Q1j | a bond | H | a bond | NH | O | NH | Q3e | OH |
| 3744 | CMe | O | Q1j | a bond | H | a bond | NH | O | a bond | Q3e | OH |

Q1a = 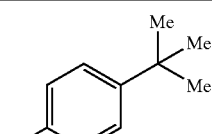

Q1b = 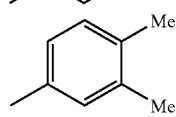

TABLE 1-continued

| No | A | B | R¹ | L¹ | R² | L² | L³ | Y | L⁴ | R³ | X |
|----|---|---|----|----|----|----|----|----|----|----|---|

Q1c =

Q1i =

Q1j =

T3a =

T3b =

T3c =

T3d =

T3e =

Q3e =

T3f =

T3g =

TABLE 1-continued

| No | A | B | R¹ | L¹ | R² | L² | L³ | Y | L⁴ | R³ | X |
|----|---|---|----|----|----|----|----|----|----|----|----|

T3h = [structure: 4-methylbenzoyl-3,5-dimethylpiperidine]

T3i = [structure: 4-methylbenzohydrazide]

T3j = [structure: N-(methylsulfonyl)-4-methylbenzamide]

64) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 64), Q1a, Q1b, Q1c, Q1i, Q1j, T3a, T3b, T3c, T3d, T3e, Q3e, T3f, T3g, T3h, T3i and T3j in Table 1 denote the following substituents).

Q1a = [structure: 4-tert-butylphenyl/cumyl]

Q1b = [structure: 3,4-dimethylphenyl]

Q1c = [structure: 3-chlorophenyl]

Q1i = [structure: 4-trifluoromethylphenyl]

Q1j = [structure: 3,4-dichlorophenyl]

T3a = [structure: 3-methyl-N-((tetrahydrofuran-2-yl)methyl)benzamide]

T3b = [structure: 3-methyl-N-(tetrahydrothiophen-2-yl)benzamide]

T3c = [structure: 3-methyl-N-(piperidin-4-yl)benzamide]

T3d = [structure: 3-methyl-N-(pyrrolidin-2-ylmethyl)benzamide]

T3e = [structure: (3-methylphenyl)(3-acetamidopyrrolidin-1-yl)methanone]

Q3e = [structure: 3-methyl-N-(2-morpholinoethyl)benzamide]

T3f = [structure: 3-methyl-N-(2-(pyrrolidin-1-yl)ethyl)benzamide]

T3g = [structure: (3-methylphenyl)(3,4-dihydroxypyrrolidin-1-yl)methanone]

T3h = [structure: (3-methylphenyl)(3,5-dimethylpiperidin-1-yl)methanone]

T3i = [structure: 3-methyl-N'-dimethylbenzohydrazide]

T3j = 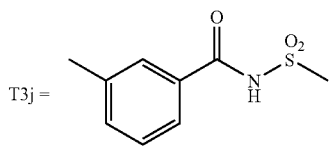

65) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 65), Q1a, Q1b, Q1c, Q1i, Q14, T3a, T3b, T3c, T3d, T3e, Q3e, T3f, T3g, T3h, T3i and T3j in Table 1 denote the following substituents).

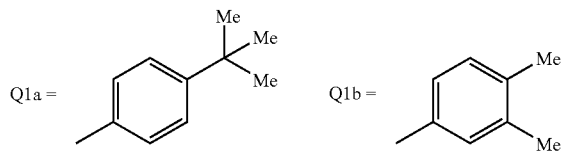

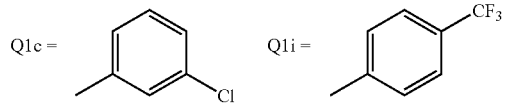

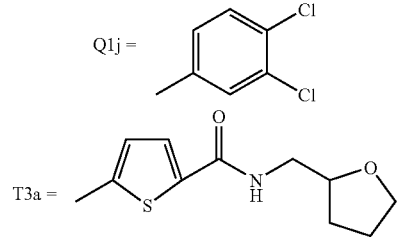

T3a = 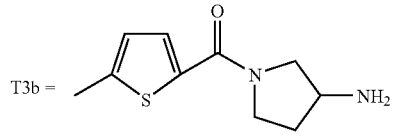

T3b = 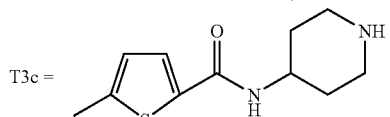

T3c = 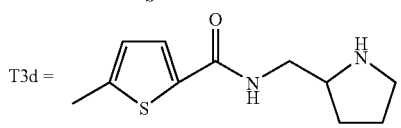

T3d = 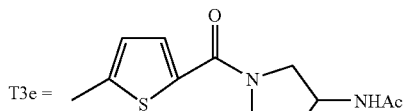

T3e = 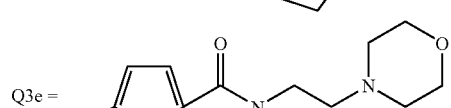

Q3e = 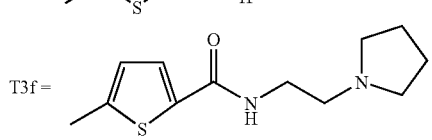

T3f =

T3g = 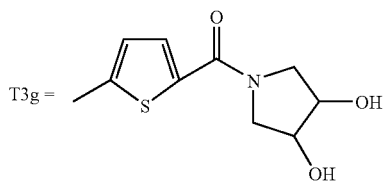

T3h = 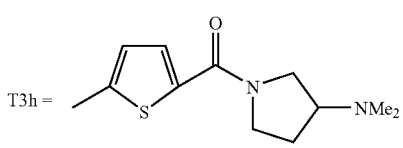

T3i = 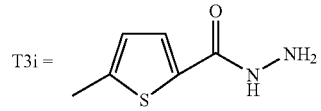

T3j = 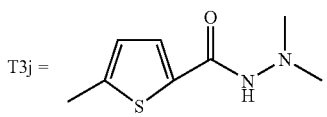

66) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 66), Q1a, Q1b, Q1c, Q1i, Q1j, T3a, T3b, T3c, T3d, T3e, Q3e, T3f, T3g, T3h, T3i and T3j in Table 1 denote the following substituents).

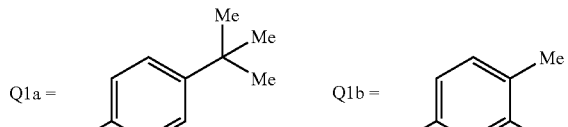

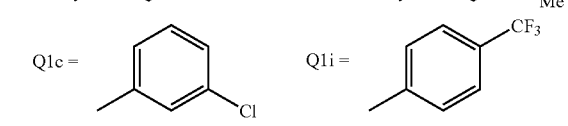

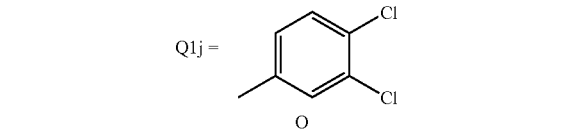

T3a = 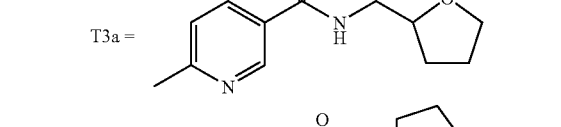

T3b = 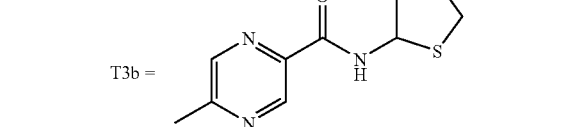

T3c = 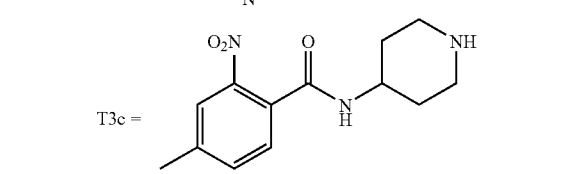

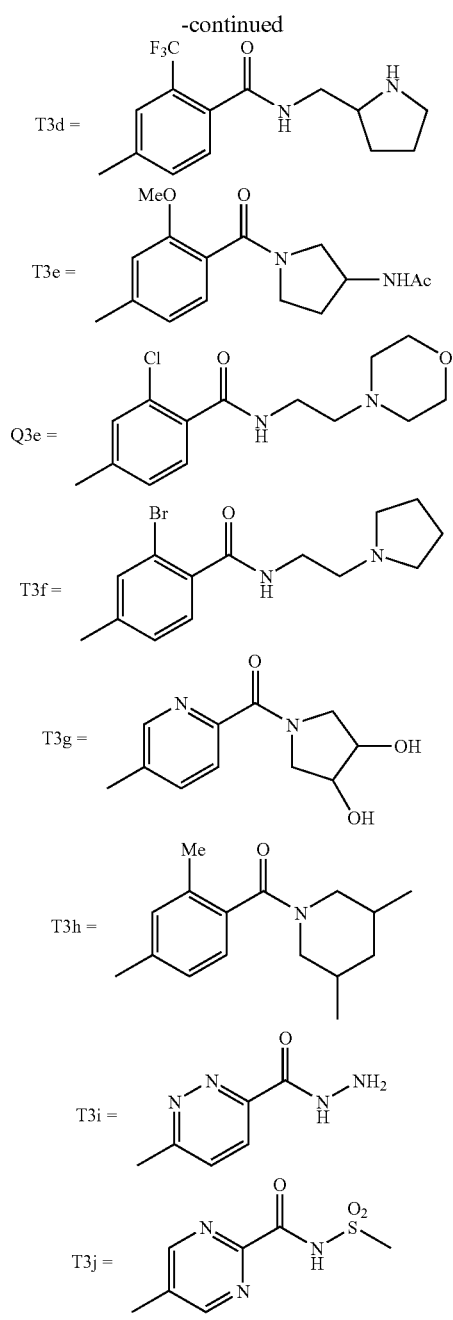
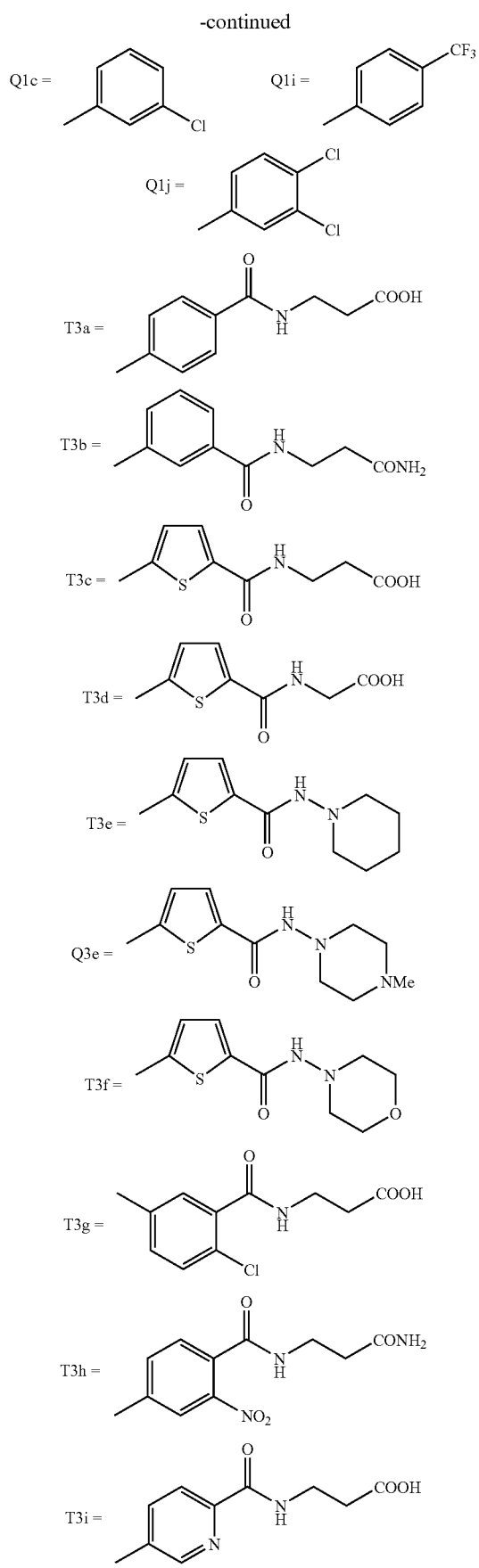
67) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 67), Q1a, Q1b, Q1c, Q1i, Q1j, T3a, T3b, T3c, T3d, T3e, Q3e, T3f, T3g, T3h, T3i and T3j in Table 1 denote the following substituents).
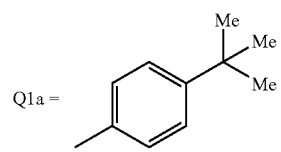
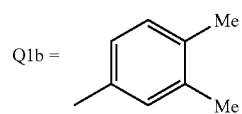

T3j = 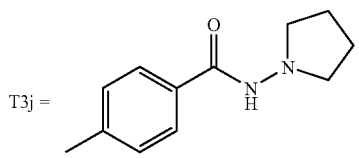

68) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 68), Q1a, Q1b, Q1c, Q1i, Q1j, T3a, T3b, T3c, T3d, T3e, Q3e, T3f, T3g, T3h, T3i and T3j in Table 1 denote the following substituents).

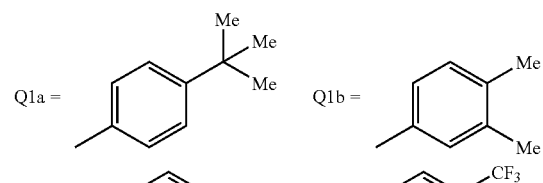

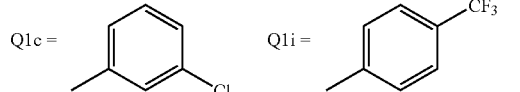

T3a = 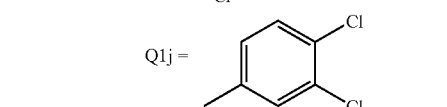

T3b = 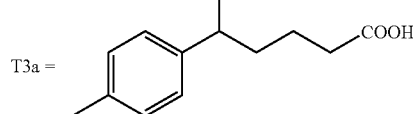

T3c = 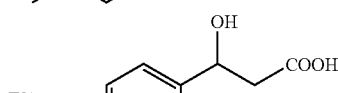

T3d = 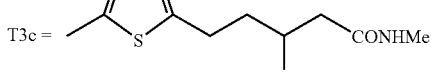

T3e = 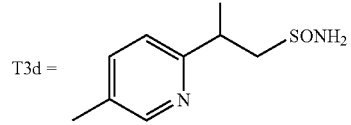

Q3e = 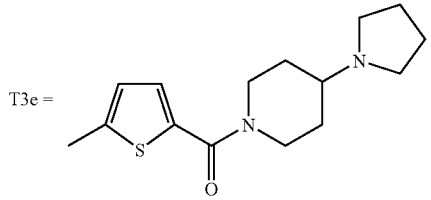

T3f = 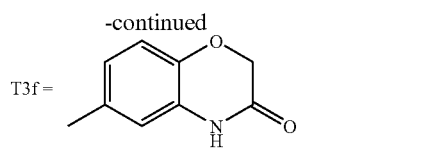

T3g = 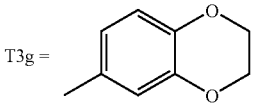  T3h = 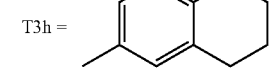

T3i = 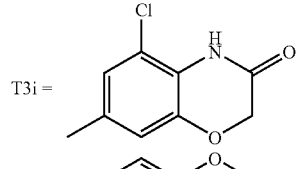

T3j = 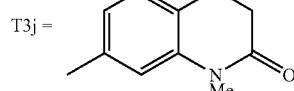

69) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 69), Q1a, Q1b, Q1c, Q1i, Q1j, T3a, T3b, T3c, T3d, T3e, Q3e, T3f, T3g, T3h, T3i and T3j in Table 1 denote the following substituents).

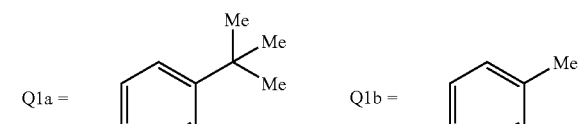

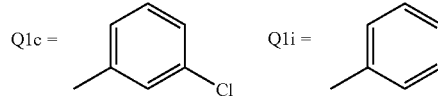

Q1j = 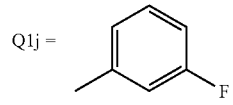

T3a = 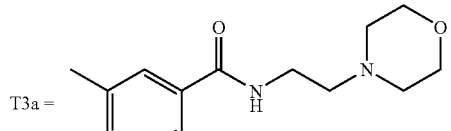

T3b = 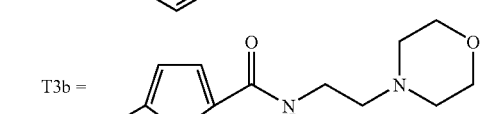

T3c = 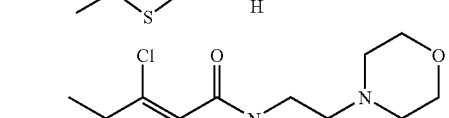

T3d = 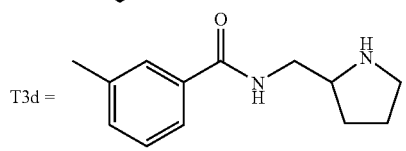

-continued

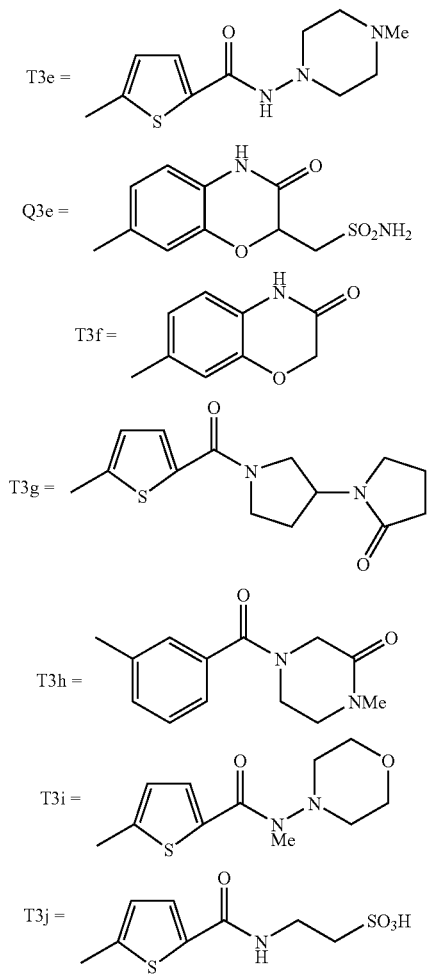

70) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 70), Q1a, Q1b, Q1c, Q1i, Q1j, T3a, T3b, T3c, T3d, T3e, Q3e, T3f, T3g, T3h, T3i and T3j in Table 1 denote the following substituents).

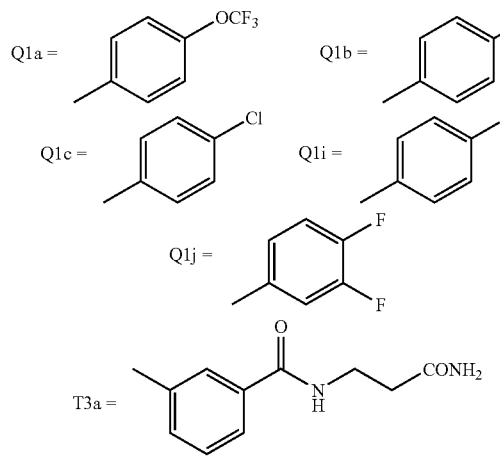

-continued

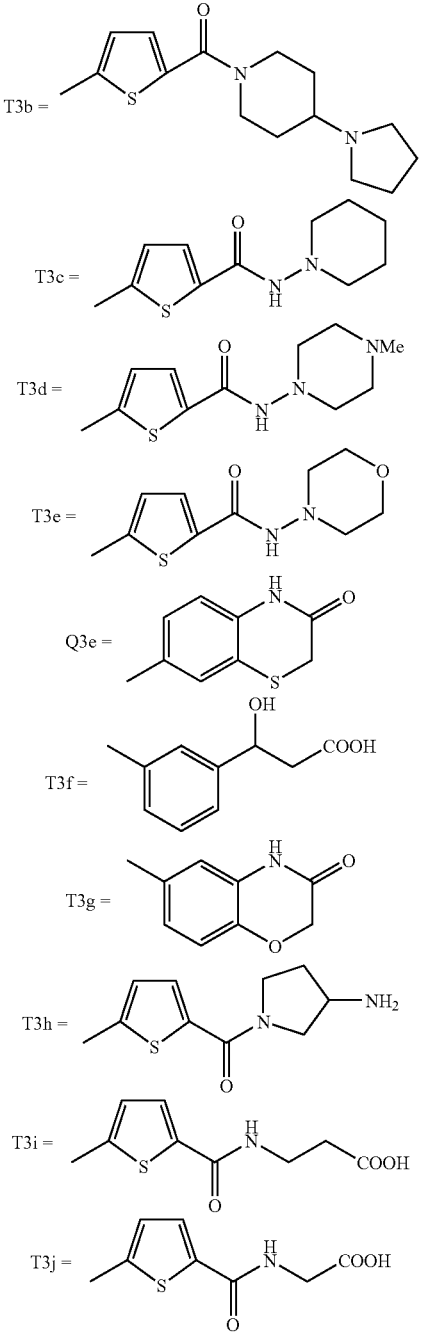

71) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 71), Q1a, Q1b, Q1c, Q1i, Q1j, T3a, T3b, T3c, T3d, T3e, Q3e, T3f, T3g, T3h, T3i and T3j in Table 1 denote the following substituents).

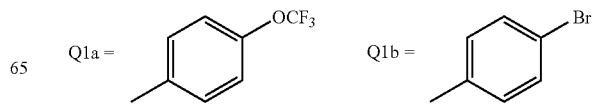

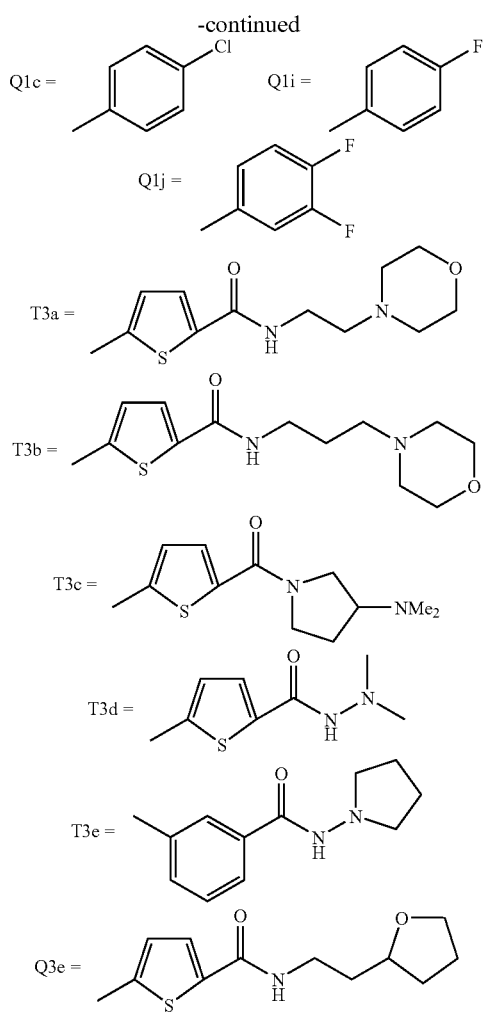

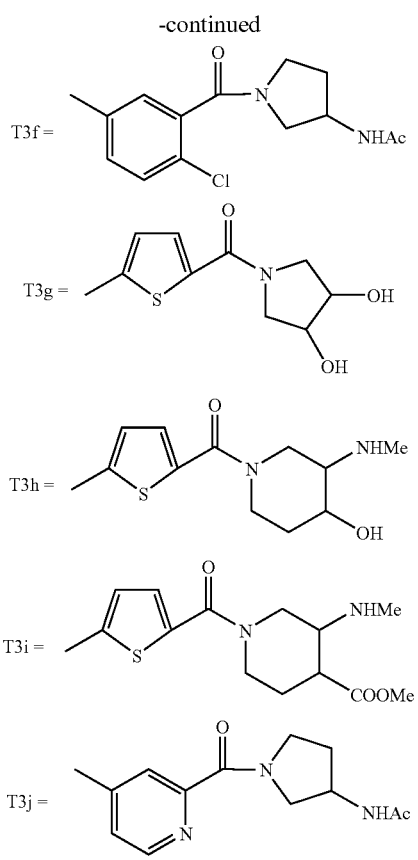

72) The compounds wherein A, B, $R^1$, $L^1$, $R^2$, $L^2$, $L^3$, Y, $L^4$, $R^3$ and X are any of the following combinations in Table 2, tautomers, prodrugs or pharmaceutically acceptable salts of the compounds or solvates thereof. The symbols in Table 2 denote the flowing substituents.

TABLE 2

| No | A | B | $R^1$ | $L^1$ | $R^2$ | $L^2$ | $L^3$ | Y | $L^4$ | $R^3$ | X |
|----|---|---|-------|-------|-------|-------|-------|---|-------|-------|---|
| 1  | N | NMe | Q1a | NH | Me | a bond | NH | S | NH | Q3a | OH |
| 2  | N | NMe | Q1a | NH | Me | a bond | NH | S | a bond | Q3a | OH |
| 3  | N | NMe | Q1a | NH | Me | a bond | NH | O | NH | Q3a | OH |
| 4  | N | NMe | Q1a | NH | Me | a bond | NH | O | a bond | Q3a | OH |
| 5  | N | NMe | Q1a | NH | H  | a bond | NH | S | NH | Q3a | OH |
| 6  | N | NMe | Q1a | NH | H  | a bond | NH | S | a bond | Q3a | OH |
| 7  | N | NMe | Q1a | NH | H  | a bond | NH | O | NH | Q3a | OH |
| 8  | N | NMe | Q1a | NH | H  | a bond | NH | O | a bond | Q3a | OH |
| 9  | N | NMe | Q1b | NH | Me | a bond | NH | S | NH | Q3a | OH |
| 10 | N | NMe | Q1b | NH | Me | a bond | NH | S | a bond | Q3a | OH |
| 11 | N | NMe | Q1b | NH | Me | a bond | NH | O | NH | Q3a | OH |
| 12 | N | NMe | Q1b | NH | Me | a bond | NH | O | a bond | Q3a | OH |
| 13 | N | NMe | Q1b | NH | H  | a bond | NH | S | NH | Q3a | OH |
| 14 | N | NMe | Q1b | NH | H  | a bond | NH | S | a bond | Q3a | OH |
| 15 | N | NMe | Q1b | NH | H  | a bond | NH | O | NH | Q3a | OH |
| 16 | N | NMe | Q1b | NH | H  | a bond | NH | O | a bond | Q3a | OH |
| 17 | N | S | Q1a | NH | Me | a bond | NH | S | NH | Q3a | OH |
| 18 | N | S | Q1a | NH | Me | a bond | NH | S | a bond | Q3a | OH |
| 19 | N | S | Q1a | NH | Me | a bond | NH | O | NH | Q3a | OH |
| 20 | N | S | Q1a | NH | Me | a bond | NH | O | a bond | Q3a | OH |
| 21 | N | S | Q1a | NH | H  | a bond | NH | S | NH | Q3a | OH |
| 22 | N | S | Q1a | NH | H  | a bond | NH | S | a bond | Q3a | OH |
| 23 | N | S | Q1a | NH | H  | a bond | NH | O | NH | Q3a | OH |
| 24 | N | S | Q1a | NH | H  | a bond | NH | O | a bond | Q3a | OH |
| 25 | N | S | Q1b | NH | Me | a bond | NH | S | NH | Q3a | OH |
| 26 | N | S | Q1b | NH | Me | a bond | NH | S | a bond | Q3a | OH |
| 27 | N | S | Q1b | NH | Me | a bond | NH | O | NH | Q3a | OH |
| 28 | N | S | Q1b | NH | Me | a bond | NH | O | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 29 | N | S | Q1b | NH | H | a bond | NH | S | NH | Q3a | OH |
| 30 | N | S | Q1b | NH | H | a bond | NH | S | a bond | Q3a | OH |
| 31 | N | S | Q1b | NH | H | a bond | NH | O | NH | Q3a | OH |
| 32 | N | S | Q1b | NH | H | a bond | NH | O | a bond | Q3a | OH |
| 33 | N | O | Q1a | NH | Me | a bond | NH | S | NH | Q3a | OH |
| 34 | N | O | Q1a | NH | Me | a bond | NH | S | a bond | Q3a | OH |
| 35 | N | O | Q1a | NH | Me | a bond | NH | O | NH | Q3a | OH |
| 36 | N | O | Q1a | NH | Me | a bond | NH | O | a bond | Q3a | OH |
| 37 | N | O | Q1a | NH | H | a bond | NH | S | NH | Q3a | OH |
| 38 | N | O | Q1a | NH | H | a bond | NH | S | a bond | Q3a | OH |
| 39 | N | O | Q1a | NH | H | a bond | NH | O | NH | Q3a | OH |
| 40 | N | O | Q1a | NH | H | a bond | NH | O | a bond | Q3a | OH |
| 41 | N | O | Q1b | NH | Me | a bond | NH | S | NH | Q3a | OH |
| 42 | N | O | Q1b | NH | Me | a bond | NH | S | a bond | Q3a | OH |
| 43 | N | O | Q1b | NH | Me | a bond | NH | O | NH | Q3a | OH |
| 44 | N | O | Q1b | NH | Me | a bond | NH | O | a bond | Q3a | OH |
| 45 | N | O | Q1b | NH | H | a bond | NH | S | NH | Q3a | OH |
| 46 | N | O | Q1b | NH | H | a bond | NH | S | a bond | Q3a | OH |
| 47 | N | O | Q1b | NH | H | a bond | NH | O | NH | Q3a | OH |
| 48 | N | O | Q1b | NH | H | a bond | NH | O | a bond | Q3a | OH |
| 49 | CH | NMe | Q1a | NH | Me | a bond | NH | S | NH | Q3a | OH |
| 50 | CH | NMe | Q1a | NH | Me | a bond | NH | S | a bond | Q3a | OH |
| 51 | CH | NMe | Q1a | NH | Me | a bond | NH | O | NH | Q3a | OH |
| 52 | CH | NMe | Q1a | NH | Me | a bond | NH | O | a bond | Q3a | OH |
| 53 | CH | NMe | Q1a | NH | H | a bond | NH | S | NH | Q3a | OH |
| 54 | CH | NMe | Q1a | NH | H | a bond | NH | S | a bond | Q3a | OH |
| 55 | CH | NMe | Q1a | NH | H | a bond | NH | O | NH | Q3a | OH |
| 56 | CH | NMe | Q1a | NH | H | a bond | NH | O | a bond | Q3a | OH |
| 57 | CH | NMe | Q1b | NH | Me | a bond | NH | S | NH | Q3a | OH |
| 58 | CH | NMe | Q1b | NH | Me | a bond | NH | S | a bond | Q3a | OH |
| 59 | CH | NMe | Q1b | NH | Me | a bond | NH | O | NH | Q3a | OH |
| 60 | CH | NMe | Q1b | NH | Me | a bond | NH | O | a bond | Q3a | OH |
| 61 | CH | NMe | Q1b | NH | H | a bond | NH | S | NH | Q3a | OH |
| 62 | CH | NMe | Q1b | NH | H | a bond | NH | S | a bond | Q3a | OH |
| 63 | CH | NMe | Q1b | NH | H | a bond | NH | O | NH | Q3a | OH |
| 64 | CH | NMe | Q1b | NH | H | a bond | NH | O | a bond | Q3a | OH |
| 65 | CH | S | Q1a | NH | Me | a bond | NH | S | NH | Q3a | OH |
| 66 | CH | S | Q1a | NH | Me | a bond | NH | S | a bond | Q3a | OH |
| 67 | CH | S | Q1a | NH | Me | a bond | NH | O | NH | Q3a | OH |
| 68 | CH | S | Q1a | NH | Me | a bond | NH | O | a bond | Q3a | OH |
| 69 | CH | S | Q1a | NH | H | a bond | NH | S | NH | Q3a | OH |
| 70 | CH | S | Q1a | NH | H | a bond | NH | S | a bond | Q3a | OH |
| 71 | CH | S | Q1a | NH | H | a bond | NH | O | NH | Q3a | OH |
| 72 | CH | S | Q1a | NH | H | a bond | NH | O | a bond | Q3a | OH |
| 73 | CH | S | Q1b | NH | Me | a bond | NH | S | NH | Q3a | OH |
| 74 | CH | S | Q1b | NH | Me | a bond | NH | S | a bond | Q3a | OH |
| 75 | CH | S | Q1b | NH | Me | a bond | NH | O | NH | Q3a | OH |
| 76 | CH | S | Q1b | NH | Me | a bond | NH | O | a bond | Q3a | OH |
| 77 | CH | S | Q1b | NH | H | a bond | NH | S | NH | Q3a | OH |
| 78 | CH | S | Q1b | NH | H | a bond | NH | S | a bond | Q3a | OH |
| 79 | CH | S | Q1b | NH | H | a bond | NH | O | NH | Q3a | OH |
| 80 | CH | S | Q1b | NH | H | a bond | NH | O | a bond | Q3a | OH |
| 81 | CH | O | Q1a | NH | Me | a bond | NH | S | NH | Q3a | OH |
| 82 | CH | O | Q1a | NH | Me | a bond | NH | S | a bond | Q3a | OH |
| 83 | CH | O | Q1a | NH | Me | a bond | NH | O | NH | Q3a | OH |
| 84 | CH | O | Q1a | NH | Me | a bond | NH | O | a bond | Q3a | OH |
| 85 | CH | O | Q1a | NH | H | a bond | NH | S | NH | Q3a | OH |
| 86 | CH | O | Q1a | NH | H | a bond | NH | S | a bond | Q3a | OH |
| 87 | CH | O | Q1a | NH | H | a bond | NH | O | NH | Q3a | OH |
| 88 | CH | O | Q1a | NH | H | a bond | NH | O | a bond | Q3a | OH |
| 89 | CH | O | Q1b | NH | Me | a bond | NH | S | NH | Q3a | OH |
| 90 | CH | O | Q1b | NH | Me | a bond | NH | S | a bond | Q3a | OH |
| 91 | CH | O | Q1b | NH | Me | a bond | NH | O | NH | Q3a | OH |
| 92 | CH | O | Q1b | NH | Me | a bond | NH | O | a bond | Q3a | OH |
| 93 | CH | O | Q1b | NH | H | a bond | NH | S | NH | Q3a | OH |
| 94 | CH | O | Q1b | NH | H | a bond | NH | S | a bond | Q3a | OH |
| 95 | CH | O | Q1b | NH | H | a bond | NH | O | NH | Q3a | OH |
| 96 | CH | O | Q1b | NH | H | a bond | NH | O | a bond | Q3a | OH |
| 97 | CMe | NMe | Q1a | NH | Me | a bond | NH | S | NH | Q3a | OH |
| 98 | CMe | NMe | Q1a | NH | Me | a bond | NH | S | a bond | Q3a | OH |
| 99 | CMe | NMe | Q1a | NH | Me | a bond | NH | O | NH | Q3a | OH |
| 100 | CMe | NMe | Q1a | NH | Me | a bond | NH | O | a bond | Q3a | OH |
| 101 | CMe | NMe | Q1a | NH | H | a bond | NH | S | NH | Q3a | OH |
| 102 | CMe | NMe | Q1a | NH | H | a bond | NH | S | a bond | Q3a | OH |
| 103 | CMe | NMe | Q1a | NH | H | a bond | NH | O | NH | Q3a | OH |
| 104 | CMe | NMe | Q1a | NH | H | a bond | NH | O | a bond | Q3a | OH |
| 105 | CMe | NMe | Q1b | NH | Me | a bond | NH | S | NH | Q3a | OH |
| 106 | CMe | NMe | Q1b | NH | Me | a bond | NH | S | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 107 | CMe | NMe | Q1b | NH | Me | a bond | NH | O | NH | Q3a | OH |
| 108 | CMe | NMe | Q1b | NH | Me | a bond | NH | O | a bond | Q3a | OH |
| 109 | CMe | NMe | Q1b | NH | H | a bond | NH | S | NH | Q3a | OH |
| 110 | CMe | NMe | Q1b | NH | H | a bond | NH | S | a bond | Q3a | OH |
| 111 | CMe | NMe | Q1b | NH | H | a bond | NH | O | NH | Q3a | OH |
| 112 | CMe | NMe | Q1b | NH | H | a bond | NH | O | a bond | Q3a | OH |
| 113 | CMe | S | Q1a | NH | Me | a bond | NH | S | NH | Q3a | OH |
| 114 | CMe | S | Q1a | NH | Me | a bond | NH | S | a bond | Q3a | OH |
| 115 | CMe | S | Q1a | NH | Me | a bond | NH | O | NH | Q3a | OH |
| 116 | CMe | S | Q1a | NH | Me | a bond | NH | O | a bond | Q3a | OH |
| 117 | CMe | S | Q1a | NH | H | a bond | NH | S | NH | Q3a | OH |
| 118 | CMe | S | Q1a | NH | H | a bond | NH | S | a bond | Q3a | OH |
| 119 | CMe | S | Q1a | NH | H | a bond | NH | O | NH | Q3a | OH |
| 120 | CMe | S | Q1a | NH | H | a bond | NH | O | a bond | Q3a | OH |
| 121 | CMe | S | Q1b | NH | Me | a bond | NH | S | NH | Q3a | OH |
| 122 | CMe | S | Q1b | NH | Me | a bond | NH | S | a bond | Q3a | OH |
| 123 | CMe | S | Q1b | NH | Me | a bond | NH | O | NH | Q3a | OH |
| 124 | CMe | S | Q1b | NH | Me | a bond | NH | O | a bond | Q3a | OH |
| 125 | CMe | S | Q1b | NH | H | a bond | NH | S | NH | Q3a | OH |
| 126 | CMe | S | Q1b | NH | H | a bond | NH | S | a bond | Q3a | OH |
| 127 | CMe | S | Q1b | NH | H | a bond | NH | O | NH | Q3a | OH |
| 128 | CMe | S | Q1b | NH | H | a bond | NH | O | a bond | Q3a | OH |
| 129 | CMe | O | Q1a | NH | Me | a bond | NH | S | NH | Q3a | OH |
| 130 | CMe | O | Q1a | NH | Me | a bond | NH | S | a bond | Q3a | OH |
| 131 | CMe | O | Q1a | NH | Me | a bond | NH | O | NH | Q3a | OH |
| 132 | CMe | O | Q1a | NH | Me | a bond | NH | O | a bond | Q3a | OH |
| 133 | CMe | O | Q1a | NH | H | a bond | NH | S | NH | Q3a | OH |
| 134 | CMe | O | Q1a | NH | H | a bond | NH | S | a bond | Q3a | OH |
| 135 | CMe | O | Q1a | NH | H | a bond | NH | O | NH | Q3a | OH |
| 136 | CMe | O | Q1a | NH | H | a bond | NH | O | a bond | Q3a | OH |
| 137 | CMe | O | Q1b | NH | Me | a bond | NH | S | NH | Q3a | OH |
| 138 | CMe | O | Q1b | NH | Me | a bond | NH | S | a bond | Q3a | OH |
| 139 | CMe | O | Q1b | NH | Me | a bond | NH | O | NH | Q3a | OH |
| 140 | CMe | O | Q1b | NH | Me | a bond | NH | O | a bond | Q3a | OH |
| 141 | CMe | O | Q1b | NH | H | a bond | NH | S | NH | Q3a | OH |
| 142 | CMe | O | Q1b | NH | H | a bond | NH | S | a bond | Q3a | OH |
| 143 | CMe | O | Q1b | NH | H | a bond | NH | O | NH | Q3a | OH |
| 144 | CMe | O | Q1b | NH | H | a bond | NH | O | a bond | Q3a | OH |
| 145 | N | NMe | Q1a | O | Me | a bond | NH | S | NH | Q3a | OH |
| 146 | N | NMe | Q1a | O | Me | a bond | NH | S | a bond | Q3a | OH |
| 147 | N | NMe | Q1a | O | Me | a bond | NH | O | NH | Q3a | OH |
| 148 | N | NMe | Q1a | O | Me | a bond | NH | O | a bond | Q3a | OH |
| 149 | N | NMe | Q1a | O | H | a bond | NH | S | NH | Q3a | OH |
| 150 | N | NMe | Q1a | O | H | a bond | NH | S | a bond | Q3a | OH |
| 151 | N | NMe | Q1a | O | H | a bond | NH | O | NH | Q3a | OH |
| 152 | N | NMe | Q1a | O | H | a bond | NH | O | a bond | Q3a | OH |
| 153 | N | NMe | Q1b | O | Me | a bond | NH | S | NH | Q3a | OH |
| 154 | N | NMe | Q1b | O | Me | a bond | NH | S | a bond | Q3a | OH |
| 155 | N | NMe | Q1b | O | Me | a bond | NH | O | NH | Q3a | OH |
| 156 | N | NMe | Q1b | O | Me | a bond | NH | O | a bond | Q3a | OH |
| 157 | N | NMe | Q1b | O | H | a bond | NH | S | NH | Q3a | OH |
| 158 | N | NMe | Q1b | O | H | a bond | NH | S | a bond | Q3a | OH |
| 159 | N | NMe | Q1b | O | H | a bond | NH | O | NH | Q3a | OH |
| 160 | N | NMe | Q1b | O | H | a bond | NH | O | a bond | Q3a | OH |
| 161 | N | S | Q1a | O | Me | a bond | NH | S | NH | Q3a | OH |
| 162 | N | S | Q1a | O | Me | a bond | NH | S | a bond | Q3a | OH |
| 163 | N | S | Q1a | O | Me | a bond | NH | O | NH | Q3a | OH |
| 164 | N | S | Q1a | O | Me | a bond | NH | O | a bond | Q3a | OH |
| 165 | N | S | Q1a | O | H | a bond | NH | S | NH | Q3a | OH |
| 166 | N | S | Q1a | O | H | a bond | NH | S | a bond | Q3a | OH |
| 167 | N | S | Q1a | O | H | a bond | NH | O | NH | Q3a | OH |
| 168 | N | S | Q1a | O | H | a bond | NH | O | a bond | Q3a | OH |
| 169 | N | S | Q1b | O | Me | a bond | NH | S | NH | Q3a | OH |
| 170 | N | S | Q1b | O | Me | a bond | NH | S | a bond | Q3a | OH |
| 171 | N | S | Q1b | O | Me | a bond | NH | O | NH | Q3a | OH |
| 172 | N | S | Q1b | O | Me | a bond | NH | O | a bond | Q3a | OH |
| 173 | N | S | Q1b | O | H | a bond | NH | S | NH | Q3a | OH |
| 174 | N | S | Q1b | O | H | a bond | NH | S | a bond | Q3a | OH |
| 175 | N | S | Q1b | O | H | a bond | NH | O | NH | Q3a | OH |
| 176 | N | S | Q1b | O | H | a bond | NH | O | a bond | Q3a | OH |
| 177 | N | O | Q1a | O | Me | a bond | NH | S | NH | Q3a | OH |
| 178 | N | O | Q1a | O | Me | a bond | NH | S | a bond | Q3a | OH |
| 179 | N | O | Q1a | O | Me | a bond | NH | O | NH | Q3a | OH |
| 180 | N | O | Q1a | O | Me | a bond | NH | O | a bond | Q3a | OH |
| 181 | N | O | Q1a | O | H | a bond | NH | S | NH | Q3a | OH |
| 182 | N | O | Q1a | O | H | a bond | NH | S | a bond | Q3a | OH |
| 183 | N | O | Q1a | O | H | a bond | NH | O | NH | Q3a | OH |
| 184 | N | O | Q1a | O | H | a bond | NH | O | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 185 | N | O | Q1b | O | Me | a bond | NH | S | NH | Q3a | OH |
| 186 | N | O | Q1b | O | Me | a bond | NH | S | a bond | Q3a | OH |
| 187 | N | O | Q1b | O | Me | a bond | NH | O | NH | Q3a | OH |
| 188 | N | O | Q1b | O | Me | a bond | NH | O | a bond | Q3a | OH |
| 189 | N | O | Q1b | O | H | a bond | NH | S | NH | Q3a | OH |
| 190 | N | O | Q1b | O | H | a bond | NH | S | a bond | Q3a | OH |
| 191 | N | O | Q1b | O | H | a bond | NH | O | NH | Q3a | OH |
| 192 | N | O | Q1b | O | H | a bond | NH | O | a bond | Q3a | OH |
| 193 | CH | NMe | Q1a | O | Me | a bond | NH | S | NH | Q3a | OH |
| 194 | CH | NMe | Q1a | O | Me | a bond | NH | S | a bond | Q3a | OH |
| 195 | CH | NMe | Q1a | O | Me | a bond | NH | O | NH | Q3a | OH |
| 196 | CH | NMe | Q1a | O | Me | a bond | NH | O | a bond | Q3a | OH |
| 197 | CH | NMe | Q1a | O | H | a bond | NH | S | NH | Q3a | OH |
| 198 | CH | NMe | Q1a | O | H | a bond | NH | S | a bond | Q3a | OH |
| 199 | CH | NMe | Q1a | O | H | a bond | NH | O | NH | Q3a | OH |
| 200 | CH | NMe | Q1a | O | H | a bond | NH | O | a bond | Q3a | OH |
| 201 | CH | NMe | Q1b | O | Me | a bond | NH | S | NH | Q3a | OH |
| 202 | CH | NMe | Q1b | O | Me | a bond | NH | S | a bond | Q3a | OH |
| 203 | CH | NMe | Q1b | O | Me | a bond | NH | O | NH | Q3a | OH |
| 204 | CH | NMe | Q1b | O | Me | a bond | NH | O | a bond | Q3a | OH |
| 205 | CH | NMe | Q1b | O | H | a bond | NH | S | NH | Q3a | OH |
| 206 | CH | NMe | Q1b | O | H | a bond | NH | S | a bond | Q3a | OH |
| 207 | CH | NMe | Q1b | O | H | a bond | NH | O | NH | Q3a | OH |
| 208 | CH | NMe | Q1b | O | H | a bond | NH | O | a bond | Q3a | OH |
| 209 | CH | S | Q1a | O | Me | a bond | NH | S | NH | Q3a | OH |
| 210 | CH | S | Q1a | O | Me | a bond | NH | S | a bond | Q3a | OH |
| 211 | CH | S | Q1a | O | Me | a bond | NH | O | NH | Q3a | OH |
| 212 | CH | S | Q1a | O | Me | a bond | NH | O | a bond | Q3a | OH |
| 213 | CH | S | Q1a | O | H | a bond | NH | S | NH | Q3a | OH |
| 214 | CH | S | Q1a | O | H | a bond | NH | S | a bond | Q3a | OH |
| 215 | CH | S | Q1a | O | H | a bond | NH | O | NH | Q3a | OH |
| 216 | CH | S | Q1a | O | H | a bond | NH | O | a bond | Q3a | OH |
| 217 | CH | S | Q1b | O | Me | a bond | NH | S | NH | Q3a | OH |
| 218 | CH | S | Q1b | O | Me | a bond | NH | S | a bond | Q3a | OH |
| 219 | CH | S | Q1b | O | Me | a bond | NH | O | NH | Q3a | OH |
| 220 | CH | S | Q1b | O | Me | a bond | NH | O | a bond | Q3a | OH |
| 221 | CH | S | Q1b | O | H | a bond | NH | S | NH | Q3a | OH |
| 222 | CH | S | Q1b | O | H | a bond | NH | S | a bond | Q3a | OH |
| 223 | CH | S | Q1b | O | H | a bond | NH | O | NH | Q3a | OH |
| 224 | CH | S | Q1b | O | H | a bond | NH | O | a bond | Q3a | OH |
| 225 | CH | O | Q1a | O | Me | a bond | NH | S | NH | Q3a | OH |
| 226 | CH | O | Q1a | O | Me | a bond | NH | S | a bond | Q3a | OH |
| 227 | CH | O | Q1a | O | Me | a bond | NH | O | NH | Q3a | OH |
| 228 | CH | O | Q1a | O | Me | a bond | NH | O | a bond | Q3a | OH |
| 229 | CH | O | Q1a | O | H | a bond | NH | S | NH | Q3a | OH |
| 230 | CH | O | Q1a | O | H | a bond | NH | S | a bond | Q3a | OH |
| 231 | CH | O | Q1a | O | H | a bond | NH | O | NH | Q3a | OH |
| 232 | CH | O | Q1a | O | H | a bond | NH | O | a bond | Q3a | OH |
| 233 | CH | O | Q1b | O | Me | a bond | NH | S | NH | Q3a | OH |
| 234 | CH | O | Q1b | O | Me | a bond | NH | S | a bond | Q3a | OH |
| 235 | CH | O | Q1b | O | Me | a bond | NH | O | NH | Q3a | OH |
| 236 | CH | O | Q1b | O | Me | a bond | NH | O | a bond | Q3a | OH |
| 237 | CH | O | Q1b | O | H | a bond | NH | S | NH | Q3a | OH |
| 238 | CH | O | Q1b | O | H | a bond | NH | S | a bond | Q3a | OH |
| 239 | CH | O | Q1b | O | H | a bond | NH | O | NH | Q3a | OH |
| 240 | CH | O | Q1b | O | H | a bond | NH | O | a bond | Q3a | OH |
| 241 | CMe | NMe | Q1a | O | Me | a bond | NH | S | NH | Q3a | OH |
| 242 | CMe | NMe | Q1a | O | Me | a bond | NH | S | a bond | Q3a | OH |
| 243 | CMe | NMe | Q1a | O | Me | a bond | NH | O | NH | Q3a | OH |
| 244 | CMe | NMe | Q1a | O | Me | a bond | NH | O | a bond | Q3a | OH |
| 245 | CMe | NMe | Q1a | O | H | a bond | NH | S | NH | Q3a | OH |
| 246 | CMe | NMe | Q1a | O | H | a bond | NH | S | a bond | Q3a | OH |
| 247 | CMe | NMe | Q1a | O | H | a bond | NH | O | NH | Q3a | OH |
| 248 | CMe | NMe | Q1a | O | H | a bond | NH | O | a bond | Q3a | OH |
| 249 | CMe | NMe | Q1b | O | Me | a bond | NH | S | NH | Q3a | OH |
| 250 | CMe | NMe | Q1b | O | Me | a bond | NH | S | a bond | Q3a | OH |
| 251 | CMe | NMe | Q1b | O | Me | a bond | NH | O | NH | Q3a | OH |
| 252 | CMe | NMe | Q1b | O | Me | a bond | NH | O | a bond | Q3a | OH |
| 253 | CMe | NMe | Q1b | O | H | a bond | NH | S | NH | Q3a | OH |
| 254 | CMe | NMe | Q1b | O | H | a bond | NH | S | a bond | Q3a | OH |
| 255 | CMe | NMe | Q1b | O | H | a bond | NH | O | NH | Q3a | OH |
| 256 | CMe | NMe | Q1b | O | H | a bond | NH | O | a bond | Q3a | OH |
| 257 | CMe | S | Q1a | O | Me | a bond | NH | S | NH | Q3a | OH |
| 258 | CMe | S | Q1a | O | Me | a bond | NH | S | a bond | Q3a | OH |
| 259 | CMe | S | Q1a | O | Me | a bond | NH | O | NH | Q3a | OH |
| 260 | CMe | S | Q1a | O | Me | a bond | NH | O | a bond | Q3a | OH |
| 261 | CMe | S | Q1a | O | H | a bond | NH | S | NH | Q3a | OH |
| 262 | CMe | S | Q1a | O | H | a bond | NH | S | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 263 | CMe | S | Q1a | O | H | a bond | NH | O | NH | Q3a | OH |
| 264 | CMe | S | Q1a | O | H | a bond | NH | O | a bond | Q3a | OH |
| 265 | CMe | S | Q1b | O | Me | a bond | NH | S | NH | Q3a | OH |
| 266 | CMe | S | Q1b | O | Me | a bond | NH | S | a bond | Q3a | OH |
| 267 | CMe | S | Q1b | O | Me | a bond | NH | O | NH | Q3a | OH |
| 268 | CMe | S | Q1b | O | Me | a bond | NH | O | a bond | Q3a | OH |
| 269 | CMe | S | Q1b | O | H | a bond | NH | S | NH | Q3a | OH |
| 270 | CMe | S | Q1b | O | H | a bond | NH | S | a bond | Q3a | OH |
| 271 | CMe | S | Q1b | O | H | a bond | NH | O | NH | Q3a | OH |
| 272 | CMe | S | Q1b | O | H | a bond | NH | O | a bond | Q3a | OH |
| 273 | CMe | O | Q1a | O | Me | a bond | NH | S | NH | Q3a | OH |
| 274 | CMe | O | Q1a | O | Me | a bond | NH | S | a bond | Q3a | OH |
| 275 | CMe | O | Q1a | O | Me | a bond | NH | O | NH | Q3a | OH |
| 276 | CMe | O | Q1a | O | Me | a bond | NH | O | a bond | Q3a | OH |
| 277 | CMe | O | Q1a | O | H | a bond | NH | S | NH | Q3a | OH |
| 278 | CMe | O | Q1a | O | H | a bond | NH | S | a bond | Q3a | OH |
| 279 | CMe | O | Q1a | O | H | a bond | NH | O | NH | Q3a | OH |
| 280 | CMe | O | Q1a | O | H | a bond | NH | O | a bond | Q3a | OH |
| 281 | CMe | O | Q1b | O | Me | a bond | NH | S | NH | Q3a | OH |
| 282 | CMe | O | Q1b | O | Me | a bond | NH | S | a bond | Q3a | OH |
| 283 | CMe | O | Q1b | O | Me | a bond | NH | O | NH | Q3a | OH |
| 284 | CMe | O | Q1b | O | Me | a bond | NH | O | a bond | Q3a | OH |
| 285 | CMe | O | Q1b | O | H | a bond | NH | S | NH | Q3a | OH |
| 286 | CMe | O | Q1b | O | H | a bond | NH | S | a bond | Q3a | OH |
| 287 | CMe | O | Q1b | O | H | a bond | NH | O | NH | Q3a | OH |
| 288 | CMe | O | Q1b | O | H | a bond | NH | O | a bond | Q3a | OH |
| 289 | N | NMe | Q1a | CH2 | Me | a bond | NH | S | NH | Q3a | OH |
| 290 | N | NMe | Q1a | CH2 | Me | a bond | NH | S | a bond | Q3a | OH |
| 291 | N | NMe | Q1a | CH2 | Me | a bond | NH | O | NH | Q3a | OH |
| 292 | N | NMe | Q1a | CH2 | Me | a bond | NH | O | a bond | Q3a | OH |
| 293 | N | NMe | Q1a | CH2 | H | a bond | NH | S | NH | Q3a | OH |
| 294 | N | NMe | Q1a | CH2 | H | a bond | NH | S | a bond | Q3a | OH |
| 295 | N | NMe | Q1a | CH2 | H | a bond | NH | O | NH | Q3a | OH |
| 296 | N | NMe | Q1a | CH2 | H | a bond | NH | O | a bond | Q3a | OH |
| 297 | N | NMe | Q1b | CH2 | Me | a bond | NH | S | NH | Q3a | OH |
| 298 | N | NMe | Q1b | CH2 | Me | a bond | NH | S | a bond | Q3a | OH |
| 299 | N | NMe | Q1b | CH2 | Me | a bond | NH | O | NH | Q3a | OH |
| 300 | N | NMe | Q1b | CH2 | Me | a bond | NH | O | a bond | Q3a | OH |
| 301 | N | NMe | Q1b | CH2 | H | a bond | NH | S | NH | Q3a | OH |
| 302 | N | NMe | Q1b | CH2 | H | a bond | NH | S | a bond | Q3a | OH |
| 303 | N | NMe | Q1b | CH2 | H | a bond | NH | O | NH | Q3a | OH |
| 304 | N | NMe | Q1b | CH2 | H | a bond | NH | O | a bond | Q3a | OH |
| 305 | N | S | Q1a | CH2 | Me | a bond | NH | S | NH | Q3a | OH |
| 306 | N | S | Q1a | CH2 | Me | a bond | NH | S | a bond | Q3a | OH |
| 307 | N | S | Q1a | CH2 | Me | a bond | NH | O | NH | Q3a | OH |
| 308 | N | S | Q1a | CH2 | Me | a bond | NH | O | a bond | Q3a | OH |
| 309 | N | S | Q1a | CH2 | H | a bond | NH | S | NH | Q3a | OH |
| 310 | N | S | Q1a | CH2 | H | a bond | NH | S | a bond | Q3a | OH |
| 311 | N | S | Q1a | CH2 | H | a bond | NH | O | NH | Q3a | OH |
| 312 | N | S | Q1a | CH2 | H | a bond | NH | O | a bond | Q3a | OH |
| 313 | N | S | Q1b | CH2 | Me | a bond | NH | S | NH | Q3a | OH |
| 314 | N | S | Q1b | CH2 | Me | a bond | NH | S | a bond | Q3a | OH |
| 315 | N | S | Q1b | CH2 | Me | a bond | NH | O | NH | Q3a | OH |
| 316 | N | S | Q1b | CH2 | Me | a bond | NH | O | a bond | Q3a | OH |
| 317 | N | S | Q1b | CH2 | H | a bond | NH | S | NH | Q3a | OH |
| 318 | N | S | Q1b | CH2 | H | a bond | NH | S | a bond | Q3a | OH |
| 319 | N | S | Q1b | CH2 | H | a bond | NH | O | NH | Q3a | OH |
| 320 | N | S | Q1b | CH2 | H | a bond | NH | O | a bond | Q3a | OH |
| 321 | N | O | Q1a | CH2 | Me | a bond | NH | S | NH | Q3a | OH |
| 322 | N | O | Q1a | CH2 | Me | a bond | NH | S | a bond | Q3a | OH |
| 323 | N | O | Q1a | CH2 | Me | a bond | NH | O | NH | Q3a | OH |
| 324 | N | O | Q1a | CH2 | Me | a bond | NH | O | a bond | Q3a | OH |
| 325 | N | O | Q1a | CH2 | H | a bond | NH | S | NH | Q3a | OH |
| 326 | N | O | Q1a | CH2 | H | a bond | NH | S | a bond | Q3a | OH |
| 327 | N | O | Q1a | CH2 | H | a bond | NH | O | NH | Q3a | OH |
| 328 | N | O | Q1a | CH2 | H | a bond | NH | O | a bond | Q3a | OH |
| 329 | N | O | Q1b | CH2 | Me | a bond | NH | S | NH | Q3a | OH |
| 330 | N | O | Q1b | CH2 | Me | a bond | NH | S | a bond | Q3a | OH |
| 331 | N | O | Q1b | CH2 | Me | a bond | NH | O | NH | Q3a | OH |
| 332 | N | O | Q1b | CH2 | Me | a bond | NH | O | a bond | Q3a | OH |
| 333 | N | O | Q1b | CH2 | H | a bond | NH | S | NH | Q3a | OH |
| 334 | N | O | Q1b | CH2 | H | a bond | NH | S | a bond | Q3a | OH |
| 335 | N | O | Q1b | CH2 | H | a bond | NH | O | NH | Q3a | OH |
| 336 | N | O | Q1b | CH2 | H | a bond | NH | O | a bond | Q3a | OH |
| 337 | CH | NMe | Q1a | CH2 | Me | a bond | NH | S | NH | Q3a | OH |
| 338 | CH | NMe | Q1a | CH2 | Me | a bond | NH | S | a bond | Q3a | OH |
| 339 | CH | NMe | Q1a | CH2 | Me | a bond | NH | O | NH | Q3 | OH |
| 340 | CH | NMe | Q1a | CH2 | Me | a bond | NH | O | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 341 | CH | NMe | Q1a | CH2 | H | a bond | NH | S | NH | Q3a | OH |
| 342 | CH | NMe | Q1a | CH2 | H | a bond | NH | S | a bond | Q3a | OH |
| 343 | CH | NMe | Q1a | CH2 | H | a bond | NH | O | NH | Q3a | OH |
| 344 | CH | NMe | Q1a | CH2 | H | a bond | NH | O | a bond | 3a | OH |
| 345 | CH | NMe | Q1b | CH2 | Me | a bond | NH | S | NH | Q3a | OH |
| 346 | CH | NMe | Q1b | CH2 | Me | a bond | NH | S | a bond | Q3a | OH |
| 347 | CH | NMe | Q1b | CH2 | Me | a bond | NH | O | NH | Q3a | OH |
| 348 | CH | NMe | Q1b | CH2 | Me | a bond | NH | O | a bond | Q3a | OH |
| 349 | CH | NMe | Q1b | CH2 | H | a bond | NH | S | NH | Q3a | OH |
| 350 | CH | NMe | Q1b | CH2 | H | a bond | NH | S | a bond | Q3a | OH |
| 351 | CH | NMe | Q1b | CH2 | H | a bond | NH | O | NH | Q3a | OH |
| 352 | CH | NMe | Q1b | CH2 | H | a bond | NH | O | a bond | Q3a | OH |
| 353 | CH | S | Q1a | CH2 | Me | a bond | NH | S | NH | Q3a | OH |
| 354 | CH | S | Q1a | CH2 | Me | a bond | NH | S | a bond | Q3a | OH |
| 355 | CH | S | Q1a | CH2 | Me | a bond | NH | O | NH | Q3a | OH |
| 356 | CH | S | Q1a | CH2 | Me | a bond | NH | O | a bond | Q3a | OH |
| 357 | CH | S | Q1a | CH2 | H | a bond | NH | S | NH | Q3a | OH |
| 358 | CH | S | Q1a | CH2 | H | a bond | NH | S | a bond | Q3a | OH |
| 359 | CH | S | Q1a | CH2 | H | a bond | NH | O | NH | Q3a | OH |
| 360 | CH | S | Q1a | CH2 | H | a bond | NH | O | a bond | Q3a | OH |
| 361 | CH | S | Q1b | CH2 | Me | a bond | NH | S | NH | Q3a | OH |
| 362 | CH | S | Q1b | CH2 | Me | a bond | NH | S | a bond | Q3a | OH |
| 363 | CH | S | Q1b | CH2 | Me | a bond | NH | O | NH | Q3a | OH |
| 364 | CH | S | Q1b | CH2 | Me | a bond | NH | O | a bond | Q3a | OH |
| 365 | CH | S | Q1b | CH2 | H | a bond | NH | S | NH | Q3a | OH |
| 366 | CH | S | Q1b | CH2 | H | a bond | NH | S | a bond | Q3a | OH |
| 367 | CH | S | Q1b | CH2 | H | a bond | NH | O | NH | Q3a | OH |
| 368 | CH | S | Q1b | CH2 | H | a bond | NH | O | a bond | Q3a | OH |
| 369 | CH | O | Q1a | CH2 | Me | a bond | NH | S | NH | Q3a | OH |
| 370 | CH | O | Q1a | CH2 | Me | a bond | NH | S | a bond | Q3a | OH |
| 371 | CH | O | Q1a | CH2 | Me | a bond | NH | O | NH | Q3a | OH |
| 372 | CH | O | Q1a | CH2 | Me | a bond | NH | O | a bond | Q3a | OH |
| 373 | CH | O | Q1a | CH2 | H | a bond | NH | S | NH | Q3a | OH |
| 374 | CH | O | Q1a | CH2 | H | a bond | NH | S | a bond | Q3a | OH |
| 375 | CH | O | Q1a | CH2 | H | a bond | NH | O | NH | Q3a | OH |
| 376 | CH | O | Q1a | CH2 | H | a bond | NH | O | a bond | Q3a | OH |
| 377 | CH | O | Q1b | CH2 | Me | a bond | NH | S | NH | Q3a | OH |
| 378 | CH | O | Q1b | CH2 | Me | a bond | NH | S | a bond | Q3a | OH |
| 379 | CH | O | Q1b | CH2 | Me | a bond | NH | O | NH | Q3a | OH |
| 380 | CH | O | Q1b | CH2 | Me | a bond | NH | O | a bond | Q3a | OH |
| 381 | CH | O | Q1b | CH2 | H | a bond | NH | S | NH | Q3a | OH |
| 382 | CH | O | Q1b | CH2 | H | a bond | NH | S | a bond | Q3a | OH |
| 383 | CH | O | Q1b | CH2 | H | a bond | NH | O | NH | Q3a | OH |
| 384 | CH | O | Q1b | CH2 | H | a bond | NH | O | a bond | Q3a | OH |
| 385 | CMe | NMe | Q1a | CH2 | Me | a bond | NH | S | NH | Q3a | OH |
| 386 | CMe | NMe | Q1a | CH2 | Me | a bond | NH | S | a bond | Q3a | OH |
| 387 | CMe | NMe | Q1a | CH2 | Me | a bond | NH | O | NH | Q3a | OH |
| 388 | CMe | NMe | Q1a | CH2 | Me | a bond | NH | O | a bond | Q3a | OH |
| 389 | CMe | NMe | Q1a | CH2 | H | a bond | NH | S | NH | Q3a | OH |
| 390 | CMe | NMe | Q1a | CH2 | H | a bond | NH | S | a bond | Q3a | OH |
| 391 | CMe | NMe | Q1a | CH2 | H | a bond | NH | O | NH | Q3a | OH |
| 392 | CMe | NMe | Q1a | CH2 | H | a bond | NH | O | a bond | Q3a | OH |
| 393 | CMe | NMe | Q1b | CH2 | Me | a bond | NH | S | NH | Q3a | OH |
| 394 | CMe | NMe | Q1b | CH2 | Me | a bond | NH | S | a bond | Q3a | OH |
| 395 | CMe | NMe | Q1b | CH2 | Me | a bond | NH | O | NH | Q3a | OH |
| 396 | CMe | NMe | Q1b | CH2 | Me | a bond | NH | O | a bond | Q3a | OH |
| 397 | CMe | NMe | Q1b | CH2 | H | a bond | NH | S | NH | Q3a | OH |
| 398 | CMe | NMe | Q1b | CH2 | H | a bond | NH | S | a bond | Q3a | OH |
| 399 | CMe | NMe | Q1b | CH2 | H | a bond | NH | O | NH | Q3a | OH |
| 400 | CMe | NMe | Q1b | CH2 | H | a bond | NH | O | a bond | Q3a | OH |
| 401 | CMe | S | Q1a | CH2 | Me | a bond | NH | S | NH | Q3a | OH |
| 402 | CMe | S | Q1a | CH2 | Me | a bond | NH | S | a bond | Q3a | OH |
| 403 | CMe | S | Q1a | CH2 | Me | a bond | NH | O | NH | Q3a | OH |
| 404 | CMe | S | Q1a | CH2 | Me | a bond | NH | O | a bond | Q3a | OH |
| 405 | CMe | S | Q1a | CH2 | H | a bond | NH | S | NH | Q3a | OH |
| 406 | CMe | S | Q1a | CH2 | H | a bond | NH | S | a bond | Q3a | OH |
| 407 | CMe | S | Q1a | CH2 | H | a bond | NH | O | NH | Q3a | OH |
| 408 | CMe | S | Q1a | CH2 | H | a bond | NH | O | a bond | Q3a | OH |
| 409 | CMe | S | Q1b | CH2 | Me | a bond | NH | S | NH | Q3a | OH |
| 410 | CMe | S | Q1b | CH2 | Me | a bond | NH | S | a bond | Q3a | OH |
| 411 | CMe | S | Q1b | CH2 | Me | a bond | NH | O | NH | Q3a | OH |
| 412 | CMe | S | Q1b | CH2 | Me | a bond | NH | O | a bond | Q3a | OH |
| 413 | CMe | S | Q1b | CH2 | H | a bond | NH | S | NH | Q3a | OH |
| 414 | CMe | S | Q1b | CH2 | H | a bond | NH | S | a bond | Q3a | OH |
| 415 | CMe | S | Q1b | CH2 | H | a bond | NH | O | NH | Q3a | OH |
| 416 | CMe | S | Q1b | CH2 | H | a bond | NH | O | a bond | Q3a | OH |
| 417 | CMe | O | Q1a | CH2 | Me | a bond | NH | S | NH | Q3a | OH |
| 418 | CMe | O | Q1a | CH2 | Me | a bond | NH | S | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 419 | CMe | O | Q1a | CH2 | Me | a bond | NH | O | NH | Q3a | OH |
| 420 | CMe | O | Q1a | CH2 | Me | a bond | NH | O | a bond | Q3a | OH |
| 421 | CMe | O | Q1a | CH2 | H | a bond | NH | S | NH | Q3a | OH |
| 422 | CMe | O | Q1a | CH2 | H | a bond | NH | S | a bond | Q3a | OH |
| 423 | CMe | O | Q1a | CH2 | H | a bond | NH | O | NH | Q3a | OH |
| 424 | CMe | O | Q1a | CH2 | H | a bond | NH | O | a bond | Q3a | OH |
| 425 | CMe | O | Q1b | CH2 | Me | a bond | NH | S | NH | Q3a | OH |
| 426 | CMe | O | Q1b | CH2 | Me | a bond | NH | S | a bond | Q3a | OH |
| 427 | CMe | O | Q1b | CH2 | Me | a bond | NH | O | NH | Q3a | OH |
| 428 | CMe | O | Q1b | CH2 | Me | a bond | NH | O | a bond | Q3a | OH |
| 429 | CMe | O | Q1b | CH2 | H | a bond | NH | S | NH | Q3a | OH |
| 430 | CMe | O | Q1b | CH2 | H | a bond | NH | S | a bond | Q3a | OH |
| 431 | CMe | O | Q1b | CH2 | H | a bond | NH | O | NH | Q3a | OH |
| 432 | CMe | O | Q1b | CH2 | H | a bond | NH | O | a bond | Q3a | OH |
| 433 | N | NMe | Q1a | a bond | Me | a bond | NH | S | CH2 | Q3a | OH |
| 434 | N | NMe | Q1a | a bond | Me | a bond | NH | O | CH2 | Q3a | OH |
| 435 | N | NMe | Q1a | a bond | H | a bond | NH | S | CH2 | Q3a | OH |
| 436 | N | NMe | Q1a | a bond | H | a bond | NH | O | CH2 | Q3a | OH |
| 437 | N | NMe | Q1b | a bond | Me | a bond | NH | S | CH2 | Q3a | OH |
| 438 | N | NMe | Q1b | a bond | Me | a bond | NH | O | CH2 | Q3a | OH |
| 439 | N | NMe | Q1b | a bond | H | a bond | NH | S | CH2 | Q3a | OH |
| 440 | N | NMe | Q1b | a bond | H | a bond | NH | O | CH2 | Q3a | OH |
| 441 | N | S | Q1a | a bond | Me | a bond | NH | S | CH2 | Q3a | OH |
| 442 | N | S | Q1a | a bond | Me | a bond | NH | O | CH2 | Q3a | OH |
| 443 | N | S | Q1a | a bond | H | a bond | NH | S | CH2 | Q3a | OH |
| 444 | N | S | Q1a | a bond | H | a bond | NH | O | CH2 | Q3a | OH |
| 445 | N | S | Q1b | a bond | Me | a bond | NH | S | CH2 | Q3a | OH |
| 446 | N | S | Q1b | a bond | Me | a bond | NH | O | CH2 | Q3a | OH |
| 447 | N | S | Q1b | a bond | H | a bond | NH | S | CH2 | Q3a | OH |
| 448 | N | S | Q1b | a bond | H | a bond | NH | O | CH2 | Q3a | OH |
| 449 | N | O | Q1a | a bond | Me | a bond | NH | S | CH2 | Q3a | OH |
| 450 | N | O | Q1a | a bond | Me | a bond | NH | O | CH2 | Q3a | OH |
| 451 | N | O | Q1a | a bond | H | a bond | NH | S | CH2 | Q3a | OH |
| 452 | N | O | Q1a | a bond | H | a bond | NH | O | CH2 | Q3a | OH |
| 453 | N | O | Q1b | a bond | Me | a bond | NH | S | CH2 | Q3a | OH |
| 454 | N | O | Q1b | a bond | Me | a bond | NH | O | CH2 | Q3a | OH |
| 455 | N | O | Q1b | a bond | H | a bond | NH | S | CH2 | Q3a | OH |
| 456 | N | O | Q1b | a bond | H | a bond | NH | O | CH2 | Q3a | OH |
| 457 | CH | NMe | Q1a | a bond | Me | a bond | NH | S | CH2 | Q3a | OH |
| 458 | CH | NMe | Q1a | a bond | Me | a bond | NH | O | CH2 | Q3a | OH |
| 459 | CH | NMe | Q1a | a bond | H | a bond | NH | S | CH2 | Q3a | OH |
| 460 | CH | NMe | Q1a | a bond | H | a bond | NH | O | CH2 | Q3a | OH |
| 461 | CH | NMe | Q1b | a bond | Me | a bond | NH | S | CH2 | Q3a | OH |
| 462 | CH | NMe | Q1b | a bond | Me | a bond | NH | O | CH2 | Q3a | OH |
| 463 | CH | NMe | Q1b | a bond | H | a bond | NH | S | CH2 | Q3a | OH |
| 464 | CH | NMe | Q1b | a bond | H | a bond | NH | O | CH2 | Q3a | OH |
| 465 | CH | S | Q1a | a bond | Me | a bond | NH | S | CH2 | Q3a | OH |
| 466 | CH | S | Q1a | a bond | Me | a bond | NH | O | CH2 | Q3a | OH |
| 467 | CH | S | Q1a | a bond | H | a bond | NH | S | CH2 | Q3a | OH |
| 468 | CH | S | Q1a | a bond | H | a bond | NH | O | CH2 | Q3a | OH |
| 469 | CH | S | Q1b | a bond | Me | a bond | NH | S | CH2 | Q3a | OH |
| 470 | CH | S | Q1b | a bond | Me | a bond | NH | O | CH2 | Q3a | OH |
| 471 | CH | S | Q1b | a bond | H | a bond | NH | S | CH2 | Q3a | OH |
| 472 | CH | S | Q1b | a bond | H | a bond | NH | O | CH2 | Q3a | OH |
| 473 | CH | O | Q1a | a bond | Me | a bond | NH | S | CH2 | Q3a | OH |
| 474 | CH | O | Q1a | a bond | Me | a bond | NH | O | CH2 | Q3a | OH |
| 475 | CH | O | Q1a | a bond | H | a bond | NH | S | CH2 | Q3a | OH |
| 476 | CH | O | Q1a | a bond | H | a bond | NH | O | CH2 | Q3a | OH |
| 477 | CH | O | Q1b | a bond | Me | a bond | NH | S | CH2 | Q3a | OH |
| 478 | CH | O | Q1b | a bond | Me | a bond | NH | O | CH2 | Q3a | OH |
| 479 | CH | O | Q1b | a bond | H | a bond | NH | S | CH2 | Q3a | OH |
| 480 | CH | O | Q1b | a bond | H | a bond | NH | O | CH2 | Q3a | OH |
| 481 | CMe | NMe | Q1a | a bond | Me | a bond | NH | S | CH2 | Q3a | OH |
| 482 | CMe | NMe | Q1a | a bond | Me | a bond | NH | O | CH2 | Q3a | OH |
| 483 | CMe | NMe | Q1a | a bond | H | a bond | NH | S | CH2 | Q3a | OH |
| 484 | CMe | NMe | Q1a | a bond | H | a bond | NH | O | CH2 | Q3a | OH |
| 485 | CMe | NMe | Q1b | a bond | Me | a bond | NH | S | CH2 | Q3a | OH |
| 486 | CMe | NMe | Q1b | a bond | Me | a bond | NH | O | CH2 | Q3a | OH |
| 487 | CMe | NMe | Q1b | a bond | H | a bond | NH | S | CH2 | Q3a | OH |
| 488 | CMe | NMe | Q1b | a bond | H | a bond | NH | O | CH2 | Q3a | OH |
| 489 | CMe | S | Q1a | a bond | Me | a bond | NH | S | CH2 | Q3a | OH |
| 490 | CMe | S | Q1a | a bond | Me | a bond | NH | O | CH2 | Q3a | OH |
| 491 | CMe | S | Q1a | a bond | H | a bond | NH | S | CH2 | Q3a | OH |
| 492 | CMe | S | Q1a | a bond | H | a bond | NH | O | CH2 | Q3a | OH |
| 493 | CMe | S | Q1b | a bond | Me | a bond | NH | S | CH2 | Q3a | OH |
| 494 | CMe | S | Q1b | a bond | Me | a bond | NH | O | CH2 | Q3a | OH |
| 495 | CMe | S | Q1b | a bond | H | a bond | NH | S | CH2 | Q3a | OH |
| 496 | CMe | S | Q1b | a bond | H | a bond | NH | O | CH2 | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 497 | CMe | O | Q1a | a bond | Me | a bond | NH | S | CH2 | Q3a | OH |
| 498 | CMe | O | Q1a | a bond | Me | a bond | NH | O | CH2 | Q3a | OH |
| 499 | CMe | O | Q1a | a bond | H | a bond | NH | S | CH2 | Q3a | OH |
| 500 | CMe | O | Q1a | a bond | H | a bond | NH | O | CH2 | Q3a | OH |
| 501 | CMe | O | Q1b | a bond | Me | a bond | NH | S | CH2 | Q3a | OH |
| 502 | CMe | O | Q1b | a bond | Me | a bond | NH | O | CH2 | Q3a | OH |
| 503 | CMe | O | Q1b | a bond | H | a bond | NH | S | CH2 | Q3a | OH |
| 504 | CMe | O | Q1b | a bond | H | a bond | NH | O | CH2 | Q3a | OH |
| 505 | N | NMe | Q1a | a bond | Me | a bond | CH2 | S | a bond | Q3a | OH |
| 506 | N | NMe | Q1a | a bond | Me | a bond | CH2 | S | NH | Q3a | OH |
| 507 | N | NMe | Q1a | a bond | Me | a bond | CH2 | O | a bond | Q3a | OH |
| 508 | N | NMe | Q1a | a bond | Me | a bond | CH2 | O | NH | Q3a | OH |
| 509 | N | NMe | Q1a | a bond | H | a bond | CH2 | S | a bond | Q3a | OH |
| 510 | N | NMe | Q1a | a bond | H | a bond | CH2 | S | NH | Q3a | OH |
| 511 | N | NMe | Q1a | a bond | H | a bond | CH2 | O | a bond | Q3a | OH |
| 512 | N | NMe | Q1a | a bond | H | a bond | CH2 | O | NH | Q3a | OH |
| 513 | N | NMe | Q1b | a bond | Me | a bond | CH2 | S | a bond | Q3a | OH |
| 514 | N | NMe | Q1b | a bond | Me | a bond | CH2 | S | NH | Q3a | OH |
| 515 | N | NMe | Q1b | a bond | Me | a bond | CH2 | O | a bond | Q3a | OH |
| 516 | N | NMe | Q1b | a bond | Me | a bond | CH2 | O | NH | Q3a | OH |
| 517 | N | NMe | Q1b | a bond | H | a bond | CH2 | S | a bond | Q3a | OH |
| 518 | N | NMe | Q1b | a bond | H | a bond | CH2 | S | NH | Q3a | OH |
| 519 | N | NMe | Q1b | a bond | H | a bond | CH2 | O | a bond | Q3a | OH |
| 520 | N | NMe | Q1b | a bond | H | a bond | CH2 | O | NH | Q3a | OH |
| 521 | N | S | Q1a | a bond | Me | a bond | CH2 | S | a bond | Q3a | OH |
| 522 | N | S | Q1a | a bond | Me | a bond | CH2 | S | NH | Q3a | OH |
| 523 | N | S | Q1a | a bond | Me | a bond | CH2 | O | a bond | Q3a | OH |
| 524 | N | S | Q1a | a bond | Me | a bond | CH2 | O | NH | Q3a | OH |
| 525 | N | S | Q1a | a bond | H | a bond | CH2 | S | a bond | Q3a | OH |
| 526 | N | S | Q1a | a bond | H | a bond | CH2 | S | NH | Q3a | OH |
| 527 | N | S | Q1a | a bond | H | a bond | CH2 | O | a bond | Q3a | OH |
| 528 | N | S | Q1a | a bond | H | a bond | CH2 | O | NH | Q3a | OH |
| 529 | N | S | Q1b | a bond | Me | a bond | CH2 | S | a bond | Q3a | OH |
| 530 | N | S | Q1b | a bond | Me | a bond | CH2 | S | NH | Q3a | OH |
| 531 | N | S | Q1b | a bond | Me | a bond | CH2 | O | a bond | Q3a | OH |
| 532 | N | S | Q1b | a bond | Me | a bond | CH2 | O | NH | Q3a | OH |
| 533 | N | S | Q1b | a bond | H | a bond | CH2 | S | a bond | Q3a | OH |
| 534 | N | S | Q1b | a bond | H | a bond | CH2 | S | NH | Q3a | OH |
| 535 | N | S | Q1b | a bond | H | a bond | CH2 | O | a bond | Q3a | OH |
| 536 | N | S | Q1b | a bond | H | a bond | CH2 | O | NH | Q3a | OH |
| 537 | N | O | Q1a | a bond | Me | a bond | CH2 | S | a bond | Q3a | OH |
| 538 | N | O | Q1a | a bond | Me | a bond | CH2 | S | NH | Q3a | OH |
| 539 | N | O | Q1a | a bond | Me | a bond | CH2 | O | a bond | Q3a | OH |
| 540 | N | O | Q1a | a bond | Me | a bond | CH2 | O | NH | Q3a | OH |
| 541 | N | O | Q1a | a bond | H | a bond | CH2 | S | a bond | Q3a | OH |
| 542 | N | O | Q1a | a bond | H | a bond | CH2 | S | NH | Q3a | OH |
| 543 | N | O | Q1a | a bond | H | a bond | CH2 | O | a bond | Q3a | OH |
| 544 | N | O | Q1a | a bond | H | a bond | CH2 | O | NH | Q3a | OH |
| 545 | N | O | Q1b | a bond | Me | a bond | CH2 | S | a bond | Q3a | OH |
| 546 | N | O | Q1b | a bond | Me | a bond | CH2 | S | NH | Q3a | OH |
| 547 | N | O | Q1b | a bond | Me | a bond | CH2 | O | a bond | Q3a | OH |
| 548 | N | O | Q1b | a bond | Me | a bond | CH2 | O | NH | Q3a | OH |
| 549 | N | O | Q1b | a bond | H | a bond | CH2 | S | a bond | Q3a | OH |
| 550 | N | O | Q1b | a bond | H | a bond | CH2 | S | NH | Q3a | OH |
| 551 | N | O | Q1b | a bond | H | a bond | CH2 | O | a bond | Q3a | OH |
| 552 | N | O | Q1b | a bond | H | a bond | CH2 | O | NH | Q3a | OH |
| 553 | CH | NMe | Q1a | a bond | Me | a bond | CH2 | S | a bond | Q3a | OH |
| 554 | CH | NMe | Q1a | a bond | Me | a bond | CH2 | S | NH | Q3a | OH |
| 555 | CH | NMe | Q1a | a bond | Me | a bond | CH2 | O | a bond | Q3a | OH |
| 556 | CH | NMe | Q1a | a bond | Me | a bond | CH2 | O | NH | Q3a | OH |
| 557 | CH | NMe | Q1a | a bond | H | a bond | CH2 | S | a bond | Q3a | OH |
| 558 | CH | NMe | Q1a | a bond | H | a bond | CH2 | S | NH | Q3a | OH |
| 559 | CH | NMe | Q1a | a bond | H | a bond | CH2 | O | a bond | Q3a | OH |
| 560 | CH | NMe | Q1a | a bond | H | a bond | CH2 | O | NH | Q3a | OH |
| 561 | CH | NMe | Q1b | a bond | Me | a bond | CH2 | S | a bond | Q3a | OH |
| 562 | CH | NMe | Q1b | a bond | Me | a bond | CH2 | S | NH | Q3a | OH |
| 563 | CH | NMe | Q1b | a bond | Me | a bond | CH2 | O | a bond | Q3a | OH |
| 564 | CH | NMe | Q1b | a bond | Me | a bond | CH2 | O | NH | Q3a | OH |
| 565 | CH | NMe | Q1b | a bond | H | a bond | CH2 | S | a bond | Q3a | OH |
| 566 | CH | NMe | Q1b | a bond | H | a bond | CH2 | S | NH | Q3a | OH |
| 567 | CH | NMe | Q1b | a bond | H | a bond | CH2 | O | a bond | Q3a | OH |
| 568 | CH | NMe | Q1b | a bond | H | a bond | CH2 | O | NH | Q3a | OH |
| 569 | CH | S | Q1a | a bond | Me | a bond | CH2 | S | a bond | Q3a | OH |
| 570 | CH | S | Q1a | a bond | Me | a bond | CH2 | S | NH | Q3a | OH |
| 571 | CH | S | Q1a | a bond | Me | a bond | CH2 | O | a bond | Q3a | OH |
| 572 | CH | S | Q1a | a bond | Me | a bond | CH2 | O | NH | Q3a | OH |
| 573 | CH | S | Q1a | a bond | H | a bond | CH2 | S | a bond | Q3a | OH |
| 574 | CH | S | Q1a | a bond | H | a bond | CH2 | S | NH | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 575 | CH | S | Q1a | a bond | H | a bond | CH2 | O | a bond | Q3a | OH |
| 576 | CH | S | Q1a | a bond | H | a bond | CH2 | O | NH | Q3a | OH |
| 577 | CH | S | Q1b | a bond | Me | a bond | CH2 | S | a bond | Q3a | OH |
| 578 | CH | S | Q1b | a bond | Me | a bond | CH2 | S | NH | Q3a | OH |
| 579 | CH | S | Q1b | a bond | Me | a bond | CH2 | O | a bond | Q3a | OH |
| 580 | CH | S | Q1b | a bond | Me | a bond | CH2 | O | NH | Q3a | OH |
| 581 | CH | S | Q1b | a bond | H | a bond | CH2 | S | a bond | Q3a | OH |
| 582 | CH | S | Q1b | a bond | H | a bond | CH2 | S | NH | Q3a | OH |
| 583 | CH | S | Q1b | a bond | H | a bond | CH2 | O | a bond | Q3a | OH |
| 584 | CH | S | Q1b | a bond | H | a bond | CH2 | O | NH | Q3a | OH |
| 585 | CH | O | Q1a | a bond | Me | a bond | CH2 | S | a bond | Q3a | OH |
| 586 | CH | O | Q1a | a bond | Me | a bond | CH2 | S | NH | Q3a | OH |
| 587 | CH | O | Q1a | a bond | Me | a bond | CH2 | O | a bond | Q3a | OH |
| 588 | CH | O | Q1a | a bond | Me | a bond | CH2 | O | NH | Q3a | OH |
| 589 | CH | O | Q1a | a bond | H | a bond | CH2 | S | a bond | Q3a | OH |
| 590 | CH | O | Q1a | a bond | H | a bond | CH2 | S | NH | Q3a | OH |
| 591 | CH | O | Q1a | a bond | H | a bond | CH2 | O | a bond | Q3a | OH |
| 592 | CH | O | Q1a | a bond | H | a bond | CH2 | O | NH | Q3a | OH |
| 593 | CH | O | Q1b | a bond | Me | a bond | CH2 | S | a bond | Q3a | OH |
| 594 | CH | O | Q1b | a bond | Me | a bond | CH2 | S | NH | Q3a | OH |
| 595 | CH | O | Q1b | a bond | Me | a bond | CH2 | O | a bond | Q3a | OH |
| 596 | CH | O | Q1b | a bond | Me | a bond | CH2 | O | NH | Q3a | OH |
| 597 | CH | O | Q1b | a bond | H | a bond | CH2 | S | a bond | Q3a | OH |
| 598 | CH | O | Q1b | a bond | H | a bond | CH2 | S | NH | Q3a | OH |
| 599 | CH | O | Q1b | a bond | H | a bond | CH2 | O | a bond | Q3a | OH |
| 600 | CH | O | Q1b | a bond | H | a bond | CH2 | O | NH | Q3a | OH |
| 601 | CMe | NMe | Q1a | a bond | Me | a bond | CH2 | S | a bond | Q3a | OH |
| 602 | CMe | NMe | Q1a | a bond | Me | a bond | CH2 | S | NH | Q3a | OH |
| 603 | CMe | NMe | Q1a | a bond | Me | a bond | CH2 | O | a bond | Q3a | OH |
| 604 | CMe | NMe | Q1a | a bond | Me | a bond | CH2 | O | NH | Q3a | OH |
| 605 | CMe | NMe | Q1a | a bond | H | a bond | CH2 | S | a bond | Q3a | OH |
| 606 | CMe | NMe | Q1a | a bond | H | a bond | CH2 | S | NH | Q3a | OH |
| 607 | CMe | NMe | Q1a | a bond | H | a bond | CH2 | O | a bond | Q3a | OH |
| 608 | CMe | NMe | Q1a | a bond | H | a bond | CH2 | O | NH | Q3a | OH |
| 609 | CMe | NMe | Q1b | a bond | Me | a bond | CH2 | S | a bond | Q3a | OH |
| 610 | CMe | NMe | Q1b | a bond | Me | a bond | CH2 | S | NH | Q3a | OH |
| 611 | CMe | NMe | Q1b | a bond | Me | a bond | CH2 | O | a bond | Q3a | OH |
| 612 | CMe | NMe | Q1b | a bond | Me | a bond | CH2 | O | NH | Q3a | OH |
| 613 | CMe | NMe | Q1b | a bond | H | a bond | CH2 | S | a bond | Q3a | OH |
| 614 | CMe | NMe | Q1b | a bond | H | a bond | CH2 | S | NH | Q3a | OH |
| 615 | CMe | NMe | Q1b | a bond | H | a bond | CH2 | O | a bond | Q3a | OH |
| 616 | CMe | NMe | Q1b | a bond | H | a bond | CH2 | O | NH | Q3a | OH |
| 617 | CMe | S | Q1a | a bond | Me | a bond | CH2 | S | a bond | Q3a | OH |
| 618 | CMe | S | Q1a | a bond | Me | a bond | CH2 | S | NH | Q3a | OH |
| 619 | CMe | S | Q1a | a bond | Me | a bond | CH2 | O | a bond | Q3a | OH |
| 620 | CMe | S | Q1a | a bond | Me | a bond | CH2 | O | NH | Q3a | OH |
| 621 | CMe | S | Q1a | a bond | H | a bond | CH2 | S | a bond | Q3a | OH |
| 622 | CMe | S | Q1a | a bond | H | a bond | CH2 | S | NH | Q3a | OH |
| 623 | CMe | S | Q1a | a bond | H | a bond | CH2 | O | a bond | Q3a | OH |
| 624 | CMe | S | Q1a | a bond | H | a bond | CH2 | O | NH | Q3a | OH |
| 625 | CMe | S | Q1b | a bond | Me | a bond | CH2 | S | a bond | Q3a | OH |
| 626 | CMe | S | Q1b | a bond | Me | a bond | CH2 | S | NH | Q3a | OH |
| 627 | CMe | S | Q1b | a bond | Me | a bond | CH2 | O | a bond | Q3a | OH |
| 628 | CMe | S | Q1b | a bond | Me | a bond | CH2 | O | NH | Q3a | OH |
| 629 | CMe | S | Q1b | a bond | H | a bond | CH2 | S | a bond | Q3a | OH |
| 630 | CMe | S | Q1b | a bond | H | a bond | CH2 | S | NH | Q3a | OH |
| 631 | CMe | S | Q1b | a bond | H | a bond | CH2 | O | a bond | Q3a | OH |
| 632 | CMe | S | Q1b | a bond | H | a bond | CH2 | O | NH | Q3a | OH |
| 633 | CMe | O | Q1a | a bond | Me | a bond | CH2 | S | a bond | Q3a | OH |
| 634 | CMe | O | Q1a | a bond | Me | a bond | CH2 | S | NH | Q3a | OH |
| 635 | CMe | O | Q1a | a bond | Me | a bond | CH2 | O | a bond | Q3a | OH |
| 636 | CMe | O | Q1a | a bond | Me | a bond | CH2 | O | NH | Q3a | OH |
| 637 | CMe | O | Q1a | a bond | H | a bond | CH2 | S | a bond | Q3a | OH |
| 638 | CMe | O | Q1a | a bond | H | a bond | CH2 | S | NH | Q3a | OH |
| 639 | CMe | O | Q1a | a bond | H | a bond | CH2 | O | a bond | Q3a | OH |
| 640 | CMe | O | Q1a | a bond | H | a bond | CH2 | O | NH | Q3a | OH |
| 641 | CMe | O | Q1b | a bond | Me | a bond | CH2 | S | a bond | Q3a | OH |
| 642 | CMe | O | Q1b | a bond | Me | a bond | CH2 | S | NH | Q3a | OH |
| 643 | CMe | O | Q1b | a bond | Me | a bond | CH2 | O | a bond | Q3a | OH |
| 644 | CMe | O | Q1b | a bond | Me | a bond | CH2 | O | NH | Q3a | OH |
| 645 | CMe | O | Q1b | a bond | H | a bond | CH2 | S | a bond | Q3a | OH |
| 646 | CMe | O | Q1b | a bond | H | a bond | CH2 | S | NH | Q3a | OH |
| 647 | CMe | O | Q1b | a bond | H | a bond | CH2 | O | a bond | Q3a | OH |
| 648 | CMe | O | Q1b | a bond | H | a bond | CH2 | O | NH | Q3a | OH |
| 649 | CMe | NH | Q1a | NH | Me | a bond | NH | S | NH | Q3a | OH |
| 650 | CMe | NH | Q1a | NH | Me | a bond | NH | S | a bond | Q3a | OH |
| 651 | CMe | NH | Q1a | NH | Me | a bond | NH | O | NH | Q3a | OH |
| 652 | CMe | NH | Q1a | NH | Me | a bond | NH | O | a bond | Q3a | OH |

TABLE 2-continued

| No | A | B | R¹ | L¹ | R² | L² | L³ | Y | L⁴ | R³ | X |
|---|---|---|---|---|---|---|---|---|---|---|---|
| 653 | CMe | NH | Q1a | NH | H | a bond | NH | S | NH | Q3a | OH |
| 654 | CMe | NH | Q1a | NH | H | a bond | NH | S | a bond | Q3a | OH |
| 655 | CMe | NH | Q1a | NH | H | a bond | NH | O | NH | Q3a | OH |
| 656 | CMe | NH | Q1a | NH | H | a bond | NH | O | a bond | Q3a | OH |
| 657 | CMe | NH | Q1b | NH | Me | a bond | NH | S | NH | Q3a | OH |
| 658 | CMe | NH | Q1b | NH | Me | a bond | NH | S | a bond | Q3a | OH |
| 659 | CMe | NH | Q1b | NH | Me | a bond | NH | O | NH | Q3a | OH |
| 660 | CMe | NH | Q1b | NH | Me | a bond | NH | O | a bond | Q3a | OH |
| 661 | CMe | NH | Q1b | NH | H | a bond | NH | S | NH | Q3a | OH |
| 662 | CMe | NH | Q1b | NH | H | a bond | NH | S | a bond | Q3a | OH |
| 663 | CMe | NH | Q1b | NH | H | a bond | NH | O | NH | Q3a | OH |
| 664 | CMe | NH | Q1b | NH | H | a bond | NH | O | a bond | Q3a | OH |
| 665 | CMe | NH | Q1a | O | Me | a bond | NH | S | NH | Q3a | OH |
| 666 | CMe | NH | Q1a | O | Me | a bond | NH | S | a bond | Q3a | OH |
| 667 | CMe | NH | Q1a | O | Me | a bond | NH | O | NH | Q3a | OH |
| 668 | CMe | NH | Q1a | O | Me | a bond | NH | O | a bond | Q3a | OH |
| 669 | CMe | NH | Q1a | O | H | a bond | NH | S | NH | Q3a | OH |
| 670 | CMe | NH | Q1a | O | H | a bond | NH | S | a bond | Q3a | OH |
| 671 | CMe | NH | Q1a | O | H | a bond | NH | O | NH | Q3a | OH |
| 672 | CMe | NH | Q1a | O | H | a bond | NH | O | a bond | Q3a | OH |
| 673 | CMe | NH | Q1b | O | Me | a bond | NH | S | NH | Q3a | OH |
| 674 | CMe | NH | Q1b | O | Me | a bond | NH | S | a bond | Q3a | OH |
| 675 | CMe | NH | Q1b | O | Me | a bond | NH | O | NH | Q3a | OH |
| 676 | CMe | NH | Q1b | O | Me | a bond | NH | O | a bond | Q3a | OH |
| 677 | CMe | NH | Q1b | O | H | a bond | NH | S | NH | Q3a | OH |
| 678 | CMe | NH | Q1b | O | H | a bond | NH | S | a bond | Q3a | OH |
| 679 | CMe | NH | Q1b | O | H | a bond | NH | O | NH | Q3a | OH |
| 680 | CMe | NH | Q1b | O | H | a bond | NH | O | a bond | Q3a | OH |
| 681 | CMe | NH | Q1a | CH2 | Me | a bond | NH | S | NH | Q3a | OH |
| 682 | CMe | NH | Q1a | CH2 | Me | a bond | NH | S | a bond | Q3a | OH |
| 683 | CMe | NH | Q1a | CH2 | Me | a bond | NH | O | NH | Q3a | OH |
| 684 | CMe | NH | Q1a | CH2 | Me | a bond | NH | O | a bond | Q3a | OH |
| 685 | CMe | NH | Q1a | CH2 | H | a bond | NH | S | NH | Q3a | OH |
| 686 | CMe | NH | Q1a | CH2 | H | a bond | NH | S | a bond | Q3a | OH |
| 687 | CMe | NH | Q1a | CH2 | H | a bond | NH | O | NH | Q3a | OH |
| 688 | CMe | NH | Q1a | CH2 | H | a bond | NH | O | a bond | Q3a | OH |
| 689 | CMe | NH | Q1b | CH2 | Me | a bond | NH | S | NH | Q3a | OH |
| 690 | CMe | NH | Q1b | CH2 | Me | a bond | NH | S | a bond | Q3a | OH |
| 691 | CMe | NH | Q1b | CH2 | Me | a bond | NH | O | NH | Q3a | OH |
| 692 | CMe | NH | Q1b | CH2 | Me | a bond | NH | O | a bond | Q3a | OH |
| 693 | CMe | NH | Q1b | CH2 | H | a bond | NH | S | NH | Q3a | OH |
| 694 | CMe | NH | Q1b | CH2 | H | a bond | NH | S | a bond | Q3a | OH |
| 695 | CMe | NH | Q1b | CH2 | H | a bond | NH | O | NH | Q3a | OH |
| 696 | CMe | NH | Q1b | CH2 | H | a bond | NH | O | a bond | Q3a | OH |
| 697 | CMe | NH | Q1a | a bond | Me | a bond | NH | S | CH2 | Q3a | OH |
| 698 | CMe | NH | Q1a | a bond | Me | a bond | NH | O | CH2 | Q3a | OH |
| 699 | CMe | NH | Q1a | a bond | H | a bond | NH | S | CH2 | Q3a | OH |
| 700 | CMe | NH | Q1a | a bond | H | a bond | NH | O | CH2 | Q3a | OH |
| 701 | CMe | NH | Q1b | a bond | Me | a bond | NH | S | CH2 | Q3a | OH |
| 702 | CMe | NH | Q1b | a bond | Me | a bond | NH | O | CH2 | Q3a | OH |
| 703 | CMe | NH | Q1b | a bond | H | a bond | NH | S | CH2 | Q3a | OH |
| 704 | CMe | NH | Q1b | a bond | H | a bond | NH | O | CH2 | Q3a | OH |
| 705 | CMe | NH | Q1a | a bond | Me | a bond | CH2 | S | a bond | Q3a | OH |
| 706 | CMe | NH | Q1a | a bond | Me | a bond | CH2 | S | NH | Q3a | OH |
| 707 | CMe | NH | Q1a | a bond | Me | a bond | CH2 | O | a bond | Q3a | OH |
| 708 | CMe | NH | Q1a | a bond | Me | a bond | CH2 | O | NH | Q3a | OH |
| 709 | CMe | NH | Q1a | a bond | H | a bond | CH2 | S | a bond | Q3a | OH |
| 710 | CMe | NH | Q1a | a bond | H | a bond | CH2 | S | NH | Q3a | OH |
| 711 | CMe | NH | Q1a | a bond | H | a bond | CH2 | O | a bond | Q3a | OH |
| 712 | CMe | NH | Q1a | a bond | H | a bond | CH2 | O | NH | Q3a | OH |
| 713 | CMe | NH | Q1b | a bond | Me | a bond | CH2 | S | a bond | Q3a | OH |
| 714 | CMe | NH | Q1b | a bond | Me | a bond | CH2 | S | NH | Q3a | OH |
| 715 | CMe | NH | Q1b | a bond | Me | a bond | CH2 | O | a bond | Q3a | OH |
| 716 | CMe | NH | Q1b | a bond | Me | a bond | CH2 | O | NH | Q3a | OH |
| 717 | CMe | NH | Q1b | a bond | H | a bond | CH2 | S | a bond | Q3a | OH |
| 718 | CMe | NH | Q1b | a bond | H | a bond | CH2 | S | NH | Q3a | OH |
| 719 | CMe | NH | Q1b | a bond | H | a bond | CH2 | O | a bond | Q3a | OH |
| 720 | CMe | NH | Q1b | a bond | H | a bond | CH2 | O | NH | Q3a | OH |

TABLE 2-continued

| No | A | B | R¹ | L¹ | R² | L² | L³ | Y | L⁴ | R³ | X |
|----|---|---|----|----|----|----|----|---|----|----|---|

Q1a = 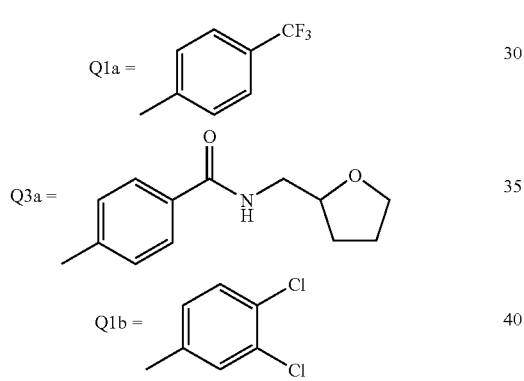

Q1b =

Q3a =

73) The compounds wherein A, B, R¹, L¹, R², L², L³, Y, L⁴, R³ and X are any of the above combinations in Table 2, tautomers, prodrugs or pharmaceutically acceptable salts of the compounds or solvates thereof (provided that in the case of 73), Q1a, Q1b and Q3a in Table 2 denote the following substituents).

Q1a =

Q3a =

Q1b =

74) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 74), Q1a, Q1b, Q1c, Q1i, Q1j, T3a, T3b, T3c, T3d, T3e, Q3e, T3f, T3g, T3h, T3i and T3j in Table 1 denote the following substituents).

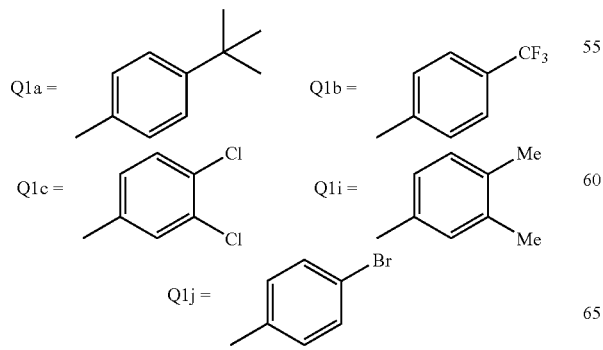

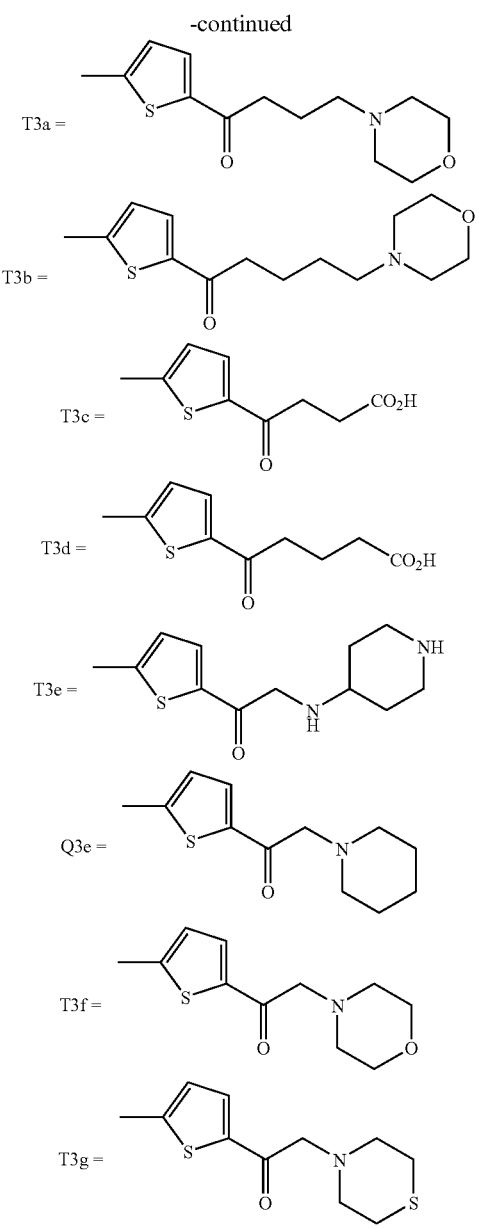

T3h = 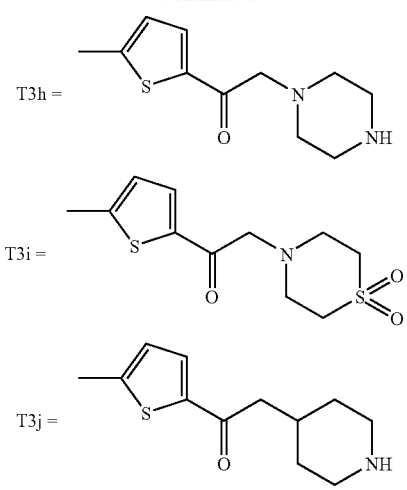

T3i =

T3j =

75) The compounds wherein A, B, R$^1$, L$^1$, R$^2$, L$^2$, L$^3$, Y, L$^4$, R$^3$ and X are any of the above combinations in Table 1, tautomers, prodrugs or pharmaceutically acceptable salts of the compounds or solvates thereof (provided that in the case of 75), Q1a, Q1b, Q1c, Q1i, Q1j, T3a, T3b, T3c, T3d, T3e, Q3e, T3f, T3g, T3h, T3i and T3j in Table 1 denote the following substituents).

Q1a = 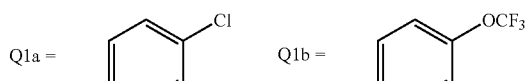 Q1b =

Q1c = Q1i =

Q1j =

T3a = 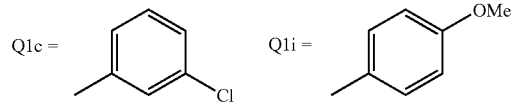

T3b = 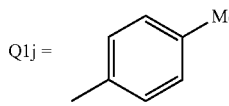

T3c = 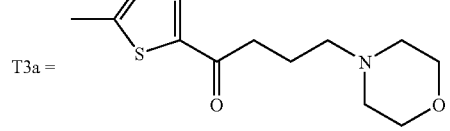

T3d = 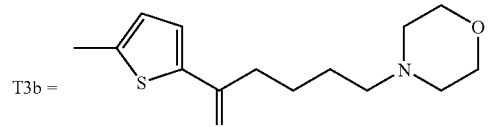

T3e = 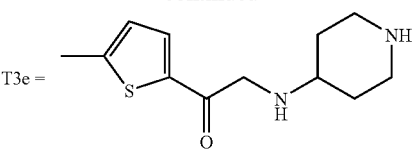

Q3e =

T3f = 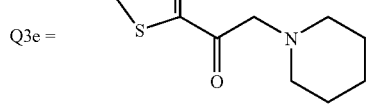

T3g = 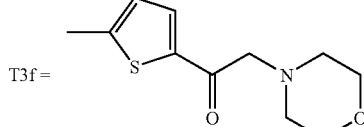

T3h = 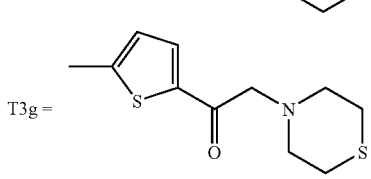

T3i = 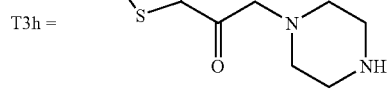

T3j = 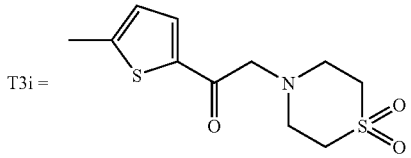

76) The compounds wherein A, B, R$^1$, L$^1$, R$^2$, L$^2$, L$^3$, Y, L$^4$, R$^3$ and X are any of the above combinations in Table 1, tautomers, prodrugs or pharmaceutically acceptable salts of the compounds or solvates thereof (provided that in the case of 76), Q1a, Q1b, Q1c, Q1i, Q1j, T3a, T3b, T3c, T3d, T3e, Q3e, T3f, T3g, T3h, T3i and T3j in Table 1 denote the following substituents).

Q1a = 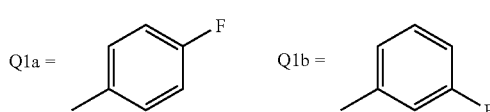 Q1b =

Q1c = Q1i =

Q1j = 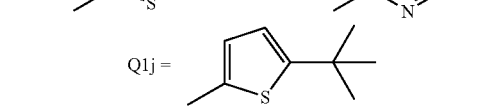

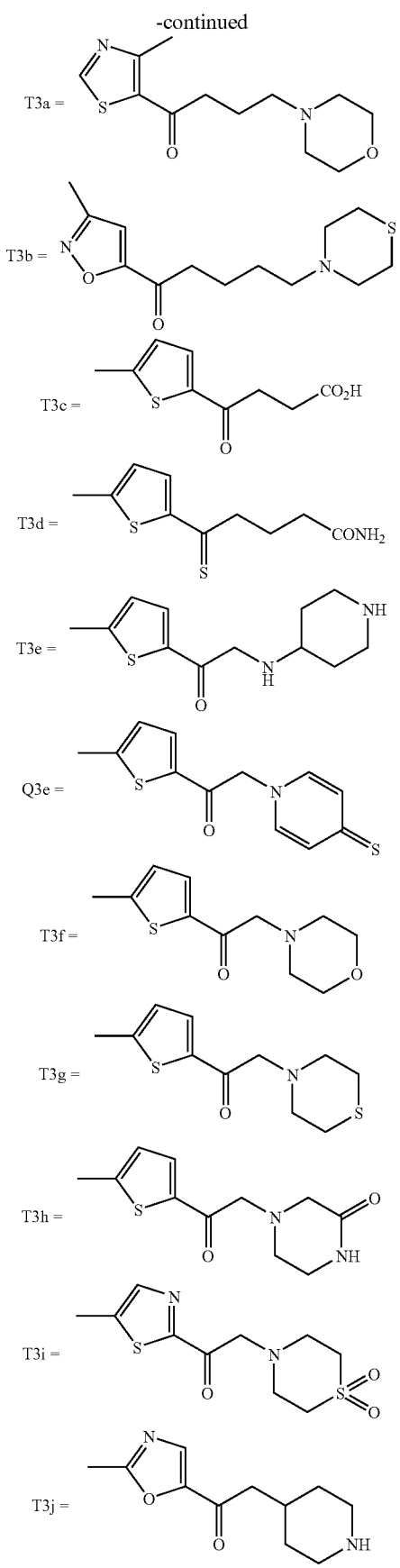
77) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 77), Q1a, Q1b, Q1c, Q1i, Q1j, T3a, T3b, T3c, T3d, T3e, Q3e, T3f, T3g, T3h, T3i and T3j in Table 1 denote the following substituents).
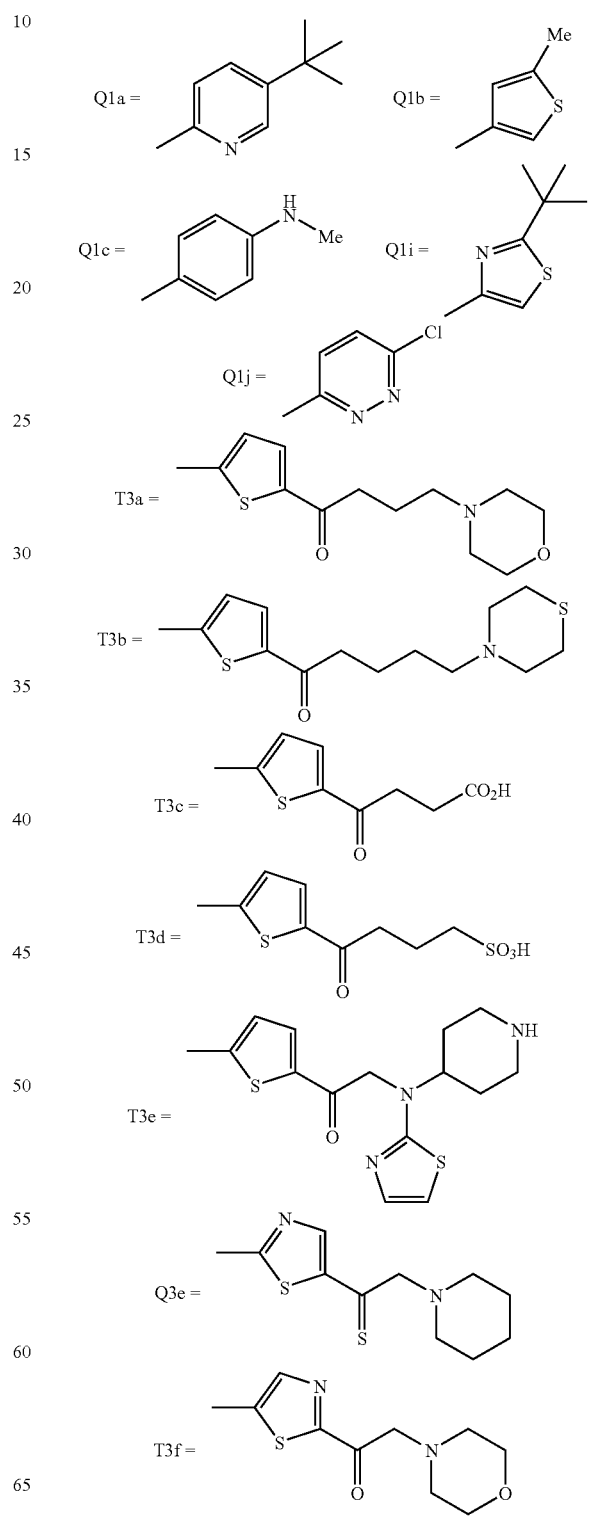

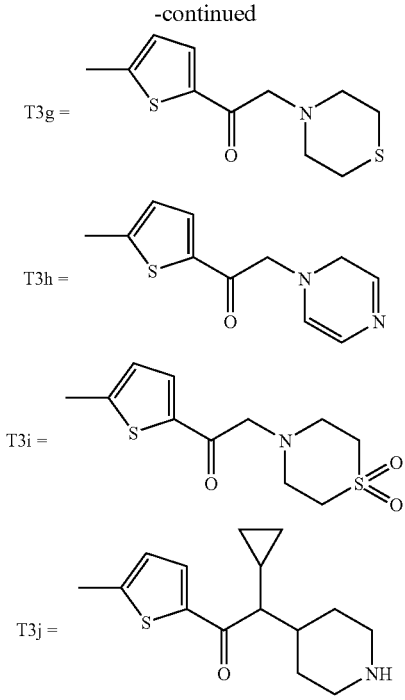

78) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 78), Q1a, Q1b, Q1c, Q1i, Q1j, T3a, T3b, T3c, T3d, T3e, Q3e, T1f, T3g, T3h, T3i and T3j in Table 1 denote the following substituents).

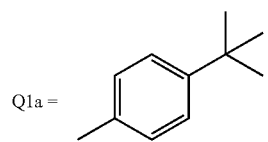
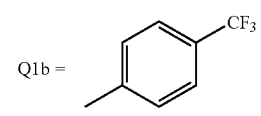
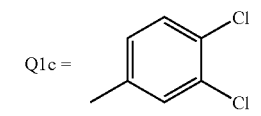
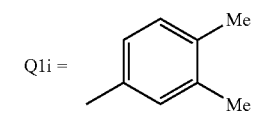
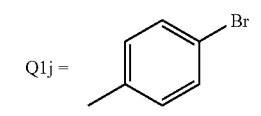
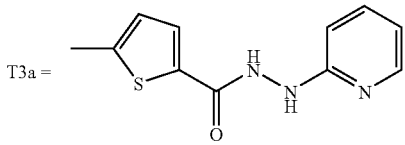

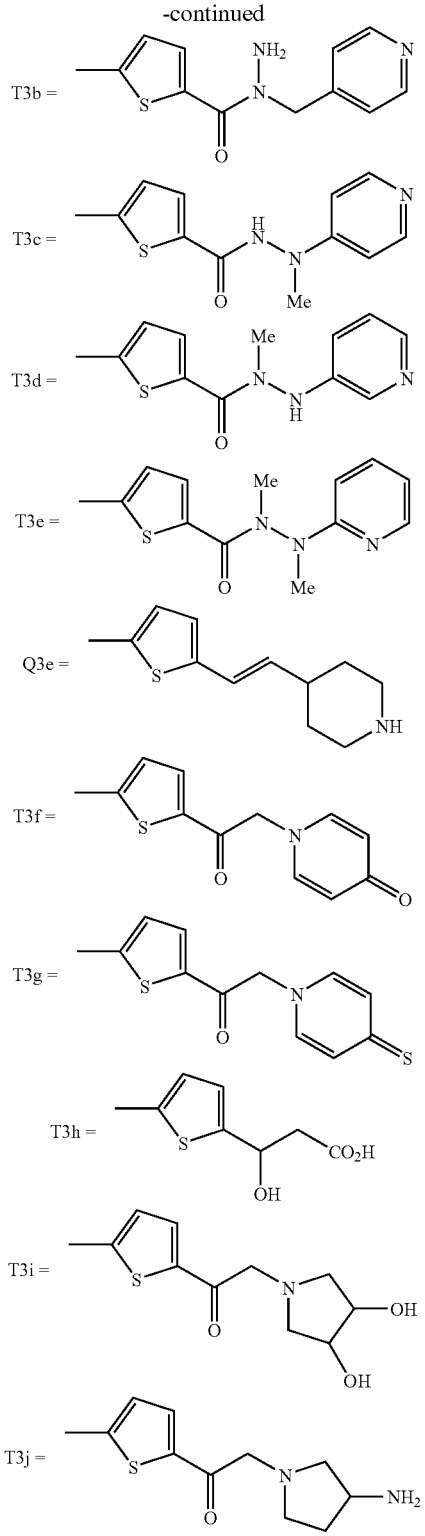

79) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 79), Q1a, Q1b, Q1c, Q1i, Q1j, T3a, T3b, T3c, T3d, T3e, Q3e, T3f, T3g, T3h, T3i and T3j in Table 1 denote the following substituents).

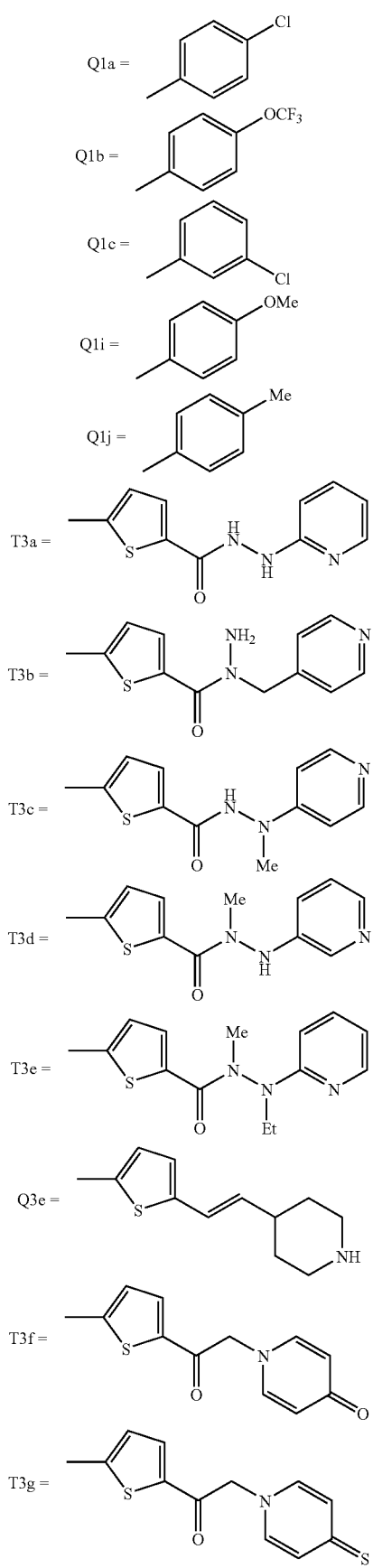
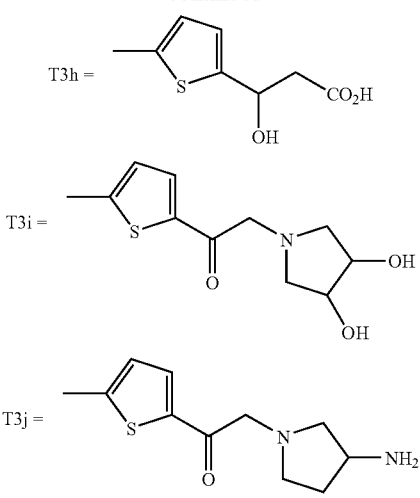
80) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 80), Q1a, Q1b, Q1c, Q1i, Q1j, T3a, T3b, T3c, T3d, T3e, Q3e, T3f, T3g, T3h, T3i and T3j in Table 1 denote the following substituents).
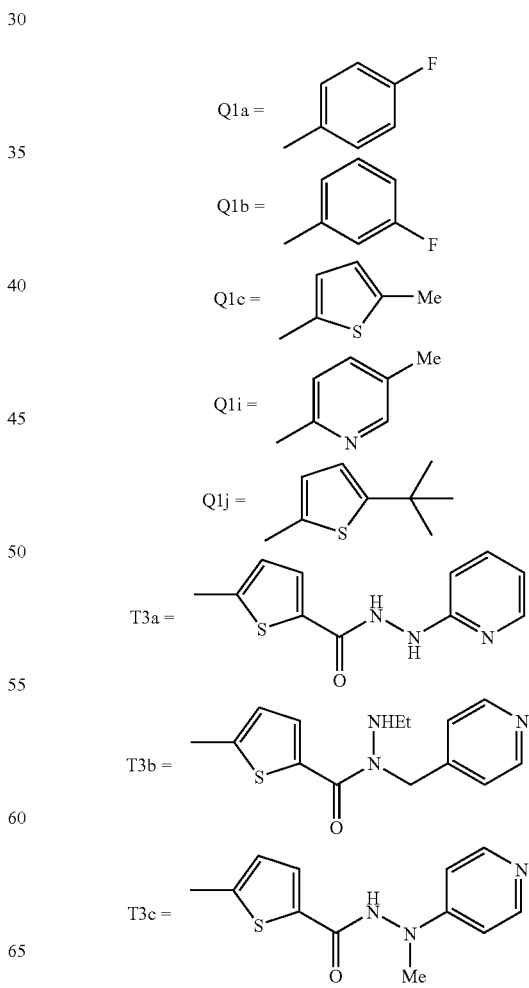

T3d = 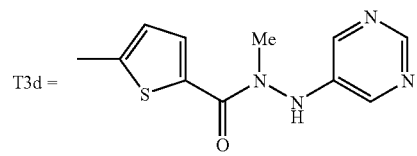

T3e = 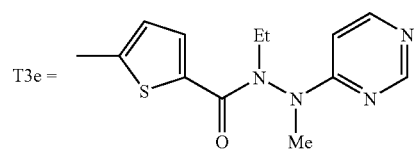

Q3e = 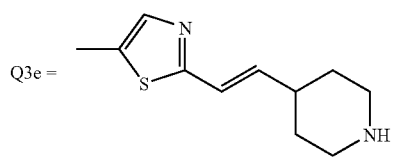

T3f = 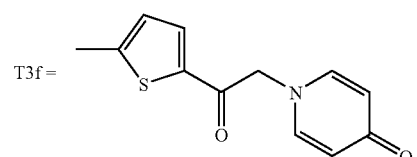

T3g = 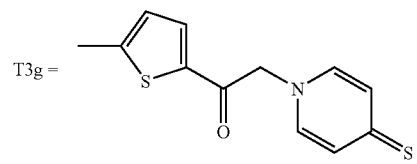

T3h = 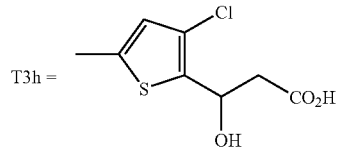

T3i = 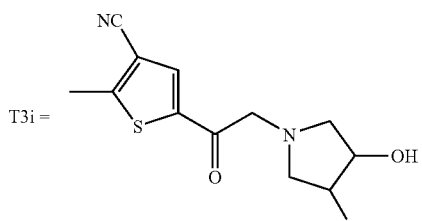

T3j = 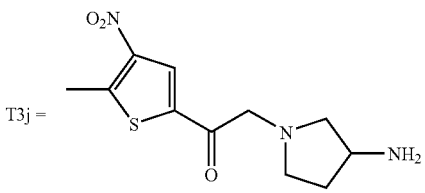

81) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 81), Q1a, Q1b, Q1c, Q1i, Q1j, T3a, T3b, T3c, T3d, T3e, Q3e, T3f, T3g, T3h, T3i and T3j in Table 1 denote the following substituents).

Q1a = 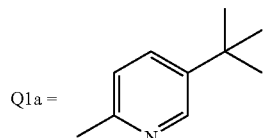

Q1b = 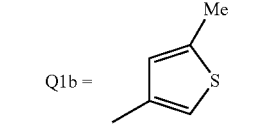

Q1c = 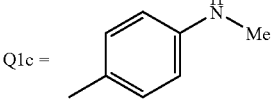

Q1i = 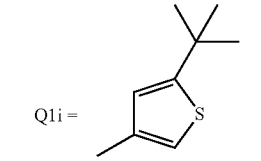

Q1j = 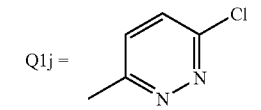

T3a = 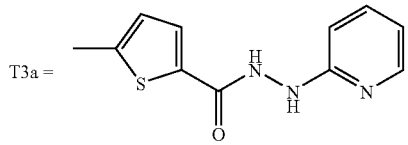

T3b = 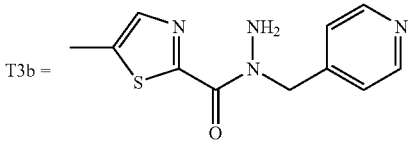

T3c = 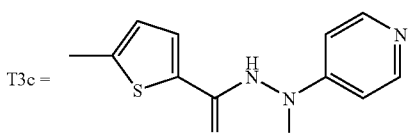

T3d = 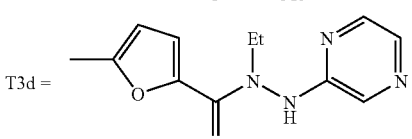

T3e = 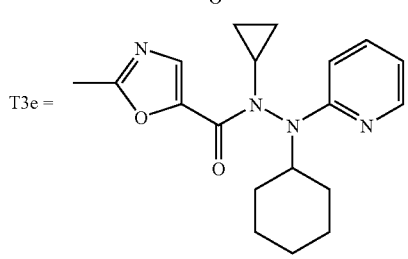

Q3e = 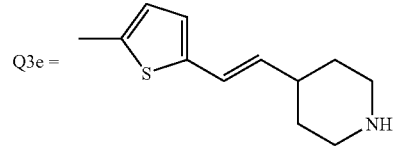

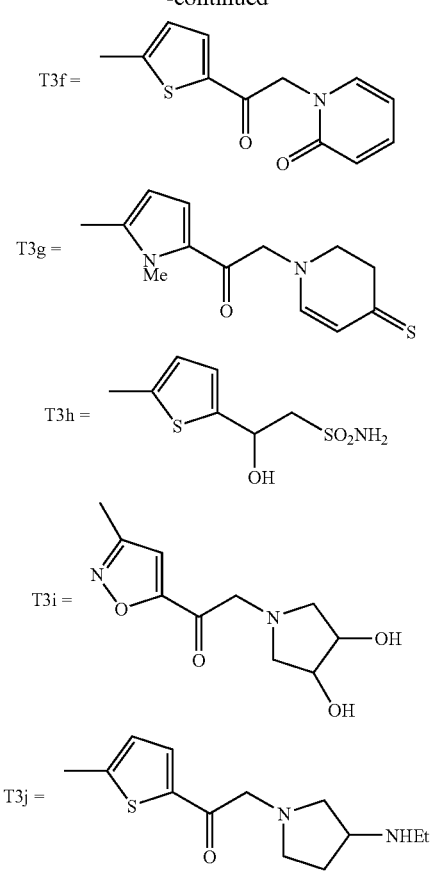

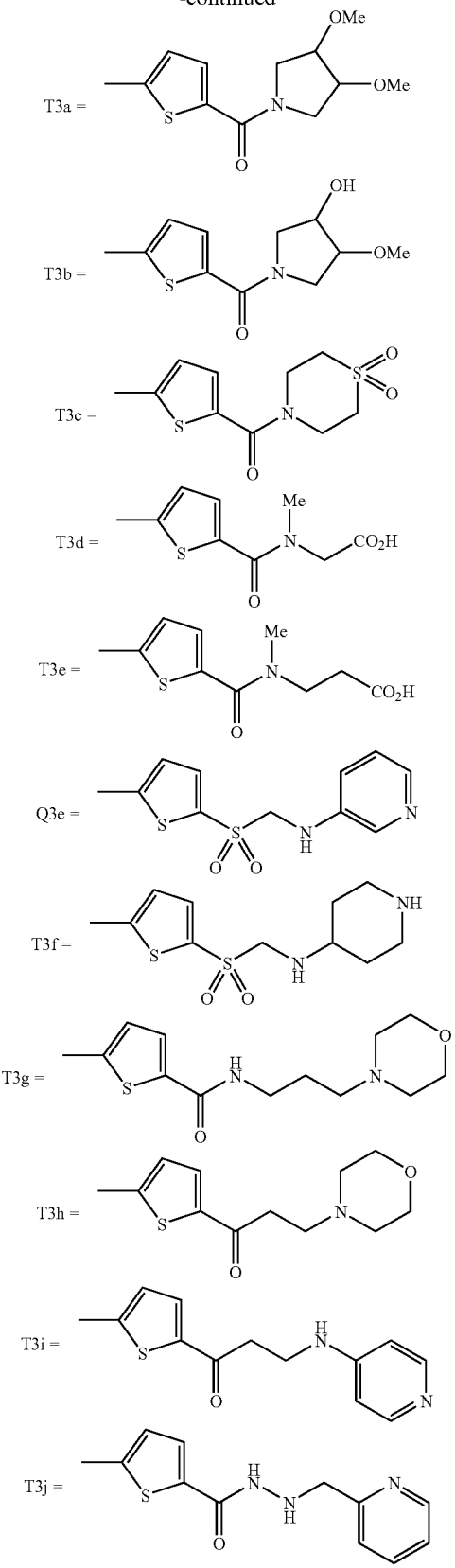

82) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 82), Q1a, Q1b, Q1c, Q1i, Q1j, T3a, T3b, T3c, T3d, T3e, Q3e, T3f, T3g, T3h, T3i and T3j in Table 1 denote the following substituents).

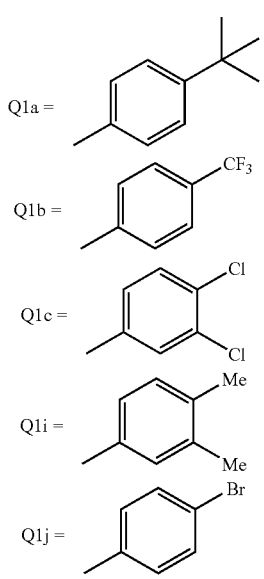

83) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 83), Q1a, Q1b, Q1c, Q1i, Q1j, T3a, T3b, T3c, T3d, T3e, Q3e, T3f, T3g, T3h, T3i and T3j in Table 1 denote the following substituents).

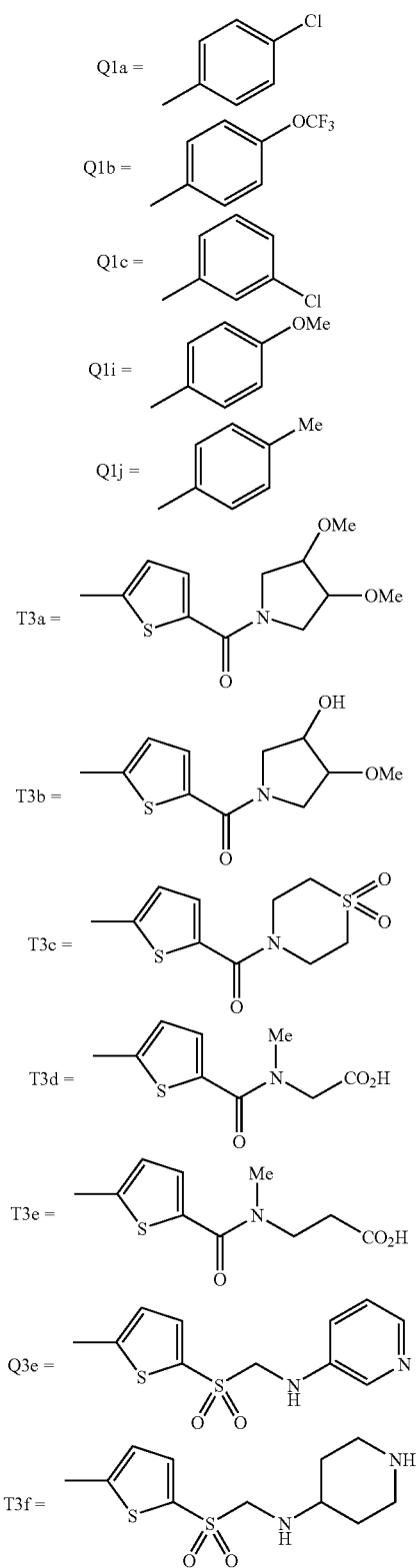

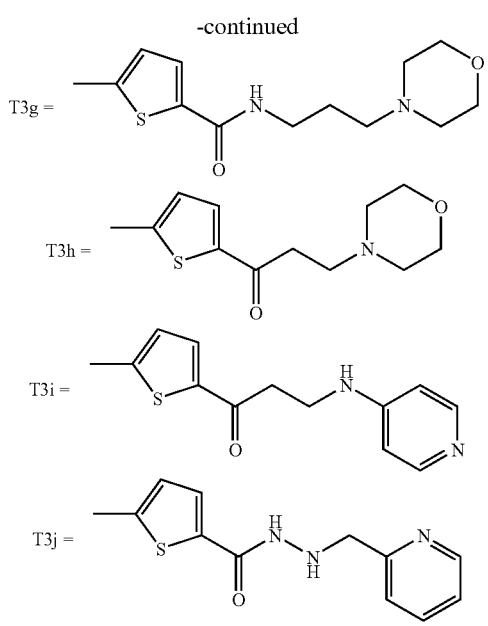

84) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 84), Q1a, Q1b, Q1c, Q1i, Q1j, T3a, T3b, T3c, T3d, T3e, Q3e, T3f, T3g, T3h, T3i and T3j in Table 1 denote the following substituents).

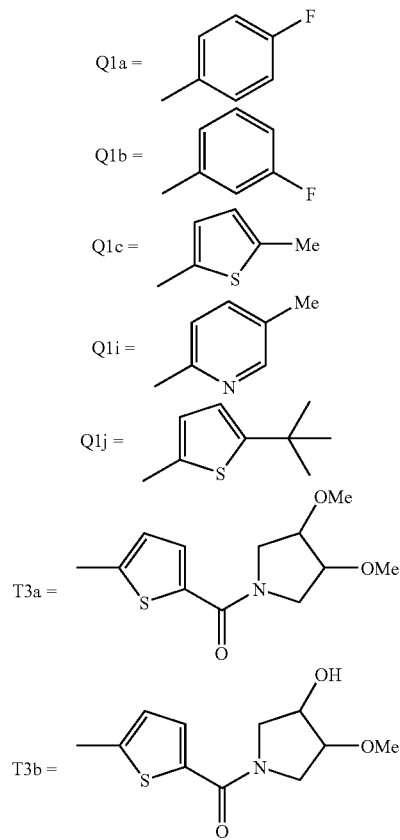

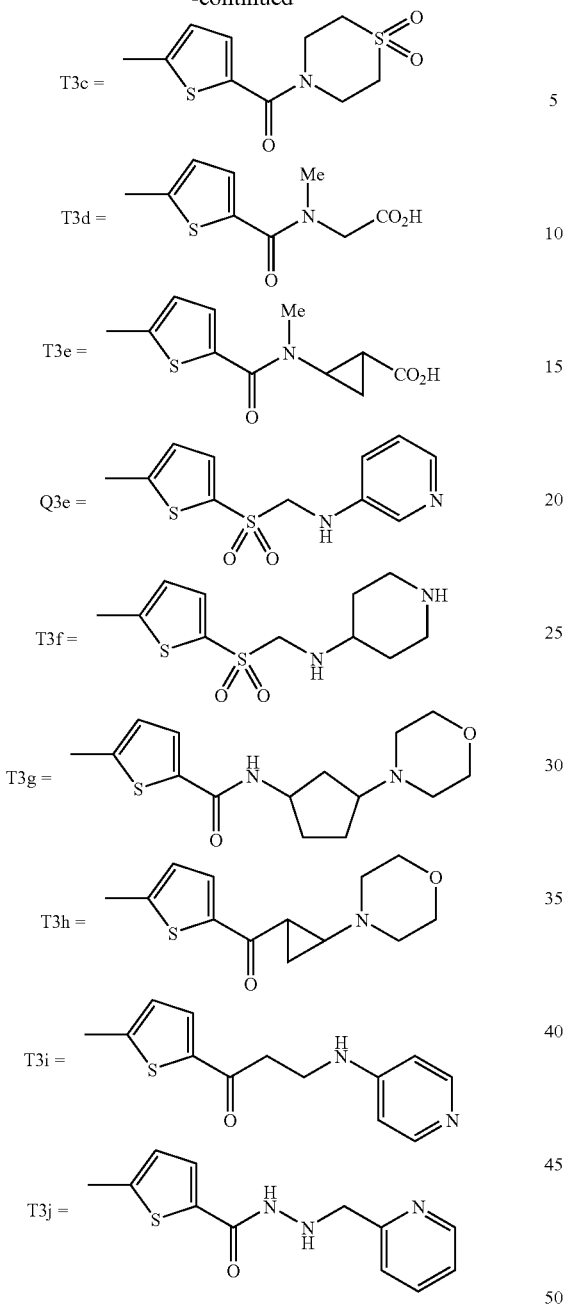
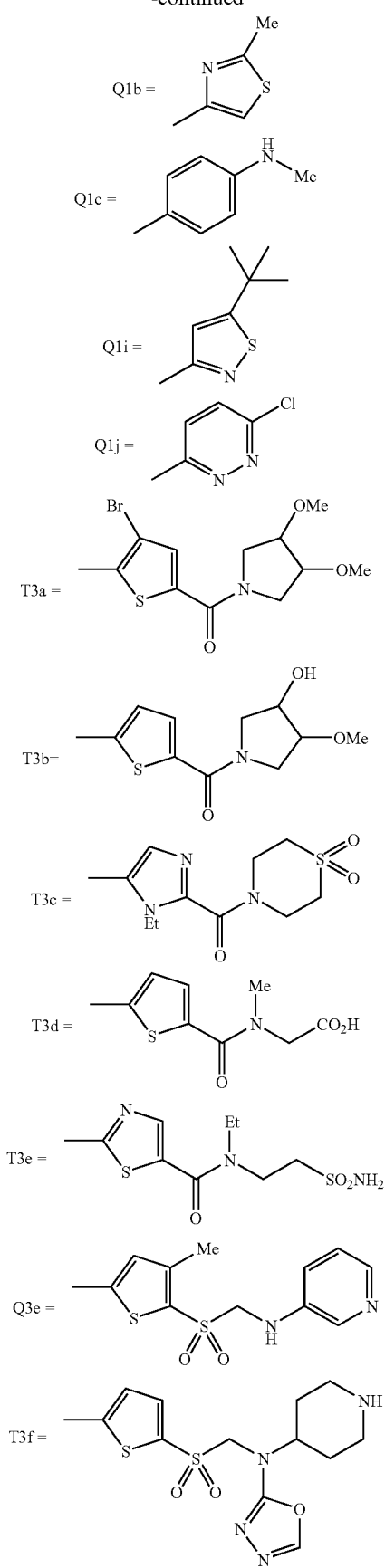
85) The compounds wherein A, B, $R^1$, $L^1$, $R^2$, $L^2$, $L^3$, Y, $L^4$, $R^3$ and X are any of the above combinations in Table 1 tautomers prodrugs or pharmaceutically acceptable salts of the compounds or solvates thereof (provided that in the case of 85), Q1a, Q1b, Q1c, Q1i, Q1j, T3a, T3b, T3c, T3d, T3e, Q3e, T3f, T3g, T3h, T3i and T3j in Table 1 denote the following substituents).

-continued

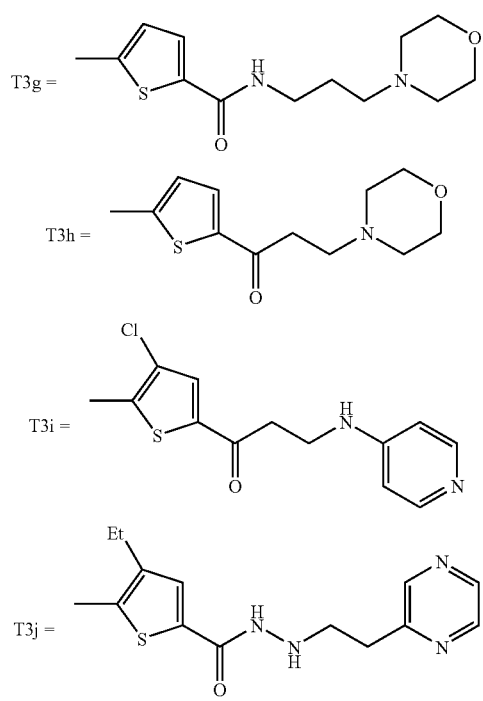

86) The compounds wherein A, B, R$^1$, L$^1$, R$^2$, L$^2$, L$^3$, Y, L$^4$, R$^3$ and X are any of the above combinations in Table 1, tautomers, prodrugs or pharmaceutically acceptable salts of the compounds or solvates thereof (provided that in the case of 86), Q1a, Q1b, Q1c, Q1i, Q1j, T3a, T3b, T3c, T3d, T3e, Q3e, T3f, T3g, T3h, T3i and T3j in Table 1 denote the following substituents.

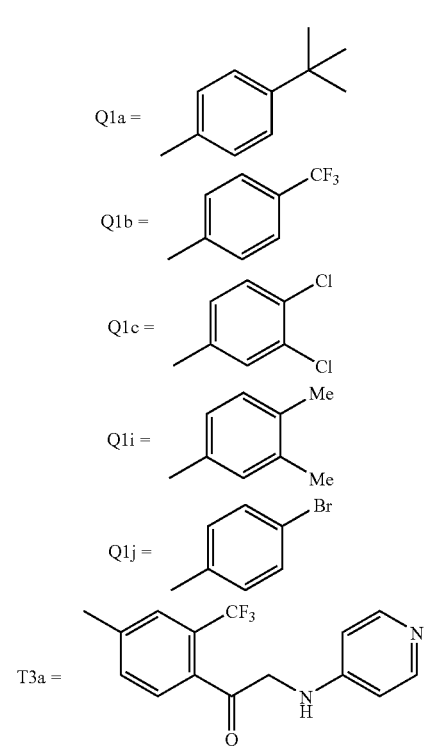

-continued

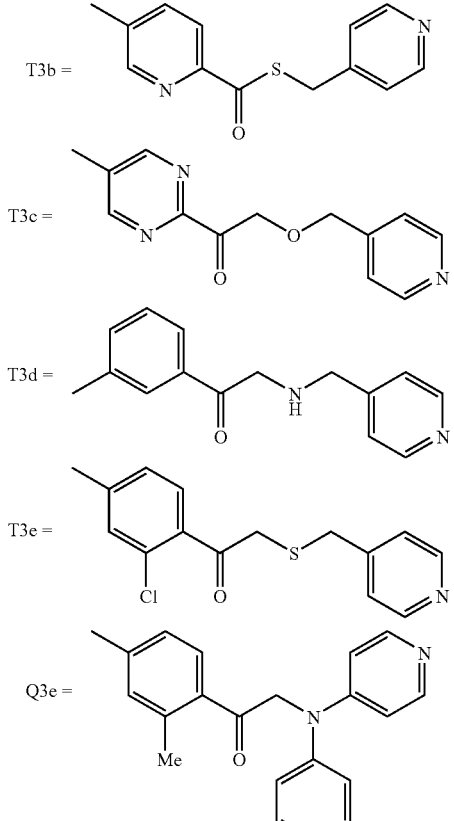

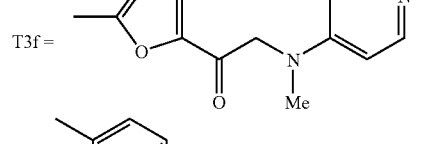

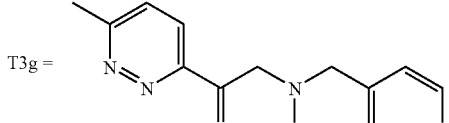

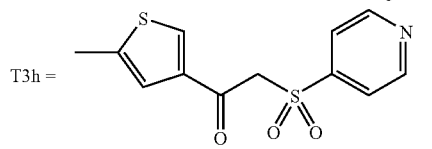

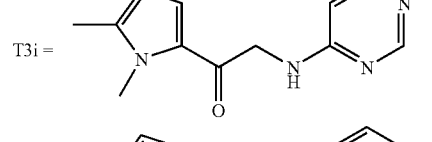

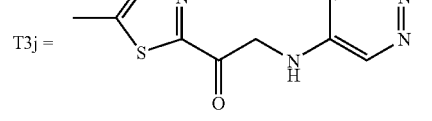

87) The compounds wherein A, B, R$^1$, L$^1$, R$^2$, L$^2$, L$^3$, Y, L$^4$, R$^3$ and X are any of the above combinations in Table 1, tautomers, prodrugs or pharmaceutically acceptable salts of the compounds or solvates thereof (provided that in the case of 87), Q1a, Q1b, Q1c, Q1i, Q1j, T3a, T3b, T3c, T3d, T3e, Q3e, T3f, T3g, T3h, T3i and T3j in Table 1 denote the following substituents.

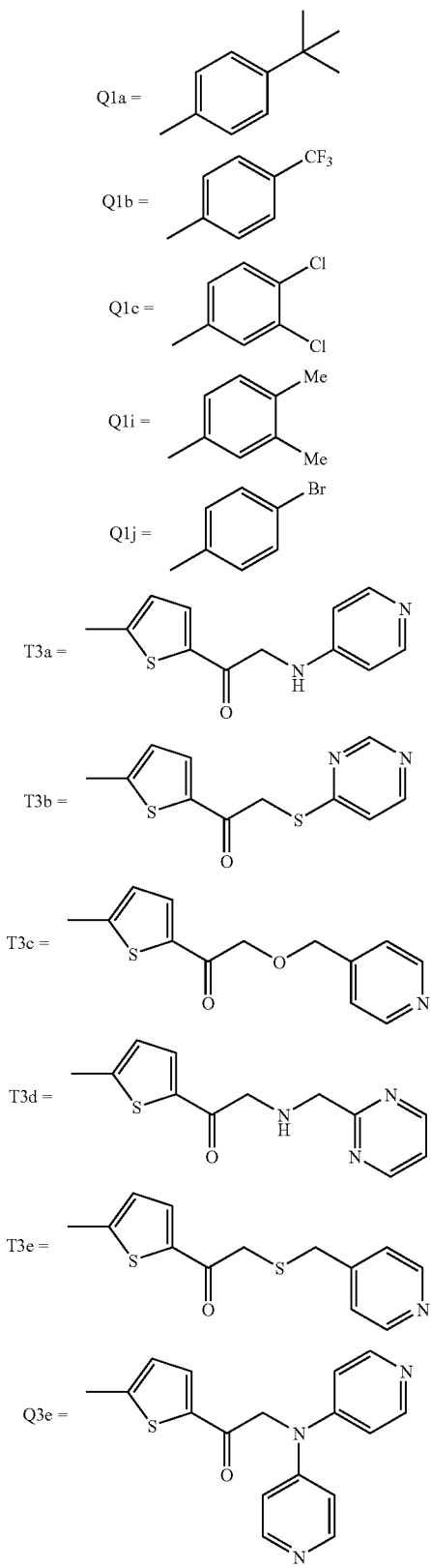

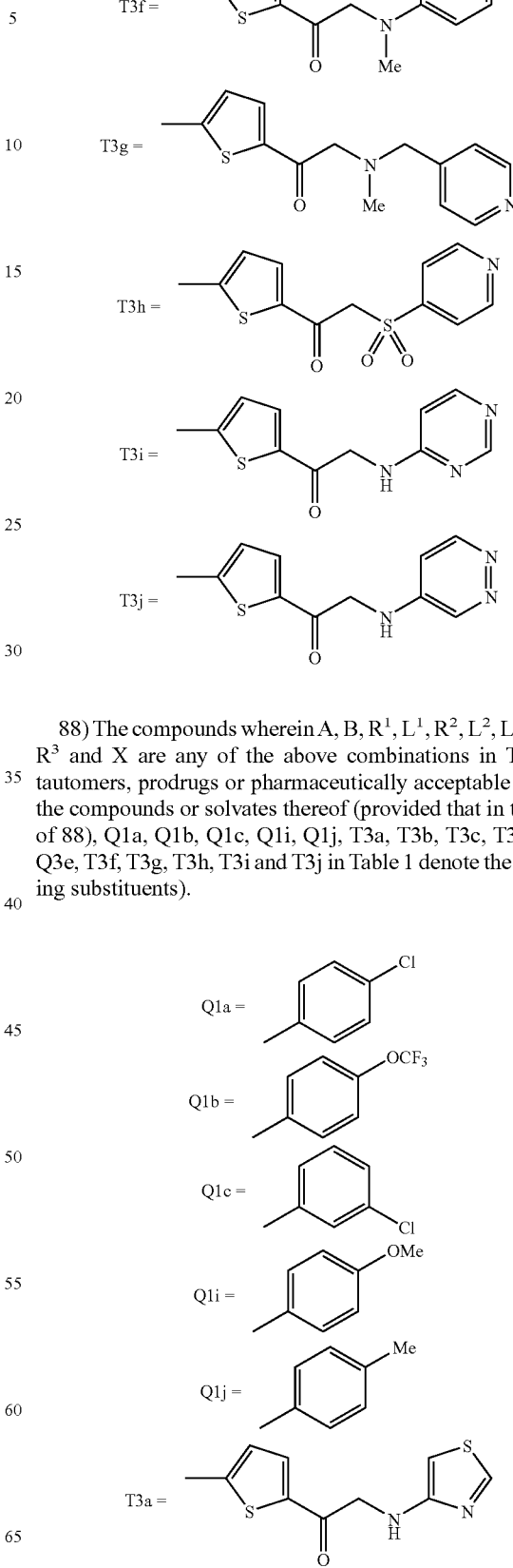

88) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 88), Q1a, Q1b, Q1c, Q1i, Q1j, T3a, T3b, T3c, T3d, T3e, Q3e, T3f, T3g, T3h, T3i and T3j in Table 1 denote the following substituents).

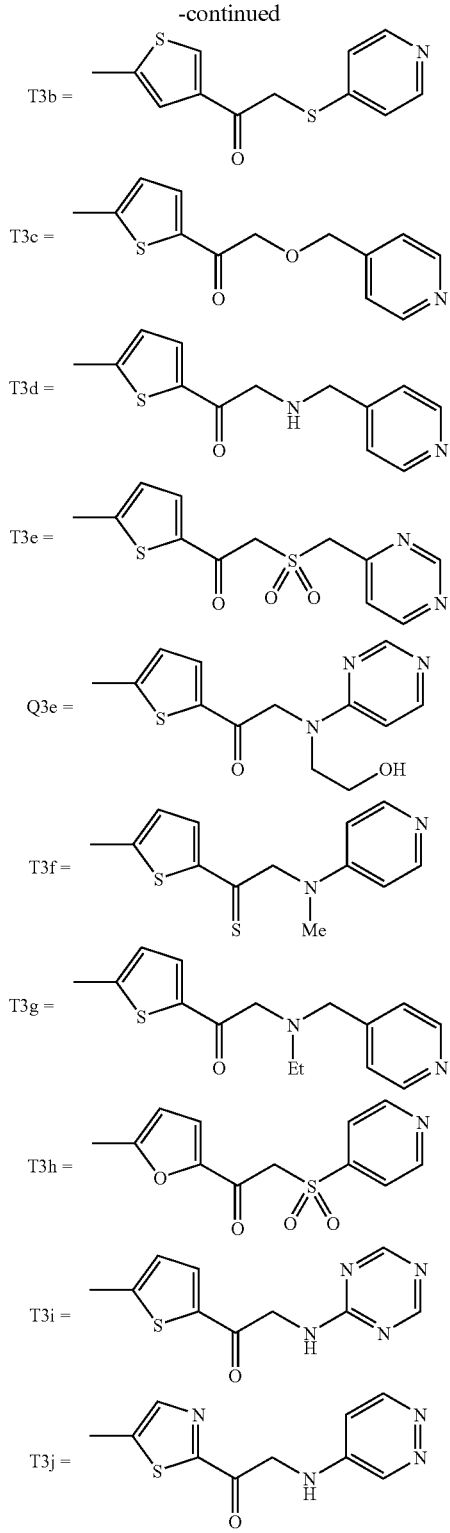
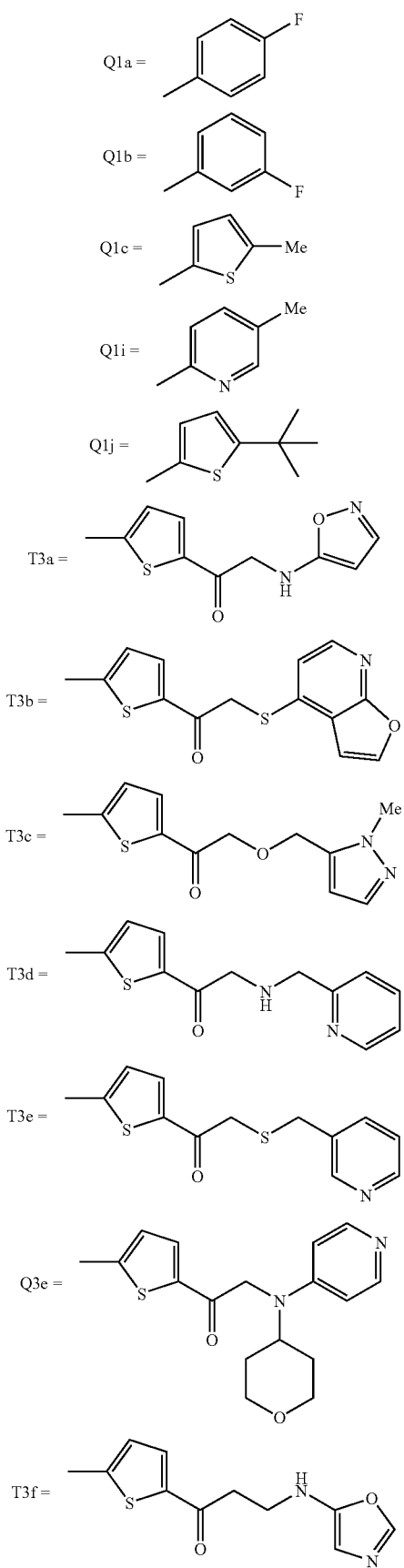
89) The compounds wherein A, B, R¹, L¹, R², L², L³, Y, L⁴, R³ and X are any of the above combinations in Table 1, tautomers, prodrugs or pharmaceutically acceptable salts of the compounds or solvates thereof (provided that in the case of 89), Q1a, Q1b, Q1c, Q1i, Q1j, T3a, T3b, T3c, T3d, T3e, Q3e, T3f, T3g, T3h, T3i and T3j in Table 1 denote the following substituents).

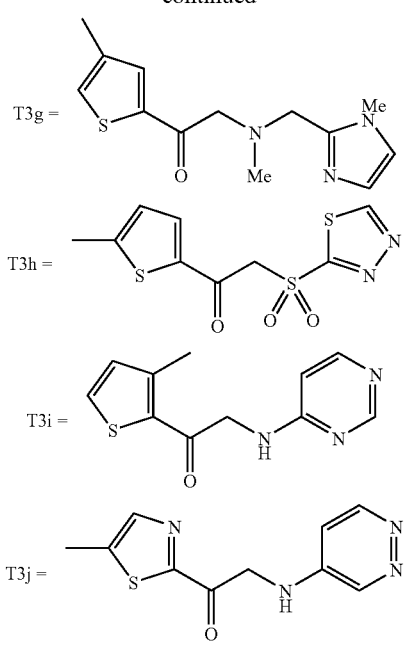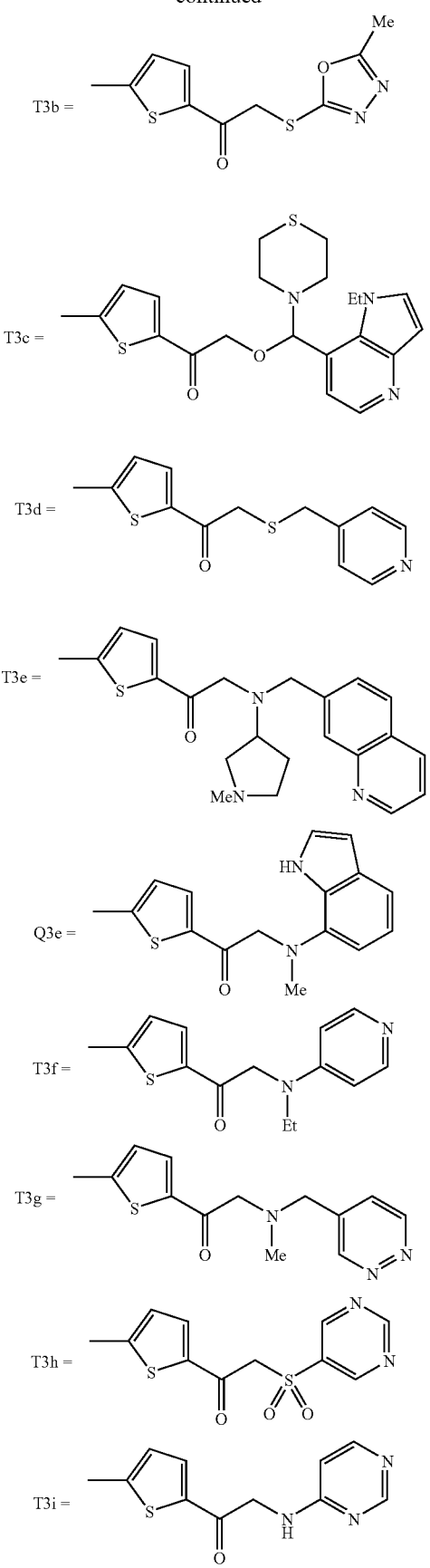
90) The compounds wherein A, B, $R^1$, $L^1$, $R^2$, $L^2$, $L^3$, Y, $L^4$, $R^3$ and X are any of the above combinations in Table 1, tautomers, prodrugs or pharmaceutically acceptable salts of the compounds or solvates thereof (provided that in the case of 90), Q1a, Q1b, Q1c, Q1i, Q1j, T3a, T3b, T3c, T3d, T3e, Q3e, T3f, T3g, T3h, T3i and T3j in Table 1 denote the following substituents).

T3j = 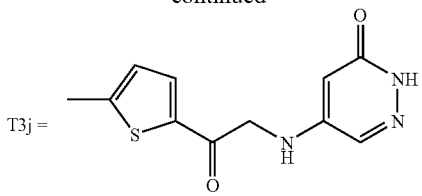

91) The compounds represented by any of 63) to 90), wherein X is converted to NH$_2$, tautomers, prodrugs or pharmaceutically acceptable salts of the compounds or solvates thereof.

92) The compounds represented by any of 63) to 90), wherein X is converted to SH, tautomers, prodrugs or pharmaceutically acceptable salts of the compounds or solvates thereof.

93) The compounds represented by any of 63) to 90), wherein X is converted to OAc, tautomers, prodrugs or pharmaceutically acceptable salts of the compounds or solvates thereof.

94) The thrombopoietin receptor activators represented by any of 1) to 93).

97) Medicaments containing the compounds represented by any of 1) to 93) or the formula (1), tautomers, prodrugs or pharmaceutically acceptable salts of the compounds or solvates thereof as an active ingredient.

In the present invention, the compounds of the present invention represented by the formula (1) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

For example, furan compounds, thiophene compounds and pyrrole compounds of the present invention may be present in the form of tetronic acid (4-hydroxy-2(5H)-furanone) analogues, thiotetronic acid (4-hydroxy-2(5H)-thiophenone) analogues and tetraminic acid (4-hydroxy-3-pyrrolin-2-one) analogues as shown below by the formulae (2), (3) and (4), mixtures thereof or mixtures of isomers thereof.

(2)

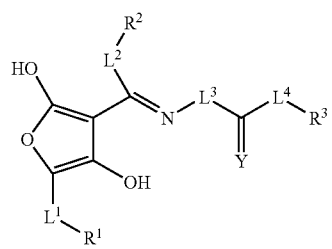 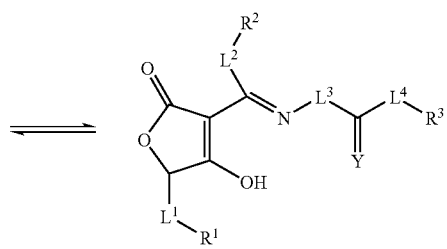

(3)

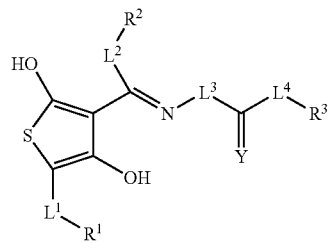 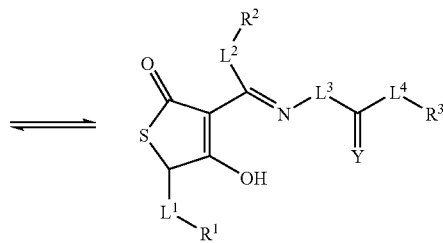

(4)

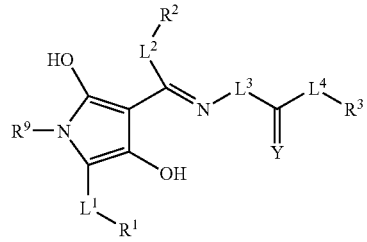 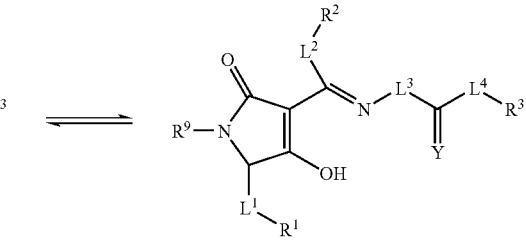

95) Preventive, therapeutic and improving agents for diseases against which activation of the thrombopoietin receptor is effective which contain the thrombopoietin receptor activators represented by 94) or the formula (1), tautomers, prodrugs or pharmaceutically acceptable salts of the activators or solvates thereof, as an active ingredient.

96) Platelet increasing agents containing the thrombopoietin receptor activators represented by 94) or the formula (1), tautomers, prodrugs or pharmaceutically acceptable salts of the activators or solvates thereof, as an active ingredient.

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary.

The pharmaceutically acceptable salts of the present invention may be, for example, salts with alkali metals (such as lithium, sodium and potassium) alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo Methods for selecting or producing appropriate prodrugs are disclosed, for example, in Design of Prodrug (Elsevier, Amsterdam 1985). In the present invention when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —OCO(t-Bu), —$OCOC_{15}H_{31}$, —OCO(m-$CO_2$Na-Ph), —$OCOCH_2CH_2CO_2Na$, —$OCOCH(NH_2)CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_{20}OCH_3$, —$NHCOCH(NH_2)CH_3$ and the like. When the compound of the present invention has a carboxyl group, carboxylic acid esters with aliphatic alcohols or carboxylic acid esters obtained by the reaction with an alcoholic free hydroxyl group of 1,2- or 1,3-digylcerides may, for example, be mentioned as prodrugs Particularly preferred prodrugs are methyl esters and ethyl esters.

The preventive, therapeutic and improving agents for diseases against which activation of the thrombopoietin receptor is effective or platelet increasing agents which contain the thrombopoietin receptor activators of the present invention tautomers, prodrugs or pharmaceutically acceptable salts of the activators or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections into an adult, though it depends on the age and conditions of the patient. The above-mentioned ranges are mere examples and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (1) are prepared by the process represented by the formula (5) illustrated below.

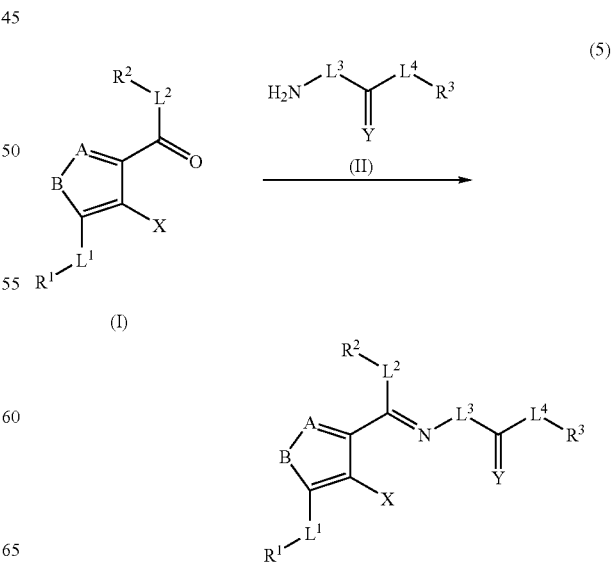

The reaction of the compound (I) with a —NH₂ compound (II) in a solvent, if necessary in the presence of a catalyst, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

For the syntheses of the intermediates (I), syntheses of the following heterocyclic compounds may be referred to.

1) Pyrazole (the formula (6))
J. Chem. Soc. Perkin. TransI, p. 81, (1985)
2) Isothiazole (the formula (7))
Liebigs. Annalen. der Chemie., 10, 1534-1546 (1979)
3) Isoxazole (the formula (8))
Synthesis, 10, 664-665 (1975)
4) Thiophene (the formula (9))
JP-A-48-026755
5) Furan (the formula (10))
J. Org. Chem., 21, 1492-1509 (1956) and EP1253146
6) Pyrrole (the formula (11))
J. Heterocyclic Chem., 30, 1253 (1993) and Tetrahedron 50(26), 7849-56 (1994)
7) Tetronic acid (4-hydroxy-2(5H-furanone) analogue (the formula (12))
Synthesis 7, 564-566 (1988) and Yakugaku Zasshi, 96(4), 536-543 (1976)
8) Tetraminic acid (4-hydroxy-3-pyrrolin-2-one) analogue (the formula (13))
Synthesis, 2, 190-192 (1987) and Agric. Biol. Chem., 43(8), 1641-1646 (1979)

(6)

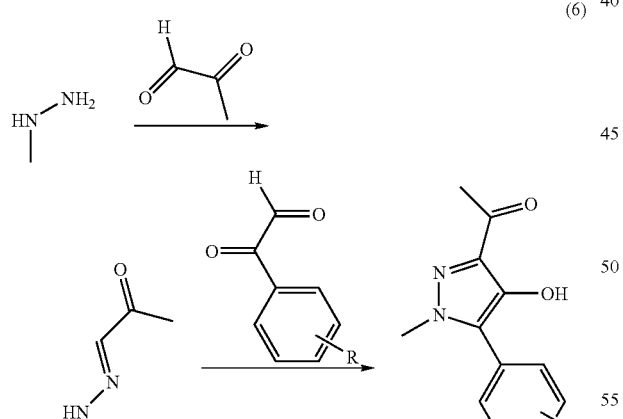

(7)

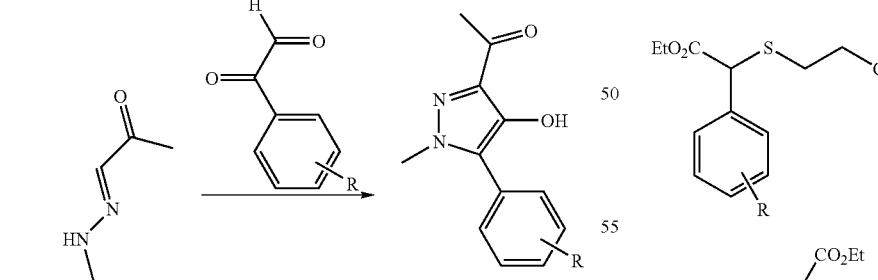

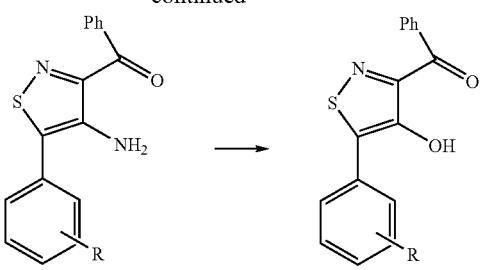

(8)

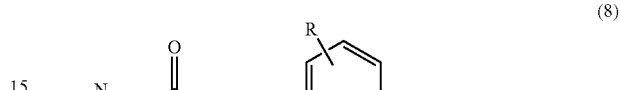

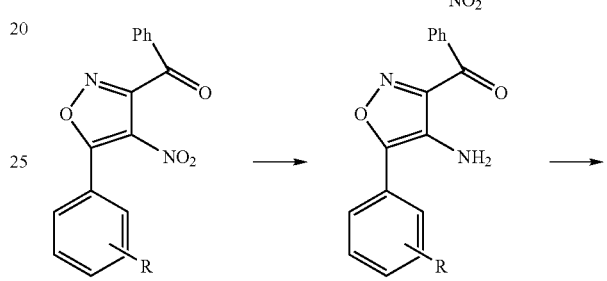

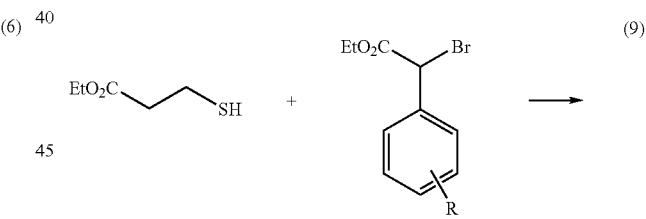

(9)

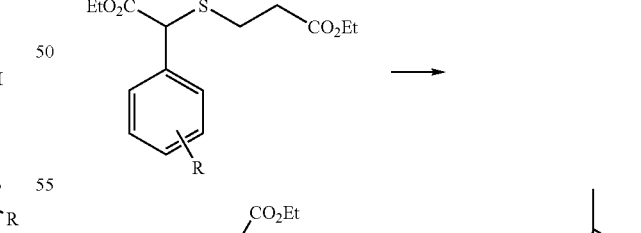

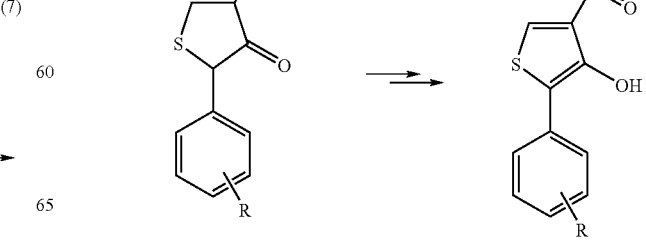

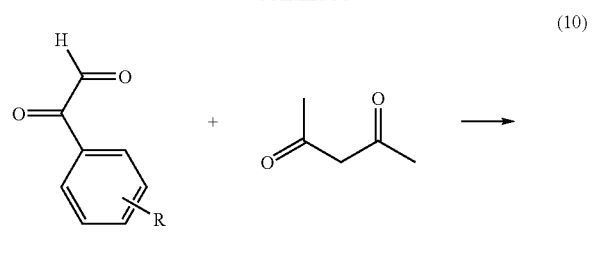
(10)
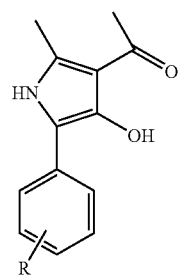
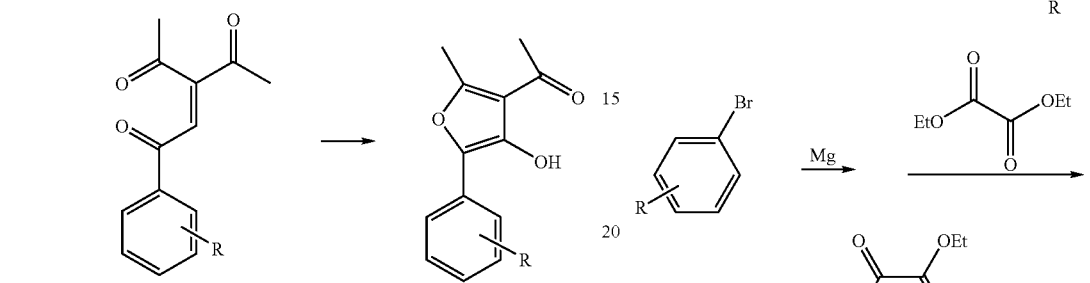
(11)
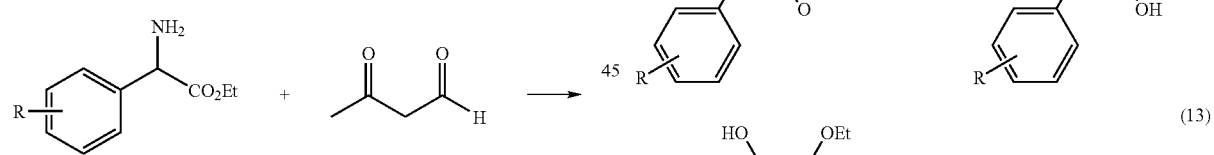
(12)
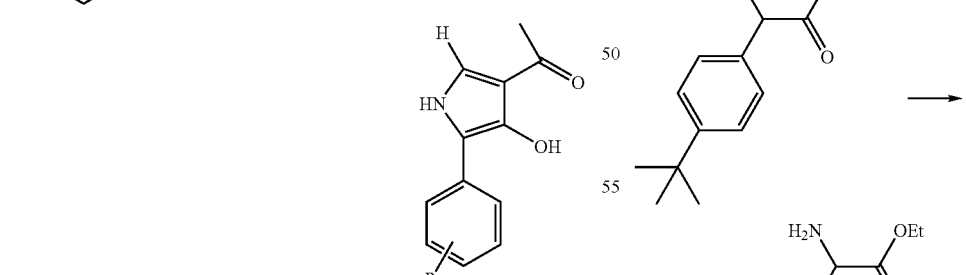
(13)
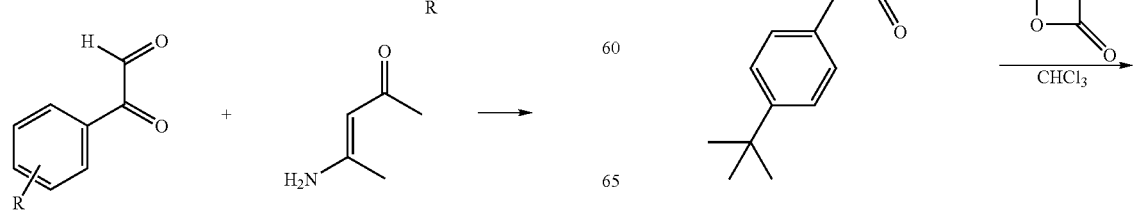

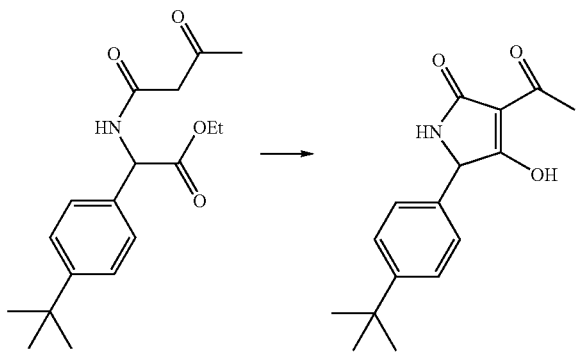

For synthesis of the —NH₂ compounds (II), for example, when $L^3$=NH, the following may be referred to.

1) $L^4$=a bond, Y=O

Synthetic Commun., 28(7), 1223-1231 (1998), J. Chem. Soc., 1225 (1948) and J. Chem. Soc., 2831 (1952)

2) $L^4$=NH, Y=O

J. Am. Chem. Soc., 46, 2813 (1924) and J. Chem. Soc., 2654 (1952)

3) $L^4$=NH, Y=S

Can. J. Chem 35, 834 (1957)

4) $L^4$=CH₂, Y=O

J. Org. Chem., 30, 2487 (1965)

5) $L^4$=O, Y=O

Bull. Soc. Chim. Belg., 68, 409, (1959)

The compounds represented by the formula (1) wherein $L^3$ is $NR^{19}$, $L^4$ is NH, and Y is O or S are prepared by the process represented by the formula (14) illustrated below.

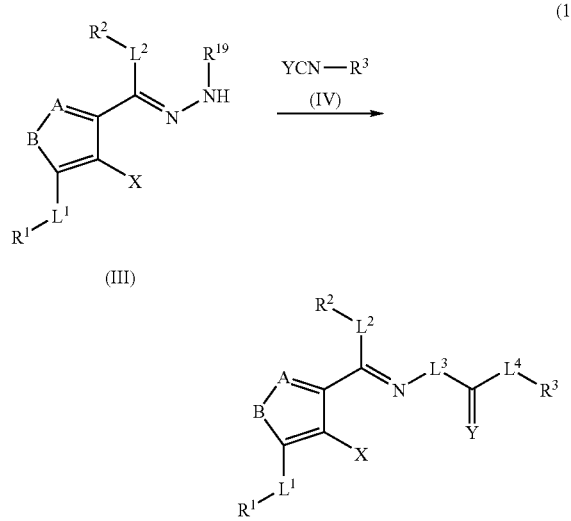

The compounds represented by the formula (1) wherein $L^3$ is $NR^{19}$, L is a bond, and Y is O or S are prepared by the process represented by the formula (15) illustrated below.

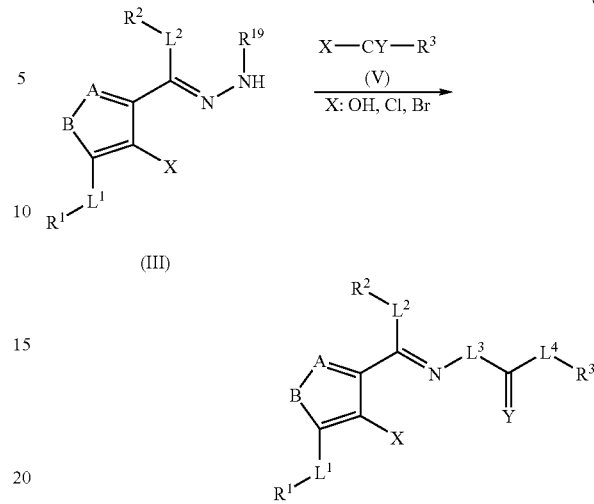

The reaction of the compound (I) with a NH₂ compound (IV) in a solvent, if necessary in the presence of a condensation agent or a catalyst, under heating with stirring gives the compound (III) as the desired product.

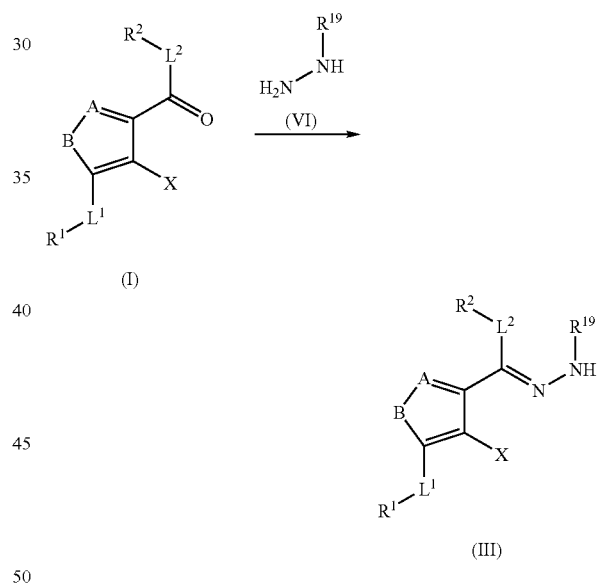

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

The ¹H-NMR analysis was carried out at 300 MHz, and the ¹³C-NMR analysis was carried out at 75 MHz. LC/MS was measured under the following conditions.

LC/MS Condition 1

Column: Waters SunFire C18 (3.5 μm, 4.6×30 mm)

Eluent: acetonitrile/0.1% aqueous formic acid (10/90→30/70)

LC/MS Condition 2
  Column: Waters SunFire C18 (3.5 μm, 4.6×30 mm)
  Eluent: acetonitrile/0.1% aqueous formic acid (10/90→60/40)
LC/MS Conditions 3
  Column: Waters SunFire C18 (3.5 μm, 4.6×30 mm)
  Eluent: acetonitrile/0.1% aqueous formic acid (10/90→85/15)
LC/MS Conditions 4
  Column: Waters Xterra MSC18 (5 μm, 4.6×50 mm)
  Eluent: acetonitrile/0.1% aqueous formic acid (10/90→30/70)
LC/MS Conditions 5
  Column: Waters Xterra MSC18 (5 μm, 4.6×50 mm)
  Eluent: acetonitrile/0.1% aqueous formic acid (10/90→60/40)
LC/MS Conditions 6
  Column: Waters Xterra MSC18 (5 μm, 4.6×50 mm)
  Eluent acetonitrile/0.1% aqueous formic acid (10/90→85/15)
LC/MS Conditions 7
  Column: Waters Xterra MSC18 (5 μm, 4.6×50 mm)
  Eluent: acetonitrile/0.1% aqueous formic acid (20/80→100/0)
LC/MS Conditions 8
  Column: Waters Xterra MSC18 (3.5 μm, 2.1×20 mm)
  Eluent: acetonitrile/0.2% aqueous formic acid (20/80→90/10)
LC/MS Conditions 9
  Column: Waters SunFire C18 (3.5 μm, 4.6×30 mm)
  Eluent: acetonitrile/0.1% aqueous formic acid (20/80→100/0)

Reference Synthetic Example 1

5-(Hydrazinocarbonyl)thiophene-2-carboxylic acid [2-(pyrrolidin-1-yl)ethyl]-amide Methyl 5-[2-(pyrrolidin-1-yl)ethylcarbamoyl]-thiophene-2-carboxylate (56 mg, 0.2 mmol) in ethanol (2.0 mL) was refluxed with heating with hydrazine monohydrate (0.10 mL) for 10 hours and allowed to cool to room temperature, and the precipitated solid was collected by filtration, washed with water and dried to give 21 mg of the desired product (yield 38%).
  Morphology: white solid
  LC/MS (ESI$^+$) m/z; 297 [M+1]$^+$
  LC/MS (ESI$^-$) m/z; 295 [M−1]$^-$ Reference Synthetic Example 2

5-(Hydrazinocarbonyl)thiophene-2-carboxylic acid(tetrahydrofuran-2-ylmethyl)amide Synthesis was carried out in the same manner as in Reference Synthetic Example 1 by using methyl 5-[(tetrahydrofuran-2-ylmethyl)carbamoyl]-thiophene-2-carboxylate to give 17 mg of the desired product (yield 32%).
  Morphology: white solid
  LC/MS (ESI$^+$) m/z; 270 [M+1]$^+$
  LC/MS (ESI$^-$) m/z; 268 [M−1]$^-$ Reference Synthetic Example 3

5-(Hydrazinocarbonyl)thiophene-2-carboxylic acid[2-(morpholin-4-yl)ethyl]amide

Synthesis was carried out in the same manner as in Reference Synthetic Example 1 by using methyl 5-[2-(morpholin-4-yl)ethylcarbamoyl]thiophene-2-carboxylate to give 30 mg of the desired product (yield 50%).
  Morphology: white solid
  LC/MS (ESI$^+$) m/z; 299 [M+1]$^+$
  LC/MS (ESI$^-$) m/z; 297 [M−1]$^-$ Reference Synthetic Example 4

2,5-Di(hydrazinocarbonyl)thiophene

Synthesis was carried out in the same manner as in Reference Synthetic Example 1 by using dimethyl thiophene-2,5-dicarboxylate to give 28 mg of the desired product.
  Morphology: pale green solid
  $^1$H-NMR (DMSO-d$_6$) δ: 4.51 (4H, s), 7.64 (2H, s), 9.88 (2H, br s).
  LC/MS (ESI$^-$) m/z; 199 [M−1]$^-$ Reference Synthetic Example 5

N-[1-(5-Hydrazinocarbonylthiophene-2-carbonyl)-pyrrolidin-3-yl]acetamide

Synthesis was carried out in the same manner as in Reference Synthetic Example 1 by using methyl 5-[3-(acetylamino)pyrrolidine-1-carbonyl]thiophene-2-carboxylate to give 37 mg of the desired product (yield 62%).
  Morphology: white solid
  LC/MS (ESI$^+$) m/z; 297 [M+1]$^+$
  LC/MS (ESI$^-$) m/z; 295 [M−1]$^-$ Reference Synthetic Example 6

2-(N,N-Dimethylhydrazinocarbonyl)-5-(hydrazinocarbonyl)thiophene

Methyl 5-(N,N-dimethylhydrazinocarbonyl)thiophene-2-carboxylate (46 mg, 0.2 mmol) in ethanol (2.0 mL) was refluexed with heating with hydrazine monohydrate (0.10 mL) for 10 hours and allowed to cool to room temperature. After addition of 3 mL of waster, the reaction solution was extracted with 10 mL of ethyl acetate, and the extract was dried over magnesium sulfate, filtered and concentrated to give 23 mg of the desired product (yield 50%).
  Morphology: colorless oil
  LC/MS (ESI$^+$) m/z; 229 [M+1]$^+$
  LC/MS (ESI$^-$) m/z; 227 [M−1]$^-$ Reference Synthetic Example 7 tert-Butyl 3-{[5-(hydrazinocarbonyl)thiophene-2-carbonyl]amino}propionate

Synthesis was carried out in the same manner as in Reference Synthetic Example 1 by using methyl 5-[2-tert butoxycarbonyl)ethylcarbamoyl]thiophene-2-carboxylate to give 37 mg of the desired product (yield 62%).
  Morphology: white solid
  LC/MS (ESI$^+$) m/z; 314 [M+1]$^+$
  LC/MS (ESI$^-$) m/z; 312 [M−1]$^-$ Reference Synthetic Example 8 tert-Butyl{[5-(hydrazinocarbonyl)thiophene-2-carbonyl]amino}acetate

Methyl 5-(tert-butoxycarbonylmethylcarbamoyl)thiophene-2-carboxylate (63 mg, 0.21 mmol) in ethanol (3.0 mL) was refluexed with heating with hydrazine monohydrate (0.13 mL) for 8 hours and allowed to cool to room temperature. The reaction mixture was concentrated under reduced pressure, and water was added. The precipitated solid was collected by filtration, washed with water and dried to give 44 mg of the desired product (yield 71%).
Morphology: white solid
LC/MS (ESI$^+$) m/z; 300 [M+1]$^+$
LC/MS (ESI$^-$) m/z; 298 [M−1]$^-$ Reference Synthetic Example 9

5-(Hydrazinocarbonyl)thiophene-2-carboxylic acid piperidin-1-ylamide

Methyl 5-piperidin-1-ylcarbamoyl)thiophene-2-carboxylate (232 mg, 0.87 mmol) in ethanol (6.0 mL) was refluexed with heating with hydrazine monohydrate (0.40 mL) for 3 hours and allowed to cool to room temperature, and the precipitated solid was collected by filtration, washed with water and dried to give 129 mg of the desired product (yield 56%).
Morphology: white solid
LC/MS (ESI$^+$) m/z; 269 [M+1]$^+$
LC/MS (ESI$^-$) m/z; 267 [M−1]$^-$ Reference Synthetic Example 10

5-(Hydrazinocarbonyl)thiophene-2-carboxylic acid (4-methylpiperazin-1-yl)amide

Methyl 5-(4-methylpiperazin-1-ylcarbamoyl)thiophene-2-carboxylate (218 mg, 0.77 mmol) in ethanol (60 mL) was refluexed with heating with hydrazine monohydrate (0.40 mL) for 6 hours and allowed to cool to room temperature, and the solvent was evaporated at 40° C. mL of diethyl ether was added to the resulting oil, and the precipitated solid was collected by filtration, washed with water and dried to give 142 mg of the desired product (yield 65%).
Morphology: pale yellow solid
LC/MS (ESI$^+$) m/z; 284 [M+1]$^+$
LC/MS (ESI$^-$) m/z; 282 [M−1]$^-$ Reference Synthetic Example 11

5-(Hydrazinocarbonyl)thiophene-2-carboxylic acid morpholin-4-ylamide

Methyl 5-(morpholin-4-ylcarbamoyl)thiophene-2-carboxylate (237 mg, 0.87 mmol) in ethanol (6.0 mL) was refluexed with heating with hydrazine monohydrate (0.40 mL) for 6 hours and allowed to cool to room temperature and the solvent was evaporated at 40° C. 5 mL of diethyl ether was added to the resulting oil, and the precipitated solid was collected by filtration, washed with water and dried to give 160 mg of the desired product (yield 68%).
Morphology: pale yellow solid
LC/MS (ESI$^+$) m/z; 271 [M+1]$^+$
LC/MS (ESI$^-$) m/z; 269 [M−1]$^-$ Reference Synthetic Example 12

5-[4-Pyrrolidin-1-yl)piperidine-1-carbonyl]thiophene-2-carbohydrazide

Methyl 5-[4-(pyrrolidin-1-yl)piperidine-1-carbonyl]thiophene-2-carboxylate (242 mg, 0.75 mmol) in ethanol (7.0 mL) was refluexed with heating with hydrazine monohydrate (0.38 mL) for 12 hours and allowed to cool to room temperature, and the solvent was evaporated at 40° C. 5 mL of diethyl ether was added to the resulting oil, and the precipitated solid was collected by filtration, washed with water and dried to give 193 mg of the desired product (yield 80%).
Morphology: pale yellow solid
LC/MS (ESI$^+$) m/z; 323 [M+1]$^+$ Reference Synthetic Example 13

2-(3,4-Dichlorophenyl)-4-(1-hydrazonoethyl)-thiophen-3-ol 2-(3,4-Dichlorophenyl)-3-hydroxy-4-(methylcarbonyl)thiophene (50 mg, 0.17 mmol) (prepared by the method disclosed in WO2004/108683) in isopropanol was stirred with hydrazine monohydrate (95 μL/0.19 mmol) at 90° C. for 1 hour, then allowed to cool to room temperature and stirred at 0° C. The precipitated solid was collected by filtration and dried to give 36 mg of the desired product (yield 69%).
Morphology: white solid
LC/MS (ESI$^+$) m/z; 301 [M+1]$^+$
LC/MS (ESI$^-$) m/z; 299 [M−1]$^-$ Reference Synthetic Example 14

3-(1-Hydrazonoethyl)-1-methyl-5-[4-(trifluoromethyl)phenyl]-1H-pyrazol-4-ol

1-[4-Hydroxy-1-methyl-5-[4-trifluoromethyl)phenyl]-1H-pyrazol-3-yl]ethanone (2.72 g, 9.57 mmol) (prepared by the method disclosed in WO2004/108683) was dissolved in 1,4-dioxane (82 mL), and hydrazine monohydrate (0.512 mL, 10.53 mmol) was added dropwise at 50° C. The reaction solution was stirred at the same temperature for 3 hours and then allowed to cools and ethyl acetate was added. The organic layer was washed with saturated aqueous sodium chloride three times, dried over anhydrous magnesium sulfate and filtered. The filtrate was dried by evaporating the solvent to give 2.90 g of the desired product (yield 102%).
Morphology: yellow solid
LC/MS (ESI$^+$) m/z; 299 [M+1]$^+$
LC/MS (ESI$^-$) m/z; 297 [M−1]$^-$ Reference Synthetic Example 15

Potassium 3-[4-(hydrazinocarbonyl)phenyl]-3-hydroxypropionate 15-a) Methyl 4-(2-tert-butoxycarbonyl-1-hydroxyethyl)benzoate Diisopropylamine (0.55 mL, 3.9 mmol) was dissolved in dry tetrahydrofuran (10 mL), and 2.66 M n-butyllithium in hexane (1.4 mL, 3.6 mmol) was added dropwise at 0° C. The reaction solution was stirred at 0° C. for 10 minutes and cooled to −78° C., and after dropwise addition of tert-butyl acetate (0.58 mL, 4.3 mmol), stirred at −78° C. for 30 minutes. Methyl 4-formylbenzoate (0.70 g, 4.3 mmol) in tetrahydrofuran (6 mL) was added dropwise at −78° C. over 5 minutes, and the reaction solution was stirred at −78° C. for 10 minutes and at 0° C. for 1 hour, then adjusted to pH 7 with acetic acid (0.43 mL, 7.5 mmol) and returned to room temperature over 12 hours. The solution was concentrated by evaporating tetrahydrofuran under reduced pressure, and ethyl acetate and water were added. The organic layer was separated and dried under reduced pressure to dryness to give 1.17 g of the crude desired product. The crude desired product was purified by silica gel column chromatography (Merck silica gel 60, 22 g, n-hexane-ethyl acetate 4:1) to give 0.84 g of the desired product (yield 84%).
Morphology: colorless solid
$^1$H-NMR (CDCl$_3$) δ: 1.45 (9H, s), 2.65 (1H, dd, J=16.5&7.0 Hz), 2.66 (1H, dd, J=16.5&5.5 Hz), 3.66 (1H, d, J=3.5 Hz), 3.91 (3H, s), 5.09-5.17 (1H, m), 7.45 (1H, d, J=8.5 Hz), 8.02 (1H, d, J=8.5 Hz).

15-b) Methyl 4-(2-carboxy-1-hydroxyethyl)benzoate

Methyl 4-(2-tert-butoxycarbonyl-1-hydroxyethyl)benzoate (140 mg, 0.50 mmol) was dissolved in trifluoroacetic acid (2.0 mL), and the resulting solution was left to stand at room temperature for 3 hours and concentrated to dryness under reduced pressure to give 113 mg of the desired product (stoichiometric yield).
Morphology: colorless solid
$^1$H-NMR (DMSO-d$_6$) δ: 2.50 (1H, dd, J=15.5&8.5 Hz: overlapped with DMSO), 2.57 (1H, dd, J=15.5&5.0 Hz), 3.82 (3H, s), 5.00 (1H, dd, J=8.5&5.0 Hz) 5.4-5.8 (1H, br s), 7.50 (1H, d, J=8.0 Hz, 7.91 (1H, d, J=8.0 Hz).

15-c) Potassium 3-[4-(hydrazinocarbonyl)phenyl]-3-hydroxypropionate

Methyl 4-(2-carboxy-1-hydroxyethyl)benzoate (110 mg, 0.49 mmol) was dissolved in methanol (2.0 mL) 0.1 M potassium hydroxide in methanol (4.9 mL, 0.49 ml) was added, and then, hydrazine monohydrate (0.24 mL, 4.9 mmol) was added at room temperature. The resulting solution was left to stand at 45° C. for 1 hour and at 60° C. for 2.5 hours, but the starting materials were little consumed The solution was concentrated under reduced pressure by evaporating methanol, and left to stand with water at 80° C. for 1 hour to force the reaction to completion. The reaction solution was concentrated to dryness to give the crude desired product.
Morphology: colorless solid
$^1$H-NMR (DMSO-d$_6$) δ: 1.93 (1H, dd, 15.0&9.5 Hz), 2.19 (1H, dd, J=15.0&3.5 Hz), 4.3-4.6 (2H, br s), 4.69 (1H, dd, J=9.5&3.5 Hz), 7.35 (1H, d, J=8.0 Hz), 7.71 (1H, d, J=80 Hz), 9.67 (1H, br s).

Reference Synthetic Examples 16 to 22

Synthesis was carried out in the same manner as in Reference Synthetic Example 1, except that Reference Synthetic Example 18 was carried out in the same manner as in Reference Synthetic Example 15, and the yields and morphology of the resulting compounds, the LC/MS conditions used for their analysis and the observed peaks and retention times are shown in Table 3.

TABLE 3

| Syn. Ex. No. | Yield (%) | Morphology | LC/MS conditions | Observed peak ESI$^+$ | Observed peak ESI$^-$ | Retention time (minute) |
|---|---|---|---|---|---|---|
| 16 | 100 | white solid | 8 | 313 | 311 | 0.47 |
| 17 | 89 | white solid | | | | |
| 18 | 100 | pale yellow solid | | | | |
| 19 | 77 | pale yellow, amorphous | 1 | 300 | 298 | 0.48 |
| 20 | 50 | white solid | | | | |
| 21 | 84 | white solid | 2 | 287 | 276 | 0.28 |
| 22 | 67 | pale yellow, amorphous | 8 | 272 (M − isobutene + 1) | | 1.30 |

Reference Synthetic Examples 23 to 26

Synthesis was carried out by the method disclosed in WO2004/108683, and the yields and morphology of the resulting compounds, the LC/MS conditions used for their analysis and the observed peaks and retention times are shown in Table 4.

TABLE 4

| Syn. Ex. No. | Morphology | LC/MS conditions | Observed peak ESI$^+$ | Observed peak ESI$^-$ | Retention time (minute) |
|---|---|---|---|---|---|
| 23 | yellow solid | 2 | 247 | 245 | 4.52 |
| 24 | yellow solid | 9 | 303 | 301 | 3.34 |
| 25 | light brown solid | 2 | 297/299 | 295/297 | 4.54 |
| 26 | pale green solid | 2 | 253/255 | 251/253 | 4.49 |

Reference Synthetic Example 27

3-(1-Hydrazonoethyl)-1-methyl-5-(3,4-dichlorophenyl)-1H-pyrazol-4-ol

Synthesis was carried out in the same manner as in Reference Synthetic Example 14 by using 1-[4-hydroxy-1-methyl-5-(3,4-dichlorophenyl)-1H-pyrazol-3-yl]ethanone (prepared by the method disclosed in WO2004/108683) to give 326 mg of the desired product (yield 100%).
Morphology: pale yellow solid
$^1$H-NMR (CDCl$_3$) δ: 2.23 (3H, s), 3.84 (3H, s), 5.24 (2H, s), 7.35 (1H, dd, J=8.5&2.0 Hz), 753 (1H, d, J=8.5 Hz), 7.61 (1H, d, J=2.0 Hz), 9.01 (1H, br s).

Reference Synthetic Example 28

5-[2-(4-Oxopyridin-1(4H)-yl)acetyl]thiophene-2-carboxylic acid

1) Synthesis of methyl 5-(2-bromoacetyl)thiophenecarboxylate 1.08 g (5.86 mmol) of methyl 5-acetylthiophenecarboxylate was dissolved in 40 ml of tetrahydrofuran, and the resulting solution was cooled to 0° C. and stirred with 2.31 g (6.15 mmol) of phenyltrimethylammonium tribromide at room temperature for 24 hours. 50 ml of water was added to terminate the reaction, and the reaction solution was extracted with 50 ml of ethyl acetate twice. The organic layer was dried over magnesium sulfate, then the magnesium sulfate was removed by filtration, and the solvent was evaporated to give 2.20 g of a light brown solid. It was recrystallized from hexane 40 ml-chloroform 7 ml to give 990 mg of methyl 5-(2-bromoacetyl)thiophenecarboxylate (yield 64%).

Morphology: light brown solid
LC/MS (ESI+) m/z; 263, 265 [M+1]+
Retention time 2.79 minutes (condition 6)

2) Methyl 5-[2-(4-oxopyridin-1(4H)-yl)acetyl]thiophene-2-carboxylate 263 mg (1.00 mmol) of methyl 5-(2-bromoacetyl)thiophenecarboxylate obtained in 1), 100 mg (1.05 mmol) of 4-hydroxypyridine and 151 mg (1.0 mmol) of potassium carbonate were stirred in 5 ml of methyl ethyl ketone at room temperature for 3 days After addition of 10 ml of water, the organic solvent was evaporated, and 20 ml of water was added. The precipitate was collected by filtration and dried to give 189 mg of methyl 5-[2-(4-oxopyridin-1(4H)-yl)acetyl]thiophene-2-carboxylate (yield 68%).

Morphology: pale purple solid
LC/MS (ESI+) m/z; 278 [M+1]+
LC/MS (ESI−) m/z; 276 [M−1]−
Retention time 1.53 minutes (condition 6)
$^1$H-NMR (CDCl$_3$) δ: 2.08 (3H, s), 5.12 (2H, s) 6.44 (2H, d, J=7.0 Hz), 7.20 (2H d, J=7.0 Hz) 7.76 (2H, d, J=2.0 Hz), 7.84 (2H, d, 2.0 Hz).
$^{13}$C-NMR (DMSO-d$_6$) δ: 52.9, 60.8, 117.1, 133.6, 134.2, 139.1, 141.9, 144.8, 161.2, 176, 187.3.

3) 5-[2-(4-Oxopyridin-1(4H)-yl)acetyl]thiophene-2-carboxylic acid 189 mg (0.68 mmol) of methyl 5-[2-(4-oxopyridin-1(4H)-yl)acetyl]thiophene-2-carboxylate obtained in 2) was dissolved in 15 ml of methanol and stirred with 2.7 ml (4 eq) of 1M aqueous sodium hydroxide at room temperature overnight. The reaction solution was cooled to 0° C. and neutralized with 2.7 ml of 1 M hydrochloric acid, and the organic solvent was evaporated. The precipitated solid was collected by filtration, washed with 2 ml of water and dried to give 129 mg of 5-[2-(4-oxopyridin-1(4H)-yl)acetyl]thiophene-2-carboxylic acid (yield 72%).

Morphology: red solid
LC/MS (ESI+) m/z; 264 [M+1]+
LC/MS (ESI−) m/z; 262 [M−1]−
Retention time 0.47 minutes (condition 6)
$^1$H-NMR (DMSO-d$_6$) δ: 5.62 (2H, s) 6.20 (2H, d, J=7.0 Hz), 7.65 (2H, d, J=7.0 Hz), 7.87 (2H, d, J=2.0 Hz), 8.06 (2H, d, J=2.0 Hz).

The structures of the compounds obtained in Reference Synthetic Examples 16 to 28 are shown below.

Reference Synthetic Example 16

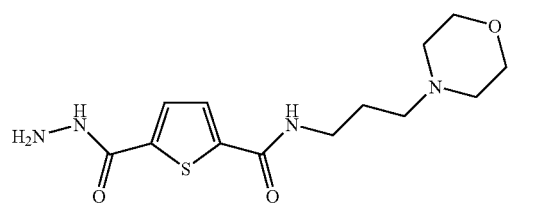

Reference Synthetic Example 17

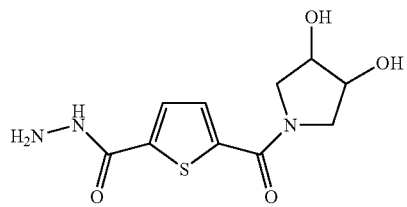

Reference Synthetic Example 18

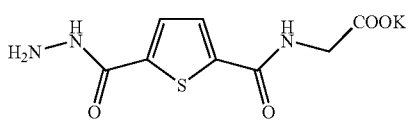

Reference Synthetic Example 19

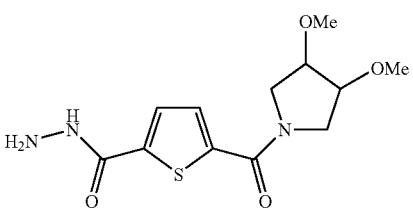

Reference Synthetic Example 20

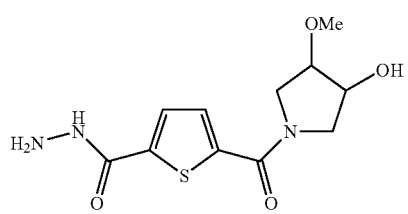

Reference Synthetic Example 21

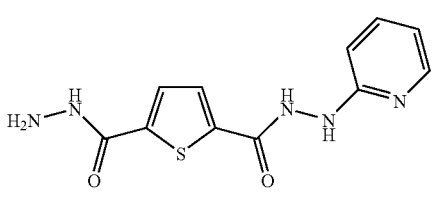

Reference Synthetic Example 22

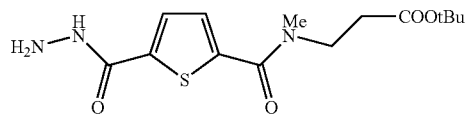

Reference Synthetic Example 23

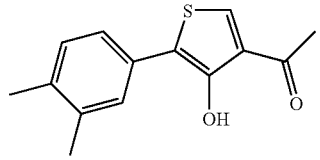

Reference Synthetic Example 24

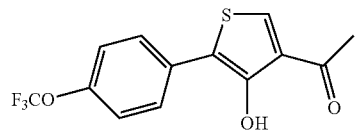

Reference Synthetic Example 25

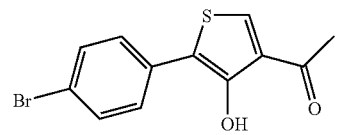

Reference Synthetic Example 26

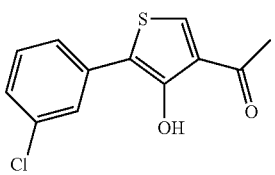

Reference Synthetic Example 27

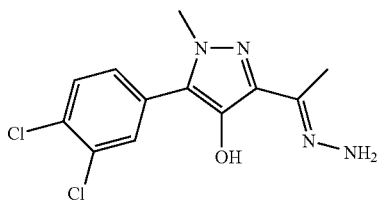

Reference Synthetic Example 28

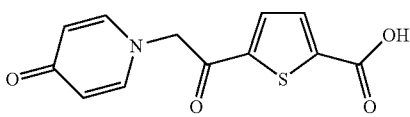

Synthetic Example 1

5-{1-[5-(3,4-Dichlorophenyl)-4-hydroxythiophen-3-yl]ethylidenehydrazinocarbonyl}thiophene-2-carboxylic acid [2-(pyrrolidin-1-yl)ethyl]amide 2-(3,4-Dichlorophenyl)-3-hydroxy-4-methylcarbonylthiophene (22 mg, 0.075 mmol) in dimethyl sulfoxide (2.0 mL) was heated with 5-(hydrazinocarbonyl)thiophene-2-carboxylic acid [2-(pyrrolidin-1-yl)ethyl]-amide (21 mg, 0.075 mmol) prepared in Reference Synthetic Example 1 at 100° C. for 24 hours. Evaporation of the solvent followed by recrystallization from chloroform (1 mL)-diethyl ether (2 mL) afforded 12 mg of the desired product (yield 29%).
Morphology: orange solid
LC/MS (ESI$^+$) m/z; 551, 553 [M+1]$^+$
LC/MS (ESI$^-$) m/z; 549, 551 [M−1]$^-$ Synthetic Example 2

5-{1-[5-(3,4-Dichlorophenyl)-4-hydroxythiophen-3-yl]ethylidenehydrazinocarbonyl}thiophene-2-carboxylic acid(tetrahydrofuran-2-ylmethyl)amide 2-(3,4-Dichlorophenyl)-3-hydroxy-4-methylcarbonylthiophene (22 mg, 0.075 mmol) in isopropanol (2.0 mL) was heated with 5-(hydrazinocarbonyl)thiophene-2-carboxylic acid (tetrahydrofuran-2-ylmethyl)amide (20 mg, 0.075 mmol) prepared in Reference Synthetic Example 2 and 3 mg of p-toluenesulfonic acid monohydrate at 105° C. for 17 hours and allowed to cool to room temperature. The precipitated solid was collected by filtration, washed with 1 mL of isopropanol and 1 mL of chloroform and dried to give 26 mg of the desired product (yield 72%).
Morphology: light brown solid
$^1$H-NMR (DMSO-d$_6$) δ: 1.50-1.70 (1H, m), 1.70-2.00 (4H, m), 3.50-4.10 (3H, m), 7.60-7.80 (2H, m), 7.86 (1H, d, J=4 Hz), 8.00 (1H, d, J=4 Hz), 8.05 (1H, brs), 8.12 (1H, s), 8.80 (1H, t, J=6 Hz), 11.4 (1H, s).
LC/MS (ESI$^+$) m/z; 538, 540 [M+1]$^+$
LC/MS (ESI$^-$) m/z; 536, 538 [M−1]$^-$ Synthetic Example 3

5-{1-[5-(3,4-Dichlorophenyl)-4-hydroxythiophen-3-yl]ethylidenehydrazinocarbonyl)thiophene-2-carboxylic acid[2-(morpholin-4-yl)ethyl]amide Synthesis was carried out in the same manner as in Synthetic Example 1 by using 5-(hydrazinocarbonyl)thiophene-2-carboxylic acid [2-(morpholin-4-yl)ethyl]amide prepared in Reference Synthetic Example 3 to give 12 mg of the desired product (yield 21%).
Morphology: white solid
$^1$H-NMR (DMSO-d$_6$) δ: 3.5-4.0 (4H, my 7.6-7.75 (3H, m), 7.80 (1H, d, J=4 Hz), 7.9-8.1 (2H, m), 8.09 (1H d, J=2 Hz), 11.4 (1H, s).
LC/MS (ESI$^+$) m/z; 567, 569 [M+1]$^+$
LC/MS (ESI$^-$) m/z; 565, 567 [M−1]$^-$ Synthetic Example 4

5-{1-[5-(3,4-Dichlorophenyl)-4-hydroxythiophen-3-yl]ethylidenehydrazinocarbonyl}thiophene-2-carbohydrazide Synthesis was carried out in the same manner as in Synthetic Example 2 by using 2,5-di(hydrazinocarbonyl)thiophene prepared in Reference Synthetic Example 4 to give 43 mg of the desired product (yield 90%).
Morphology: pale yellow solid
$^1$H-NMR (DMSO-d$_6$) δ: 7.60-7.75 (2H, m), 7.77 (1H, d), 8.00 (1H, d), 8.05 (1H, brs), 8.13 (1H, s).
LC/MS (ESI$^+$) m/z; 469, 471 [M+1]$^+$
LC/MS (ESI$^-$) m/z; 467, 469 [M−1]$^-$ Synthetic Example 5

N-[1-{5-{1-[5-(3,4-Dichlorophenyl)4-hydroxythiophen-3-yl]ethylidenehydrazinocarbonyl}thiophene-2-carbonyl]pyrrolidin-3-yl]acetamide Synthesis was carried out in the same manner as in Synthetic Example 2 by using N-[1-(5-hydrazinocarbonylthiophene-2-carbonyl)-pyrrolidin-3-yl]acetamide prepared in Reference Synthetic Example 5 to give 53 mg of the desired product (yield 93%).
Morphology: pale yellow solid
$^1$H-NMR (DMSO-d$_6$) δ: 1.81 (3H, ds), 2.0-2.3 (1H, m), 3.5-4.2 (4H, m), 4.30 (1H, brs), 7.5-7.8 (3H, m), 7.9-8.1 (2H, m), 8.12 (1H, s) 8.19 (1H, t, J=6 Hz, 11.5 (1H, s).
LC/MS (ESI$^+$) m/z; 565, 567 [M+1]$^+$
LC/MS (ESI$^-$) m/z; 563, 565 [M−1]$^-$ Synthetic Example 6

5-{1-[5-(3,4-Dichlorophenyl)-4-hydroxythiophen-3-yl]ethylidenehydrazinocarbonyl}thiophene-2-carboxylic acid(N,N-dimethyl)hydrazide Synthesis was carried out in the same manner as in Synthetic Example 2 by using 2-(N,N-dimethylhydrazinocarbonyl)-5-(hydrazinocarbonyl thiophene prepared in Reference Synthetic Example 6 to give 14 mg of the desired product (yield 28%).
Morphology: pale yellow solid
(DMSO-d$_6$) δ: 2.60 (3H, s) 262 (3H, s), 7.6-7.75 (2H, m), 7.8-8.2 (4H, m).
LC/MS (ESI$^+$) m/z; 497, 499 [M+1]$^+$
LC/MS (ESI$^-$) m/z; 495, 497 [M−1]$^-$

Synthetic Example 7

3-[5-{1-[5-(3,4-Dichlorophenyl)-4-hydroxythiophen-3-yl]ethylidenehydrazinocarbonyl}thiophene-2-carbonyl)amino]propionic acid 7-a) tert-Butyl 3-[(5-{1-[5-(3,4-dichlorophenyl)-4-hydroxythiophen-3-yl]ethylidenehydrazinocarbonyl}thiophene-2-carbonyl)amino]propionate 2-(3,4-Dichlorophenyl)-3-hydroxy-4-methylcarbonylthiophene (24 mg, 0.083 mmol) in isopropanol (2.0 mL) was heated with tert-butyl 3-{[5-(hydrazinocarbonyl)thiophene-2-carbonyl]amino}propionate (18 mg, 0.057 mmol) prepared in Reference Synthetic Example 7 and 6 mg of p-toluenesulfonic acid monohydrate at 100° C. for 8 hours and allowed to cool to room temperature. Water was added to the reaction mixture, and the precipitated solid was collected by filtration, washed with water, methanol and chloroform and dried to give 28 mg of the desired product (yield 85%).
Morphology: pale yellow solid
LC/MS (ESI$^-$) m/z; 580, 582 [M−1]$^-$ 7-b) 3-[(5-{1-[5-(3,4-Dichlorophenyl)-4-hydroxythiophen-3-yl]ethylidenehydrazinocarbonyl}thiophene-2-carbonyl)amino]propionic acid Synthesis was carried out in the same manner as in Synthetic Example 8 by using tert-butyl 3-[(5-{1-[5-(3,4-dichlorophenyl)-4-hydroxythiophen-3-yl]ethylidenehydrazinocarbonyl}thiophene-2-carbonyl)amino]propionate to give 14 mg of the desired product (yield 55%).
Morphology: pale yellow solid
$^1$H-NMR (DMSO-d$_6$) δ: 2.40-2.60 (5H, m, overlapped_with_DMSO), 3.45 (2H, dd, J=12.3, 6.7 Hz), 7.66 (1H, d, J=8.6 Hz), 7.70 (1H, dd, J=8.6, 2.0 Hz), 7.80 (1H, d, J=4.0 Hz), 8.00 (1H, d, J=4.0 Hz), 8.05 (1H, brs), 8.12 (1H, s), 8.80 (1H, t, J=5.4 Hz), 11.44 (1H, s).
LC/MS (ESI$^+$) m/z; 526, 528 [M+1]$^+$
LC/MS (ESI$^-$) m/z; 524, 526 [M−1]$^-$

Synthetic Example 8

[(5-{1-[5-(3,4-Dichlorophenyl)-4-hydroxythiophen-3-yl]ethylidenehydrazinocarbonyl}thiophene-2-carbonyl)amino]acetic acid 8-a) tert-Butyl[(5-{1-[5-(3,4-dichlorophenyl)-4-hydroxythiophen-3-yl]ethylidenehydrazinocarbonyl}thiophene-2-carbonyl)amino]acetate 2-(3,4-Dichlorophenyl)-3-hydroxy-4-methylcarbonylthiophene (49 mg, 0.17 mmol) in isopropanol (2.0 mL) was heated with tert-butyl{[5-(hydrazinocarbonyl)thiophene-2-carbonyl]amino}acetate (44 mg, 0.15 mmol) prepared in Reference Synthetic Example 8 and 3 mg of p-toluenesulfonic acid monohydrate at 100° C. for 8 hours and allowed to cool to room temperature. Water was added to the reaction mixture, and the precipitated solid was collected by filtration, washed with water, methanol and chloroform and dried to give 69 mg of the desired product (yield 83%).
Morphology: pale yellow solid
LC/MS (ESI$^-$) m/z; 566, 568 [M−1]$^-$ 8-b) [(5-{1-[5-(3,4-Dichlorophenyl)-4-hydroxythiophen-3-yl]ethylidenehydrazinocarbonyl}thiophene-2-carbonyl)amino]acetic acid tert-Butyl[(5-{1-[5-(3,4-dichlorophenyl)-4-hydroxythiophen-3-yl]ethylidenehydrazinocarbonyl}thiophene-2-carbonyl)amino]acetate (69 mg, 0.12 mmol) in CH$_2$Cl$_2$ (4.0 mL) was stirred with trifluoroacetic acid (0.14 mL) at room temperature for 4 days. The reaction mixture was concentrated under reduced pressure, and chloroform was added. The precipitated solid was collected by filtration, washed with chloroform and dried to give 35 mg of the desired product (yield 56%).
Morphology: pale yellow solid
$^1$H-NMR (DMSO-D$_6$) δ: 2.48 (3H, s, overlapped_with_DMSO), 3.92 (2H, brd, J=5.8 Hz), 7.65 (1H, d, J=8.5 Hz), 7.68 (1H, brd, J=8.5 Hz), 7.86 (1H, d, J=3.8 Hz), 8.03 (1H, d, J=3.8 Hz), 8.05 (1H, brs), 8.13 (1H, s), 9.11 (1H, t, J=5.8 Hz), 11.48 (1H, s).
LC/MS (ESI$^+$) m/z; 512, 514 [M+1]$^+$
LC/MS (ESI$^-$) m/z; 510, 512 [M−1]$^-$

Synthetic Example 9

5-{1-[5-(3,4-Dichlorophenyl)-4-hydroxythiophen-3-yl]ethylidenehydrazinocarbonyl}thiophene-2-carboxylic acid piperidin-1-ylamide 2-(3,4-Dichlorophenyl)-3-hydroxy-4-methylcarbonylthiophene (29 mg, 0.1 mmol) in dimethyl sulfoxide (4.0 mL) was heated with 5-(hydrazinocarbonyl)thiophene-2-carboxylic acid piperidin-1-ylamide (27 mg, 0.1 mmol) prepared in Reference Synthetic Example 9 at 100° C. for 20 hours and allowed to cool to room temperature. 2 mL of water was added, and the precipitated solid was collected by filtration, washed with 1 mL of chloroform and dried to give 47 mg of the desired product (yield 87%).
Morphology: yellow solid
LC/MS (ESI$^+$) m/z; 537, 539 [M+1]$^+$
LC/MS (ESI$^-$) m/z; 535, 537 [M−1]$^-$

Synthetic Example 10

5-{1-[5-(3,4-D-chlorophenyl)-4-hydroxythiophen-3-yl]ethylidenehydrazinocarbonyl}thiophene-2-carboxylic acid(4-methylpiperazin-1-yl)amide 2-(3,4-Dichlorophenyl)-3-hydroxy-4-methylcarbonylthiophene (29 mg, 0.1 mmol) in dimethyl sulfoxide (4.0 mL) was heated with 5-(hydrazinocarbonyl)thiophene-2-carboxylic acid(4-methylpiperazin-1-yl)amide (28 mg, 0.1 mmol) prepared in Reference Synthetic Example 10 at 100° C. for 20 hours and allowed to cool to room temperature 2 mL of water was added and the precipitated solid was collected by filtration, washed with 1 mL of chloroform and dried to give 50 mg of the desired product (yield 93%).
Morphology: pale orange solid
LC/MS (ESI$^+$) m/z; 552, 554 [M+1]$^+$
LC/MS (ESI$^-$) m/z; 550, 552 [M−1]$^-$

Synthetic Example 11

5-{1-[5-(3,4-Dichlorophenyl)-4-hydroxythiophen-3-yl]ethylidenehydrazinocarbonyl}thiophene-2-carboxylic acid morpholin-4-ylamide 2-(3,4-Dichlorophenyl)-3-hydroxy-4-methylcarbonylthiophene (29 mg, 0.1 mmol) in dimethyl sulfoxide (4.0 mL)

was heated with 5-(hydrazinocarbonyl)thiophene-2-carboxylic acid morpholin-4-ylamide (27 mg, 0.1 mmol) prepared in Reference Synthetic Example 11 at 100° C. for 20 hours and allowed to cool to room temperature 2 mL of water was added, and the precipitated solid was collected by filtration, washed with chloroform and dried Synthesis was carried out in the same manner as in Reference Synthetic Example by using to give 40 mg of the desired product (yield 73%).
Morphology: yellow solid
LC/MS (ESI$^+$) m/z; 539, 541 [M+1]$^+$
LC/MS (ESI$^-$) m/z; 537, 539 [M−1]$^-$ Synthetic Example 12

5-{1-[5-(3,4-Dichlorophenyl)-4-hydroxythiophen-3-yl]ethylidenehydrazinocarbonyl}-2-[4-pyrrolidin-1-yl]piperidine-1-carbonyl]thiophene 2-(3,4-Dichlorophenyl)-3-hydroxy-4-methylcarbonylthiophene (29 mg, 0.1 mmol) in isopropanol (4.0 mL) was heated with 5-[4-pyrrolidin-1-yl)piperidine-1-carbonyl]thiophene-2-carbohydrazide (21 mg, 0.1 mmol) prepared in Reference Synthetic Example 12 and 6 mg of p-toluenesulfonic acid monohydrate at 100° C. for 13 hours and allowed to cool to room temperature. The precipitated solid was collected by filtration, washed with 1 mL of chloroform and dried to give 21 mg of the desired product (yield 36%).
Morphology: pale orange solid
LC/MS (ESI$^+$) m/z; 591, 593 [M+1]$^+$
LC/MS (ESI$^-$) m/z; 589, 591 [M−1]$^-$ Synthetic Example 13

N-(2-Carbamoylethyl)-3-[(2-{1-[5-(3,4-dichlorophenyl)-4-hydroxythiophen-3-yl]ethylidene}hydrazinecarbothioamido]benzamide 3-Amino-N-(2-carbamoylethyl)benzamide (31 mg, 0.15 mmol) in dimethylformamide (0.3 mL) was stirred with thiocarbonyldiimidazole (27 mg, 0.15 mmol) at room temperature for 1 hour and then with 2-(3,4-dichlorophenyl)-4-(1-hydrazonoethyl)-thiophen-3-ol prepared in Reference Synthetic Example 13 at 40° C. for 3 hours. Methanol and water were added to the reaction solution, and the resulting crystals were collected by filtration washed and dried to give 29 mg of the desired product (yield 53%).
Morphology: white solid
LC/MS (ESI$^+$) m/z; 550, 552 [M+1]$^+$
LC/MS (ESI$^-$) m/z; 548, 550 [M−1]$^-$ Synthetic Example 14

N-(2-Carbamoylethyl)-3-({1-[4-hydroxy-1-methyl-5-(4-trifluoromethylphenyl)-1H-pyrazol-3-yl]ethylidene}hydrazinecarbothioamido)benzamide 3-Amino-N-(2-carbamoylethyl)benzamide (56 mg, 0.27 mmol) was stirred with a dimethylformamide solution of thiocarbonyldiimidazole (0.1 M, 2.25 mL, 0.225 mmol) at room temperature for 1.5 hours, and then with a dimethylformamide solution of 3-(1-hydrazonoethyl)-1-methyl-5-[4-(trifluoromethyl)phenyl]-1H-pyrazol-4-ol prepared in Reference Synthetic Example 14 (0.1 M, 1.8 mL, 0.18 mmol) at 40° C. for 1 hour, and then stirred at room temperature for 17 hours. After addition of water and saturated aqueous sodium chlorides the solution was extracted with ethyl acetate, and the extract was dried over anhydrous sodium sulfate and filtered. The solvent was evaporated, and chloroform and hexane were added to the residue. The precipitated solid was collected by filtration, washed with hexane and dried to give 102.7 mg of the desired product (yield 100%).
Morphology: yellow solid
LC/MS (ESI$^+$) m/z; 548 [M+1]$^+$
LC/MS (ESI$^-$) m/z; 546 [M−1]$^-$ Synthetic Example 15

3-[2-Chloro-5-(2-{1-[4-hydroxy-1-methyl-5-(4-trifluoromethylphenyl)-1H-pyrazol-3-yl]ethylidene}hydrazinecarbothioamido)benzoylamino]propionic acid Ethyl 3-(5-amino-2-chlorobenzoylamino)propionate (122.8 mg, 0.45 mmol) was stirred with a dimethylformamide solution of thiocarbonyldiimidazole (0.1 M, 4.5 mL) at room temperature for 1 hour and with a dimethylformamide solution of 3-(1-hydrazonoethyl)-1-methyl-5-[4-(trifluoromethyl)phenyl]-1H-pyrazol-4-ol prepared in Reference Synthetic Example 14 (0.1 M, 3.0 mL) at room temperature for 6 hours. Water (3.0 mL) was added, and the precipitated solid was removed by filtration. The filtrate was separated by thin layer chromatography to give 57.0 mg of a crude product. An ethanol solution (1.0 mL) of the crude product (26.0 mg, 0.0435 mmol) was stirred with 1 M aqueous sodium hydroxide (131 μL, 0.131 mmol), and the precipitated solid was collected by filtration, washed with water and dried to give 14.6 mg of the desired product (yield 20%).
Morphology: yellow solid
LC/MS (ESI$^+$) m/z; 583, 585 [M+1]$^+$
LC/MS (ESI$^-$) m/z; 581, 583 [M−1]$^-$ Synthetic Example 16

6-(2-{1-[5-(3,4-Dichlorophenyl)-4-hydroxythiophen-3-yl]ethylidene}hydrazinecarbothioamido)-2,3-dihydrobenzo[1,4]dioxine 2-(3,4-Dichlorophenyl)-4-(1-hydrazonoethyl)-thiophen-3-ol (25 mg, 0.08 mmol) prepared in Reference Synthetic Example 13 in dimethylformamide (0.25 mL) was stirred with 6-isothiocyanato-2,3-dihydrobenzo[1,4]dioxine (24 mg, 0.13 mmol, at 30° C. for 4 hours. Methanol and water were added to the reaction solution, and the resulting crystals were collected by filtration, washed and dried to give 28 mg of the desired product (yield 65%).
Morphology: colorless solid
LC/MS (ESI$^-$) m/z; 492, 494 [M−1]$^-$ Synthetic Example 17

6-[2-{1-{5-(3,4-Dichlorophenyl)-4-hydroxythiophen-3-yl}ethylidene}hydrazinecarbothiamido]-4H-benzo[1,4]oxazin-3-one Synthesis was carried out in the same manner as in Synthetic Example 13 by using 6-amino-4H-benzo[1,4]oxazin-3-one (yield 55%).
Morphology: light brown solid
LC/MS (ESI$^+$) m/z; 507, 509 [M+1]$^+$
LC/MS (ESI$^-$) m/z; 505, 507 [M−1]$^-$

Synthetic Example 18

7-(2-{1-[5-(3,4-Dichlorophenyl)4-hydroxythiophen-3-yl]ethylidene}hydrazinecarbothioamido)-4H-benzo[1,4]oxazin-3-one Synthesis was carried out in the same manner as in Synthetic Example 13 by using 7-amino-4H-benzo[1,4]oxazin-3-one (yield 73%).

Morphology: white solid
LC/MS (ESI$^+$) m/z; 507, 509 [M+1]$^+$
LC/MS (ESI$^-$) m/z; 505, 507 [M−1]$^-$

Synthetic Example 19

7-(2-{1-[4-Hydroxy-1-methyl-5-(4-trifluoromethylphenyl)-1H-pyrazol-3-yl]ethylidene}hydrazinecarbothioamido)-4H-benzo[1,4]oxazin-3-one 7-Amino-4H-benzo[1,4]oxazin-3-one (33 mg, 0.203 mmol) was stirred with a dimethylformamide solution of thiocarbonyldiimidazole (0.1 M, 2.03 mL, 0.203 mmol) at room temperature for 1 hour and then with a dimethylformamide solution of 3-(1-hydrazonoethyl)-1-methyl-5-[4-(trifluoromethyl)phenyl]-1H-pyrazol-4-ol prepared in Reference Synthetic Example 14 (0.1 M, 1.36 mL, 0.135 mmol) at room temperature for 4 hours Water was added, and the precipitated solid was collected by filtration, washed with water and dried. After addition of chloroform, the solid was collected by filtration washed with chloroform and dried to give 33.6 mg of the desired product (yield 49%).

Morphology: pale yellow solid
LC/MS (ESI$^+$) m/z; 505 [M+1]$^+$
LC/MS (ESI$^-$) m/z; 503 [M−1]$^-$

Synthetic Example 20

3-(4-{1-[5-(3,4-Dichlorophenyl)-4-hydroxy-thiophen-3-yl]-ethylidenehydrazinocarbonyl}phenyl)-3-hydroxypropionic acid Crude potassium 3-[4-(hydrazinocarbonyl)phenyl]-3-hydroxypropionate prepared in Reference Synthetic Example 15 suspended in dimethylformamide (3.0 mL) was stirred with 1.0 M hydrogen chloride-methanol (0.5 mL) and 2-(3,4-dichlorophenyl)-3-hydroxy-4-methylcarbonylthiophene (0.15 g, 0.54 mmol) under reduced pressure at room temperature for 4 hours. The resulting solid was collected by filtration and dissolved in dimethyl sulfoxide (2.0 mL) and stirred with 2-(3,4-dichlorophenyl)-3-hydroxy-4-methylcarbonylthiophene (99 mg, 0.34 mmol) at 100° C. for 2.5 hours. Water and methanol were added, and the resulting precipitate was collected by filtration and washed with chloroform to give 80 mg of the desired product (yield 33% for the two steps).

Morphology: gray solid
$^1$H-NMR (DMSO-d$_6$) δ: 2.21-2.63 (2H), 4.92 (1H, dd, J=9.0&4.5 Hz), 7.49 (1H, d, J=8.0 Hz), 7.63 (1H, d, J=8.5 Hz), 7.69 (1H, dd, J=8.5&2.0 Hz), 7.88 (1H, d, J=8.5 Hz), 8.07 (1H, s), 8.12 (1H, br s).
LC/MS (ESI$^+$) m/z; 493, 495 [M+1]$^+$
LC/MS (ESI$^-$) m/z; 491, 493 [M−1]$^-$

Synthetic Example 21

5-{1-[5-(3,4-Dichlorophenyl)-4-hydroxythiophen-3-yl]ethylidenehydrazinocarbonyl}thiophene-2-carboxyacid (4-methylpiperazin-1-yl)amide potassium salt 5-{1-[5-(3,4-Dichlorophenyl)-4-hydroxythiophen-3-yl]ethylidenehydrazinocarbonyl}thiophene-2-carboxylic acid (4-methylpiperazin-1-yl)amide (11 mg, 0.02 mmol) suspended in methanol (0.33 mL) was sonicated with 0.1 M potassium hydroxide-methanol (0.2 mL, 0.02 mmol) in an ultrasonic cleaner for 10 seconds, and the reaction solution was concentrated to give the desired product (11 mg, yield 93%).

Morphology: red solid

Synthetic Examples 22 to 29

Synthesis was carried out in the same manner as in Synthetic Example 1, and the yields and morphology of the resulting compounds the LC/MS conditions used for their analysis and the observed peaks and retention times are shown in Table 5.

In Synthetic Examples 22 to 29, the desired products were prepared by mixing 1 equivalent of 2-(4-t-butylphenyl)-3-hydroxy-4-methylcarbonylthiophene (prepared by the method disclosed in WO2004/108683) with 1 equivalent of the corresponding hydrazides in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 5

| Syn. Ex. No. | Yield (%) | Morphology | LC/MS conditions | Observed peak ESI$^+$ | Observed peak ESI$^-$ | Retention time (minute) |
|---|---|---|---|---|---|---|
| 22 | 50 | pale yellow solid | 3 | 569 | 567 | 2.48 |
| 23 | 49 | pale yellow solid | 3 | 555 | 553 | 2.48 |
| 24 | 43 | pale yellow solid | 3 | 485 | 483 | 3.63 |
| 25 | 27 | brown solid | 3 | 579 | 577 | 2.55 |
| 26 | 46 | yellow solid | 3 | 527 | 525 | 3.63 |
| 27 | 71 | yellow solid | 3 | 514 | 512 | 3.50 |
| 28 | 52 | yellow solid | 3 | 500 | 498 | 3.54 |
| 29 | 30 | pale yellow solid | 3 | 528 | 526 | 3.35 |

Synthetic Examples 30 to 38

Synthesis was carried out in the same manner as in Synthetic Example 1, and the yields and morphology of the resulting compounds, the LC/MS conditions used for their analysis and the observed peaks and retention times are shown in Table 6.

In Synthetic Examples 30 to 38, the desired products were prepared by mixing 1 equivalent of 2-(4-trifluoromethylphenyl)-3-hydroxy-4-methylcarbonylthiophene (prepared by the method disclosed in WO2004/108683) with the corresponding hydrazides, if necessary with heating and subsequent cooling, and if necessary, concentrating the reaction mixture, adding a poor solvent such as ethanol, methanol, water, chloroform, ether or hexane and collecting the resulting crystals by filtration.

TABLE 6

| Syn. Ex. No. | Yield (%) | Morphology | LC/MS conditions | Observed peak ESI+ | Observed peak ESI− | Retention time (minute) |
|---|---|---|---|---|---|---|
| 30 | 48 | light brown solid | 3 | 497 | 495 | 3.47 |
| 31 | 32 | brown solid | 3 | 591 | 589 | 2.43 |
| 32 | 76 | light brown solid | 3 | 581 | 579 | 2.42 |
| 33 | 79 | light brown solid | 3 | 567 | 565 | 2.42 |
| 34 | 66 | colorless solid | 3 | 539 | 537 | 3.42 |
| 35 | 54 | yellow solid | | | | |
| 36 | 50 | yellow solid | | | | |
| 37 | 56 | yellow solid | | | | |
| 38 | 33 | pale yellow solid | 8 | 568 | 566 | 4.78 |

Synthetic Example 39

3-(5-{1-[4-Hydroxy-5-(4-trifluoromethylphenyl)thiophen-3-yl]ethylidenehydrazinocarbonyl}-N-methylthiophene-2-carboxamido)propionic acid 39-a) t-Butyl 3-(5-{1-[4-Hydroxy-5-(4-trifluoromethylphenyl)thiophen-3-yl]ethylidenehydrazinocarbonyl}-N-methylthiophene-2-carboxamido)propionate 2-(4-Trifluoromethylphenyl)-3-hydroxy-4-methylcarbonylthiophene (35 mg, 0.122 mmol) and the hydrazide (40 mg, 0.122 mmol) prepared in Reference Synthetic Example 22 suspended in dimethylformamide (1 mL) were stirred with concentrated hydrochloric acid (10 mL) for 12 hours. After addition of water, the resulting solid was collected by filtration and dried to give the desired product (yield 62%).
Morphology: white solid 39-b) 3-(5-{1-[4-Hydroxy-5-(4-trifluoromethylphenyl)thiophen-3-yl]ethylidenehydrazinocarbonyl}-N-methylthiophene-2-carboxamido)propionic acid t-Butyl 3-(5-{1-[4-Hydroxy-5-(4-trifluoromethylphenyl)thiophen-3-yl]ethylidenehydrazinocarbonyl}-N-methylthiophene-2-carboxamido)propionate (30 mg, 0.05 mmol) was stirred with trifluoroacetic acid (300 μL) at room temperature for 15 minutes. The reaction solution was concentrated, and after addition of ether the resulting solid was collected by filtration to give the desired product (yield 56%).
Morphology: white solid
LC/MS (ESI+) m/z; 540 [M+1]+
LC/MS (ESI−) m/z; 538 [M−1]−
Retention time: 4.03 minutes (condition 5)

Synthetic Examples 40 to 47

Synthesis was carried out in the same manner as in Synthetic Example 1, and the yields and morphology of the resulting compounds, the LC/MS conditions used for their analysis and the observed peaks and retention times are shown in Table 7.

The desired products were prepared by mixing 2-(4-chlorophenyl)3-hydroxy-4-methylcarbonylthiophene (prepared the method disclosed in WO2004/105683) in Synthetic Examples 40 to 46, or 1 equivalent of 1-[4-hydroxy-1-methyl-5-(4-trifluoromethylphenyl)-1H-pyrazol-3-yl]ethanone in Synthetic Examples 47 to 54, with the corresponding hydrazides in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 7

| Syn. Ex. No. | Yield (%) | Morphology | LC/MS conditions | Observed peak ESI+ | Observed peak ESI− | Retention time (minute) |
|---|---|---|---|---|---|---|
| 40 | 40 | light brown solid | 3 | 547/549 | 545/547 | 2.37 |
| 41 | 56 | colorless solid | 3 | 533/535 | 531/533 | 2.37 |
| 42 | 62 | pale yellow solid | 2 | 505/507 | 503/505 | 4.00 |
| 43 | 65 | brown solid | 3 | 557/559 | 555/557 | 2.40 |
| 44 | 57 | yellow solid | 3 | 506/508 | 504/506 | 3.09 |
| 45 | 57 | yellow solid | 8 | 492/494 | 490/492 | 4.55 |
| 46 | 63 | ocher solid | 8 | 478/480 | 476/478 | 4.47 |
| 47 | 42 | yellow solid | 2 | 495 | 493 | 3.30, 3.62 |
| 48 | 31 | red solid | 2 | 589 | 587 | 2.33, 2.54 |
| 49 | 79 | orange solid | 2 | 579 | 577 | 2.49 |
| 50 | 93 | orange solid | 2 | 565 | 563 | 2.49 |
| 51 | 74 | pale yellow solid | 2 | 537 | 535 | 3.30, 3.59 |
| 52 | 37 | pale yellow solid | 2 | 538 | 536 | 3.32 |
| 53 | 56 | pale yellow solid | 2 | 524 | 522 | 3.57 |
| 54 | 58 | pale yellow solid | 2 | 510 | 508 | 3.55 |

Synthetic Example 55

N-(2-Carbamoylethyl)-3-(2-{1-[5-(3,4-dichlorophenyl)-4-hydroxy-1-methyl-1H-pyrazol-3-yl]ethylidene}hydrazinecarbothioamido)benzamide Synthesis was carried out in the same manner as in Synthetic Example 14 by using 3-(1-hydrazonoethyl)-1-methyl-5-(3,4-dichlorophenyl)-1H-pyrazol-4-ol prepared in Reference Synthetic Example 27 to give 74.3 mg of the desired product (yield 81%).
Morphology: pale yellow solid
LC/MS (ESI+) m/z; 548, 550 [M+1]+
LC/MS (ESI−) m/z; 546, 548 [M−1]−

Synthetic Examples 56 to 58

Synthesis was carried out in the same manner as in Synthetic Example 1, and the yields and morphology of the resulting compounds, the LC/MS conditions used for their analysis and the observed peaks and retention times are shown in Table 8.

In Synthetic Examples 56 to 58, the desired products were prepared by mixing 1 equivalent of 2-(3,4-dichlorophenyl)-3-hydroxy-4-methylcarbonylthiophene (prepared by the method disclosed in WO2004/108683) with 1 equivalent of the corresponding hydrazides in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 8

| Syn. Ex. No. | Yield (%) | Morphology | LC/MS conditions | Observed peak ESI+ | Observed peak ESI- | Retention time (minute) |
|---|---|---|---|---|---|---|
| 56 | 48 | pale yellow solid | 8 | 554/556 | 552/554 | 4.80 |
| 57 | 37 | pale yellow solid | 8 | 568/570 | 566/568 | 5.02 |
| 58 | 66 | pale yellow solid | 2 | 546/548 | 544/546 | 3.69 |

TABLE 9

| Syn. Ex. No. | Yield (%) | Morphology | LC/MS conditions | Observed peak ESI+ | Observed peak ESI- | Retention time (minute) |
|---|---|---|---|---|---|---|
| 60 | 80 | pale yellow solid | 2 | 541 | 539 | 2.85 |
| 61 | 85 | pale yellow solid | 2 | 527 | 525 | 2.82 |
| 62 | 41 | yellow solid | 2 | 457 | 455 | 4.14 |
| 63 | 59 | brown solid | 2 | 551 | 549 | 2.82 |
| 64 | 40 | yellow solid | 2 | 499 | 497 | 4.07 |
| 65 | 41 | yellow solid | 2 | 486 | 484 | 3.97 |
| 66 | 69 | yellow solid | 2 | 472 | 470 | 4.02 |
| 67 | 54 | pale yellow solid | 2 | 597 | 595 | 2.99 |
| 68 | 64 | pale yellow solid | 2 | 583 | 581 | 3.00 |
| 69 | 59 | pale yellow solid | 2 | 513 | 511 | 4.34 |
| 70 | 67 | brown solid | 8 | 607 | 605 | 4.12 |
| 71 | 73 | pale yellow solid | 2 | 555 | 553 | 4.25 |
| 72 | 37 | yellow solid | 8 | 556 | 554 | 4.48 |
| 73 | 56 | yellow solid | 3 | 528 | 526 | 3.37 |
| 74 | 36 | yellow solid | 3 | 542 | 540 | 3.38 |

Synthetic Example 59

3-(5-{1-[4-Hydroxy-5-(3,4-dichlorophenyl)thiophen-3-yl]ethylidenehydrazinocarbonyl]-N-methylthiophene-2-carboxamido)propionic acid 59-a) t-Butyl 3-(5-{1-[4-hydroxy-5-(3,4-dichlorophenyl)thiophen-3-yl]ethylidenehydrazinocarbonyl]-N-methylthiophene-2-carboxamido)propionate Synthesis was carried out in the same manner as in Synthetic Example 39 by using the hydrazide (40 mg, 0.122 mmol) prepared in Reference Synthetic Example 22 to give the desired product (yield 45%).
Morphology: white solid 59-b) 3-(5-{1-[4-Hydroxy-5-(3,4-dichlorophenyl)thiophen-3-yl]ethylidenehydrazinocarbonyl]-N-methylthiophene-2-carboxamido)propionic acid Synthesis was carried out in the same manner as in Synthetic Example 39 by using t-butyl 3-(5-{1-[4-hydroxy-5-(3,4-dichlorophenyl)thiophen-3-yl]ethylidenehydrazinocarbonyl]-N-methylthiophene-2-carboxamido)propionate (30 mg, 0.05 mmol) to give the desired product (yield 100%).
Morphology: white solid
LC/MS (ESI+) m/z; 540, 542 [M+1]+
LC/MS (ESI-) m/z; 538, 540 [M-1]-
Retention time: 4.27 minutes (condition 5)

Synthetic Examples 60 to 74

Synthesis was carried out in the same manner as in Synthetic Example 1, and the yields and morphology of the resulting compounds, the LC/MS conditions used for their analysis and the observed peaks and retention times are shown in Table 9.

The desired products were prepared by mixing 1 equivalent of 2-(3,4-dimethylphenyl)-3-hydroxy-4-methylcarbonylthiophene prepared in Reference Synthetic Example 23 in Synthetic Examples 60 to 66, or 1 equivalent of 2-(4-trifluoromethoxyphenyl)-3-hydroxy-4-methylcarbonylthiophene prepared in Reference Synthetic Example 24 in Synthetic Examples 67 to 74, with 1 equivalent of the corresponding hydrazides in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

Synthetic Example 75

3-(5-{1-[4-Hydroxy-5-(4-trifluoromethoxyphenyl)thiophen-3-yl]ethylidenehydrazinocarbonyl}-N-methylthiophene-2-carboxamido)propionic acid 75-a) t-Butyl 3-(5-{1-[4-hydroxy-5-(4-trifluoromethoxyphenyl)thiophen-3-yl]ethylidenehydrazinocarbonyl}-N-methylthiophene-2-carboxamido)propionate Synthesis was carried out in the same manner as in Synthetic Example 39 by using 2-(4-trifluoromethoxyphenyl)-3-hydroxy-4-methylcarbonylthiophene (37 mg, 0.122 mmol) and the hydrazide (40 mg, 0.122 mmol) prepared in Reference Synthetic Example 22 to give the desired product (yield 40%).
Morphology: white solid 75-b) 3-(5-{1-[4-Hydroxy-5-(4-trifluoromethoxyphenyl)thiophen-3-yl]ethylidenehydrazinocarbonyl}-N-methylthiophene-2-carboxamido)propionic acid Synthesis was carried out in the same manner as in Synthetic Example 39 by using t-butyl 3-(5-{1-[4-hydroxy-5-(4-trifluoromethoxyphenyl)thiophen-3-yl]ethylidenehydrazinocarbonyl}-N-methylthiophene-2-carboxamido)propionate (30 mg, 0.05 mmol) to give the desired product (yield 65%).
Morphology: white solid
LC/MS (ESI+) m/z; 556 [M+1]+
LC/MS (ESI-) m/z; 554 [M-1]-
Retention time: 4.10 minutes (condition 5)

Synthetic Examples 76 to 92

Synthesis was carried out in the same manner as in Synthetic Example 1, and the yields and morphology of the resulting compounds, the LC/MS conditions used for their analysis and the observed peaks and retention times are shown in Table 10.

The desired products were prepared by mixing 1 equivalent of 2-(4-bromophenyl)-3-hydroxy-4-methylcarbonylthiophene prepared in Reference Synthetic Example 25 in Synthetic Examples 76 to 84, or 1 equivalent of 2-(3-chlorophenyl)-3-hydroxy-4-methylcarbonylthiophene prepared in Reference Synthetic Example 26 in Synthetic Examples 85 to 92, with 1 equivalent of the corresponding hydrazides in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water chloroform, ether or hexane and collecting the resulting crystals by filtration.

TABLE 10

| Syn. Ex. No. | Yield (%) | Morphology | LC/MS conditions | Observed peak ESI+ | Observed peak ESI− | Retention time (minute) |
| --- | --- | --- | --- | --- | --- | --- |
| 76 | 75 | pale yellow solid | 8 | 507/509 | 505/507 | 4.72 |
| 77 | 26 | brown solid | 8 | 601/603 | 599/601 | 4.03 |
| 78 | 66 | yellow solid | 8 | 591/593 | 589/591 | 3.95 |
| 79 | 66 | yellow solid | 8 | 577/579 | 575/577 | 4.02 |
| 80 | 53 | pale brown solid | 2 | 549/551 | 547/549 | 4.15 |
| 81 | 52 | light brown solid | 2 | 550/552 | 548/550 | 3.82 |
| 82 | 98 | yellow solid | 2 | 538/536 | 536/534 | 3.97 |
| 83 | 98 | yellow solid | 2 | 522/524 | 520/522 | 4.03 |
| 84 | 45 | white solid | 8 | 578/580 | 576/578 | 4.78 |
| 85 | 76 | yellow solid | 3 | 463/465 | 461/463 | 3.34 |
| 86 | 52 | yellow solid | 3 | 547/549 | 545/547 | 2.30 |
| 87 | 66 | yellow solid | 3 | 533/535 | 531/533 | 2.27 |
| 88 | 43 | brown solid | 3 | 557/559 | 555/557 | 2.30 |
| 89 | 68 | pale yellow solid | 3 | 505/507 | 503/505 | 3.32 |
| 90 | 72 | yellow solid | 3 | 506/508 | 504/506 | 3.07 |

TABLE 10-continued

| Syn. Ex. No. | Yield (%) | Morphology | LC/MS conditions | Observed peak ESI+ | Observed peak ESI− | Retention time (minute) |
| --- | --- | --- | --- | --- | --- | --- |
| 91 | 51 | pale yellow solid | 3 | 492/494 | 490/492 | 3.25 |
| 92 | 64 | dark yellow solid | 3 | 478/480 | 476/478 | 3.29 |

Synthetic Example 93

N-[1-{5-(3,4-Dichlorophenyl)-4-hydroxythiophen-3-yl}ethylidene]-5-{2-(4-oxopyridin-1(4H)yl)acetyl}thiophene-2-carbohydrazide 37 mg (0.12 mmol) of 2-(3,4-dichlorophenyl)-4-(1-hydrazonoethyl)-thiophen-3-ol prepared in Reference Synthetic Example 13, 40 mg (0.15 mmol) of 5-[2-(4-Oxopyridin-1(4H)-yl)acetyl]thiophene-2-carboxylic acid prepared in Reference Synthetic Example 28, 32 mg (0.17 mmol) of 1-[3-(3-(dimethylamino)propyl]-3-ethylcarbodiimide hydrochloride and 22 mg (0.16 mmol) of hydroxybenzotriazole were stirred with 3 ml of dioxane and then with 23 μl (0.17 mmol) of triethylamine at room temperature for 7 days. After addition of water, the precipitated solid was collected by filtration, washed with 2 ml of chloroform, 2 ml of methanol, 5 ml of water and 2 ml of methanol to give 14.5 mg of the desired product (yield 22%).

Morphology: brown solid
LC/MS (ESI+) m/z; 546, 548 [M+1]+
LC/MS (ESI−) m/z; 544, 546 [M−1]−
Retention time 3.23 minutes (condition 6)

The structural formulae of the compounds obtained in the Synthetic Examples are given below.

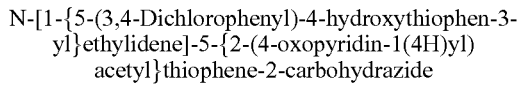

Synthetic Example 1

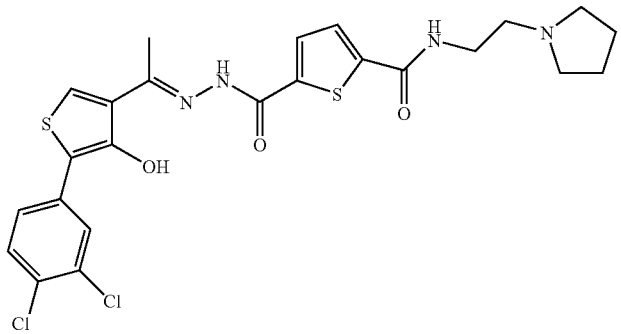

Synthetic Example 2

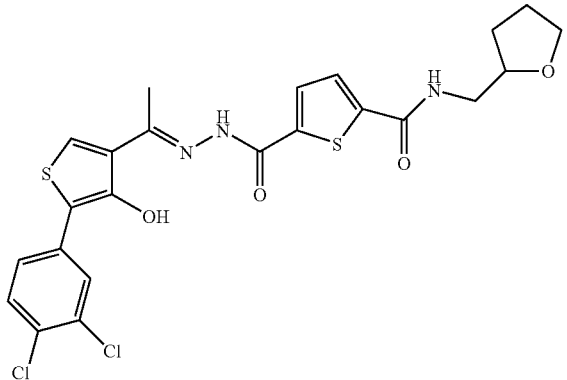

-continued
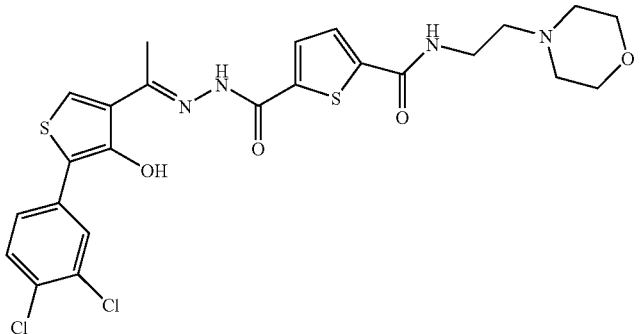
Synthetic Example 3
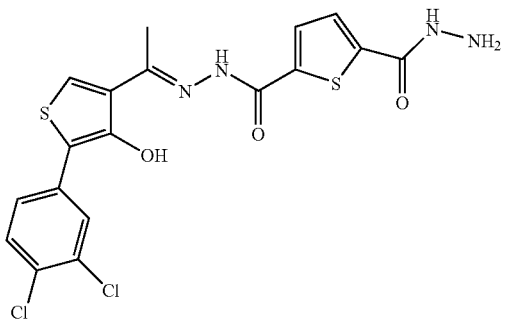
Synthetic Example 4
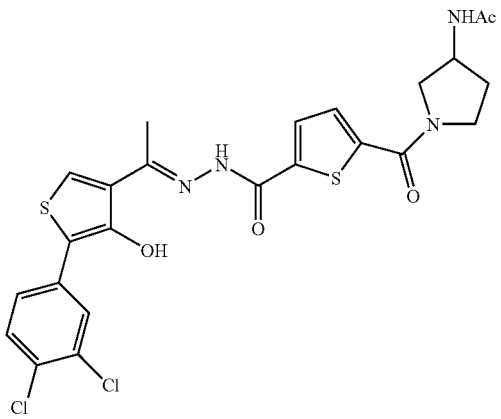
Synthetic Example 5
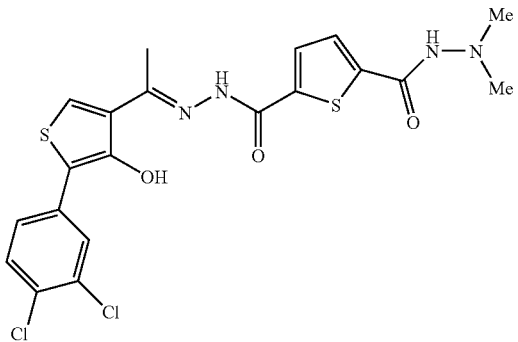
Synthetic Example 6

-continued
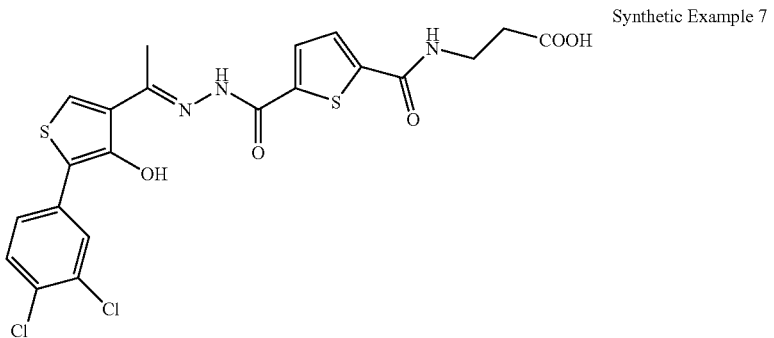
Synthetic Example 7
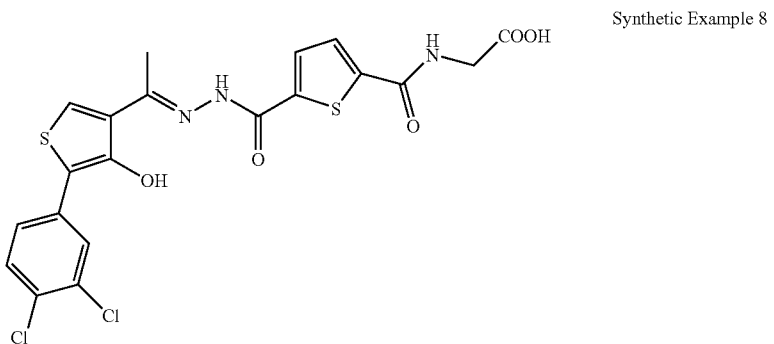
Synthetic Example 8
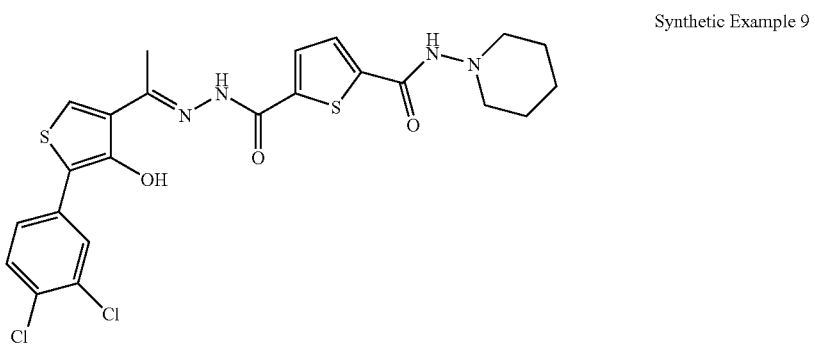
Synthetic Example 9
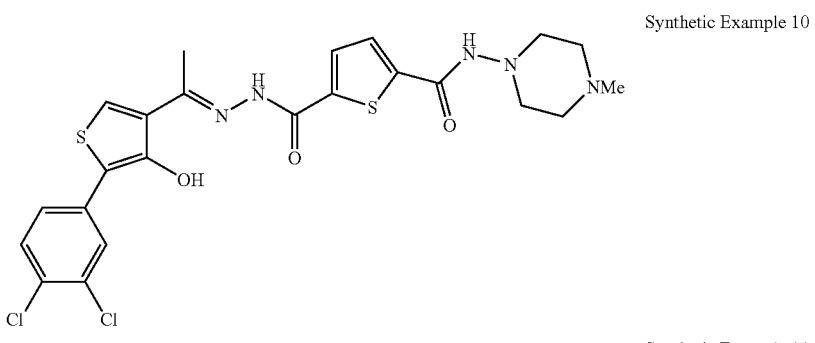
Synthetic Example 10
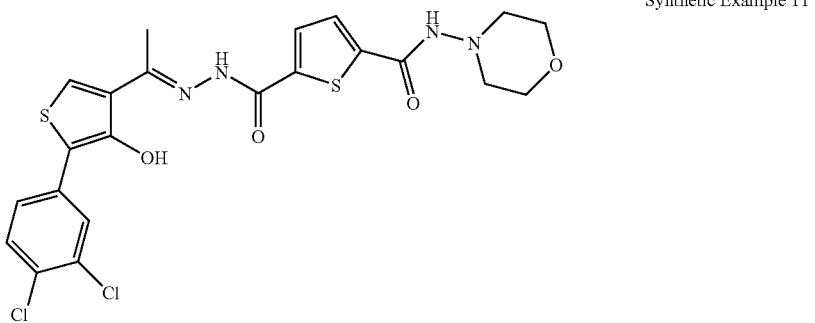
Synthetic Example 11

-continued
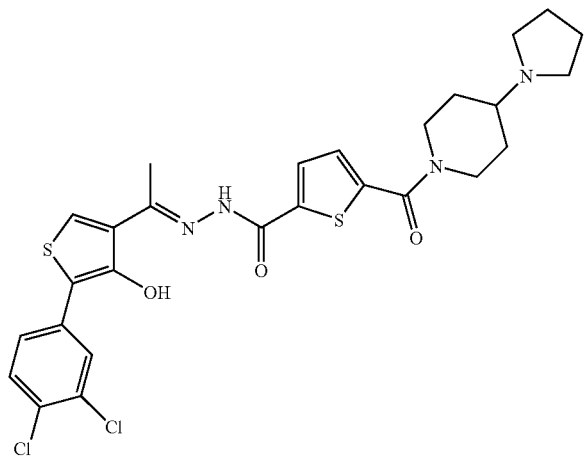
Synthetic Example 12
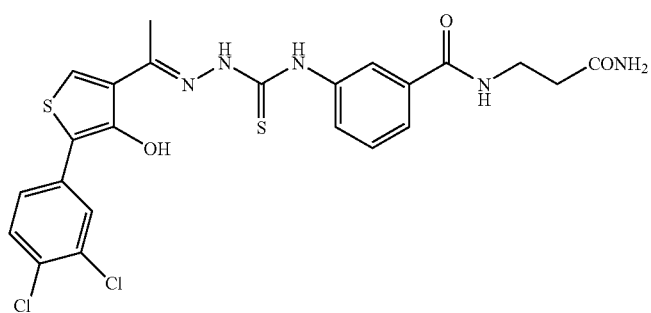
Synthetic Example 13
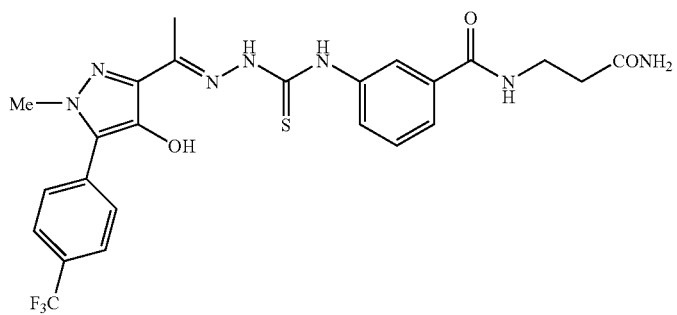
Synthetic Example 14
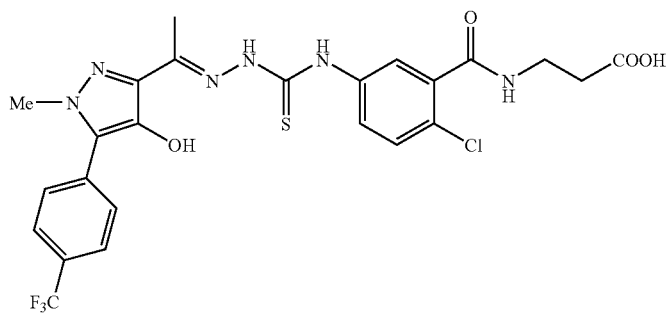
Synthetic Example 15

-continued
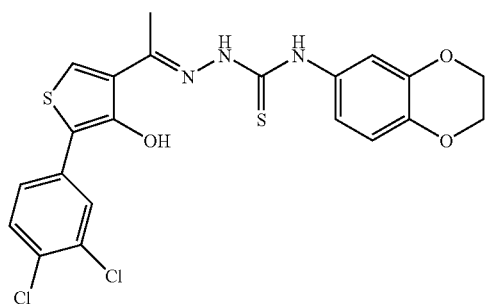
Synthetic Example 16
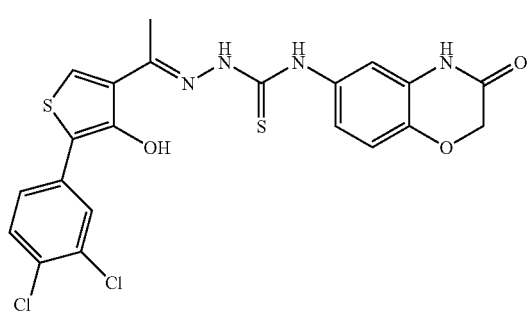
Synthetic Example 17
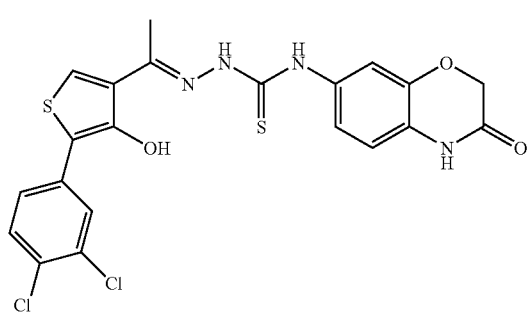
Synthetic Example 18
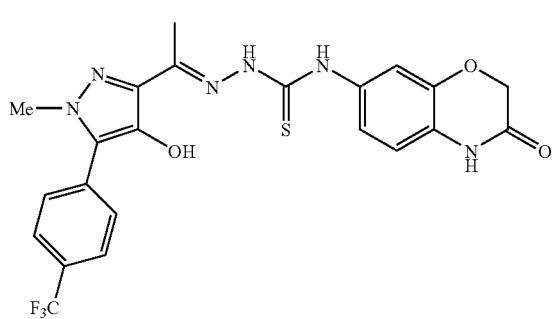
Synthetic Example 19
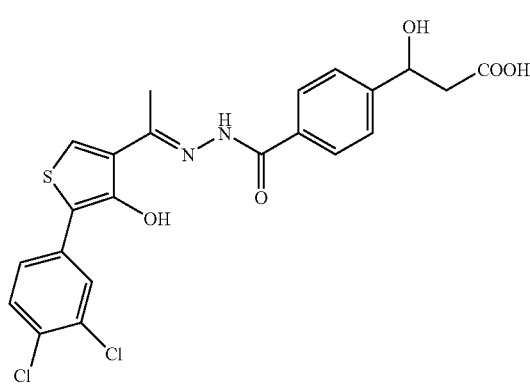
Synthetic Example 20

Synthetic Example 21
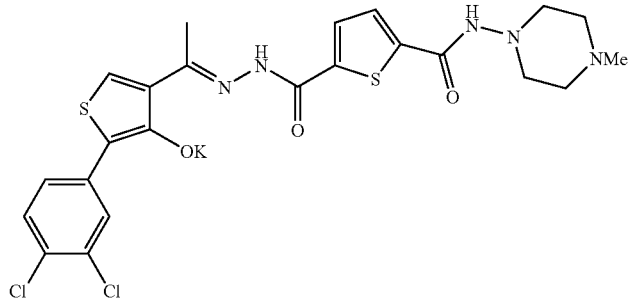
Synthetic Example 22
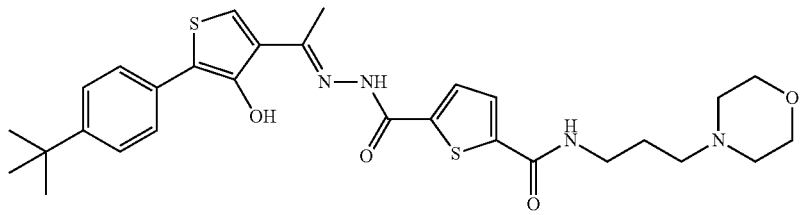
Synthetic Example 23
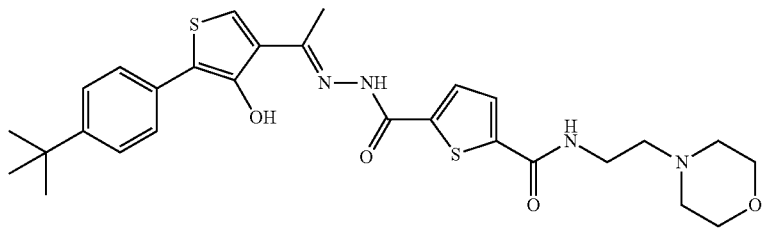
Synthetic Example 24
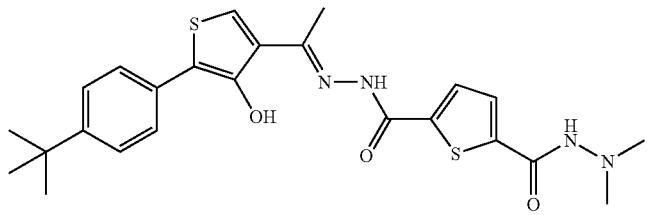
Synthetic Example 25
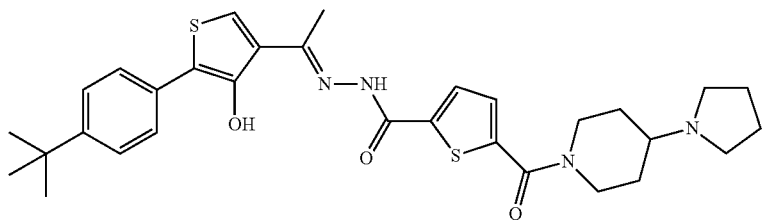
Synthetic Example 26
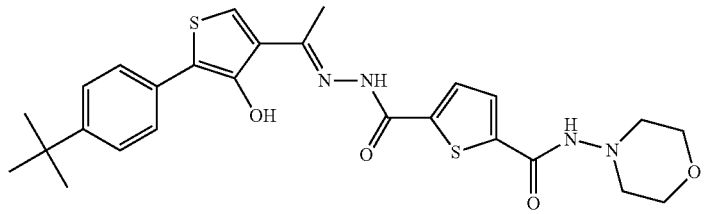

-continued
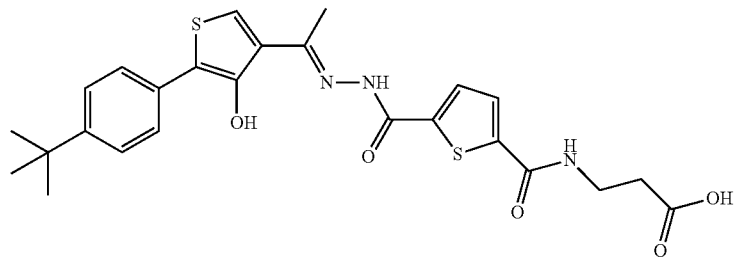
Synthetic Example 27
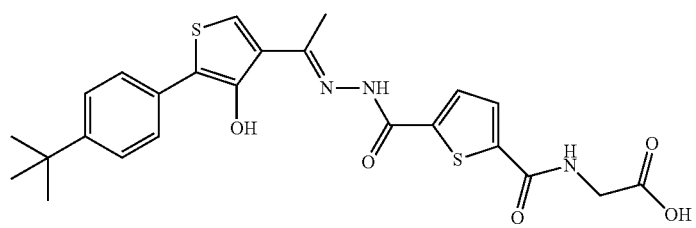
Synthetic Example 28
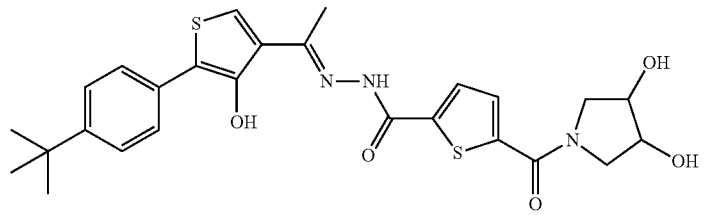
Synthetic Example 29
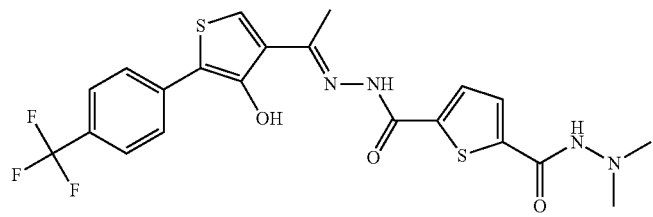
Synthetic Example 30
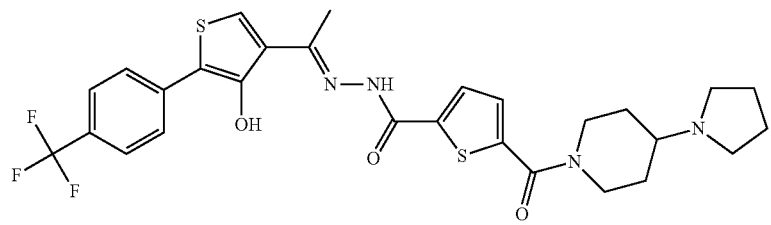
Synthetic Example 31
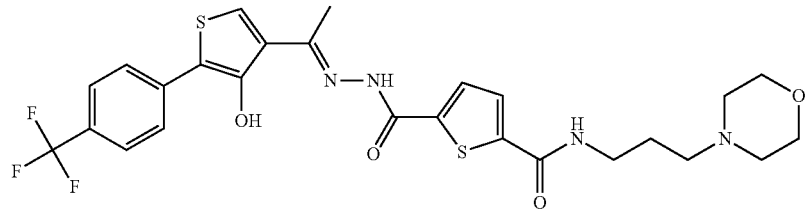
Synthetic Example 32
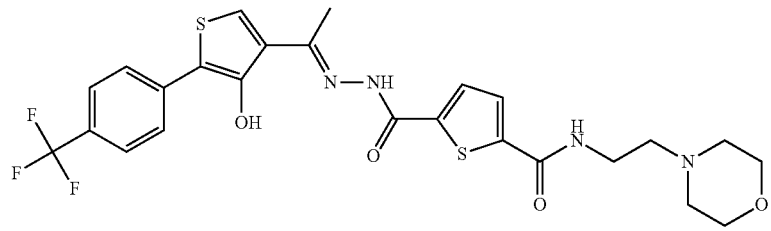
Synthetic Example 33

-continued
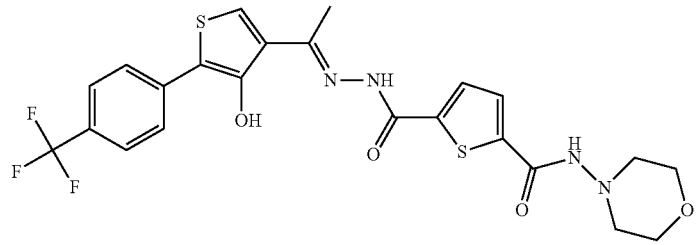
Synthetic Example 34
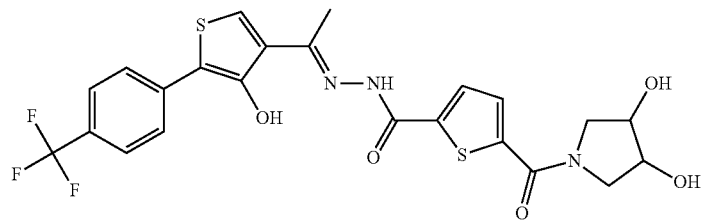
Synthetic Example 35
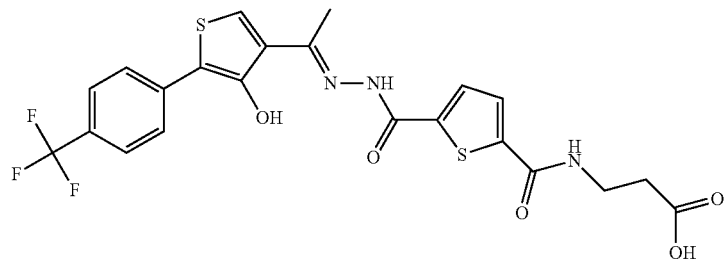
Synthetic Example 36
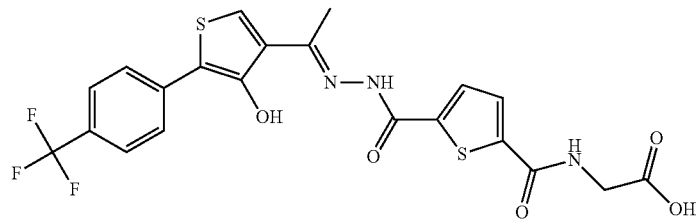
Synthetic Example 37
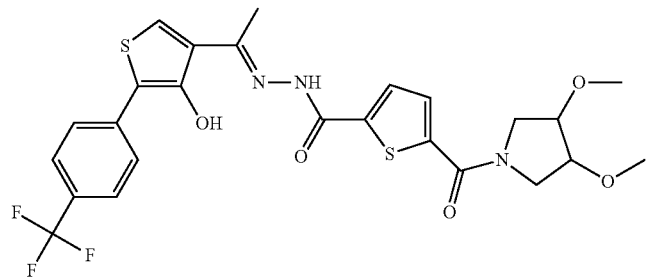
Synthetic Example 38
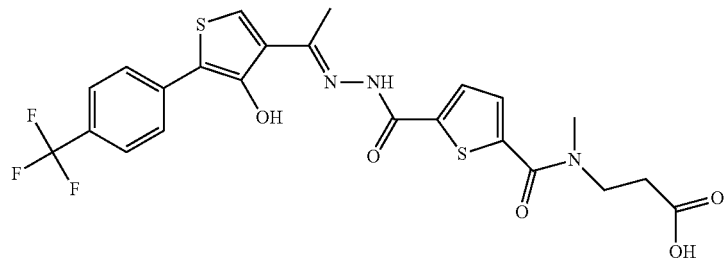
Synthetic Example 39

-continued
Synthetic Example 40
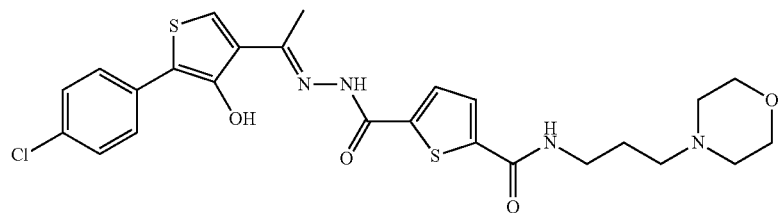
Synthetic Example 41
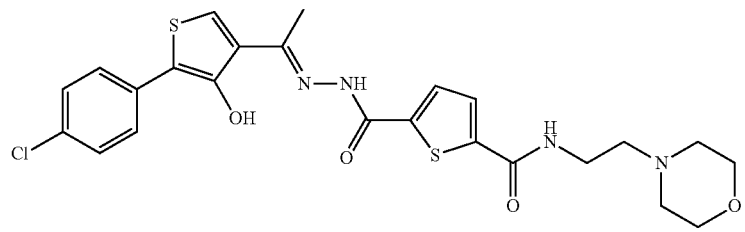
Synthetic Example 42
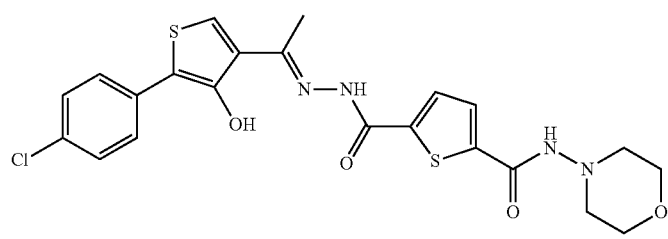
Synthetic Example 43
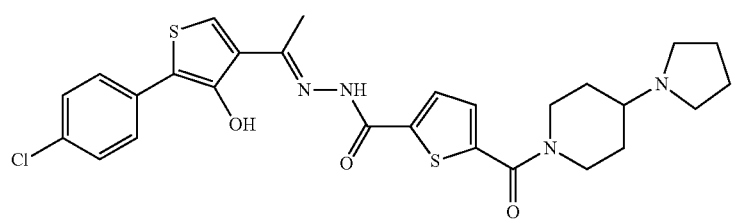
Synthetic Example 44
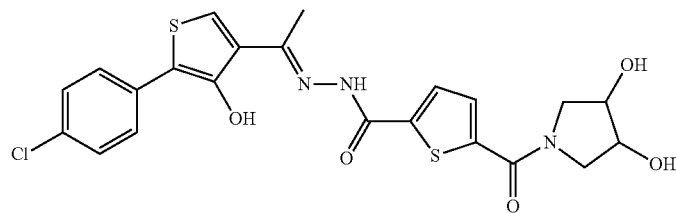
Synthetic Example 45
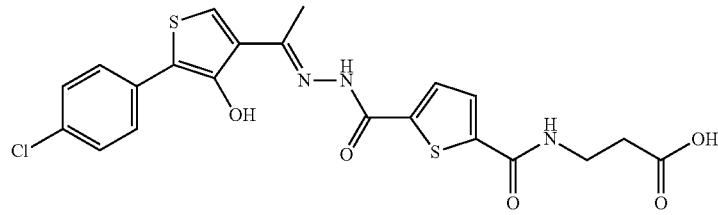
Synthetic Example 46
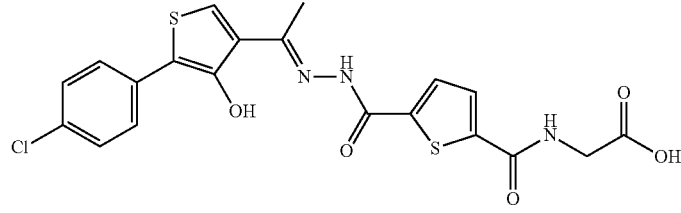

-continued
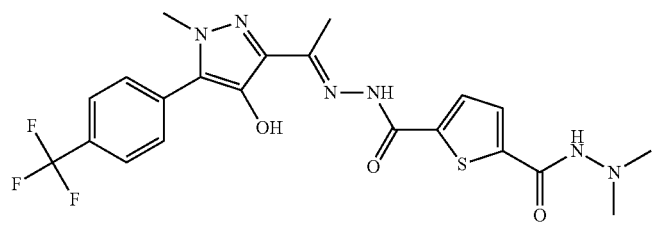
Synthetic Example 47
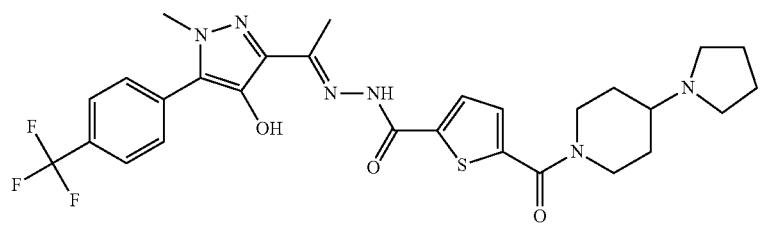
Synthetic Example 48
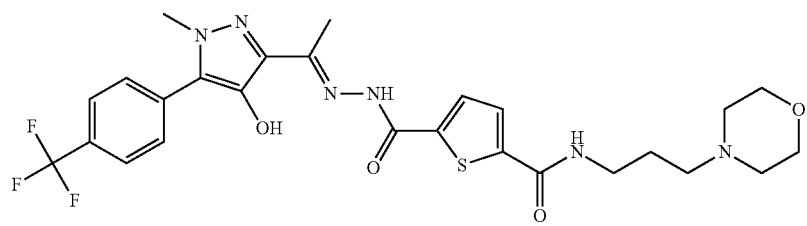
Synthetic Example 49
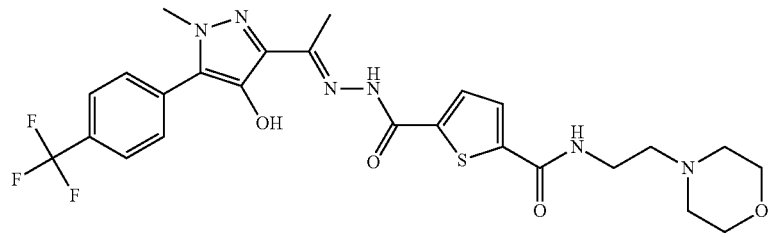
Synthetic Example 50
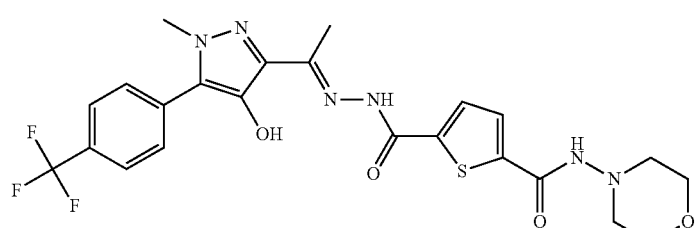
Synthetic Example 51
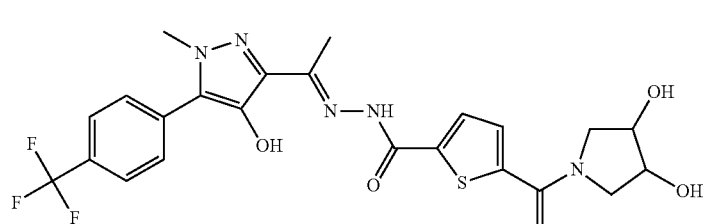
Synthetic Example 52
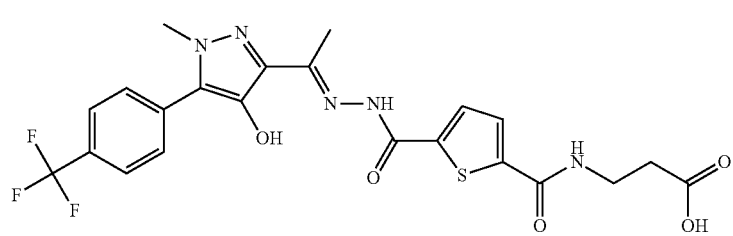
Synthetic Example 53

-continued
Synthetic Example 54
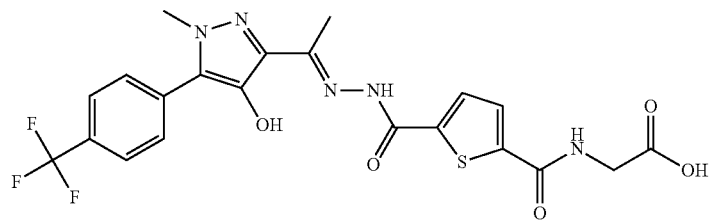
Synthetic Example 55
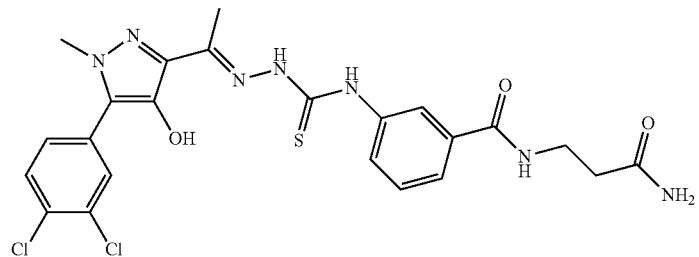
Synthetic Example 56
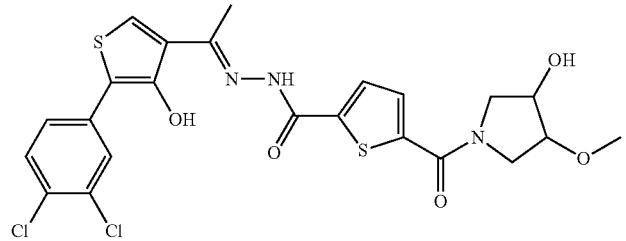
Synthetic Example 57
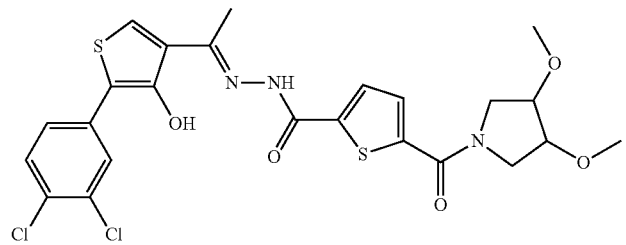
Synthetic Example 58
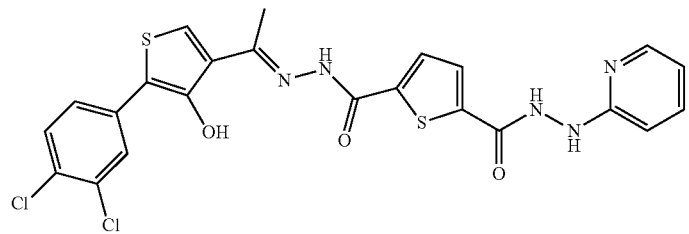
Synthetic Example 59
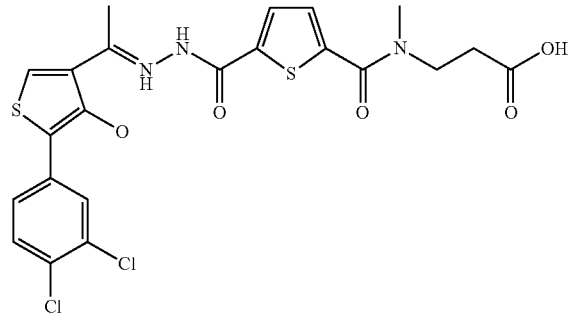

-continued
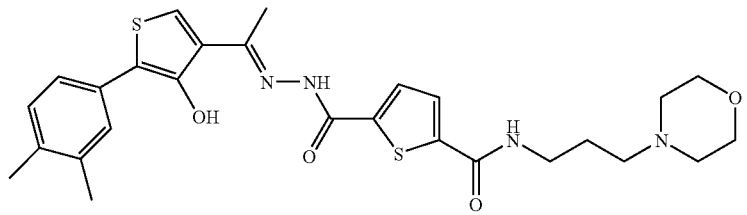
Synthetic Example 60
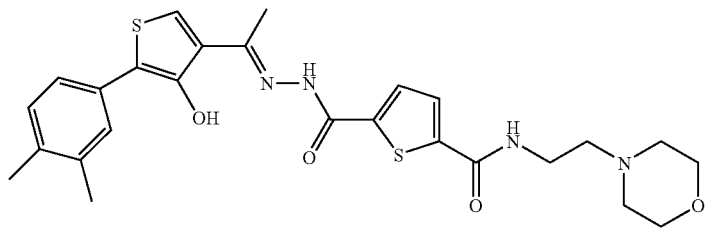
Synthetic Example 61
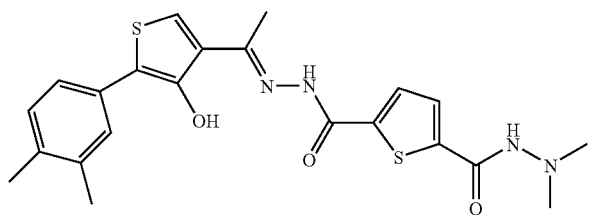
Synthetic Example 62
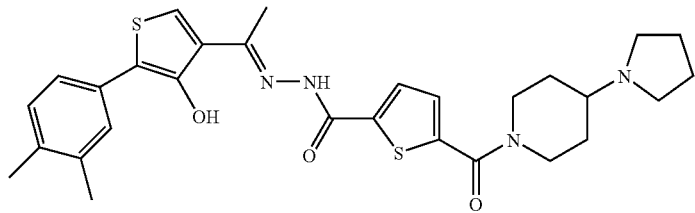
Synthetic Example 63
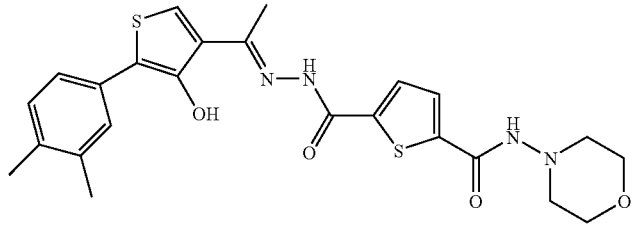
Synthetic Example 64
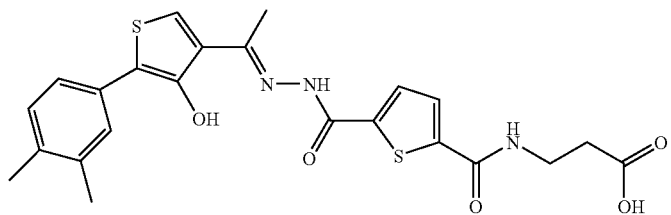
Synthetic Example 65
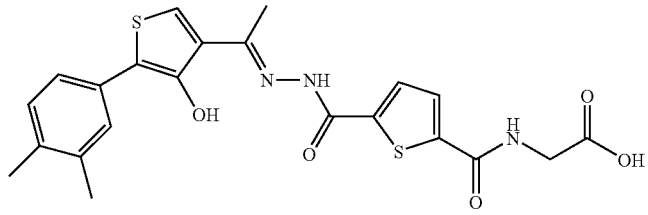
Synthetic Example 66

-continued
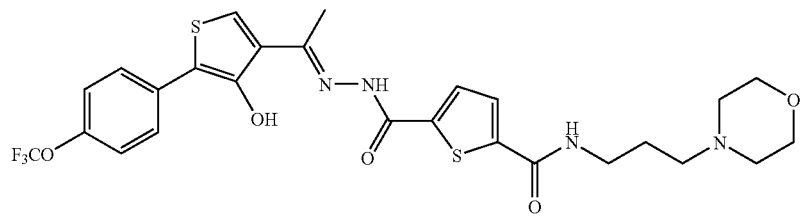
Synthetic Example 67
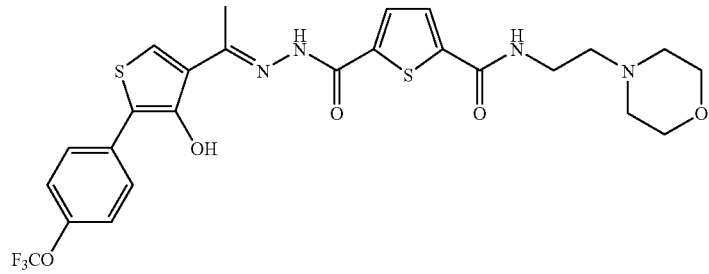
Synthetic Example 68
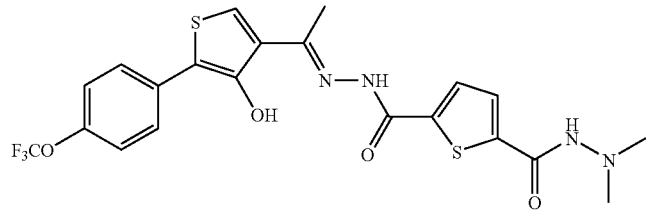
Synthetic Example 69
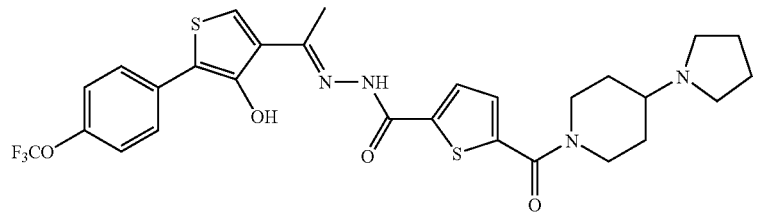
Synthetic Example 70
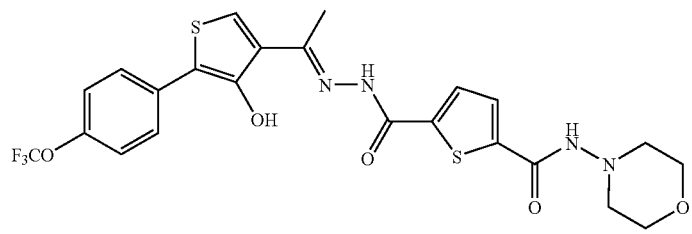
Synthetic Example 71
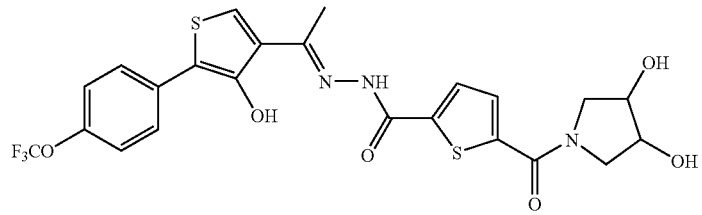
Synthetic Example 72
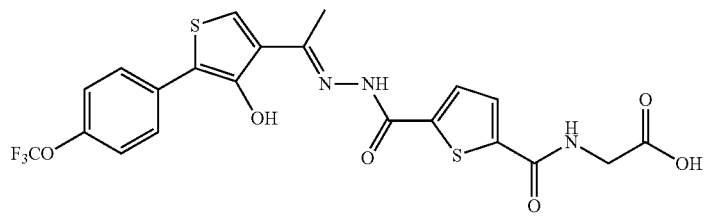
Synthetic Example 73

-continued
Synthetic Example 74
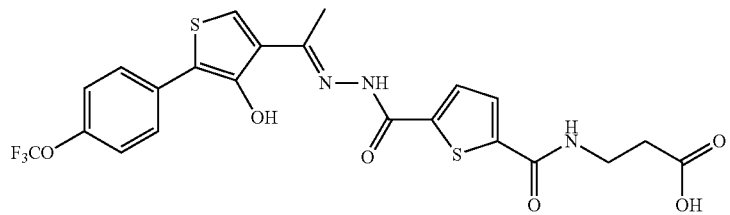
Synthetic Example 75
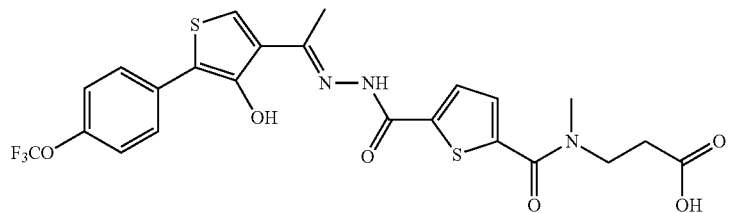
Synthetic Example 76
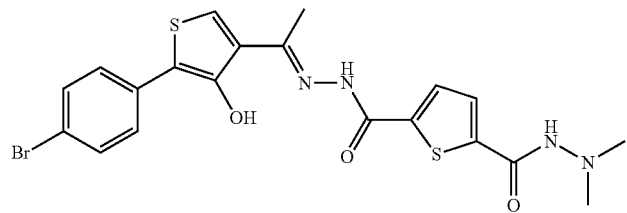
Synthetic Example 77
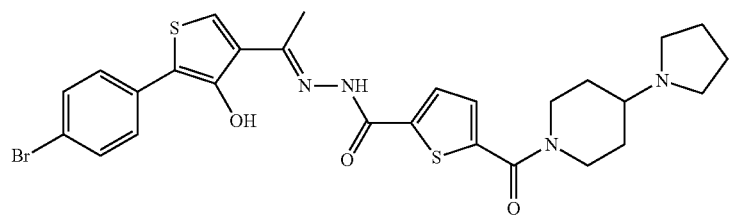
Synthetic Example 78
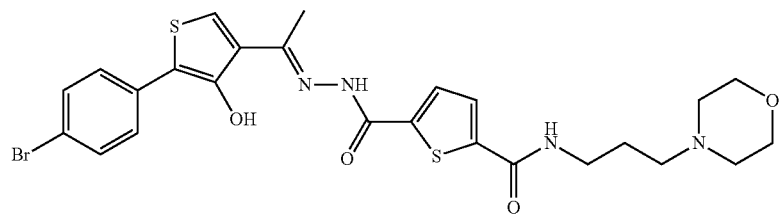
Synthetic Example 79
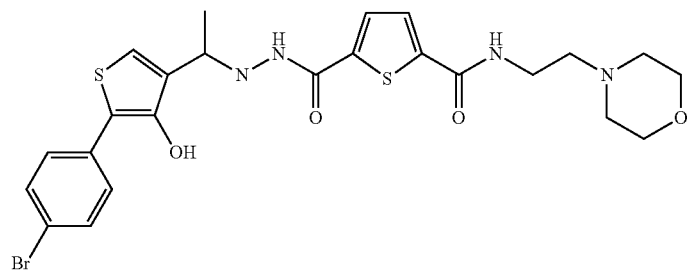

-continued
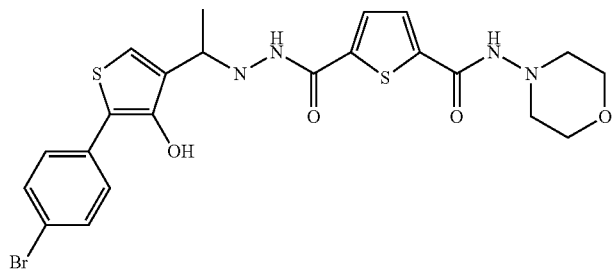
Synthetic Example 80
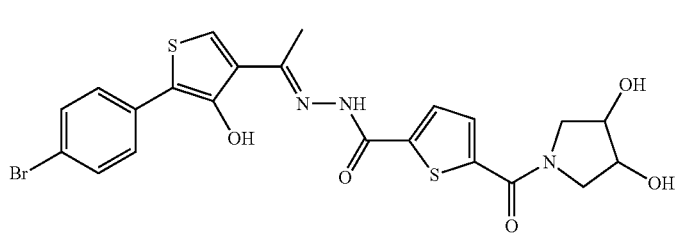
Synthetic Example 81
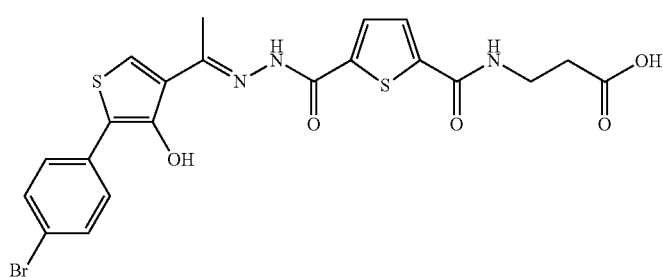
Synthetic Example 82
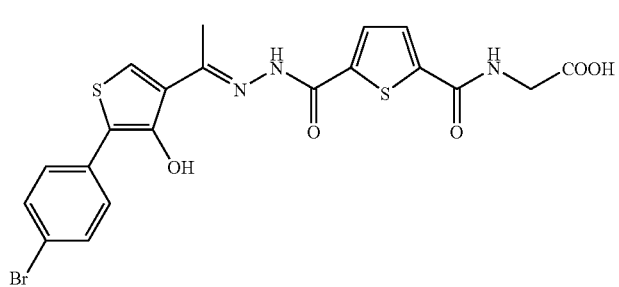
Synthetic Example 83
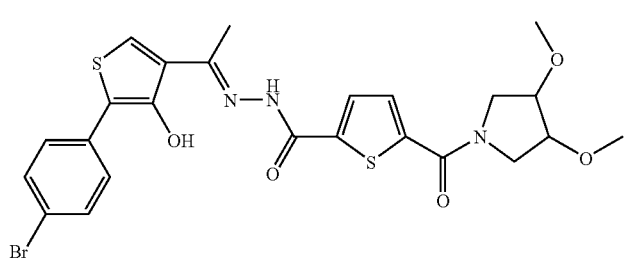
Synthetic Example 84
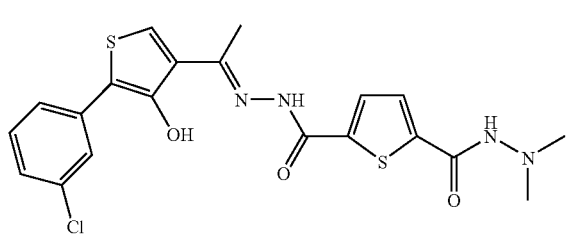
Synthetic Example 85

-continued
Synthetic Example 86
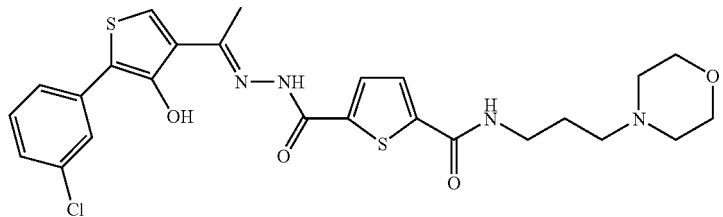
Synthetic Example 87
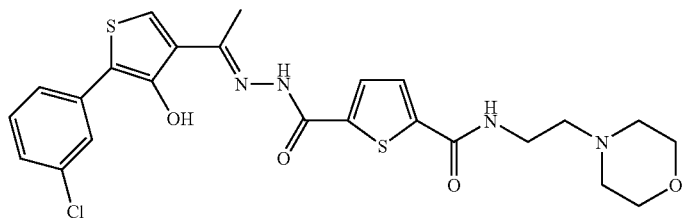
Synthetic Example 88
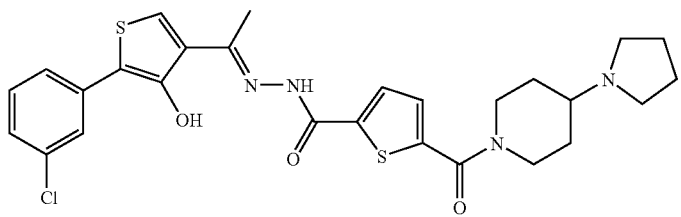
Synthetic Example 89
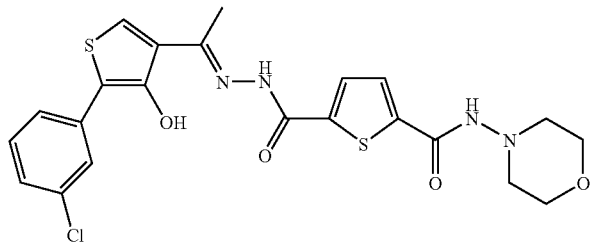
Synthetic Example 90
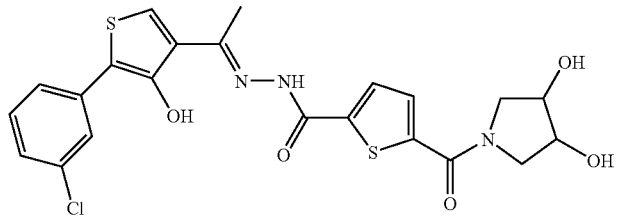
Synthetic Example 91
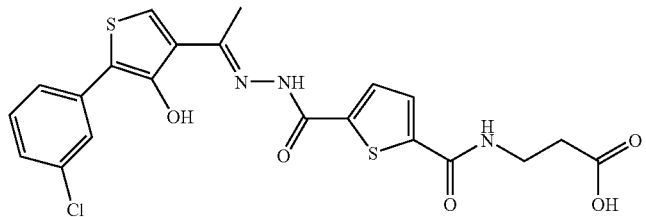
Synthetic Example 92
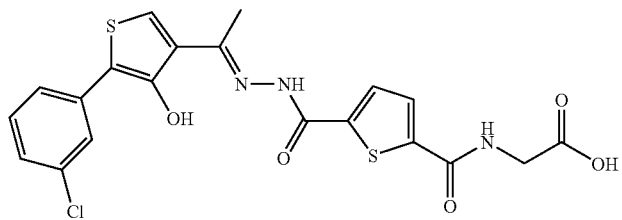

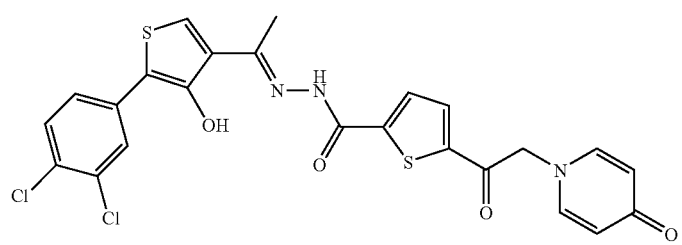

Synthetic Example 93

Assay Example 1

Stimulation of Proliferation of a Thrombopoietin-Dependent Cell Line

The response of thrombopoietin receptor to the compound of Synthetic Example 2 of the present invention was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in IMDM (GIBCO) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6 \times 10^4$ cells/ml. The cell suspension was transferred to a 96-well tissue culture plate (CORNING) in 100-µl aliquots. Then either thrombopoietin (Pepro Tech EC, or the compound of Synthetic Example 2 dissolved in dimethyl sulfoxide was diluted 83-fold with IMDM containing 10% fetal bovine serum and added to the aforementioned cell suspension in 20-µl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-µl aliquot of 5 mM WST-8 reagent solution was added to each well of the tissue culture plate, and the plate was incubated at 37° C. for 4 hours. The formazan pigment generated was detected by measuring the absorbance at 450 nm with a 96-well microplate reader (Nihon Molecular Devices, Spectramax 190). FIG. 1 shows the results with UT7/EPO-mpl cells, while FIG. 2 shows data obtained with UT7/EPO cells expressing no thrombopoietin receptor.

Figure 2:
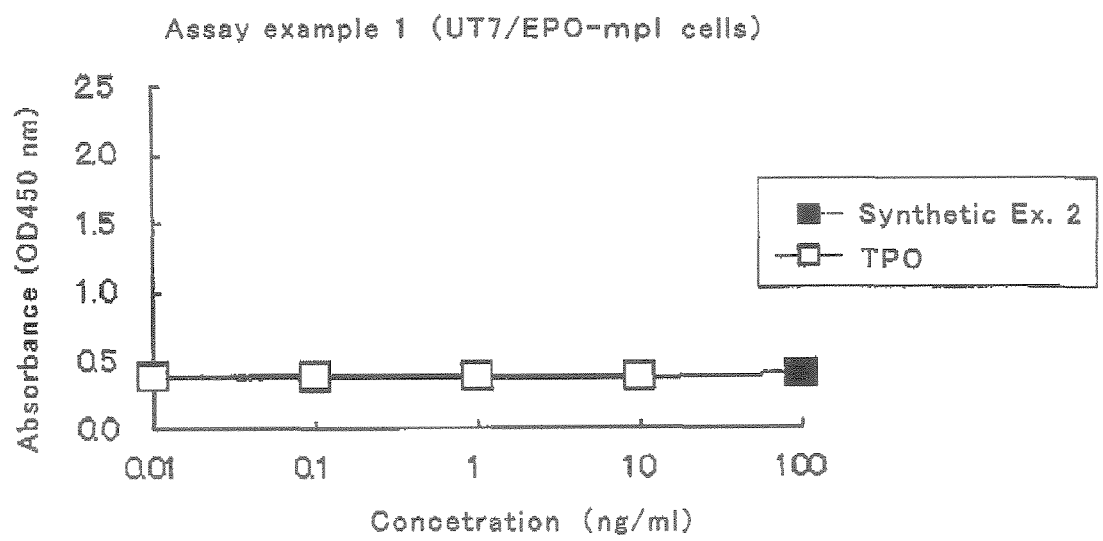
FIG. 2 shows the proliferation of UT7/EPO cells when stimulated by the compound of the present invention (Synthetic Example 2).

FIG. 1 demonstrates that proliferation of thrombopoietin-responsive UT7/EPO-mpl cells was stimulated by the compound of Synthetic Example 2 in a concentration-dependent manner, while no effect of this compound on proliferation was observed with UT7/EPO, the mother cell line, as shown in FIG. 2. These results indicate that the compound of Synthetic Example 2 of the present invention acts on the thrombopoietin receptor selectively as an activator.

Assay Example 2

The compounds of the following Synthetic Examples were tested according to the method of Assay Example 1 to determine the concentration of each compound that yields a growth rate corresponding to 50% of the growth of human leukemic cell line UT-7/EPO-mpl observed in the presence of 10 ng/mL TPO ($EC_{50}$). The results are summarized in Table 11.

TABLE 11

| Synthetic Ex. No. | $EC_{50}$ (ng/mL) |
|---|---|
| 1 | 2.7 |
| 2 | 2.1 |
| 4 | 1.5 |
| 5 | 0.32 |
| 7 | 2.3 |
| 8 | 2.2 |
| 9 | 5.6 |
| 10 | 3.1 |
| 11 | 0.35 |
| 12 | 0.40 |
| 13 | 2.9 |
| 14 | 2.7 |
| 15 | 7.7 |
| 16 | 32 |
| 17 | 16 |
| 18 | 16 |
| 19 | 23 |
| 20 | 3.0 |
| 24 | 1.1 |
| 35 | 0.27 |
| 45 | 3.2 |
| 49 | 1.6 |
| 55 | 3.1 |
| 58 | 0.85 |
| 65 | 2.0 |
| 75 | 3.3 |
| 84 | 2.9 |
| 90 | 0.33 |
| 93 | 0.37 |

Formulation Example 1

A granule preparation containing the following ingredients is prepared.

| Ingredients | |
|---|---|
| Compound represented by the formula (1) | 10 mg |
| Lactose | 700 mg |
| Corn Starch | 274 mg |
| HPC-L | 16 mg |
| | 1000 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
| --- | --- |
| Compound represented by the formula (1) | 10 mg |
| Lactose | 79 mg |
| Corn Starch | 10 mg |
| Magnesium Stearate | 1 mg |
| | 100 mg |

A compound represented by the formula (1) and lactose are sifted through a 60-mesh sieve Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
| --- | --- |
| Compound represented by the formula (1) | 15 mg |
| Lactose | 90 mg |
| Corn Starch | 42 mg |
| HPC-L | 3 mg |
| | 150 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
| --- | --- |
| Compound represented by the formula (1) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (1), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
| --- | --- |
| Compound represented by the formula (1) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The entire disclosures of Japanese Patent Application No. 2004-361150 filed on Dec. 14, 2004 and Japanese Patent Application No. 2005-134643 filed on May 2, 2005 including specifications, claims, drawings and summaries are incorporated herein by reference in their entireties.

The invention claimed is:

1. A compound represented by the formula (1), a tautomer thereof, or a pharmaceutically acceptable salt thereof:

$$(1)$$

wherein
  A is a nitrogen atom or CH,
    when A is a nitrogen atom, B is $NR^9$, wherein $R^9$ is a $C_{1-10}$ alkyl group, and
    when A is CH, B is a sulfur atom,
  $R^1$ is a phenyl group, wherein said phenyl group is substituted with one or more substituents selected from the group consisting of: a halogen atom, an unsubstituted $C_{1-10}$ alkyl group, a $C_{1-10}$ alkyl group substituted with one or more halogen atom, an unsubstituted $C_{1-10}$ alkoxy group, and a $C_{1-10}$ alkoxy group substituted with one or more halogen atom,
  $L^1$ is a bond,
  X is OH,
  $R^2$ is a $C_{1-6}$ alkyl group,
  $L^2$ is a bond, $L^3$ is NH,
$L^4$ is a bond or NH,
Y is an oxygen atom or a sulfur atom, and
$R^3$ is
  a dihydrobenzo[1,4]dioxine group,
  a benzo[1,4]oxazinone group, and
  a thienyl group, wherein said thienyl group is substituted with a 2-(4-oxopyridin-1(4H)-yl)acetyl group) or a substituent represented by $CONR^{29}R^{30}$, where
    $R^{29}$ is a hydrogen atom or a $C_{1-10}$ alkyl group, and
    $R^{30}$ is selected from the group consisting of
      an unsubstituted amino group,
      a pyridyl-substituted amino group,
      a mono-$C_{1-10}$ alkylamino group,
      a di-$C_{1-10}$ alkylamino group,
      a N-methylpiperazinyl group,
      a piperidino group,
      a morpholino group, and
      a $C_{1-10}$ alkyl group substituted with one or more substituents selected from the group consisting of: a carboxyl group, a carbamoyl group, a pyrrolidinyl group, a tetrahydrofuryl group and a morpholino group, or
    $R^{29}$ and $R^{30}$ mean, together with each other, —$(CH_2)_{m3}$-G-$(CH_2)_{m4}$—, wherein
      G is $CR^{31}R^{32}$, wherein $R^{31}$ is a hydrogen atom, and $R^{32}$ is a $C_{1-10}$ alkylcarbonylamino group or a pyrrolidinyl group, and each of m3 and m4 is independently an integer of from 0 to 5, provided that m3+m4 is 3, 4 or 5), or
    $NR^{29}R^{30}$, as a whole, is selected from the group consisting of a di-substituted piperidino group or a di-substituted pyrrolidinyl group, wherein the substitutents independently selected from the group consisting of: a hydroxyl group and a $C_{1-10}$ alkoxy group.

2. The compound, a tautomer thereof, or a pharmaceutically acceptable salt thereof, according to claim 1, wherein
  $R^1$ is a phenyl group, wherein said phenyl group is substituted with one or more substituents selected from the group consisting of: a halogen atom, an unsubstituted $C_{1-10}$ alkyl group, a trifluoromethyl group and a trifluoromethoxy group,
  $R^2$ is a methyl group,
  $L^4$ is a bond,
  Y is an oxygen atom, and
  $R^3$ is a thienyl group, wherein said thienyl group is substituted with a substituent represented by $CONR^{29}R^{30}$, where
    $R^{29}$ is a hydrogen atom or a methyl group, and
    $R^{30}$ is selected from the group consisting of
      an unsubstituted amino group,
      a di-methylamino group,
      a N-methylpiperazinyl group,
      a piperidino group,
      a morpholino group, and
      a methyl group or an ethyl group substituted with one or more substituents selected from the group consisting of: a carboxyl group, a carbamoyl group, a pyrrolidinyl group, a tetrahydrofuryl group and a morpholino group, or
    R29 and R30 mean, together with each other, —$(CH_2)_{m3}$-G-$(CH_2)_{m4}$—, wherein
      G is $CR^{31}R^{32}$, wherein $R^{31}$ is a hydrogen atom, and $R^{32}$ is a methylcarbonylamino group or a pyrrolidinyl group, and each of m3 and m4 is independently an integer of from 1 to 2, provided that m3+m4 is 3 or 4), or
    $NR^{29}R^{30}$, as a whole, is a di-substituted piperidino group or a di-substituted pyrrolidinyl group, wherein the substitutents independently selected from the group consisting of: a hydroxyl group and a methoxy group.

3. The compound, a tautomer thereof, or a pharmaceutically acceptable salt thereof, according to claim 2, wherein A is CH and B is a sulfur atom.

4. The compound, a tautomer thereof, or a pharmaceutically acceptable salt thereof, according to claim 2, wherein A is a nitrogen atom, B is $NR^9$ where $R^9$ is a methyl group.

5. The compound, a tautomer thereof, or a pharmaceutically acceptable salt thereof, according to claim 3, wherein $R^{30}$ is selected from the group consisting of
  an unsubstituted amino group,
  a di-methylamino group,
  a N-methylpiperazinyl group,
  a piperidino group,
  a morpholino group, and
  a methyl group or an ethyl group substituted with one or more substituents selected from the group consisting of: a pyrrolidinyl group, a tetrahydrofuryl group and a morpholino group.

6. The compound, a tautomer thereof, or a pharmaceutically acceptable salt thereof, according to claim 3, wherein $R^{30}$ is a methyl group or an ethyl group substituted with one or more substituents selected from the group consisting of: a carboxyl group and a carbamoyl group.

7. The compound, a tautomer thereof, or a pharmaceutically acceptable salt thereof, according to claim 3, wherein $R^{29}$ and $R^{30}$ mean, together with each other, —$(CH_2)_{m3}$-G-$(CH_2)_{m4}$—, wherein G is $CR^{31}R^{32}$, wherein $R^{31}$ is a hydrogen atom, and $R^{32}$ is a methylcarbonylamino group or a pyrrolidinyl group, and each of m3 and m4 is independently an integer of from 1 to 2, provided that m3+m4 is 3 or 4.

8. The compound, a tautomer thereof, or a pharmaceutically acceptable salt thereof, according to claim 3, wherein $NR^{29}R^{30}$, as a whole, is a di-substituted piperidino group or a di-substituted pyrrolidinyl group, wherein the substitutents independently selected from the group consisting of: a hydroxyl group and a methoxy group.

9. A composition comprising the compound according to claim 1, a tautomer, or pharmaceutically acceptable salt of the compound, as an active ingredient and at least one additive selected from the group consisting of an oral medicine, an excipient, a lubricant, a binder, a disintegrant, a humectant, a plasticizer, and a coating agent.

* * * * *